US009879232B2

(12) United States Patent
Yeo et al.

(10) Patent No.: US 9,879,232 B2
(45) **Date of Patent: *Jan. 30, 2018**

(54) ATTENUATED VACCINIA VIRUS KVAC103 STRAIN

(71) Applicant: Korea Centers for Disease Control and Prevention, Chungcheongbuk-do (KR)

(72) Inventors: Sang Gu Yeo, Seoul (KR); Ho Sun Son, Daejeon (KR); June Woo Lee, Seoul (KR); Seung Bin Cha, Seoul (KR); Sun Hwa Lee, Seoul (KR); Kwi Sung Park, Daejeon (KR); Sang Won Lee, Seoul (KR)

(73) Assignee: KOREA CENTERS FOR DISEASE CONTROL AND PREVENTION, Chungcheongbuk-Do (KR)

(*) Notice: Subject to any disclaimer, the term of this patent is extended or adjusted under 35 U.S.C. 154(b) by 0 days.

This patent is subject to a terminal disclaimer.

(21) Appl. No.: 14/883,757

(22) Filed: Oct. 15, 2015

(65) Prior Publication Data

US 2016/0106829 A1 Apr. 21, 2016

(30) Foreign Application Priority Data

Oct. 16, 2014 (KR) ........................ 10-2014-0140150

(51) Int. Cl.
*C12N 7/00* (2006.01)
*A61K 39/12* (2006.01)
*A61K 39/00* (2006.01)

(52) U.S. Cl.
CPC ................ *C12N 7/00* (2013.01); *A61K 39/12* (2013.01); *A61K 2039/5254* (2013.01); *C12N 2710/24121* (2013.01); *C12N 2710/24134* (2013.01); *C12N 2710/24164* (2013.01)

(58) Field of Classification Search
CPC ........... C12N 2710/24121; C12N 2710/24134; C12N 7/00; C12N 15/86; C12N 2710/24164; C12N 2710/24143; C12N 2710/24171; A61K 2039/5254; A61K 39/12; A61K 39/285
See application file for complete search history.

(56) References Cited

U.S. PATENT DOCUMENTS

| | | | |
|---|---|---|---|
| 8,741,308 | B2 | 6/2014 | Howley et al. |
| 9,012,214 | B2 | 4/2015 | Tangy et al. |
| 2012/0328650 | A1 | 12/2012 | Chaplin et al. |

FOREIGN PATENT DOCUMENTS

| | | | |
|---|---|---|---|
| KR | 20040108798 | A | 12/2004 |
| KR | 20050024359 | A | 3/2005 |
| KR | 20080032016 | A | 4/2008 |
| WO | WO 2010/031837 | A1 | 3/2010 |

OTHER PUBLICATIONS

"Construction of Recombinant Vaccinia Virus: Cloning into the Thymidine Kinase Locus." Byrd CM, Hruby DE. Isaacs SN, Ed. In: Vaccinia Virus and Poxvirology: Methods and Protocols. 2004. Humana Press: Totowa, NJ. pp. 31-40. 978-1-59259-789-5. http//dx.doi.org/10.1385/1-59259-789-0:031.*

Son HS, Yeo SG, Lee SW. Development of a Recombinant Viral Vector Using the Highly Attenuated Korean Vaccinia Virus Strain, KVAC103. Abstract F034. International Meeting of the Federation of Korean Microbiological Societies. Oct. 17-18, 2013. http://www.msk.or.kr/mskfile/fkms2013.pdf. p. 264.*

Stickl et al. "MVA-Stage Vaccination Against Smallpox," Dtsch Med Wochenschr 1974; 99(47): 2386-2392. Abstract.

Hendrickson et al., "Orthopoxvirus Genome Evolution: The Role of Gene Loss," Viruses 2010, 2, 1933-1967.

Rosel et al., "Conserved TAAATG Sequence at the Transcriptional and Translational Initiation Sites of Vaccinia Virus Late Genes Deduced by Structural and Functional Analysis of the HindIII H Genome Fragment," Journal of Virology, vol. 60, No. 2, Nov. 1986, 436-449.

Yuen et al., "Early promoter-binding factor from vaccinia virions," Proc. Natl. Acad. Sci. USA, vol. 84, Sep. 1987, 6069-6073.

Davison et al., "Structure of Vaccinia Virus Late Promoters," J. Mol. Biol. (1989) 210, 771-784.

Davison et al., "Structure of Vaccinia Virus Early Promoters," J. Mol. Biol. (1989) 210, 749-769.

Chakrabarti et al., "Compact, Synthetic, Vaccinia Virus Early/Late Promoter for Protein Expression," BioTechniques 23. Dec. 1997, 1084-1097.

* cited by examiner

*Primary Examiner* — Rachel B Gill
(74) *Attorney, Agent, or Firm* — RatnerPrestia

(57) ABSTRACT

The attenuated vaccinia virus strain KVAC103 was obtained by subculturing a vaccinia virus strain 103 times in VERO cells. The attenuated vaccinia virus strain KVAC103 has significantly low toxicity, shows reduced skin lesions, and, at the same time, induces effectively immune responses to poxvirus. Thus, it can be used as a poxvirus vaccine while causing less side effects.

9 Claims, 9 Drawing Sheets
(4 of 9 Drawing Sheet(s) Filed in Color)

【Figure 1】
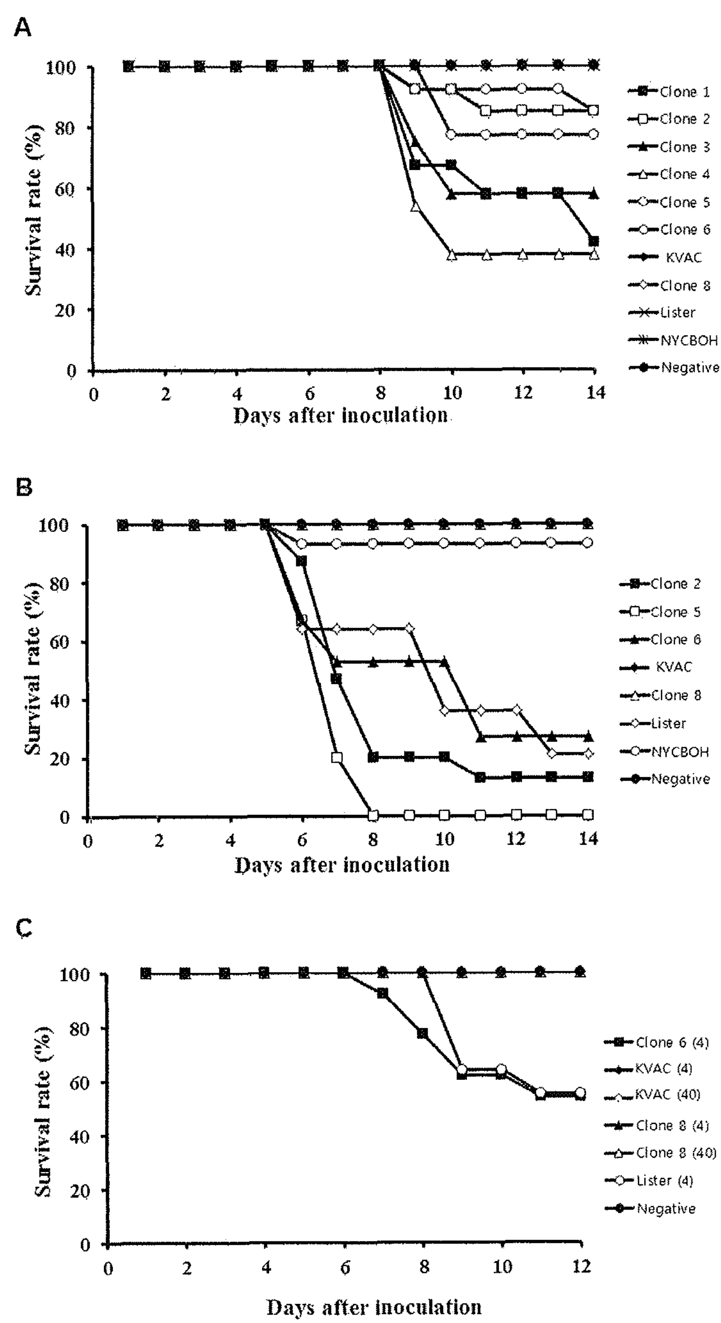

【Figure 2】
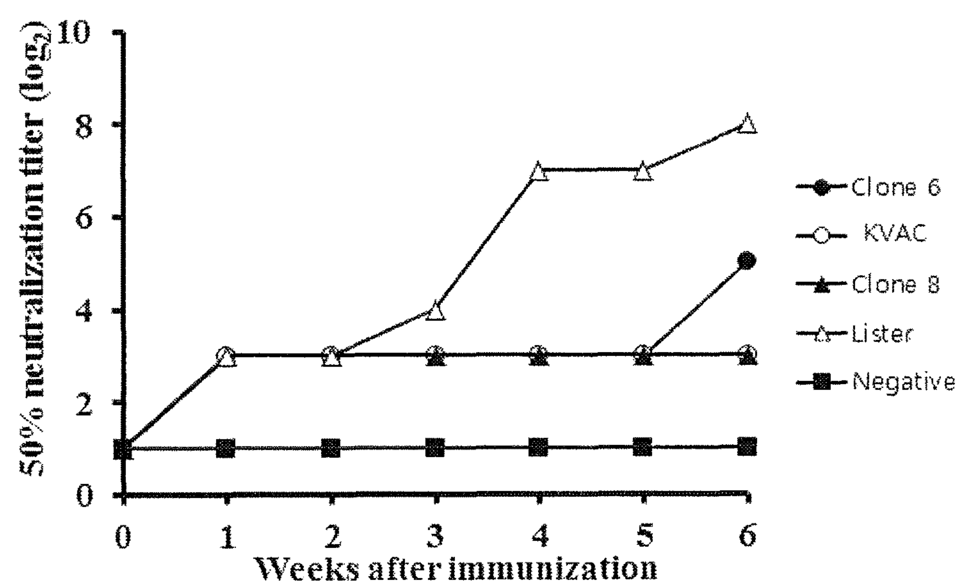

【Figure 3】
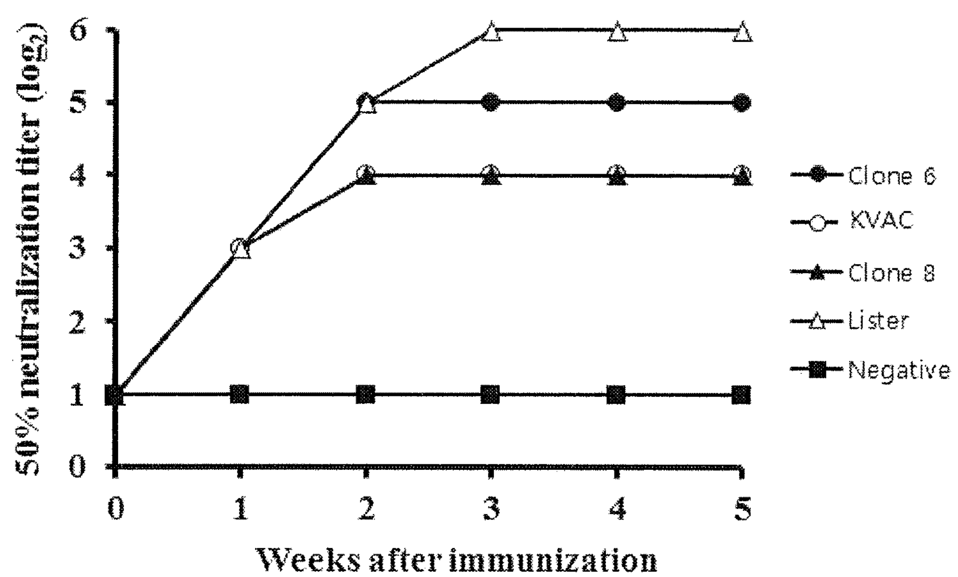

【Figure 4】
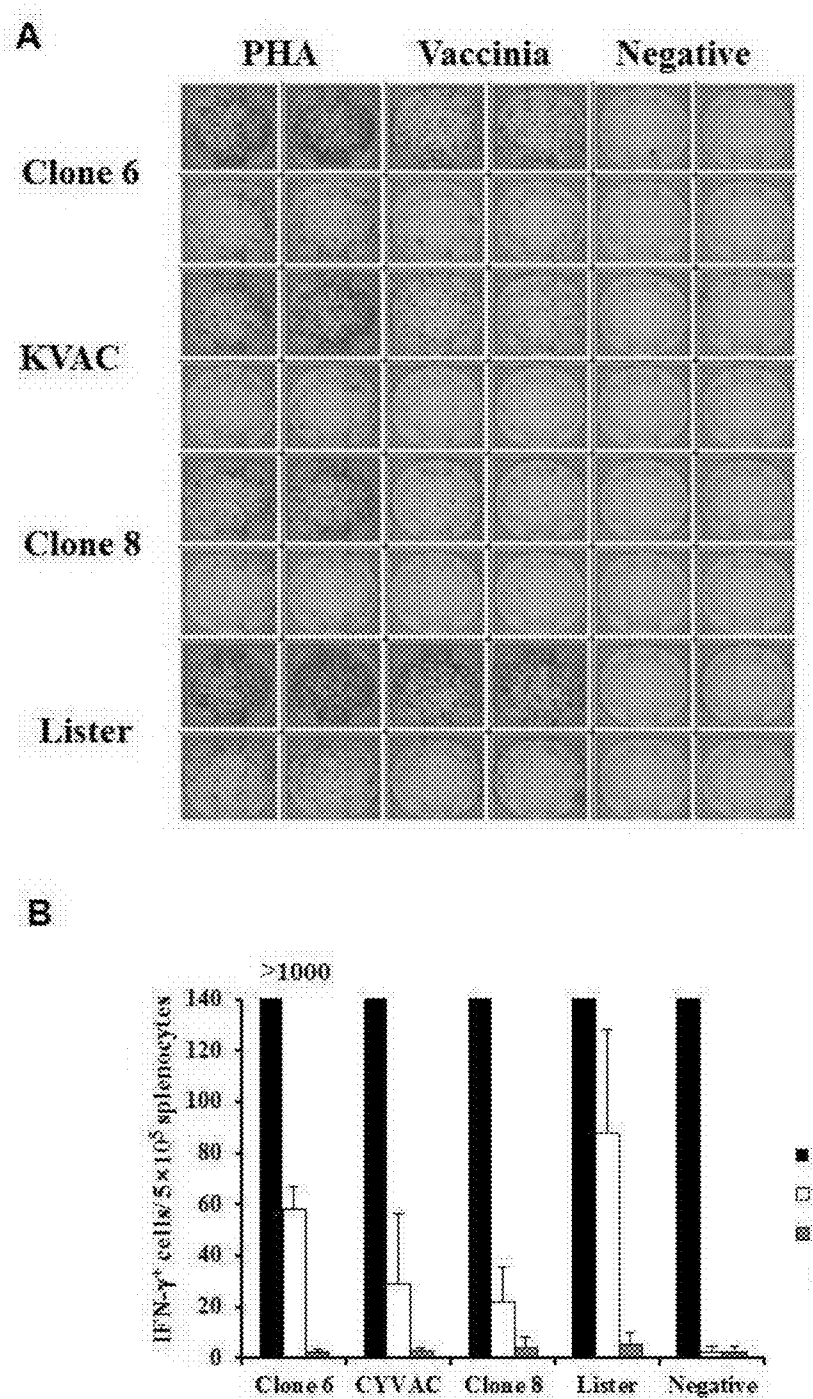

【Figure 5A】
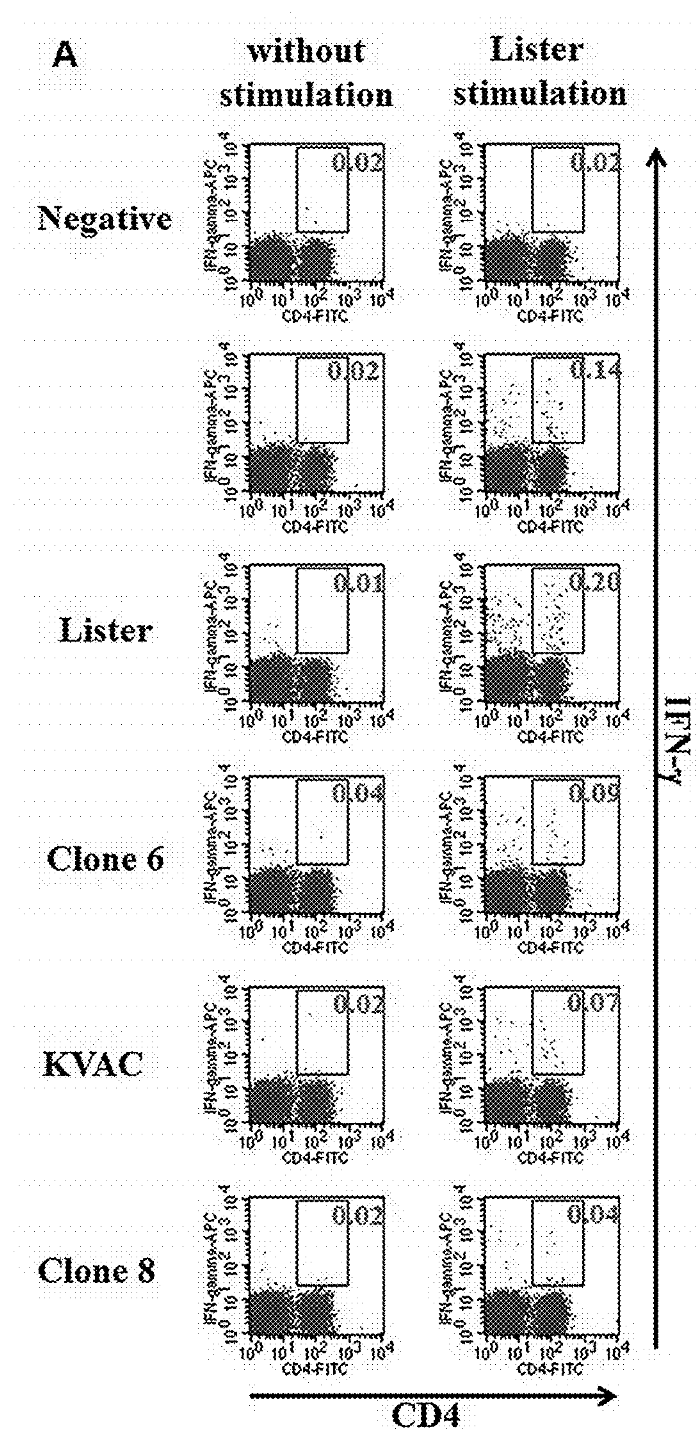

【Figure 5B】
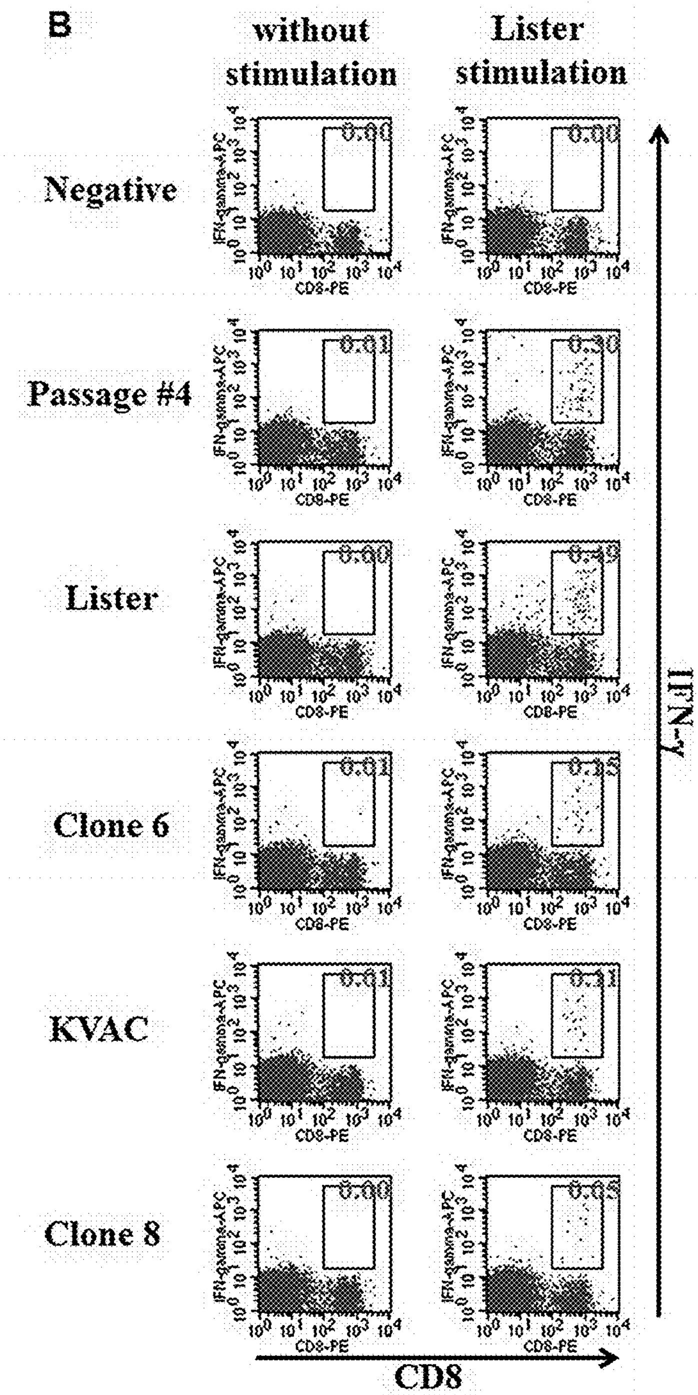

【Figure 6】
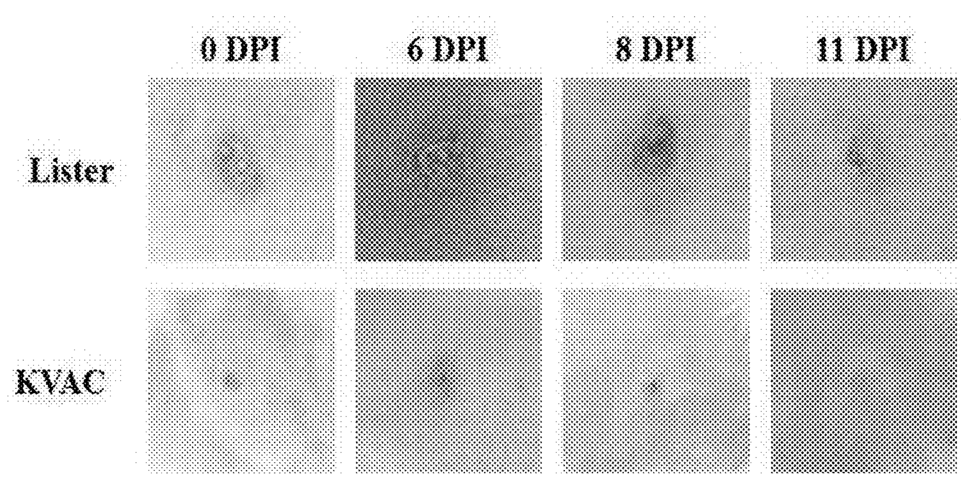

【Figure 7】

Reference Sequence for analysis is VACV107 (Genbank:DQ121394)

>20k Deletion region [C9L - F3L]

```
                                         15195
VACV107 CATGTCTACTATTTGTGTATTCTTCTAATGGGG TAGCTGTCTCCAATTTTTGCGTAATGGAT
                                         15024
KVAC103 CATGTCTACTATTTGTGTATTCTTCTAATGGGGATTTGGTAGACCTCCTACTACGTATAATTT
                                           34632
VACV107 TCCCCGTGGAACCAACGCTCAACAGATGT GGGATTTGGTAGACCTCCTACTACGTATAATTT
```

19,437 bp deletion compared to VACV107
( 34,632 - 15,195 = 19,437 bp)

>2.5 kb Deletion region [A25L - A26L]

```
                                           139978
VACV107 AATTAGGATCTTCTAATGGATTGTATGGCTTGATA GCATCATCTTTATCATTATTAGGGGGAT
                                           120359
KVAC103 AATTAGGATCTTCTAATGGATTGTATGGCTTGATAACTTCGTGAATAATGTTTCTATGTTTTCTA
                                           142484
VACV107 CATTTTAGGATAGGCTTTCATAAAGTCCCTA ATAACTTCGTGAATAATGTTTCTATGTTTTCTA
```

2,506 bp deletion compared to VACV107
( 142,484 - 139,978 = 2,506 bp)

【Figure 8】
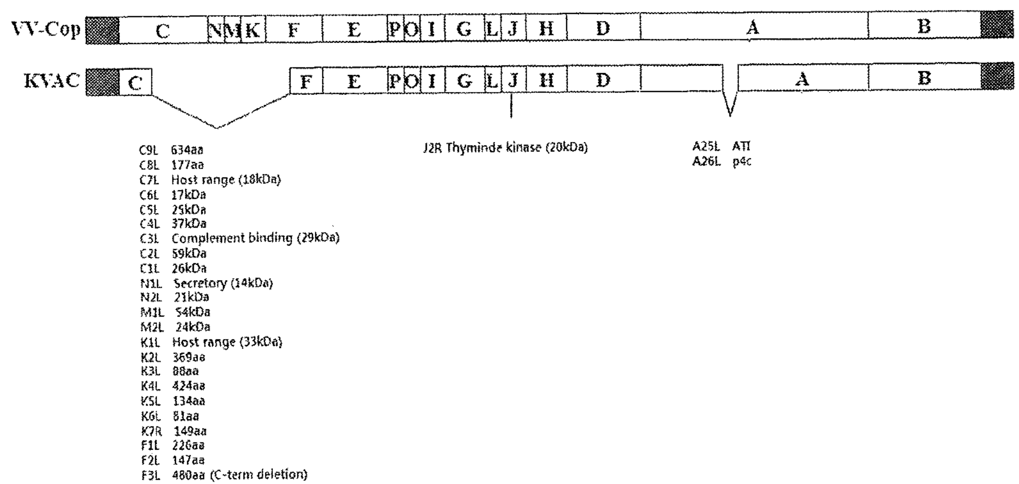

ATTENUATED VACCINIA VIRUS KVAC103 STRAIN

CROSS REFERENCE TO RELATED APPLICATION

This application claims priority to Korean Patent Application No. 10-2014-0140150, filed Oct. 16, 2014, the contents of such application being incorporated by reference herein.

BACKGROUND OF THE INVENTION

Field of the Invention

The present invention relates to the novel attenuated vaccinia virus strain KVAC103 having reduced toxicity and side effects.

Description of the Prior Art

Vaccinia virus is an enveloped DNA virus which has an about 120-180 kb double-stranded linear DNA genome encoding about 200 different genes (Hendrickson et al., 2010). Each of the genes is composed of a short 5'-promoter, a single ORF encoding a protein without intron, a short 3'-polyadenylation site. These proteins are expressed in a promoter-dependent manner in the intermediate-early (IE), early (E) or late (L) stage of viral infection. The sequences of the early and late promoters have been well characterized through functional experiments (Rosel et al., 1986; Yuen et al., 1987; Davision et al., 1989a and 1989b; Chakrabarti et al., 1997).

Since vaccinia virus was first used as a vaccine for smallpox by Edward Jenner in the 18$^{th}$ century, it has become a general term for immunomodulators such that it would give the etymology of the word “vaccine”. Smallpox is an acute contagious disease caused by the variola virus. In smallpox caused by the variola major virus, maculopapular exanthema appears after an incubation of 7-17 days (12 days on average), and then progresses to blisters, pus blisters, etc. Smallpox has a mortality rate of 30% or higher, and the survivors are left with scars on the face. The variola virus that causes smallpox belongs to the Orthopoxvirus genus together with monkeypox, cowpox and vaccinia virus. Orthopoxviruses have the characteristic of inducing strong cross-immunity therebetween, and thus a vaccine produced from the vaccinia virus, which is less pathogenic than variola virus, has been used in a global program for the eradication of smallpox. The effect of the vaccine was demonstrated by the 1980's World Health Organization (WHO) declaration of eradication of smallpox (WHO Declaration of global eradication of smallpox, Wkly Epideminol Rec 1980:55:148). The variola virus that causes smallpox is characterized in that: 1) it is stable in an aerosol state; 2) it is easy to mass-produce; 3) it is contagious in a small amount; 4) it is highly contagious among humans; 5) it has a long incubation period of 7-17 days; and 6) it has high mortality rate. Due to such characteristics, there have been concerns over the potential for the variola virus to be developed as biological weapons. Due to the uncertainty over the eradication of smallpox and the danger of developing the variola virus into biological terror weapons, countries have retained smallpox vaccines for use in case of emergency. As is known, in the case of the USA, the first-generation smallpox vaccine produced from cows has been used for some risk groups. Some developed countries including Japan have also taken their own measures, and for example, developed smallpox vaccine by themselves in order to meet the demand for smallpox vaccines in their countries, or purchased the first-generation smallpox vaccine.

Vaccinia virus used in the early years had a good immunogenic efficacy and greatly contributed to the eradication of smallpox, but people vaccinated with the vaccinia virus sometimes showed serious side effects such as systemic infection or progressive infection. To reduce such side effects, Virulence-attenuated vaccinia virus strains including MVA, NYVAC, and LC16m8 were developed. Among them, modified vaccinia virus Ankara (MVA) as disclosed in Korean Patent No. 1009102970000 is an attenuated virus strain obtained by Subculturing the vaccinia virus CVA strain 500 times or more in chick embryo fibroblasts (CEFs), and it does not proliferate in most mammalian cells and has a 30 kb deleted region in six regions in the genome. This virus showed excellent safety in animal models, and thus have been developed as a smallpox vaccine and a vaccine delivery vehicle by Bavarian Nordic (Denmark). LC16m8, an attenuated virus developed by the Chiba Serum Institute of Japan, forms small plaques and shows reduced virulence. It was found to have a mutation in the B5R gene in the genome sequence. NYVAC is a virus strain obtained by deleting 18 ORFs from five regions containing 18 ORFs in the genome of the Copenhagen strain by a genetic engineering technique, and has been developed as various recombinant viral delivery vehicles.

SUMMARY OF THE INVENTION

An aspect of the present invention provides a novel attenuated vaccinia virus strain in order to develop a highly pure, safe poxvirus vaccine which can be produced by cell culture.

The present inventors subcultured vaccinia virus 103 times in Vero cells, thereby isolating and identifying the novel attenuated vaccinia virus strain KVAC103 which has excellent immunogenicity while having reduced toxicity due to virulence attenuation.

BRIEF DESCRIPTION OF THE DRAWINGS

The patent or application file contains at least one drawing executed in color. Copies of this patent or patent application publication with the color drawing(s) will be provided by the Office upon request and payment of the necessary fee.

FIG. 1 shows the survival rates of 5-day-old suckling mice after selected vaccinia virus clones were inoculated into the brains of the mice in order to compare the safety of the clones.

FIG. 2 shows the results of evaluating humoral immunogenicity by a plaque reduction neutralization test (PRNT50) after mouse immunization with each of selected vaccinia virus clones.

FIG. 3 shows the results of evaluating humoral immunogenicity by a plaque reduction neutralization test (PRNT50) after rabbit immunization with each of selected vaccinia virus clones.

FIG. 4 shows the results of performing ICS (intracellular cytokine staining) to evaluate cell-mediated immunogenicity in mice after immunization with viruses.

FIGS. 5A and 5B shows the results of an ELISPOT immunoassay to evaluate cell-mediated immunogenicity in mice after immunization with viruses.

FIG. 6 shows the results of analyzing the skin toxicity of the attenuated vaccinia virus strain KVAC103 in rabbits.

FIG. 7 shows a comparison between the nucleotide sequence of a deletion region in the genome of the novel attenuated virus strain KVAC103 (corresponding to nucleotide residues 14992-15054 and 120327-120391 of SEQ ID NO: 1) and the entire nucleotide sequence of reference strain VACV107 (corresponding to nucleotide residues 15163-15224, 34601-34662, 139946-140008 and 142453-142516 of SEQ ID NO: 7).

FIG. 8 is a gene map showing the deletion region of the genome of KVAC103.

DETAILED DESCRIPTION OF THE INVENTION

Hereinafter, the present invention will be described in detail. However, the present invention can be embodied in different forms and is not limited to the embodiments described herein.

In one aspect, the present invention relates to the attenuated vaccinia virus strain KVAC103 (accession No. KCCM11574P).

In an embodiment of the present invention, the attenuated vaccinia virus strain KVAC103 may be one wherein a gene having a nucleotide sequence represented by SEQ ID NO: 1 is deleted or damaged.

In one aspect, the present invention relates to an immunogenic composition for preventing or treating poxvirus infection, the composition containing the attenuated vaccinia virus strain KVAC103 (accession No. KCCM11574P) as an active ingredient.

In an embodiment of the present invention, the attenuated vaccinia virus strain KVAC103 may be attenuated by subculture.

In an embodiment, the composition may contain at least one pharmaceutically acceptable carrier or excipient.

For preparation of the preventive composition (i.e., vaccine) of the present invention, the attenuated vaccinia virus according to the present invention is converted into a physiologically acceptable form. This can be done based on the experience in the preparation of poxvirus vaccines used for vaccination against smallpox (as described by Stickl, H. et al. Dtsch. med. Wschr. 99, 2386-2392 [1974]). For the preparation of vaccine shots, for example, virus particles are lyophilized in 100 ml of phosphate-buffered saline (PBS) in the presence of 2% peptone and 1% human albumin in an ampoule, preferably a glass ampoule. Alternatively, the vaccine shots are produced by stepwise freeze-drying of the virus in a formulation. This formulation can contain additional additives such as mannitol, dextran, sugar, glycine, lactose or polyvinylpyrrolidone or other aids, such as antioxidants or inert gas, stabilizers or recombinant proteins (for example, human serum albumin) suitable for in vivo administration. The glass ampoule is then sealed and can be stored between 4° C. and room temperature for several months. However, as long as no immediate need exists, the ampoule can preferably be stored at temperatures below −20° C.

The therapeutically effective dose of the therapeutic composition of the present invention can vary depending on various factors, for example, an administration method, a target area, the subject's conditions, etc. Thus, when the composition is to be used in the human body, the dose of the composition should be suitably determined by taking into consideration both safety and efficiency. It is also possible to estimate the dose for human administration from the effective dose determined through an animal test. Such considerations to be taken in the determination of the effective dose are described, for example, in Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The composition of the present invention may also comprise a carrier, a diluent, an excipient, or a combination of two or more thereof, which are commonly used in biological formulations. The pharmaceutically acceptable carrier for use in the present invention is not specifically limited, as long as it is suitable for in vivo delivery of the composition. Examples of a pharmaceutically acceptable carrier that may be used in the present invention include the compounds described in Merck Index, 13$^{th}$ ed., Merck & Co. Inc., physiological saline, sterile water, Ringer's solution, buffered saline, dextrose solution, maltodextrin solution, glycerol, ethanol, and mixtures containing one or more of these components. If necessary, the composition may contain other conventional additives such as antioxidants, buffers, bacteriostatic agents and the like. In addition, the composition can be prepared into injectable formulations, such as aqueous solutions, suspensions and emulsions, pills, capsules, granules or tablets, by adding diluents, dispersing agents, surfactants, binders and lubricants thereto. Furthermore, the pharmaceutical composition may preferably be formulated according to each disease or component by a suitable method known in the art or by using the method disclosed in Remington's Pharmaceutical Science (Mack Publishing Company, Easton Pa., 18th, 1990).

The composition of the present invention may further comprise pharmaceutically acceptable additives. Examples of pharmaceutically acceptable additives that may be used in the present invention include starch, gelatinized starch, microcrystalline cellulose, lactose, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, starch sodium glycolate, carnauba wax, synthetic aluminum silicate, stearic acid, magnesium stearate, aluminum stearate, calcium stearate, white sugar, dextrose, sorbitol, talc, etc. The pharmaceutically acceptable additives that are used in the present invention are preferably contained in an amount of 0.1-90 parts by weight based on the total weight of the composition, but are not limited thereto.

The therapeutic composition of the present invention may be administered orally or parenterally (for example, intravenous, subcutaneous, intraperitoneal or topical application) according to the intended method. The dose of the composition of the present invention can vary depending on various factors, including the subject's weight, age, sex and health conditions, diet, administration time, administration method, excretion rate and the severity of the disease. The daily dose of the composition according to the present invention is 0.0001-10 mg/ml, preferably 0.0001-5 mg/ml, and is preferably administered once or several times a day.

In one aspect, the present invention relates to a method for preventing or treating poxvirus infection in mammals excluding humans, the method comprising a step of administering the composition of the present invention to the mammals.

In an embodiment of the present invention, the poxvirus may be Orthopoxvirus.

For vaccination or therapy, the lyophilisate of the composition can be dissolved in 0.1-0.5 ml of an aqueous solution, preferably physiological saline or Tris buffer, and administered either systemically or locally, i.e. parenterally, subcutaneously, intramuscularly, or any other administration routes known to those skilled in the art. The mode of administration, the dose and the number of administrations can be optimized by those skilled in the art in a known manner. However, most commonly, a patient is vaccinated with a second shot about one month to six weeks after the first vaccination shot.

Hereinafter, the present invention will be described in further detail with reference to the following examples. It is to be understood, however, that these examples are for illustrative purposes only and are not intended to limit the scope of the present invention.

EXAMPLES

Example 1: Establishment of Attenuated Vaccinia Virus Strain 1-1: Subculture of Vaccinia Virus To make an attenuated vaccinia virus, a Korean smallpox vaccine obtained from the Korea National Institute of Health was used as a parent strain, and subcultured in monkey kidney-derived Vero cells (ATCC CCL-81). Specifically, Vero cells cultured as a monolayer in a T75 flask were infected with 2 ml of the virus for 2 hours, after which the supernatant was removed, and the cells were cultured in 1% FBS-containing DMEM medium for 2-3 days while they were observed. A cytopathic effect (CPE) in the entire cells was observed by a phase contrast microscope, and the virus was harvested. To harvest the virus, the T-flask containing the infected cells was sealed, and freezing at −80° C. and thawing at room temperature was repeated twice to lyse the cells, after which the lysed cells were centrifuged at 1800 rpm for 5 minutes to remove the precipitate, and the supernatant containing the virus was collected. Infection of Vero cells with the virus-containing supernatant and subculture of the cells was repeated 103 times. As a result, viral stock containing various genetic variants was obtained.

1-2: Separation of Attenuated Viral Plaques

Each of the viral stocks of Example 1-1 was serially diluted 10-fold, and Vero cells cultured as a monolayer in a 6-well plate were infected with the diluted viral stock for 2 hours. Then, a 1:3 mixture of 4% agarose gel (Gibco-BRL, Cat#18300-012) and 1% FBS-containing DMEM was overlaid on the cells. Thereafter, the cells were cultured for 3 days, and then stained with 0.06% neutral red dye solution (Sigma, N2889) diluted in DMEM. Based on the results of the staining, plaques thought to have a suitable shape and size were selected, and previously prepared Vero cells were infected with the selected plaques and cultured for 3 days, thereby obtaining clones showing a cytopathic effect (CPE).

Example 2: Selection of Attenuated Virus Strain 2-1: Examination of Cerebral Toxicity To compare the safety of isolated vaccinia virus clones selected after subculture, the clones were inoculated into the brains of suckling mice, and then the survival rate of the mice was evaluated. In the experiment, 5-day-old Balb/C suckling mice purchased from Orient Co., Ltd. (Korea) were used. The mice were stabilized for at least two days after purchase but before use in the experiment. Each mouse of each mouse group consisting of 12-15 suckling mice (5 days old) was inoculated with 10 PFU of the virus by an intracerebral route and observed for 14 days. Clones having low toxicity were selected (FIG. 1).

2-2: Analysis of Humoral Immune Response

Mice were immunized by injection with each of the selected vaccinia virus clones. 1, 2, 3, 4 and 5 weeks after immunization, immunogenicity was analyzed by ELISA. Specifically, each mouse group consisting of 5 female Balb/C mice of 4-weeks was inoculated with the virus. Inoculation was performed by a scarification method in which the tail was picked up 3-4 times with a bifurcated needle. Thereafter, clones showing excellent humoral immune activity were selected (FIG. 2).

2-3: Measurement of Neutralizing Antibody Titer

Blood was collected at one-week intervals from the eyeball of vaccinia clone-immunized mice for 6 weeks and from the ear vein of vaccinia clone-rabbits for 5 weeks. Serum was separated from the blood and inactivated at 56° C. for 30 minutes. One day before the experiment, BSC-40 cells were seeded in a 12-well plate. The antibody-containing mouse serums was serially diluted 2-fold and were mixed with 50 PFU of the vaccinia virus Lister strain at a ratio of 1:1, and the mixture was incubated at 37° C. for 1 hours. Then, the cells were infected with the incubated mixture for 2 hours. After the supernatant was removed, the cells were cultured in DMEM+1% FES medium containing carboxymethyl cellulose (CMC) for 2 days, and then stained with 0.06% crystal violet solution. Based on the results of the staining, the number of the plaques was measured to determine a serum concentration corresponding to a 50% or more reduction in the plaque number (FIG. 3).

2-4: Analysis of Cell-Mediated Immune Response

To analyze cell-mediated immunogenicity, 5 mice/group were inoculated with $6.5\times10^6$ PFU of the isolated virus strain. 4 weeks after immunization, the spleen was taken from the mice, and cells were extracted from the spleen. Using the extracted cells, cell-mediated immunogenicity was evaluated by ELISPOT and ICS (intracellular cytokine staining). Specifically, $5\times10^5$ splenocytes/well were cultured and stimulated with 0.1 MOI of the vaccinia Lister strain in vitro, and the number of splenocytes secreting IFN-γ was measured by ELISPOT and ICS (intracellular cytokine staining) (FIGS. 4, 5A and 5B).

As a result, clone 7 (KVAC) showed a decrease in the mouse cerebral toxicity compared to the conventional vaccine strain, had a constant plaque size and shape, and would be highly useful as a vaccine as proven by the immunogenicity test. Thus, this clone was named “KVAC103”, and deposited with the Korean Culture Center of Microorganisms (KCCM), in accordance with the Budapest Treaty on the International Recognition of the Deposit of Microorganisms, on Oct. 1, 2014 under the accession number KCCM11574P, that all restrictions imposed by the depositor on the availability to the public of the deposited material will be irrevocably removed upon the granting of a patent.

2-5: Skin Toxicity Test

To compare safety between the conventional vaccine and the novel clones, each of the selected KVAC103 vaccinia virus and the vaccinia virus Lister strain was inoculated into the skin of rabbits, and then the size of lesions generated after inoculation was compared. As the rabbits, about 2-month-old female New Zealand white rabbits (weight: about 2 kg) were used. Inoculation of the rabbits was performed similar to inoculation of humans. Specifically, an area having a diameter of 5 cm or more on both sides of the back was shaved, and the shaved skin was inoculated with $10^5$ PFU of the virus by a scarification method in which the skin was lightly picked 10 times or more with a smallpox vaccine inoculation device (bifurcated needle). Then, the skin was observed for 2 weeks. As a result, it could be seen that the skin toxicity of the attenuated vaccinia virus strain KVAC103 of the present invention was very low (FIG. 6).

Example 3: Characterization of Attenuated Vaccinia Virus Strain KVAC103

3-1: Analysis of Entire Genome Sequence of KVAC103

To analyze the nucleotide sequence of KVAC103, PCR amplification was performed. A vaccinia virus reference sequence for primer design was used based on the genome sequence (Genbank: DQ121394; 189,421 bp) of the VACV107 strain. The primers used were designed such that PCR products of the entire nucleotide sequence would be produced with a size of about 1,000-1,500 bp and the calculated melting temperature (Tm) would be between 53° C. and 55° C. (Table 1). For PCR amplification, the genomic DNA (20 ng/μl) of the virus was used as a template, and 10 pmole of each primer, 2.5 U of Taq polymerase (Cosmogenetech, Korea), 1× buffer and dNTP (each 2.5 mM) were mixed with distilled water to a total volume of 50 μl and used in PCR amplification. The PCR reaction was performed under the following conditions: 95° C. for 3 min; and then 35 cycles, each consisting of 95° C. for 1 min, 50° C. for 30 sec, and 72° C. for 80 sec; and then 72° C. for 3 min. Each of the PCR products was electrophoresed on agarose gel, and then the electrophoresis product bands were excised. Each PCR product was purified using a gel elution kit (Cosmogenetech, Korea), and the entire nucleotide sequence of KVAC103 was determined using both end primers. As a result, the entire nucleotide sequence (167122 bp) of KVAC103 could be determined, and the determined nucleotide sequence is shown in SEQ ID NO: 1.

TABLE 1

| PCR product No. | Primer name | Sequence (5'->3') | Tm (° C.) |
|---|---|---|---|
| 1 | 1-23F | GGT ACA CTT TTT TAA TTC GTG GT | 53.1 |
| | 1223-1200R | AAG ATT CTT CCT CCA AAC AGT TAA | 53.6 |
| 2 | 1102-1125F | GTA GTC TTG AGT ATT GGT ATT ACT | 53.6 |
| | 2328-2305R | ATA AGA TAG ATT CCA TCA TCG TGA | 53.6 |
| 3 | 2217-2237F | TGT CTG TCT GAA TGT ATG GCT | 53.9 |
| | 3446-3423R | TTC TGT CAA CAA TGT CTG TCA TAT | 53.6 |
| 4 | 3327-3347R | TGT AAT GGA GAG TTA CCT CGT | 53.9 |
| | 4563-4544R | TAT CCT CTG CAC GAC TAC TT | 53.4 |
| 5 | 4454-4474F | GCC ATT GTT CGA TAC GTG ATT | 53.9 |
| | 5679-5656R | AGA ATA GCT ATG GAT TAT TGT GGT | 53.6 |
| 6 | 5565-5588F | TTG ATA AGT TGT GAC ACG TTT CAA | 53.6 |
| | 6700-6677R | CCT ATT AAA GGA GTA TGT CAT GAA | 53.6 |
| 7 | 6584-6607F | GCT AAA GCT ATC TAT ACT ATC AGA | 53.6 |
| | 7823-7803R | ATG GCT TAT TAT CGA GGA GAC | 53.9 |
| 8 | 7697-7717F | CAT TAC GAT AGT ATG CAG GCA | 53.9 |
| | 8906-8886R | TCG GAG GAT TCT CTA TTA TCG | 53.9 |
| 9 | 8759-8783F | TTA GTA GAT AAC ATA CCA CAC CAT T | 54.0 |
| | 9995-9976R | TCG ATA GCG TTA CCA CTA TC | 53.4 |
| 10 | 9878-9898F | ACA CAC ACT GAG AAA CAG CAT | 53.9 |
| | 11041-11020R | CAA TTG CCG TTC TAG ACA TAT C | 54.4 |
| 11 | 10892-10915F | CAA CCA AGT AAT GAT CAT CTA TTG | 53.6 |
| | 12106-12083R | GGA TAA TGC ATA CTG TTA GTC TTA | 53.6 |
| 12 | 11993-12012F | TCG CGG ATA TGG AAT TCG AT | 53.4 |
| | 13227-13204R | CAA GAT GAG AAT CCT ATT TCT CAT | 53.6 |
| 13 | 13115-13138F | ATT CTC CAG AAG ATG TTA CAA TGT | 53.6 |
| | 14336-14313R | AAT GTG TAG TAT TGT ACC ACT ATG | 53.6 |
| 14 | 14223-14246F | CCG AAT GTC ATA TAC TCA ATT AGT | 53.6 |
| | 15466-15443R | CAT GAT GGT AGT AAT AAA GGA TCT | 53.6 |
| 15 | 15365-15385F | ACC TCC GTT AAT ACC TCC ATT | 53.9 |
| | 16607-16584R | GAT GAA GGA GCT ACA TTA TAT AGA | 53.6 |
| 16 | 16472-16496F | GGT TAT CAT CAT TGT CAT TAT CTA C | 54.0 |
| | 17714-17691R | ACT AAT AGT ACT GAC ACT ACA GTA | 53.6 |
| 17 | 17577-17600F | TAT CTT ATC GTT AAC CAT GAT TGG | 53.6 |
| | 18818-18798R | GTT GGC TTA TTC CAT AGT AGC | 53.9 |
| 18 | 18696-18716F | CTG AAT GGA TGA ACG AAT ACC | 53.9 |
| | 19937-19917R | GAG AGA ATG GAT TAT GTG TGC | 53.9 |

TABLE 1-continued

| PCR product No. | Primer name | Sequence (5'->3') | Tm (° C.) |
|---|---|---|---|
| 19 | 19793-19816F | ATT GGT CTG TGT TAC ATA TCT CTT | 53.6 |
| | 21023-21000R | CGA CAC AAT AGA TAT ATC TGA TTG | 53.6 |
| 20 | 20882-20905F | CAC ATT ATC ATC TGT TAG AGT AGT | 53.6 |
| | 22126-22106R | GTA ACT CAT AAG TCA CTG CCA | 53.9 |
| 21 | 22019-22039F | ATG TTA TCC TGG ACA TCG TAC | 53.9 |
| | 23257-23236R | CTA TAT AAT GCG TCG ATG TCA G | 54.4 |
| 22 | 23133-23153F | TTT ACG TTA ACG TCT TCG TGG | 53.9 |
| | 24366-24342R | GAT CTA ATG ATT GAT CTA TAT GGT G | 54.0 |
| 23 | 24298-24318F | GTA CTC ATT ATC ATT CGG CAG | 53.9 |
| | 25496-25479R | CTT TGT ACT TAT GCA TCC GGA | 53.9 |
| 24 | 25392-25415F | AAT ACT TCG TAA GAT ACT CCT TCA | 53.6 |
| | 26638-26618R | ATG CTA CAA GCT ATC GAA CCT | 53.9 |
| 25 | 26522-26542F | TGG AGA GTA TCC TCT ATG AAG | 53.9 |
| | 27770-27745R | CGA CAT TAA TAT CTA TTC TGC TAA TC | 54.4 |
| 26 | 27661-27684F | TTG TAT AGG AGT CAG ACT TGT ATT | 53.6 |
| | 28899-28876R | ATG ATG GCT CCT AGT ATG TTT AAT | 53.6 |
| 27 | 28785-28805F | CTT GTT CGT CGA CAT CTA TCT | 53.9 |
| | 30018-29998R | GGC AGA GTA TAC GAG AAT GAT | 53.9 |
| 28 | 29926-29946F | ATG CAT CTT AAC ACT CTC TGC | 53.9 |
| | 31182-31163R | AGG AGT ACG AGT TAG AGT AG | 53.4 |
| 29 | 31055-31075F | TAT GAA GAA CTC CTC CTA GGA | 53.9 |
| | 32309-32289R | CGT CTC CTT CCT CTA TAT TGA | 53.9 |
| 30 | 32188-32211F | GCA CTC ATG ATT CAC GTT ATA TAA | 53.6 |
| | 33442-33419R | TAG CAA TAA TGT TGA TCA CGA CTA | 53.6 |
| 31 | 33346-33369F | CGT TGA TAG ATA ATC GAG TAT GTT | 53.6 |
| | 34553-34533R | GAT TCC AAT TCC TCC GAT GAA | 53.9 |
| 32 | 34440-34459F | AAC CAA CGC TCA ACA GAT GT | 53.4 |
| | 35657-35637R | ATA GAA TTC GTC GCG GAT AGA | 53.9 |
| 33 | 35576-35596F | CCA TGA AAT CAA ACG GAT TGG | 53.9 |
| | 36865-36846R | ATA TCC AAC AGA GTC GCT AG | 53.4 |
| 34 | 36712-36732F | GGA TTC ACA AAT GTT ACG CAC | 53.9 |
| | 37933-37913R | TTA ATA TGA CGC TCG TCA TGG | 53.9 |
| 35 | 37832-37852F | TGT AAC ATC CTT CTC TTC CCT | 53.9 |
| | 39090-39067R | GCA TTA GAA GAA TTC ATC ATG TGT | 53.6 |
| 36 | 39014-39034F | ATT GGG TGA AGA ATG GAA ACC | 53.9 |
| | 40269-40249R | ATG GGT GTT GCC AAT GAT TCA | 53.9 |
| 37 | 40117-40137F | TAA CAA TCT AAC TGA CGG AGC | 53.9 |
| | 41346-41326R | GCA TTC CAT CGA GAT CAA AGA | 53.9 |
| 38 | 41165-41185F | GGA TAC GAA GAT GCT ATC CAT | 53.9 |
| | 42423-42403R | TAT ACT GGC CCA ATA ACT GTG | 53.9 |
| 39 | 42336-42356F | TAC GCA TCC ATC CAA ATA ACC | 53.9 |
| | 43516-43496R | AGT CGA CGA CGA ATA TGT TCA | 53.9 |
| 40 | 43372-43391F | GCT AGA TAC CCA ATC TCT CT | 53.4 |
| | 44611-44591R | TAG ACG AAG ATG ACA TCA TGG | 53.9 |
| 41 | 44505-44525F | CGA TTC TAG AAT ATC ATC GGC | 53.9 |
| | 45678-45655R | GAT AGT TAA TTC CAA TGT TAC GTG | 53.6 |
| 42 | 45506-45526F | GAT TAT CCA ATT GAG AAG CGC | 53.9 |
| | 46835-46816R | GAC ACA TCG TGT GAT TTC GA | 53.4 |
| 43 | 46697-46717F | CAC ATA AAC CTC TGG CAC TTA | 53.9 |
| | 47961-47933R | AAT AGG AAT CCT GAT CAG AAT ACT T | 54.0 |

TABLE 1-continued

| PCR product No. | Primer name | Sequence (5'->3') | Tm (° C.) |
|---|---|---|---|
| 44 | 47863-47886F | ATA TGA TAT TCG TTC ACA CTA GGT | 53.6 |
| | 49107-49084R | CTA TAC ATT CTA CGT TAG TAA TGG | 53.6 |
| 45 | 49021-49041F | TAT CGA TGT CGA TCT CGT CTA | 53.9 |
| | 50317-50294R | TAC GTC ATC ATT AGA TTC TGA TTC | 53.6 |
| 46 | 50182-50205F | ATA CTA GTC GCG TTA ATA GTA CTA | 53.6 |
| | 51395-51372R | ATG TGA TAT GAT TAA GGG TAC TAG | 53.6 |
| 47 | 51220-51240F | AGT TAG GAC ACG GTG TAT TGT | 53.9 |
| | 52462-52442R | GAG GGT ATC TTC TTC AGA TTC | 53.9 |
| 48 | 52214-52237F | ATT CGT TAT AGA ATG CAT CCA ATG | 53.6 |
| | 53487-53467R | CTA TGC CTG TAT CTT TCT TGC | 53.9 |
| 49 | 53302-53325F | GAG AAC TTA TAG GCG TAA ATT ATG | 53.6 |
| | 54575-54555R | ATC CGT CTT GGT TAG ATG GAT | 53.9 |
| 50 | 54432-54452F | CCT AGT ATT CTT CCA TCG CTA | 53.9 |
| | 55722-55699R | ATT ATA GAT TGG AAT GGA AGT CAG | 53.6 |
| 51 | 55623-55643F | GTT CTC TGG TAG ATA CGT ATC | 53.9 |
| | 56898-56878R | TCC GTG TTT ACA GAG ATA GAC | 53.9 |
| 52 | 56764-56784F | CAG ATT CTT ATA TAC CGC CTC | 53.9 |
| | 57989-57969R | CCA CAG GTA ATT ATG TGA CTG | 53.9 |
| 53 | 57873-57896F | ATG TAT CAT TAG GTA AAG TAG GAC | 53.6 |
| | 59155-59135R | GGA TGT TCG GTG CAT TAA TTG | 53.9 |
| 54 | 59075-59094F | TCA CCA TTT CGA CAT CTG GA | 53.4 |
| | 60342-60322R | CTT AAT CGG TCA ACG ATG TTG | 53.9 |
| 55 | 60225-60245F | TCC GTA TAC CAA CAT GTC TGA | 53.9 |
| | 61479-61459R | TGA GAA TGT AGT CAA GGC TAC | 53.9 |
| 56 | 61360-61380F | GTA GCT CCT ACA GGA ATA TCT | 53.9 |
| | 62639-62618R | GAC GAA TCG TCA ATC TAT GTG | 53.9 |
| 57 | 62523-62543F | AGC GTT CGT CAA CAT ACT ATG | 53.9 |
| | 63785-63765R | TTG GCC AAG GCA ATT ATC ACA | 53.9 |
| 58 | 63656-63676F | TAT CTC CAG AGA GTC CGA TAA | 53.9 |
| | 64896-64876R | GTG GAA CCG TAT ACC AGT AAT | 53.9 |
| 59 | 64772-64795F | CTA TTC TTG ATC TCA TCA TTC CAT | 53.6 |
| | 66069-66049R | GAT GAT AGC ATA GAG GGT ATC | 53.9 |
| 60 | 65949-65968F | TAC CGG AGA TAT AGC TTC CA | 53.4 |
| | 67260-67240R | GCG TCT AAA CAC AAT CTT GGT | 53.9 |
| 61 | 67125-67148F | AAC TGG AAA GCT AGA CTT GAT TAT | 53.6 |
| | 68325-68302R | CTA TTT AAC TTG CAA GAT CTA TCC | 53.6 |
| 62 | 68164-68188F | AGT TAT TCA TCG TCG TCT ACT ATT | 53.6 |
| | 69504-69481R | TGT AAG AGA ATA CAT TAA CGC AGT | 53.6 |
| 63 | 1-24F | CAT CTA TAT TGC TAC ATA ATC CAG | 53.6 |
| | 1224-1200R | CAT TCT GGA AGA TGG ATT TAT CTT A | 54.0 |
| 64 | 1102-1120F | GAT GAC AGG GAA CGG CTA A | 54.9 |
| | 2321-2299R | CCA ATC TAT TGA GCA AGA ATA CC | 54.9 |
| 65 | 2199-2222F | CTT TTG TAG ACA CGA CTA AAC ATT | 53.6 |
| | 3438-3415R | ATA TCG GGA TCG AAT ATC GTA ATT | 53.6 |
| 66 | 3302-3324F | TTA CCG TTT GTA CTT ACT GGA AT | 53.1 |
| | 4530-4510R | TTA TAA CAC GGC CGT ATA CAC | 53.9 |
| 67 | 4418-4440F | GAA CAT GTA GAT TTA TCG GAG GA | 54.9 |
| | 5613-5591R | CTT CTT CCA TAA ATC CGG TAA CA | 54.9 |
| 68 | 5499-5519F | CAA GAC GTT AGA GAC AAG AGA | 53.9 |
| | 6732-6710R | TGT TAA GTT ACG TTG AGG TTC TA | 53.1 |

TABLE 1-continued

| PCR product No. | Primer name | Sequence (5'->3') | Tm (° C.) |
|---|---|---|---|
| 69 | 6571-6589F | GTG TTC CAA CTC GTG TGC T | 54.9 |
| | 7801-7781R | GGT GAG CCT ATT ATA GTA GCT | 53.9 |
| 70 | 7684-7707F | CAT ATG TGG TAT TCA CTA TAT CAG | 53.6 |
| | 8924-8904R | CAG TAT TAC CAG GAG TCT TCA | 53.9 |
| 71 | 8811-8830F | CCG TCA TTC ATC TAG AAT GG | 53.4 |
| | 10043-10021R | ACA TGA CAA TCT TAA TGA GGA AG | 53.1 |
| 72 | 9909-9929F | GAG TGT TCG AAT GCC AAT GTT | 53.9 |
| | 11093-11075R | GGT CGA AGT ATA GCA GGA C | 54.9 |
| 73 | 10991-11012F | CTG ATC GTC TAG ACG ATA TAG T | 54.4 |
| | 12230-12208R | ACG AGG TGA TAG AAA TAT ACC AG | 54.9 |
| 74 | 12113-12134F | ATC TTG TTT CGG TGG CTG ATT A | 54.4 |
| | 13350-13329R | GAT GTT TGA GTT GTC ATC CAT G | 54.4 |
| 75 | 13227-13250F | ATA TGT TCT TCA TGC CTA AAC GAA | 53.6 |
| | 14404-14382R | CTA CAC ACC GAT TGA TAC ATA TC | 54.9 |
| 76 | 14292-14314F | CTA ACT GCT GTG TGT ATG AAA TG | 54.9 |
| | 15530-15505R | ATA CTC TAT ATC GGT AGT ATA TCT C | 54.0 |
| 77 | 15401-15423F | GTT AGT CAT GAA CCA ATA CAA CG | 54.9 |
| | 16632-16607R | CAT GAC TAA TGA TAA TAT CTG TAG CA | 54.4 |
| 78 | 16504-16529F | GAA ATT TGA TTG TAT ACT TTC GGT TC | 54.4 |
| | 17742-17721R | TAG CTC TGA TAG ATG AAG CGA T | 54.4 |
| 79 | 17628-17648F | CAT TTA TTG CCT GGT GAT TGG | 53.9 |
| | 18818-18801R | CAG TGT TCC GGT ACG TGA | 54.3 |
| 80 | 18672-18690F | CCA GAC TCT AAG GAT CCA G | 54.9 |
| | 19900-19880R | TGA TTG AAG TCG TCA TAT CCC | 53.9 |
| 81 | 19779-19801F | GAA CCG GAA GAA TTG AAT CTT AG | 54.9 |
| | 21014-20995R | : TTG TAC GCC TAC TAT AGC CT | 53.4 |
| 82 | 20879-20900F | TCC AGT TGA ACG TAG TAG TAA G | 54.4 |
| | 22110-22086R | ACG ATA ACG TTA TTG AGG ATA TTA C | 54.0 |
| 83 | 22075-22096F | GAC GAA GAA ACG TAA TAT CCT C | 54.4 |
| | 23297-23275R | CAT CTC CGT GGT TAT ATA CGA TT | 54.9 |
| 84 | 23180-23201F | ATC CAA TTC CTC CGG CAT TAT A | 54.4 |
| | 24401-24380R | ACC AGA GAT TAA GAA GAT ACC G | 54.4 |
| 85 | 24273-24294F | GGA ATA CCG ATG TGT CTA CAT A | 54.4 |
| | 25490-25469R | TTA ACG ATA TTG TCG GTA GCC A | 54.4 |
| 86 | 25371-25389F | AGA GCT CGA TGA TAG CGA C | 54.9 |
| | 26593-26572R | CGT GAT CTA CGA CTA TAG ATA G | 54.4 |
| 87 | 26485-26506F | AGA GCT TAT ATG GCA ACG ACT A | 54.4 |
| | 27709-27689R | CAG AGA TGT ATT AGG CCT TGA | 53.9 |
| 88 | 27560-27584F | CGA CTA GAA TTA GTC AAT CTT ATT C | 54.0 |
| | 28769-28748R | CAT TAT TGG CGT ATT GAT GTC C | 54.4 |
| 89 | 28658-28682F | GGA AAT CAA CAT AAT ATC ATA GTC G | 54.0 |
| | 29866-29846R | ATG AAC AGG CCA GAT GTT ATC | 53.9 |
| 90 | 29751-29769F | GGA CCT TCC AAC TGT GGA T | 54.9 |
| | 30981-30963R | GGA TCT ATA CCG CAC ACA C | 54.9 |
| 91 | 30871-30889F | AGT AGC CAG TTG GCT GCT A | 54.9 |
| | 32100-32079R | CCA CGT AAG TGA ATA GGT AAT C | 54.4 |
| 92 | 31999-32017F | CTC TTC GGG TTG TAG GTA C | 54.9 |
| | 33213-33192R | CAA TGA CAC AAG GTT CTG TCA A | 54.4 |
| 93 | 33088-33110F | CAT TTA TCG CTA ACA TGC ATT TG | 53.1 |
| | 34315-34295R | ATC ACG GTC ATA AGT TCT CCA | 53.9 |

TABLE 1-continued

| PCR product No. | Primer name | Sequence (5'->3') | Tm (° C.) |
|---|---|---|---|
| 94 | 34205-34228F | CGA TAA CGT CAT TAA TTA TAA CGG | 53.6 |
| | 35439-35416R | GAC ATC TCT TGA AGA ATA GAG TAT | 53.6 |
| 95 | 35321-35345F | AAC GAT TAC ACA CAG GAT GAA TTA A | 54.0 |
| | 36556-36536R | TTG TCG TCG TCT AAT CAT GAG | 53.9 |
| 96 | 35321-35345F | AAC GAT TAC ACA CAG GAT GAA TTA A | 54.0 |
| | 36556-36536R | TTG TCG TCG TCT AAT CAT GAG | 53.9 |
| 97 | 36433-36453F | AGG TAG TTG CTG CTC GTA TAA | 53.9 |
| | 37613-37591R | ACT GTT ATA CGT TCA TCA CTT TC | 53.1 |
| 98 | 37498-37519F | ATC GAT CCT CAC TTT GAA GAG T | 54.4 |
| | 38693-38675R | GGC GTA GAT GGT CGA GTA T | 54.9 |
| 99 | 38538-38561F | CAT AGA GGA TGT TAT TAC GAA TCA | 53.6 |
| | 39797-39774R | TGT TCG TAC ATA GTT AAT AAC GAG | 53.6 |
| 100 | 39605-39626F | TAG TAG CCA TAC GTC TCA GAA T | 54.4 |
| | 40834-40816R | CGT AAG CGA TAG CTG GTT G | 54.9 |
| 101 | 40703-40723F | ACA CTG TTC ACA TCC TTC CAA | 53.9 |
| | 41935-41912R | AAT CTT TGC TCA CAT ATC ACA TAG | 53.6 |
| 102 | 41825-41846F | GAT TCG GCT GAT CTA TTA TCT C | 54.4 |
| | 43036-43015R | GGA TGA CTC TAT TAA ACG GTC T | 54.4 |
| 103 | 42916-42934F | AGC CTG ATT GTC TGG ACC A | 54.9 |
| | 44083-44062R | GTA TTG CGG AGA TTA TTG TCT C | 54.4 |
| 104 | 43984-44005F | CAT CTA CAT CAT CCG TGG ATA T | 54.4 |
| | 45218-45197R | CCG ATT TCT ATC AAT TCC AAG G | 54.4 |
| 105 | 45112-45132F | ACT CCA GAA CAT CTT CCA TAG | 53.9 |
| | 46317-46294R | TGG TAG ATG AAG ATC ATA TTC ACA | 53.6 |
| 106 | 46197-46217F | TTG GTA CGT TGA TTT CTA GCC | 53.9 |
| | 47428-47408R | CTA GTG ACT CTC CAT CTT CTT | 53.9 |
| 107 | 47320-47343F | CGA TTA TAA GAT TAA ATG GCA GAC | 53.6 |
| | 48562-48541R | CCG AAG ATA TTG TAT CCG ATT C | 54.4 |
| 108 | 48465-48485F | TTG TTG GAG AAC TTG ATA CGC | 53.9 |
| | 49697-49673R | GAT AGT AAG TCC GTA TAT CCT TAA T | 54.0 |
| 109 | 49582-49603F | GTT CCA TAT TAG CAG TCA TTC C | 54.4 |
| | 50804-50783R | TAA TCC CTT CGT ATA CAC TCA G | 54.4 |
| 110 | 50681-50701F | AAT AGA TGT ATC GCA CGC TCT | 53.9 |
| | 51890-51869R | GAT TCC ACA GCC AAT GAA CAT | 53.9 |
| 111 | 51774-51794F | TAG TAC GGG CGC TGT AAT TAA | 53.9 |
| | 53001-52981R | GTG GAG ATA TTA CAG GAG AAG | 53.9 |
| 112 | 52881-52905F | GTT GTA ATG TTA TCC AAC ATA TCA C | 54.0 |
| | 54132-54108R | GAT ATC AAT CTC TTA TTC CTA GAC T | 54.0 |
| 113 | 54023-54043F | GGT TAC ATT CAC TGC AGC ATT | 53.9 |
| | 55266-55247R | GAT AAT AGT GGC CGG TGA AT | 53.4 |
| 114 | 55154-55174F | ACA ACG TGG TAG ATA GAG AAC | 53.9 |
| | 56339-56319R | CTC GTC TTC TTC TAC ATC AAC | 53.9 |
| 115 | 56225-56245F | TTG GAC AAT CTG ACC ATC CAT | 53.9 |
| | 57355-57335R | AAG TAA TTA CGA GCC GTT GCT | 53.9 |
| 116 | 57208-57232F | CGA ATG AAC AAA GTG GAA TAT AAA C | 54.0 |
| | 58446-58426R | TTA TCA GAA CGA GGT AAC TCC | 53.9 |
| 117 | 58319-58338F | TTG CTA CGC TAT CAC TAT CG | 53.4 |
| | 59497-59478R | ATG ATC CCG GTT CAA CTT CT | 53.4 |
| 118 | 59394-59416F | GAT GGA GTA TAA TCT TTA TGC CG | 54.9 |
| | 60640-60618R | ATA GTT CTG TTT CTC GAC ATA CC | 54.9 |

TABLE 1-continued

| PCR product No. | Primer name | Sequence (5'->3') | Tm (° C.) |
|---|---|---|---|
| 119 | 60527-60547F | CCG GTA CTG GTT TAG ATA TTC | 53.9 |
| | 61770-61750R | TAC ACG CAC TTC GCA TAT CAT | 53.9 |
| 120 | 61634-61657F | TAA TAT TGA TCC GGG CTA TTA CAT | 53.6 |
| | 62875-62851R | GAA GAA CTG TAG TGT ATT CAT ATT G | 54.0 |
| 121 | 62759-62779F | TAG AAG TCA AGG ATA ACT CCG | 53.9 |
| | 63980-63959R | GGA TGA TAT CTT CGA ACA ACA G | 54.4 |
| 122 | 63869-63892F | ACT ATG CAC ATT ATT CTA TCC AAG | 53.6 |
| | 65111-65088R | CTA ATG AAT TCT AGA CTC ACT CTA | 53.6 |
| 123 | 65003-65026F | ATA TAT CAC AAT TGG AAG CGT TGA | 53.6 |
| | 66221-66201R | ATG TCA GAG AAT GTC ATG TCG | 53.9 |
| 124 | 66118-66138F | GGA AGA TTA GTC AGA CCA TTC | 53.9 |
| | 67375-67355R | : AAG GCT TAT CCG TTT CAG GAT | 53.9 |
| 125 | 67249-67272F | ATC GAT ACA TAT ATG CAA TTC GCT | 53.6 |
| | 68474-68455R | TTA TGG AGT TCG ATC GCC TT | 53.4 |
| 126 | 68333-68354F | CTA CGT TCA GAT TCC AAT TCA C | 54.4 |
| | 69556-69538R | GAC AAC TGA GTG AAT GCC G | 54.9 |
| 127 | 138802-138825F | ATT ATT ACG TCT ACA GTC GTT CAA | 53.6 |
| | 140039-140019R | TTC TTC TAC TAA CTC CCG AAG | 53.9 |
| 128 | 139916-139936F | GTA ATA GGC TTA GGC AAA TGC | 53.9 |
| | 141149-141126R | AGT TGA TAG GTT AGA ACA TCA CAT | 53.6 |
| 129 | 141032-141052F | ATG TGG ATG GAC AGT AGG TAA | 53.9 |
| | 142302-142322R | GGA CTT TAT GAA AGC CTA TCC | 53.9 |
| 130 | 142202-142222F | CGC TAG CAT GGT CTT ATG ATA | 53.9 |
| | 143438-143415R | GGA TGT AAT TCT AGG TTA GAA TCA | 53.6 |
| 131 | 143347-143367F | TTA CAC GCA TCA GAC AAT GCT | 53.9 |
| | 144769-144746R | AAT CAT CAT GAT ATA TAC CTC CTC | 53.6 |
| 132 | 144492-144515F | TAG TAA AGC TGC AAT TAC ACA CTT | 53.6 |
| | 145817-145797R | TCC TCC CTA CTA ACA ACC TTA | 53.9 |
| 133 | 145664-145684F | ATC CTC CCG TTA AAA CCA TTC | 53.9 |
| | 146930-146907R | TAA CAC ATA GTA CAG ATT GAG TAC | 53.6 |
| 134 | 146831-146851F | CAA CTA AAC AGT ACG ACG GAT | 53.9 |
| | 148074-148051R | AAG GAT TGG ATG AAT AGT TAG GAT | 53.6 |
| 135 | 147963-147989F | CGT AAT GAA CAG ACT ATT TAT CAG | 53.6 |
| | 149211-149191R | GAG AAT GAA TCC ATT CCG TAC | 53.9 |
| 136 | 149084-149107F | GAG CAT TAG TAT TTC TGT GGA TTA | 53.6 |
| | 150345-150322R | GTG TAT AAT ACG TCG TCT AAT AAG | 53.6 |
| 137 | 150192-150215F | TCA ACG ATA TTC TAA CTC TTG ACA | 53.6 |
| | 151465-151445R | GTG TGG TGT ACT CGA TTA AGA | 53.9 |
| 138 | 151358-151378F | GTA ATG GTA ACT TCG AAA CCG | 53.9 |
| | 152592-152572R | TAC GTA GAA GCA ACA CTA GAC | 53.9 |
| 139 | 152425-152445F | TAC GGT ATC GCG ATT AGT GTA | 53.9 |
| | 153660-153640R | GAC ACG ATA CAT TTA CTG AGC | 53.9 |
| 140 | 153505-153524F | GCA CGT TAA CCG TAG ATG AA | 53.4 |
| | 154795-154772R | GCC AAT AAT TCC GTA ATC ATG AAT | 53.6 |
| 141 | 154671-154691F | TTA CCG TGT TGC TTA CAT TGC | 53.9 |
| | 155921-155901R | GTA TTA ACC GCG CAA CCA ATA | 53.9 |
| 142 | 155792-155813F | CAC ACT ACA CTG TCG AAT TTG | 53.9 |
| | 157100-157081R | CGT GCA ACC ATC CAA AGA TT | 53.4 |
| 143 | 156973-156993F | TCC ACA TCT ATA GAC GAC GAT | 53.9 |
| | 158221-158201R | CAA CTC AGT CTG ATA GTT CTC | 53.9 |

TABLE 1-continued

| PCR product No. | Primer name | Sequence (5'->3') | Tm (° C.) |
|---|---|---|---|
| 144 | 158129-158152F | ATC ATG TGT AGA TCA AAC TTG GAT | 53.6 |
| | 159376-159353R | GTA CAT TAT GTT CGT CTA CAA GAA | 53.6 |
| 145 | 159264-159287F | AGT ACT CTC TCA TAA AGT GGA TTA | 53.6 |
| | 160493-160473R | GAG TCT TGT CAT CGT CAT CTA | 53.9 |
| 146 | 160385-160405F | TAT CTG GAT AAT GCG GTA TCC | 53.9 |
| | 161696-161673R | TCA TAG ATA TGC AAT CGT ATA CAG | 53.6 |
| 147 | 161562-161585F | AAT TCG GTA CTA TAG AAG AAC TCA | 53.6 |
| | 162801-162778R | TGA ATA ATA CAC TAA CCA AGT AGC | 53.6 |
| 148 | 162697-162717F | GAC TTG ATC CAT TTC CTC CAT | 53.9 |
| | 163964-163941R | GAA TTT GTA CAT GTA TTG TAC GCT | 53.6 |
| 149 | 163835-163858F | TAT CTT CAC GTA GAT ATA GGT GTA | 53.6 |
| | 165082-165062R | ATC AGT GTC ATT TGT AGG CGA | 53.9 |
| 150 | 164962-164982F | ATC TTA CGA CTC TCC ATA CGA | 53.9 |
| | 166199-166179R | TAA TAG TGT CGA ATA GAC CGG | 53.9 |
| 151 | 166091-166111F | AAG CTT CGT CGT AGA AAC ACT | 53.9 |
| | 167414-167394R | CCA TGA TTT CGG TTG TAC ACA | 53.9 |
| 152 | 167292-167312F | ATT ACG ACA AGT TTC GGC ACA | 53.9 |
| | 168654-168634R | ATT CTC TAC CAG TCT GAG GTA | 53.9 |
| 153 | 168505-168525F | ACT AAG AAC ACG TAT ACG GCA | 53.9 |
| | 169812-169792R | TCC ACG TTG TTG ATA TCG TGT | 53.9 |
| 154 | 169631-169650F | GAA GAC AGT TAC GGT TGT AC | 53.4 |
| | 170994-170974R | TCA TAG TGG GTA CAG TAC ATG | 53.9 |
| 155 | 170872-170892F | TAG TGC TCG ACA GTG TAT ACT | 53.9 |
| | 172171-172151R | CCA TTA AGT GTA TCC ATC ACC | 53.9 |
| 156 | 172069-172089F | ACA GGC TAT TTA CAA GAT GCG | 53.9 |
| | 173320-173300R | ATG CGG ATA TGT CGT ATG TTC | 53.9 |
| 157 | 173078-173101F | ACT TCA GTG ACA GTA GTC AAA TAA | 53.6 |
| | 174421-174402R | CGT GAT ATA CCC TAG CCA TA | 53.4 |
| 158 | 174323-174343F | CTA ATA GCA CGA TCG TGG TTA | 53.9 |
| | 175665-175645R | GTC TTG AAA CTG TTG CTC CAA | 53.9 |
| 159 | 175559-175582F | ATA CAA GAG TGG AAA CTC ACA TAT | 53.6 |
| | 176896-176877R | CCA CTA GTA CAG AAG TTG CT | 53.4 |
| 160 | 176800-176820F | AAT TCA GAT GTG AGT GTC GAC | 53.9 |
| | 178144-178124R | CTG CGT TTA CGT TAC TAG CAA | 53.9 |
| 161 | 178021-178041F | ATC GTG TCT GTC TCA GAA TCA | 53.9 |
| | 179428-179405R | TAA GGT AGG TGA TTC AGT TCT ATA | 53.6 |
| 162 | 179288-179308F | ATT ACA ATA GCA TGA TCC GCG | 53.9 |
| | 180639-180616R | AGT ATA GGC GTT AAT CCA TGA TTA | 53.6 |
| 163 | 180502-180525F | GTT AGA TAA TTG TGG TAA TAC ACC | 53.6 |
| | 181757-181737R | CAG TAG ATG CGA GTA AGT CTT | 53.9 |
| 164 | 181579-181599F | TGG TAA CTG TGT TAC ATG TGC | 53.9 |
| | 182827-182807R | GAG GAA TGA GAG TGT CTT ATC | 53.9 |
| 165 | 182676-182699F | ACC AAG GTA GTT AGT TAA TAC ACA | 53.6 |
| | 183996-183973R | TAC ATA CAG GTA CGA AAT ACG TAA | 53.6 |
| 166 | 183869-183889F | TAT GCA ATC AAT GGT CTC GGA | 53.9 |
| | 185155-185135R | ACG CCT GAT ATG TAG ACA TTC | 53.9 |
| 167 | 185027-185047F | CAG ATA CGC CTT AAT CCT AGA | 53.9 |
| | 186289-186269R | TGT TGC ACA ATC GTT CCA TGA | 53.9 |
| 168 | 186151-186171F | TAT GGA GCA AAC ATT AAC GCG | 53.9 |
| | 187445-187425R | CTA TTG TGA GTC GTG TTA CAC | 53.9 |

TABLE 1-continued

| PCR product No. | Primer name | Sequence (5'->3') | Tm (° C.) |
|---|---|---|---|
| 169 | 187318-187338F | ATG CGA TAG CAA GAC TAA CAC | 53.9 |
| | 188444-188464R | ATC TGA CTC GGA CTC TGT AAT | 53.9 |
| 170 | 188303-188323F | AGT CTT CAG CAA TCA TCC TCA | 53.9 |
| | 189118-189099R | GGA ATA TAG TGT CCG GTA CA | 53.4 |

3-2: Characterization of KVAC103 by Comparison of Nucleotide Sequences

The novel attenuated virus strain KVAC103 was characterized by comparing the entire nucleotide sequence of KVAC103 with the entire nucleotide of VACV107 (Genbank: DQ121394). As a result, it was shown that the attenuated virus strain KVAC103 had a 19.5 kb [C9L-F3L] deletion region on the left and a 2.5 kb [A25L-A26L] deletion region on the right (FIGS. 7 and 8). Thus, the identity of the attenuated strain KVAC103 could be identified by amplifying the deletion regions in the genome by PCR and determining the nucleotide sequences of the PCR products. The 19.5 kb deletion region of KVAC103 was amplified using a primer pair of 15F (SEQ ID NO: 2) and 35R (SEQ ID NO: 3), and the 2.5 kb deletion region was amplified using a primer pair of 140F (SEQ ID NO: 4) and 143R (SEQ ID NO: 5). The amplification products were separated on agarose gel, and then sequenced, thereby identifying deleted sequence of KVAC103. In addition, the wild-type vaccinia virus DNA was identified by PCR amplification using a primer pair of 15F (SEQ ID NO: 2) and 16R (SEQ ID NO: 6).

TABLE 2

| Region amplified | Primer name | Primer sequence (5'->3') | SEQ ID NO. |
|---|---|---|---|
| 19.5 kb deletion region | 15F | AGG AAC AGG ATC ATT GTC ATT ACA | 2 |
| | 35R | TGA ACT AAA TGT TCC AGA TGA GGA | 3 |
| 2.5 kb deletion region | 140F | AGT TCT GCA TTC AAT TCG GTG AGT | 4 |
| | 143R | AAT TGT ACC AAC GGT TCA AGA TGT | 5 |

TABLE 2-continued

| Region amplified | Primer name | Primer sequence (5'->3') | SEQ ID NO. |
|---|---|---|---|
| Wild-type vaccinia virus | 15F | AGG AAC AGG ATC ATT GTC ATT ACA | 2 |
| | 16R | TCG TTT ATC AAC ACT ACC GTT AGA | 6 |

3-3: Optimization of KVAC103 Culture Conditions

The proliferation levels of the virus in Vero cells (ATCC CCL-81), in various culture media and at various serum concentrations, were analyzed to determine the optimum culture conditions. Specifically, Vero cells were seeded in a 12-well plate, and then cultured with 1% FBS (Gibco #16000)-containing DMEM (Gendepot #CM0027050), Advanced-DMEM (Gibco #12491), OptiMEMI (Gibco #31985), VP-SFM (Gibco #11681) or OptiPro-SFM (Gibco #2309) medium for 24 hours. Then, the cells were infected with KVAC103 at a titer of 100 PFU/well for 2 hours. Thereafter, the medium in each well was replaced with the same medium containing 0%, 1%, 2% or 5% FBS, followed by culture for 3 days. The medium was removed, and the virus plaques were observed by staining with crystal violet solution. As a result, it was shown that the plaques were the clearest and largest in the OptiMEMI medium containing 1% FBS. Under such culture conditions, the proliferation of the virus was smooth, indicating that these conditions are suitable for the replication of KVAC103 and the production of a recombinant virus.

As described above, the attenuated vaccinia virus strain KVAC103 according to the present invention has reduced toxicity, shows reduced skin lesions, and effectively induces humoral and cell-mediated immune responses. Thus, it can be expected that the attenuated vaccinia virus strain KVAC103 can be effectively used as a vaccine composition which has excellent immunogenic effect together with reduced toxicity.

Accession Number

Depository authority: Korean Culture Center of Microorganisms;

Accession number: KCCM11574P;

Deposit date: Oct. 1, 2014.

What is claimed is:

1. The attenuated vaccinia virus strain KVAC103 (Korean Culture Center of Microorganisms [KCCM] accession number KCCM11574P) which has a nucleotide sequence represented by SEQ ID NO: 1.

2. An immunogenic composition for inhibiting or treating symptoms associated with a poxvirus infection, the composition containing the attenuated vaccinia virus strain KVAC103 (accession number KCCM11574P) of claim 1 as an active ingredient.

3. The composition of claim 2, which contains at least one pharmaceutically acceptable carrier or excipient.

4. The composition of claim 2, wherein the attenuated vaccinia virus strain KVAC103 is one attenuated by subculture.

5. A method for inhibiting or treating symptoms associated with a poxvirus infection in mammals excluding humans, the method comprising a step of administering the composition of claim 2 to the mammals.

6. An immunogenic composition for inhibiting or treating symptoms associated with a poxvirus infection, the composition containing the attenuated vaccinia virus strain KVAC103 (accession number KCCM11574P) of claim 1 as an active ingredient and at least one pharmaceutically acceptable carrier or excipient.

7. The composition of claim 6, wherein the attenuated vaccinia virus strain KVAC103 is one attenuated by subculture.

8. A method for inhibiting or treating symptoms associated with a poxvirus infection in mammals excluding humans, the method comprising a step of administering the composition of claim 6 to the mammals.

9. An attenuated vaccinia virus, wherein the genome of said attenuated vaccinia virus comprises a nucleotide deletion from 15,195 to 34,632 and from 139,978 to 142,484 as compared to SEQ ID NO: 7.

* * * * *

SEQUENCE LISTING

<160> NUMBER OF SEQ ID NOS: 7

<210> SEQ ID NO 1
<211> LENGTH: 167122
<212> TYPE: DNA
<213> ORGANISM: Vaccinia virus

<400> SEQUENCE: 1

```
accctactca tccaatttca gatgaataga gttatcgatt cagacacacg ctttgagttt      60
tgttgaatcg atgagtgaag tatcatcggt tgcaccttca gatgccgatc cgtcgacata     120
cttgaatcca tccttgacct caagttcaga tgattccttg cacatgtctc cgatacgaac     180
gctaaactct agattcttga cacattttgt attgacgatc gttgaaccga tgatatcttc     240
gtaactcact ttcttatgag agatgttaga cccgagtact ggatgggtct tgatgtcgct     300
gtctttctct tcttcgctac atctgatgtc gatagacacc tcacagtctt tgatcatagc     360
aagagcttct tcacgagtga tcgcgggaga gtccttacct tgtcctgggg acacgctgga     420
caatctagca ttcactgtgt ttccatcagc ggattctgag atggatttaa tctgaggaca     480
tttggtgaat ccaaagttca ttctcagacc tccaccgatg atggagtaat aagtggtagg     540
aggatctaca tcctcgactg atgtggaatc atcttctgat tccacctcgg gatctggatc     600
tgactcggac tctgtaattt ccgttacgga ttggcaaatc ttatcattgg tcggtgtttg     660
gtcttgcttt gtgactttga taataacatc gattcccata tgatgtttgt tttcttcttc     720
cgtacacgag gaggaggatg aggatgattg ctgaaaactg gcaggcatag cagctgccgc     780
caggcacatg catgccagga cgatatattg tttcataatt gctattgatt gagtactgtt     840
ctttatgatt ctacttcctt accgtgcaat aaattagaat atattttcta cttttacgag     900
aaattaatta ttgtatttat tatttatggg tgaaaaactt actataaaaa gtgggtgggt     960
ttggaattag tgatcagttt atgtatatcg caactaccgg gcatatggct atcgacatcg    1020
agaacattac ccacatgata agagattgta tcagtttcgt agtcttgagt attggtatta    1080
ctatatagta tatagatgtc gcccactaga gttacagtct ccgaatgcgg catgatagta    1140
tcattctttg ctttcgttaa ctgtttggag gaagaatctt tgttattgca tttaatctcg    1200
aaattcagag tgcacacctt tctcctgtaa agaaacctga agtcgctacc ttattaagaa    1260
cggagaagta tccatcacga aagacgggat tacagtcttt atgattcata gtaatagtta    1320
gttccgacgt tgagatggat tcgctgagac cggtagtggt cgtccgagta cacgatgtgt    1380
cgttaacggg atacagatta atttccacat cgatatagtt aaaggttatt actgggtacg    1440
ggttcgcatt tatctgcgga agagacggtg tgagaatatg ttccgagacc acacggagaa    1500
cagatgacgt ctccggatac tccgtatcct attccacatt ttgtttggga aacacatgcc    1560
ttgcatccgg atgatccttt gagaagacaa taatatccgg gagagcattc acagattcta    1620
ttgtgagtcg tgttacacga tcgcgtcttc cgttacaact tagacaagcg ggtaaatgat    1680
tattgcgaga tgtgaaggta cccgaaccac acggcgtaca ttgtgtgtta gtcttgctat    1740
cgcataatct ggaagcgtat gttcccagac acaaattatg gcgtttgtat tcgttgtctt    1800
tacactttcc atcggatggt gcatgcggtg ctatatctct tccgtttatt attatacatg    1860
agagaaacaa tatatacgag tataatacgg acttcatgat ttaataatgt agtaatcgtc    1920
gtcttgttcc tgtttcctac ttctccaatc atatagatat tttctttcta tcatggataa    1980
tatttgtaat ggttctttcc gtacaacata ctgtttagat gatattgcgc ataatttccg    2040
gaggcaaata cgatagtcta gattgaccga tggtagactc taatttattg agtgctttgt    2100
cgacgagttt acttttacgc tccatcgata gatggcactg ttctatgaga tcgtcgtaca    2160
tgggaaatga aatgtgactg tctgaatgta tggctttaag atagctgtga taccgtatac    2220
aggtcggtgt cggagattcg gaatcgtctt taaggcgact tatgtcacga tgatggaatc    2280
```

```
tatcttatcg aatgatatat ttttcataaa tacactttta tagtcctcgt ttaaacagaa   2340
tttactatgt agttccgcga atgactcgtc ccttaatagg cagtaggcta gtatcttttt   2400
tacgtagtaa tcgtcgtagg gagagacatc ttgtagaaca acgatttaat cataggtaga   2460
gatactttca gtctgtggtg gatgatgtca ttcacaacat ccgccttgta tatgatgttt   2520
ctgttttcaa acaccaagtc gaataccgtc tttagtcgga aggttgatgt cgtatccgat   2580
gtatgaggca acattgttgt tacaattttg aaaggcggta ttatagtatt cgtctttctg   2640
aatgtcgaac ctatctaata gataccgtag tatattgaga gtgtatcctt gattatgttt   2700
tatgaataga taaagtagat gttgtccttc ttccttttgt tcgtgccaat tgagtaacat   2760
tatgagaata tgacctgttg cacaatcgtt ccatgatggg tgtacaatca agattattac   2820
gtatcctcga gataaaagag catacaccac acgaggacta tgtttggtat actgttgaag   2880
gtaagtgtgt aaccgcgtta atgtttgctc cataatctat tatcgcgtag atgaatcgct   2940
tctcggctcg catcttagtg tgacttaact tgtaataatt gctttcgtag aacgtggata   3000
tgtgtttaca gtagtaatga agagaagtga gttcatcctc gtcggcgcaa ttagggtcgg   3060
atcctttgta cagaacgtaa tagtttaagc tcccattgaa tttatatcta agataacaca   3120
gcaatagatc ggatgattta ctaaagtcat caatggtgtc cgttagtata tcaaagatct   3180
tgttatcgat tgatagtggt catccttgct atcaaagtta cgcatgccgt ggtgtaacaa   3240
tatctttaat acagatggat taaatcgtgt attcatcgta tagcaatgta atggagagtt   3300
acctcgttta ttcagatcgc agtgtttaat aactagctta aacagatgag acgatgtatc   3360
tacatcaaag aacgtaaaat acatatgaca gacattgttg acagaaacgt gaccttcatt   3420
cttaccgtcg tccataaata cgttaggtat gtaccacata ctgtcgcgaa cgatgcgtac   3480
aatctcgtcc atctcataat gatttacttt ttcataatta aagatgtgaa agaaaaacag   3540
aacaatatat ttttttagta atgtttatgc gagacatata aaataaactc cgtgtttatg   3600
atgccggtaa atgtttttat catcttggac ggaatcgatt ttgtaatatg tcatggaaac   3660
aaatgaaaca ggacattatc gctccatgat aaattattta atggagtaat aaagtatctc   3720
catgggtaat ttcgaaatca agttatcgtc tgtattaatg ttgtccacta tggagtcgat   3780
cctctcattg ttctttacag tttctgtaat gatggacgtt agttcttttt tgtaccattt   3840
gatgtcggat tctttgcgta tctcaatctg tggcgtctgt ttcgtttaaa gaatatatca   3900
aacatggaga cgcctgatat gtagacattc ttcattctat taatgtctac tctatagcgc   3960
tttagttcct tatgacgacc ggagatatca tacttacttt agaaggaaaa tcatcatcta   4020
ggattaaggc gtatctgata caggcgaata atggttcagg atatagatag cgtatatctc   4080
tattaaatgc gtcaatcata gtctctagag tgggatggta actcagtaat aaatcaacta   4140
tcctcgtttt gttttctctt tggtaactgc ttttctggat ggccgtattg attatcgagc   4200
gtgatgttgt aacactcgct ccatattcca ataaccgctt tgcaaattgt atattattga   4260
catcgaccgc gtaatatagt agagttatcg atcatatcta tattatccat gtacttgctt   4320
agtatatcaa atacatctat cagtatggtt tcataacagt gatacccgca attattaaat   4380
ctcgataata tcagaccgta catacataga cggccattgt tcgatacgtg atttacagcc   4440
gcgtgtccat attttccacg ataaacctta cgacgtttac atcgacgaga ttattattaa   4500
caaagtagtc gtgcagagga tagttgttgt ccgttatcca acatgcattg aatgataggt   4560
atacttacca tatcgccgta atgtaagtag tttatcaaca tggcttgtac gatggattca   4620
tcctgttgtc taaatctctt tagaatgtta tcgatgatgt agtggttata ttctctggaa   4680
```

```
tcgtacgaag taatactacg cattacgtcg acaagagtat gacgtctctc aataaggaag   4740
attaacgatt tccatgtcta cattatatgg ggttactcta aatcgcttgt ttagataata   4800
cgcctctaat atagggctga cgtcgtatac tctacacgtg tccacatcct ttattaataa   4860
tttaacaatc tctatatcta tggttgagaa agaccagtag tattggatgg gtaaagatcc   4920
tccttcgtct ctgccatgaa tggaaacatt gttattgatc aaacatttaa ttacatcctt   4980
ggatagagat tgagattctc tatgagacga tatatagtaa tgaagagagt tcttacacat   5040
atcactgtcg tacatacagg tacaaaatac gaaaccggtg ctgtaacatt ctgatttaag   5100
aagccatagc aatacttctg gtctcggatt aggcgtcgtt acgtatatat ccaccaatcc   5160
gagaccattg attgcataat tcgtattctt ggacggacgt atccgtttat ccacaattag   5220
gtattttagc agacgtaagt cgatattata cgaatacaga tcgaaatcat ttatattcga   5280
cttgagttcg ttagaggaat tcgaatagct ggatatcagt agatgcacaa tctgagattt   5340
gacgtatcta tgcttactgt atgctcctag cggagttaat ccttcgttgt ttctacaaag   5400
tctctcgact ccgcgagaga gtaacagccg aacaatctta atgtctgtat cgcatttatt   5460
ggagacgtaa caatgtagcg cattgtttcc tcgtctatct atatgttttg ataagttgtg   5520
acacgtttca atctctggtt ttattttttt gtacgtcaca tcttcatcca gtagacgaca   5580
tagaatagtg cactctctac cacaataatc catagctatt ctggtgctaa ttattcctat   5640
ttcacgaagg caatcattcc tcataagatg ataaaaagtg tagtgagaga gcatgaagga   5700
gatttagtat ttagcagtgc ggatatgatc caagagggtg agatagtcgt tctcgttcag   5760
aatctttcgc agcataagta gtatgtcgat atacttatcg ttgaagactc ttccagagac   5820
gatagctgat tgagtacaaa gtccaatgat tgcacgaagt tcttcggcgg ttttcatgga   5880
gtcatttctg atgaaacatt taatgatctc cacgcaattg tcccacggaa gtgaatcctt   5940
caactcacca ccaaagagct ccgttgcatc agttctgaaa gagatgagaa gcctgtagag   6000
agaccctgcg ctttctctat gggtccatct atgagaaacc cacaggatgt attcagtcag   6060
acaatgtctg acgtcggcca cggtattcag ggagtcctta gtagcgtggc aatgacaggg   6120
tctgaactgg gcacaaggaa aggccattgt gaaggtagac gaaggttaac ctgatggtag   6180
acctgtagcc gtctatgcta atagagggct ttaatttcca tttttttaat ggggttgtgg   6240
atgaggaatg agagtgatat catattgaga tacgtagtta tgtagaggtg tatttcctat   6300
attatttact ttcggtttca tattttacca actctttaat aaatttcttt tcacgatgca   6360
tcttattaaa tgacgttttc tcataagtgg acatatagat gcaaaagtaa tgaagaaaag   6420
tattacctct atcatctaca taattagggt ctgctccttt ttttaacaac ttatacagta   6480
cgtagtagta gtttatcggt tttaaatcaa gtctagaata tatagtggat taatatattt   6540
ttatattagc taaagctatc tatactatca gaaagcatat cattctcaac ttcatcatga   6600
gttaaatatt tgtgtaatgg aatgtgacca tcactgtcat gacatactcc tttaataggt   6660
tttttaaaac agatgattca aatccttcat tcattagata acagtgtaac ggagtcgtac   6720
cttctactag tttgtttata tcacagcatt ctacaaacag tctaaacaat agagaagacg   6780
gacagacttt aacgtataaa tgacacatgt tatcgatatt cgttgatgaa ttattattaa   6840
acgtagttat gataaatgat tctaacgaca tctctcgcta gagataaaat ctagtatcgt   6900
atcatactcg catagcatag tttttcataa ttaatacaat atttaaaaga cttattcgga   6960
aagtatttta atacatgtat catcgatgga gatccatatg aggagtcact tgtagttctt   7020
```

-continued

```
cagtagtaat aacagtgcta tcatcgatag tataattata tgttgttgta attggagtaa   7080
ctgttggtag ttcttccgtg gaatcaataa ttatactaac agcaatagta taattatata   7140
aatatgttcc gttgatatca catattttaa tgaactcatt tctaacaccc tcagctatat   7200
ctgtccaatt aaatgtagcc aacaatctac tacgttctct ttgattgact acttgtacgg   7260
tagcgacgct acactatctt tattgtcttc tacatgctcc aattgaatgt catgatacaa   7320
cgcagttttt cttatgcatg tttcataaca ccacgaacat gtcgcagtaa gataatttct   7380
gtaaattcat gattgccggt cataaacaag cccgtcaata attgtggcta tatattcagt   7440
ttatagagca aaataattaa gcacaatagc gcttaatctc aaaatatgtt atgtttattt   7500
ttttcatatt aaacatactg gttaaaatcc tctaaaggct gatcttcatc tataaatcaa   7560
gatcataatt acatttagac agtggtttca tgtttataaa aatgttcttt ttgtgtgaat   7620
aaggaatata ctaatcaata atcaaccatc gaccccatta cgatagtatg caggcaaccc   7680
cccattagag aggtacgtgt aatcagtctc tccagtttta gtatttttat aagtcattgt   7740
tacataaacg gcttttaaac agtctcctcg ataataagcc atatctggaa atttattaaa   7800
tactcgagtc attttacgca cggtcaaaaa agtaagtaat gtcgacgact tcttacattc   7860
tatagaaaca cctagaatac tcattttctt ttggaaaata tcctcagact ctgatttgaa   7920
caatgcacga cctatagtaa accgtgacca ataagttata ttagtcaatg gtatatccaa   7980
accatcaggt gtggatagta cgccgatagt ccagtctttg gtatcgatag tgtagttatt   8040
gaactgagaa gttaccgtat agtctttttg gtcatctcta aacaaggaaa ctaatacctc   8100
tacactattg aacgatttat cttccgtaat gggtggaata acgggaatat aaagtggact   8160
agcgatggat gaagtcacga atataagaca cgctattaat ccgtatatca tcattttgat   8220
attacttata ataacgattt gtttaatttt tagtttatac tattaattgt aaatgatatt   8280
attatttttt taagtattat cagctttagt ttatactatt actatttgta atatttagac   8340
atagataaac gtgataaaag tctatttgtt tatatttatt gcggatagca gtatttccct   8400
ataaaaagta tacgtcctgt gttgtcttta atcatgtaca tgaatggatg gtttatgtag   8460
accttcgtac gatataccat cgaaaagtta gtcataaata ctcctgtaac ggccgatgct   8520
tctgtatact cctcattaac atctataaac gtcgtatgta gaaatttttc tacagtgata   8580
gtttcattac acatcttgct aaaatctgca taatatccga atatattagt aagtcctaaa   8640
ttttctaaaa tcggtaccag attatacggt tctgtcattt ccactttaaa ctttggcata   8700
tacaagtcta tacttttagt agataacata ccacaccatt ttttaaattt ttcatctgtt   8760
atattttttt ctatgttata tataccttct atgtcgtccg gtagtataat taccatacta   8820
gagttcccct cgtatggaat atcgataata gagaatcctc cgaataattc attaatatgt   8880
acatattgca agttattctc ggtacccacc atcatatcaa cgctggtaac tatattctta   8940
gaaatataaa acttgtctgt atatgtaaga tgtttagaaa atggatattt ccacattgct   9000
ttaaaatgga cggcgctaac aactgtcata cgagtattaa tggatagcgg actagtcaat   9060
aaggaattaa ttttaccatt tgtcattgtc ttaacccatt cgttgattag ttcctttgtt   9120
tggttagcat tattaaagtt tacagtttga aaatcgtctt ttattttttg taggaaggag   9180
gcatggaact cgatactatc gctaccgtat attttatttg cggtagctag tgtcgcacaa   9240
tacggaatat ctacgtccat gtcattattg tcatcgggtg tattctcatt catattctct   9300
atatattttg atagttgttc agctgtagaa ccagctgctc catgatttag aatagataaa   9360
gtagataaaa tagaaactgg agaaatcaaa acattttcat ccgtgtgttt tacgattagt   9420
```

```
tctttaaaga tatccatggt atagaccaaa caataacgat aacgatatat atcataaata   9480
aataatgtta aatttcagtt tatgtttgta ccccgtattc atacttaaca aattggtatt   9540
gcgtacacaa tcaatcatat tacataccat taataatgca agcataaaaa atcgttagta   9600
gatgtttcta aatataggtt ccgtaagcaa agaatataag aatgaagcgg taatgataaa   9660
atcaatcgtt atctaaaatg atcatactca tttattttat tctattatat taacacatac   9720
atttttaaca gcaacacatt caatattgta ttgttatttt tatattattt acacaattaa   9780
caatatatta ttagtttata ttactgaatt aataatataa aattcccaat cttgtcataa   9840
acacacactg agaaacagca taaacacaaa atccatcaaa aatgttgata aattatctga   9900
tgttgttgtt cgctgctatg ataatcagat cattcgccga tagtggtaac gctatcgaaa   9960
cgacattgcc agaaattaca aacgctacaa cagatattcc agctatcaga ttatgcggtc  10020
cagagggaga tggatattgt ttacacggtg actgtatcca cgctagagat attgacggta  10080
tgtattgtag atgctctcat ggttatacag gcattagatg tcagcatgta gtattagtag  10140
actatcaacg ttcagaaaac ccaaacacta caacgtcata tatcccatct cccggtattg  10200
tgcttgtatt agtaggcatt attattatta cgtgttgtct attatctgtt tataggttca  10260
ctcgaagaac taataaacta cctttacaag atatggttgt gccataattt ttataaattt  10320
ttttatgagt atttttacaa aaatgtataa agtgtatgtc ttatgtatat ttataaaaat  10380
gctaaatatg cgatgtatct atgttatttg tatttatcta aacaatacct ctacctctag  10440
atattataca aaaatttttt atttcggcat attaaagtaa aatctagtta ccttgaaaat  10500
gaatacagtg ggtggttccg tatcaccagt aagaacataa tagtcaaata cagtatccga  10560
ttgagatttt gcatacaata ctagtctaga aagaaatttg taatcatttt ctgtgacggg  10620
agtccatata tctgtatcat cgtctagttt atcagtgtcc catgctatat tcctgttatc  10680
atcattagtt aatgaaaata actctcgtgc ttcagaaaag tcaaatattg tatccataca  10740
tacatctcca aaactatcgc ttatacgttt atctttaacg atacctatac ctagatggtt  10800
atttactaac agacattttc cagatctatt gactataact cctatagttt ccacatcaac  10860
caagtaatga tcatctattg ttatataaca ataacataac tcttttccat ttttatcagt  10920
atgtatatct atatcaacgt cgtcgttgta gtgaatagta gtcattgatc tattatatga  10980
aacggatatg tctagaacgg caattgtttt acgtccagtt aacactttct ttgatttaaa  11040
gtctagagtc tttgcaaaca taatatcctt atccgacttt atatttcctg tagggtggta  11100
taattttatt ttgcctccac atatcggtgt ttccaaatat attactagac aatattccat  11160
atagttatta gttaagggta cccaattaga acacgtacgc ttattatcat catttggatc  11220
gtatttcata aaagttattg tactatcgat gtcaacacat tctacatttt ttaatcgtct  11280
atatagtatt tttctgatat tttctataat atcagaattg tcttccatcg gaagttgtat  11340
actatcggaa tcagttacat gtttaaataa ttctctgatg tcattcctta tacaatcaaa  11400
ttcattatta aacagtttaa tagtctgtag acctttatcg tcgtaaatat ccattgtctt  11460
attagttacg cttattttta tgtgttttac gttgctttat tatattttat aagaatgatt  11520
gtttgacgaa tcacgagaac tattaagaca cattattagg tatatattat aaaaaagttt  11580
ttgattacga tgttataaga ggaaaagagg acacattaac atcatacatc aattaactac  11640
attcttataa catcgtaatc aaaagaattg caattttgat gtataacaac tgtcaatggg  11700
ttatggaatt gtatattaca tattatacgg tatgttggta acgacaaata ccggtcggta  11760
```

```
attgtctgcc ggtgtaatag aattatatat atctatctat tacaccggcc ttgtatacat  11820
aataataagt tgtggtagta tgatctccat atttataatt taggactttg tattcagtat  11880
ttttggaatc ataaaaaata aaaaaaagtt ttactaattt aaaatttaaa aagtatttac  11940
atttttttca ctgtttagtc gcggatatgg aattcgatcc tgccaaaatc aatacatcat  12000
ctatagatca tgtaacaata ttacaataca tagatgaacc aaatgatata agactaacag  12060
tatgcattat ccgaaatatt aataacatta catattatat caatatcaca aaaataaata  12120
cacatttggc taatcaattt cgggcttgga aaaaacgtat cgccggaagg gactatatga  12180
ctaacttatc tagagataca ggaatacaac aatcaaaact tactgaaact atacgtaact  12240
gtcaaaaaaa tagaaacata tatggtctat atatacacta caatttagtt attaatgtgg  12300
ttattgattg gataaccgat gtgattgttc aatcaatatt aagagggttg gtaaattggt  12360
acatagctaa taatacctat actccaaata cacccaataa tacaacaacc atttctgagt  12420
tggatatcat caaaatactg gataaatacg aggacgtgta tagagtaagt aaagaaaaag  12480
aatgtggaat ttgctatgaa gttgtttact caaaacgata gatactttgg tttattggat  12540
tcgtgtaatc atatattttg cataacatgt atcaatatat ggcatagaac acgaagagaa  12600
accggtgcgt cggataattg tcctatatgt cgtacccgtt ttagaaacat aacaatgagc  12660
aagttctata agctagttaa ctaataaata aaaagtttaa tttgttgacg acgtatgtcg  12720
ttatttttc tcgtataaaa gattaatttg attctaatat aatctttagt attggataaa  12780
tatcaattca aattaattcc attagattat atcataaata aaaatagtag cacacaacta  12840
cttcagccaa atattctttt ttgaaacgcc atctatcgta gtgaggacac aagtgaacct  12900
ataattatca aatttattag tatcagtcac atgaaggact ttctgtagag tgacgattcc  12960
actatctgtg gtacgaacgg tttcatcttc tttgatgcca tcacccagat gttctataaa  13020
cttggtatcc tcgtccgatt tcatatcctt tgctaaccaa tacatatagc taaactcagg  13080
catatgttcc acacatcctg aacaatgaaa ttctccagaa gatgttacaa tgtctagatt  13140
tggacatttg gtttcaccgc gttaacatat gagtgaacac acccatacat gaaagcgatg  13200
agaaatagga ttctcatctt gccaaaatat cactagaaaa aatttattta tcaattttaa  13260
aggtataaaa aatacttatt gttgctcgaa tattttgtat ttgatggtat acggaagatt  13320
agaaatgtag gtattatcat caactgattc tatggtttta tgtattctat catgtttcac  13380
tattgcgttg gaaataatat catatgcttc cacatatatt ttattttgtt ttaactcata  13440
atactcacgt aattctggat tattggcata tctatgaata attttagctc catgatcagt  13500
aaatattaat gagaacatag tattaccacc taccattatt tttttcatct cattcaattc  13560
ttaattgcaa agatctatat aatcattata gcgttgactt atggactctg gaatcttaga  13620
cgatgtacag tcatctataa tcatggcata tttaatacat tgttttatag catagtcgtt  13680
atctacgatg ttagatattt ctctcaatga atcaatcaca taatctaatg taggtttatg  13740
acataatagc attttcagca gttcaatgtt tttagattcg ttgatggcaa tggctataca  13800
tgtatatccg ttatttgatc taatgttgac atctgaaccg gattctagca gtaaagatac  13860
tagagattgt ttattatatc taacagcctt gtgaagaagt gtttctcctc gtttgtcaat  13920
catgttaatg tctttaagat aaggtaggca aatgtttata gtactaagaa ttgggcaagc  13980
ataagacatg tcacaaagac cctttttttgt atgtataagt gtagaaatta taacatccat  14040
agttggattt acataggtgt ccaatcggga tctctccatc atcgagataa ttgatggcat  14100
ctcccttcct tttttagtag atatttcatc gtgtaagaat caatattaat atttctaaag  14160
```

```
tatccgtgta tagcctcttt atttaccaca gctccatatt ccactagagg gatatcgccg  14220
aatgtcatat actcaattag tatatgttgg gaggacatcc gagttcattg ttttcaatat  14280
caaaaagatg gtttccttat catttctcca tagtggtaca atactacaca ttattccgtg  14340
cggctttcca ttttccaaaa acaatttgac caaatctaaa tctacatctt tattgtatct  14400
ataatcacta tttagataat cagccataat tcctcgagtg caacatgtta gatcgtctat  14460
atatgaataa gccgtgttat ctattccttt cattaacaat ttaacaatgt ctatatctat  14520
ataagatgac ttaatataat attgaagagc tgtacaatag tttttatcta taaaagacgg  14580
cttgattccg tgattaatta gacatttaac aacttccgga cgcacatatg ctctcgtatc  14640
cgactttgaa tacagatgag agatggatat acagatgcaa tacggtaccg caatttcgta  14700
gttgataatc atcatacgcg tatcagtact cgtcctcata aagaacactg cagccatttt  14760
ctatgaacaa atcaataatt ttaggaacag gatcattgtc attacataat tttctataac  14820
tgaacgatgg ttttcacatt taacactcaa gtcaaatcca tgttctacca acacctttat  14880
caagtcaacg tctacatttt tggatttcat atagctgaat atattaaagt catttatgtt  14940
gctaaatcca gtggcttcta gtagagccat cgctatatcc tttaacttta acatgtctac  15000
tatttgtgta ttcttctaat ggggatttgg tagacctcct actacgtata atttattgtt  15060
agcgggtatc ccgctagcat acagtctggg gctattcatc ggaggaattg gaatccaatt  15120
gtttgatata taatttaccg ctatagcatt gttatgtatt tcattgttca tccatccacc  15180
gatgagatat actacttctc caacatgagt acttgtacac atatggaata tatctataat  15240
ttgatccatg ttcataggat actctatgaa tggatacttg tatgatttgc gtggttgttt  15300
atcacaatga aatattttgg tacagtctag tatccatttt acattattta tacctctggg  15360
agaaagataa tttgacctga ttacattttt gataaggagt agcagatttc ctaatttatt  15420
tcttcgcctc atataccact taatgacaaa atcaactaca taatcctcat ctggaacatt  15480
tagttcatcg ctttctagaa taagtttcat agatagataa tcaaaattgt ctatgatgtc  15540
atcttccagt tccaaaaagt gtttggcaat aaagtttta gtatgacata agagattgga  15600
tagtccgtat tctataccca tcatgtaaca ctcgacacaa tattcctttc taaaatctcg  15660
taagataaag tttatacaag tgtagatgat aaattctaca gaggttaata tagaagcacg  15720
taataaattg acgacgttat gactatctat atataccttt ccagtatacg agtaaataac  15780
tatagaagtt aaactgtgaa tgtcaaggtc tagacaaacc ctcgtaactg gatctttatt  15840
tttcgtgtat ttttgacgta aatgtgtgcg aaagtaagga gataactttt tcaatatcgt  15900
agaattgact attatattgc cacctatagc atcaataatt gttttgaatt tcttagtcat  15960
agacaatgct aatatattct tacagtacac agtattgaca aaatcggcat ttatgtttct  16020
ttaaaagtca acatctagag aaaaatgatt atctttttga gacataactc ccattttttg  16080
gtattcaccc acacgttttt cgaaaaaatt agtttttcct tccaatgata tattttccat  16140
gaaatcaaac ggattggtaa cattataaat ttttttaaat cccaattcag aaatcaatct  16200
atccgcgacg aattctatat atgttttcat catttcacaa ttcattccta taagtttaac  16260
tggaagagcc gcagtaagaa attcttgttc aatggatacc gcatctgtta taatagatct  16320
aacggtttct tcactcggtg gatgcaataa atgtttaaac atcaaacatg cgaaatcgca  16380
gtgcagaccc tcgtctctac taattagttc gttggaaaac gtgagtccgg gcattaggcc  16440
acgcttttta agccaaaata tggaagcgaa tgatccggaa aagaagattc cttctactgc  16500
```

```
agcaaaggca ataagtctct ctccataacc ggcgctgtca tgtatccact tttgagccca  16560

atcggccttc tttttacac aaggcattgt ttctatggca ttaaagagat agttttttc  16620

attactatct ttaacataag tatcgatcaa aagactatac atttccgaat gaatgttttc  16680

aatggccatc tgaaatccgt agaaacatct agcctcggta atctgtactt ctgtacaaaa  16740

tcgttccgcc aaattttcat tcactattcc gtcactggct gcaaaaaacg ccaatacatg  16800

ttttataaaa tatttttcgt ctggtgttag tttattccaa tcattgatat ctttagatat  16860

atctacttct tccactgtcc aaaatgatgc ctctgccttt ttatacatgt tccagatgtc  16920

atgatattgg attgggaaaa taacaaatct atttggattt ggtgcaagga tgggttccat  16980

aactaaatta acaataacaa taaatttttt ttcagttatc tatatgcctg tacttggatc  17040

ttttgtacat cgatatcgcc gcaatcacta caataattac aagtattatt gatagcattg  17100

ttattagtac tatcataatt aaattatcta cattcatggg tgctgaataa tcgttattat  17160

catcattatc attttgtaat tgtgacatca tactagataa atcgtttgcg agattgttgt  17220

gggaagcggg catggaggat gcattatcat tattatttaa cgccttccat ttggattcac  17280

aaatgttacg cacattcaac attttatgga aactataatt ttgtgaaaac agataacaag  17340

aaaactcgtc atcgttcaaa tttttaacga tagtaaaccg attaaacgtc gagctaattt  17400

ctaacgctag cgactctgtt ggatatgggt ttccagatat atatcttttc agttccccta  17460

cgtatctata atcatctgta ggaaatggaa gatatttcca tttatctact gttcctaata  17520

tcatatgtgg tggtgtagta gaaccattaa gcgcgaaaga tgttatttcg catcgtattt  17580

taacttcgca ataatttctg gttagataac gcactctacc agtcaagtca atgatattag  17640

cctttacaga tatattcata gtagtcgtaa cgatgactcc atcttttaga tgcgatactc  17700

ctttgtatgt accagaatct tcgtaccgca aactcgatat atttaaacaa gttaatgaga  17760

tattaacgcg ttttatgaat gatgatatat aaccagaagt tttatcctcg gtggctagcg  17820

ctataacctt atcattataa taccaactag tgtgattaat atgtgacacg ttagtgtggg  17880

tacaaatatg tacattatcg tctacgtcgt attcgataca tccgcataca gccaacaaat  17940

ataaaatgac aaatactcta acgacgttcg tacccatctt gatgcggttt aataaatgtt  18000

ttgatttcaa tttattgtaa aaaaagattc ggttttatac tgttcgatat tctcattgct  18060

tatattttca tctatcatct ccacacagtc aaatccgtgg ttagcatgca cctcatcaac  18120

cggtaaaaga ctatcggact cttctatcat tataactcta gaatatttaa tttggtcatt  18180

attaatcaag tcaattatct tatttttaac aaacgtgagt attttactca tttttttataa  18240

aaacttttag aaatatacag actctatcgt gtgtctatat cttcttttta tatccaatgt  18300

atttatgtct gatttttctt catttatcat atataatggt ccaaattcta cacgtgcttc  18360

ggattcatcc agatcattaa ggttcttata attgtaacat ccttctcttc cctcttctac  18420

atcttccttc ttattcttat tcttagcgtc acagaatcta ccacagcagg atcccatgac  18480

gagcgtcata ttaaactaat tcattttcaa ttataatata tgattagtaa tgaccattaa  18540

aataaaaaat attcttcata accggcaaga aagtgaaaag ttcacattga aactatgtca  18600

gtagtataca tcatgaaatg atgatatata tatactctat tttggtggag gattatatga  18660

tataattcgt ggataatcat ttttaagaca catttcttca ttcgtaaatc ttttcacgtt  18720

aaatgagtgt ccatattttg caatttcttc atatgatggc ggtgtacgtg gacgaggctg  18780

ctcctgttct tgttgtagtc gccgactgtc gtgtctgcgt ttagatccct ccattatcgc  18840

gattgcgtag atggagtact attatatacc ttgtaattaa attttttat taattaaacg  18900
```

```
tataaaaacg ttccgtatct gtatttaaga gccagatttc gtctaataga acaaatagct  18960
acagtaaaaa taactagaat aattgctaca cccactagaa accacggatc gtaatacggc  19020
aatcggtttt cgataatagg tggaacgtat attttattta aggacttaac aattgtctgt  19080
aaaccacaat ttgcttccgc ggatcctgta ttaactatct gtaaaagcat atgttgaccg  19140
ggcggagccg aacattctcc gatatctaat ttctgtatat ctataatatt attaacctcc  19200
gcatacgcat tacagttctt ttctagcttg gataccgcac taggtacatc gtctagatct  19260
attcctattt cctcagcgat agctcttcta tccttttccg gaagcaatga aatcacttca  19320
ataaatgatt caaccatgag tgtgaaacta agtcgagaat tactcatgca tttgttagtt  19380
attcggagcg cgcaattttt aaactgtcct ataacctctc ctatatgaat agcacaagtg  19440
acattagtag ggatagaatg ttgagctaat ttttgtaaat aactatctat aaaaagatta  19500
tacaaagttt taaactcttt agtttccgcc atttatccag tctgagaaaa tgtctctcat  19560
aataaatttt tccaagaaac taattgggtg aagaatggaa acctttaatc tatatttatt  19620
acagtctgtc ttggtacaca tgatgaattc ttctaatgct gtactaaatt cgatatcttt  19680
ttcgatttct ggatatgttt ttaataaagt atgaacaaag aaatggaaat cgtaatacca  19740
gttatgttca actttgaaat tgttttttat tttcttgtta atgattccag ccacttggga  19800
aaagtcaaag tcgtttaatg ccgatttaat acgttcatta aaaacaaact ttttatcctt  19860
tagatgaatt attattggtt cattggaatc aaaaagtaag atattatcgg gtttaagatc  19920
tgcgtgtaaa aagttgtcgc aacagggtag ttcgtagatt ttaatgtata acagagccat  19980
ctgtaaaaag ataaacttta tgtattgtac caaagattta aatcctaatt tgatagctaa  20040
ctcggtatct actttatctg ccgaatacag tgctagggga aaaattataa tgtttcctct  20100
ttcatattcg tagttagttc tcttttcatg ttcgaaaaag tgaaacatgc ggttaaaata  20160
gtttataaca ttaatattac tgttaataac tgccggataa aagtgggata gtaatttcac  20220
gaatttgata ctgtcctttc tctcgttaaa cgcctttaaa aaaactttag aagaatatct  20280
caatgagagt tcctgaccat ccatagtttg tatcaataat agcaacatat gaagaacccg  20340
tttatacaga gtatgtaaaa atgttaattt atagtttaat cccatggccc acgcacacac  20400
gattaatttt ttttcatctc cctttagatt gttgtataga aatttgggta ctgtgaactc  20460
cgccgtagtt tccatgggac tatataattt tgtggcctcg aatacaaatt ttactacata  20520
gttatctatc ttaaagacta taccatatcc tcctgtagat atgtgataaa aatcgtcgtt  20580
tataggataa aatcgtttat ccttttgttg gaaaaaggat gaattaatgt aatcattctc  20640
ttctatcttt agtagtgttt ccttattaaa attcttaaaa taatttaaca atctaactga  20700
cggagcccaa ttttggtgta aatctaattg ggacattata ttgttaaaat acaaacagtc  20760
tcctaatata acagtatctg ataatctatg gggagacatc cattgatatt caggggatga  20820
atcattggca acacccattt attgtacaaa aagccccaat ttacaaacga aagtccaggt  20880
ttgatagaga caaactatta actattttgt ctctgttttt aacacctcca cagtttttaa  20940
tttctttagt aatgaaatta ttcacaatat cagtatcttc tttatctacc agagatttta  21000
ctaacttgat aaccttggct gtctcattca atagggtagt gatatttgta tgtgtgatat  21060
tgatatcttt ttgaattgtt tcttttagaa gtgattcttt gatggtgcca gcatacgaat  21120
tacaataatg cagaaactcg gttaacatgc aggaattata gtaagccaat tccaattgtt  21180
gcctgtgttg tattagagtg tcaatatgag caatggtgtc cttgcgtttc tctgatagaa  21240
```

```
tgcgagcagc gattttggcg ttatcatttg acgatatttc tggaatgacg aatcctgttt  21300
ctactaactt tttggtagga caaagtgaaa caatcaagaa gatagcttct cctcctattt  21360
gtggaagaaa ttgaactcct ctagatgatc tactgacgat agtatctcct tgacagatat  21420
tggaccgaat tacagaagta cctggaatgt aaagccctga aaccccctca ttttttaagc  21480
agattgttgc cgtaaatcct gcactatgcc caagatagag agctcctttg gtgaatccat  21540
ctctatgttt cagtttaacc aagaaacagt cagctggtct aaaatttcca tctctatcta  21600
atacagcatc taacttgatg tcaggaacta tgaccggttt aatgttatat gtaacattga  21660
gtaaatcctt aagttcataa tcatcactgt catcagttat gtacgatcca aacaatgttt  21720
ctaccggcat agtggatacg aagatgctat ccatcagaat gtttccctga ttagtatttt  21780
ctatatagct attcttcttt aaacgatttt ccaaatcagt aactatgttc attttttttag  21840
gagtaggacg cctagccagt atggaagagg attttctaga tcctctcttc aacatctttg  21900
atctcgatgg aatgcaaaac cccatagtga aacaaccaac gataaaaata atattgtttt  21960
tcacttttta taattttacc atctgactca tggattcatt aatatcttta taagagctac  22020
taacgtataa ttctttataa ctgaactgag atatatacac cggatctatg gtttccataa  22080
ttgagtaaat gaatgctcgg caataactaa tggcaaatgt atagaacaac gaaattatac  22140
tagagttgtt aaagttaata ttttctatga gctgttccaa taaattattt gttgtaactg  22200
cgttcaagtc ataaatcatc ttgatactat ccagtaaacc gtttttaagt tctggaatat  22260
tatcatccca ttgtaaagcc cctaattcga ctatcgaata tcctgctctg atagcagttt  22320
caatatcgac ggacgtcaat actgtaataa aggtggtagt attgtcatca tcgtgataaa  22380
ctactggaat atggtcgtta gtaggtacgg taactttaca caacgcgata tataactttc  22440
cttttgtacc atttttaacg tagttgggac gtcctgcagg gtattgtttt gaagaaatga  22500
tatcgagaac agatttgata cgatatttgt tggattcctg attattcact ataatataat  22560
ctagacagat agatgattcg ataaatagag aaggtatatc gttggtagga taatacatcc  22620
ccattccagt attctcggat actctattga tgacactagt taagaacatg tcttctattc  22680
tagaaaacga aaacatccta catggactca ttaaaacttc taacgctcct gattgtgtct  22740
cgaatgcctc gtacaaggat ttcaaggatg ccatagattc tttgaccaac gatttagaat  22800
tgcgtttagc atctgatttt tttattaaat cgaatggtcg gctctctggt ttgctacccc  22860
aatgataaca atagtcttgt aaagataaac cgcaagaaaa tttatacgca tccatccaaa  22920
taaccctagc accatcggat gatattaatg tattattata gattttccat ccacaattat  22980
tgggccagta tactgttagc aacggtatat cgaatagatt actcatgtaa cctactagaa  23040
tgatagttcg tgtactagtc ataatatctt taatccaatc taagaaattt aaaattagat  23100
tttttacact gttaaagtta acaaaggtat tacccggata cgtggatatc atatatggca  23160
ttggtccatt atcagtaata gctccataaa ctgatacggc gatggttttt atatgtgttt  23220
gatctaacga ggaagaaatt cgcgcccaca attcatctct agatatgtat ttaatatcaa  23280
acggtaacac atcaatttcg ggacgcgtat atgtttctaa atttttaatc caaatataat  23340
gatgacctat atgccctatt atcatactgt caactatagt acacctaggg aacttacgat  23400
acatctgttt cctgtaatcg ttaaatttta caaatctata acatgctaaa ccttttgacg  23460
acaaccattc attaatttct gatatggaat ctgtattctc aataccgtat cgttctaaag  23520
ccagtgctat atctccctgt tcgtgagaac gctttcgtat aatatcgatc aacggataat  23580
ctgaagtttt tggagaataa tatgactcat gatctatttc gtccataaac aatctagaca  23640
```

```
taggaattgg aggcgatgat cttaattttg tgcaatgagt cgtcaatcct ataacttcta  23700
atcttgtaat attcatcatc gacataatac tatctatgtt atcatcgtat attagtatac  23760
cacggccttc ttcatttcgt gccaaaatga tatacagtct taaatagtta cgcaatatct  23820
caatagtttc ataattgtta gctgttttca tcaagatttg taccctgttt aacatgatgg  23880
cgttctataa cgtctctatt ttctattttt aattttttaa atttttaacg atttactgtg  23940
gctagatacc caatctctct caaatatttt tttagcctcg cttacaagct gtttatctat  24000
actattaaaa ctgacgaatc cgtgattttg gtaatgggtt ccgtcgaaat ttgccgaagt  24060
gatatgaaca tattcgtcgt cgactatcaa caattttgta ttattctgaa tagtgaaaac  24120
cttcacagat agatcatttt gaacacacaa cgcatctaga cttttggcgg ttgccataga  24180
atatacgtcg ttcttatccc aattaccaac tagaagtctg atcttaactc ctctattaat  24240
ggctgcttct ataatggagt tgtaaatgtc gggccaatag tagctattac cgtcgacacg  24300
tgtagtggga actatggcca aatgttcaat atctatacta gtcttagccg acttgagttt  24360
atcaataact acatcggtat ctagatctct agaatatccc aataggtgtt ccggagaatc  24420
agtaaagaac actccaccta taggattctt aatatgatac gcagtgctaa ctggcaaaca  24480
acaagccgca gagcataaat tcaaccatga attttttgcg ctattaaagg ctttaaaagt  24540
atcaaatctt ctacgaagat ctgtggccag cgggggataa tcagaatata cacctaacgt  24600
tttaatcgta tgtatagatc ctccagtaaa tgacgcgttt cctacataac atctttcatc  24660
atctgacacc caaaaacaac cgagtagtag tcccacatta ttttttttat ctatattaac  24720
ggttataaaa tttatatccg ggcagtgact ttgtagctct cccagatttc ttttccctcg  24780
ttcatctagc aaaactatta ttttaatccc tttttcagat gcctctttta gtttatcaaa  24840
aataagcgcg cccctagtcg tactcagagg attacaacaa aaagatgcta tgtatatata  24900
tttcttagct agagtgataa tttcgttaaa acattcaaat gttgttaaat gatcggatct  24960
aaaatccata ttttctggta gtgtttctac cagcctacat tttgctcctg caggtaccgg  25020
tgcaaatggc cacatttagt taacataaaa acttatacat cctgttctat caacgattct  25080
agaatatcat cggctatatc gctaaaattt tcatcaaagt cgacatcaca acctaactca  25140
gtcaatatat taagaagttc catgatgtca tcttcgtcta tttctatatc cgtatccatt  25200
gtagattgtt gaccgattat cgagtttaaa tcattactaa tactcaatcc ttcagaatac  25260
aatctgtgtt tcattgtaaa tttataggcg gtgtatttaa gttggtagat tttcaattat  25320
gtattaatat agcaacagta gttcttgctc ctccttgatt ctagcatcct cttcattatt  25380
ttcttctacg tacataaaca tgtccaatac gttagacaac acaccgacaa tggcggccgc  25440
cacagacacg aatatgacta aaccgatgac catttaaaaa cccctctcta gctttcactt  25500
aaactgtatc gatcattctt ttagcacatg tataatataa aaacattatt ctatttcgaa  25560
tttaggcttc caaaaatttt tcatccgtaa accgataata atatatatag acttgttaat  25620
agtcggaata aatagattaa tgcttaaact atcatcatct ccacgattag agatacaata  25680
tttacattct ttttgctgtt tcgaaacttt atcaatacac gttaatacaa acccaggaag  25740
gagatattga aactgaggct gttgaaaatg aaacggtgaa tacaataatt cagataatgt  25800
aaaatcatga ttccgtattc tgatgatatt agaactgcta atggatgtcg atggtatgta  25860
tctaggagta tctattttaa caaagcatcg atttgctaat atacaattat ccttttgatt  25920
aattgttatt ttattcatat tcttaaaagg tttcatattt atcaattctt ctacattaaa  25980
```

```
aatttccatt tttaatttat gtagccccgc aatactcctc attacgtttc attttttgtc  26040
tataatatcc attttgttca tctcggtaca tagattatcc aattgagaag cgcatttagt  26100
agttttgtac attttaagtt tattgacaaa tcgtcgaaaa ctagttatag ttaacatttt  26160
attatttgat accctgatat taatacccct gccgttacta ttatttataa ctgatgtaac  26220
ccacgtaaca ttagaattaa ttatcgatag taatgcatca acgcttccaa aattgtctat  26280
tataaactca ccgataattt ttttattgca tgttttcata ttcattagga ttatcaaatc  26340
tttaatctta ttacgattgt atgcgttgat attacaagac gtcattctaa aagacggagg  26400
atttccatca aatgccagac aatcacgtac aaagtacatg gaaataggtt ttgttctatt  26460
gcgcatcata gatttatata gaacacccgt agaaatacta atttgtttta ctctataaaa  26520
tactaatgca tctatttcat cgttttgtat aacgtctttc caagtgtcaa attccaaatt  26580
tttttcattg atagtaccaa attcttctat ctctttaact acttgcatag ataggtaatt  26640
acagtgatgc ctacatgccg ttttttgaaa ctgaatagat gcgtctagaa gcgatgctac  26700
gctagtcaca atcaccactt tcatatttag aatatatgta tgtaaaaata tagtagaatt  26760
tcattttgtt tttttctatg ctataaatga attctcattt tgcatctgct catactccgt  26820
tttatatcaa taccaaagaa ggaagatatc tggttctaaa agccgttaaa gtatgcgatg  26880
ttagaactgt agaatgcgaa ggaagtaaag cttcctgcgt actcaaagta gataaaccct  26940
catcgcccgc gtgtgagaga agaccttcgt ccccgtccag atgcgagaga atgaataacc  27000
ctggaaaaca agttccgttt atgagaacgg acatgctaca aaatatgttc gcggctaatc  27060
gcgataatgt agcttctaga cttttgtcct aaaatactat tatatccttt tcgatattaa  27120
taaatccgtg tcgtccaggt tttttatctc tttcagtatg tgaatagata ggtattttat  27180
ctctattcat catcgaattt aagagatccg ataaacattg tttgtattct ccagatgtca  27240
gcatctgata caacaatata tgtgcacata aacctctggc acttatttca tgtaccttcc  27300
ccttatcact aaggagaata gtatttgaga aatatgtata catgatatta tcatgaatta  27360
gatatacaga atttgtaaca ctctcgaaat cacacgatgt gtcggcgtta agatctaata  27420
tatcactcga taacacattt tcatctagat acactagaca ttttttaaag ctaaaatagt  27480
ctttagtagt gacagtaact atgcgattat tttcatcgat gatacatttc atcggcatat  27540
tattacgctt accatcaaag actataccat gtgtatatct aacgtattct agcatggttg  27600
ccatacgcgc attaaacttt tcaggatctt tggatagatc ttccaatcta tctatttgag  27660
aaaacatttt tatcatgttc aatagttgaa acgtcggatc cactatatag atattatcta  27720
taaagatttt aggaactacg ttcatggtat cctggcgaat attaaaacta tcaatgatat  27780
gattatcgtt ttcatctttt atcaccatat agtttctaag atatgggatt ttacttaata  27840
taatattatt tcccgtgata aattttatta gaaaggccaa atctataaga aaagtcctag  27900
aattagtctg aagaatatct atatcgccgt atagtatatt tggattaatt agatatagag  27960
aatatgatcc gtaacatata caacttttat tatggcgtct aagatattct tccatcaact  28020
tattaacatt tttgactagg gaagatacat tatgacgtcc cattactttt gccttgtcta  28080
ttactgcgac gttcatagaa tttagcatat ctcttgccaa ttcttccatt gatgttacat  28140
tataagaaat tttagatgaa attacatttg gagctttaat agtaagaact cctaatatgt  28200
ccgtgtatgt ggtcactaat acagattgta gttctataat cgtaaataat ttacctatat  28260
tatatgtttg agtctgttta gaaaagtagc taagtatacg atcttttatt tctgatgcag  28320
atgtattaac atcggaaaaa aatctttttt tattcttttt tactaaagat acaaatatgt  28380
```

```
ctttgttaaa aacagttatt ttctgaatat ttctagcttg taattttaac atatgatatt  28440
cgttcacact aggtactctg cctaaatagg tttctataat ctttaatgta atattaggaa  28500
aagtattctg atcaggattc ctattcattt tgaggattta aaactctgat tattgtctaa  28560
tatggtctct acgcaaactt tttcacagag cgatagagtt tttgataact cgtttttctt  28620
aagaaatata aaactactgt ctccagagct cgctctatct tttattttat ctaattcgat  28680
acaaactcct gatactggtt cagaaagtaa ttcattaatt ttcagtcctt tatagaagat  28740
atttaatata gataatacaa aatcttcagt ttttgatatc gatctgattg atcctagaac  28800
tagatatatt aataacgtgc tcattaggca gtttatggca gcttgataat tagatatagt  28860
atattccagt tcatatttat tagataccgc attgcccaga ttttgatatt ctatgaattc  28920
ctctgaaaat aaatccaaaa taactagaca ttctattttt tgtggattag tgtactctct  28980
tccctctatc atgttcacta ctggtgtcca cgatgataaa tatctagagg gaatataata  29040
tagtccatag gatgccaatc tagcaatgtc gaataactgt aatttgattc ttcgttcttc  29100
attatgaatt gattcttgag gtataaacct aacacaaatt atattattag acttttcgta  29160
tgtaatgtct ttcatgttat aagtttttaa tcctggaata gaatctattt taatgaggct  29220
tttaaacgca gagttctcca acgagtcaaa gcataatact ctgttgtttt tcttatatac  29280
gatgttacga ttttcttctt tgaatggaat aggtttttga attagtttat aattacaaca  29340
taatagataa ggaagtgtgc aaatagtacg cggaaaaaac ataatagctc ccctgttttc  29400
atccatggtt ttaagtaaat gatcactggc ttctttagtc aatggatatt cgaacattaa  29460
ccgtttcatc atcattggac agaatccata ttttttaatg taaagagtga tcaaatcatt  29520
gtgtttattg taccatcttg ttgtaaatgt gtattcggtt atcggatctg ctcctttttc  29580
tattaaagta tcgatatcga tctcgtctaa gaattcaact atatcgacat atttcatttg  29640
tatacacata accattacta acgtagaatg tataggaaga gatgtaacgg gaacagggtt  29700
tgttgattcg caaactattc taatacataa ttcttctgtt aatacgtctt gcacgtaatc  29760
tattatagat gccaagatat ctatataatt attttgtaag atgatgttaa ctatgtgatc  29820
tatataagta gtgtaataat tcatgtattt tgatatatgt tccaactctg tctttgtgat  29880
gtctagtttc gtaatatcta tagcatcctc aaaaaaatata ttcgcatata ttcccaagtc  29940
ttcagttcta tcttctaaaa aatcttcaac gtatggaata taataatcta ttttacctct  30000
tctgatatca ttaatgatat agtttttgac actatcttct gtcaattgat tcttattcac  30060
tatatctaag aaacggatag cgtccctagg acgaactact gccattaata tctctattat  30120
agcttctgga cataattcat ctattatacc agaattaatg ggaactattc cgtatctatc  30180
taacatagtt ttaagaaagt cagaatctaa gacttgatgt tcatatattg gttcatacat  30240
gaaatgatct ctattgatga tagtgactat ttcattctct gaaaattggt aactcattct  30300
atatatgctt tccttgttga tgaaggatag aatatactca atagaatttg taccaacaaa  30360
ctgttctctt atgaatcgta tatcatcatc tgaaataatc atgtaaggca tacatttaac  30420
aattagagac ttgtctcctg ttatcaatat actattcttg tgataattta tgtgtgaggc  30480
aaatttgtcc acgttcttta attttgttat agtagatatc aaatccaatg gagctacagt  30540
tcttggctta aacagatata gtttttctgg aacaaattct acaacattat tataaaggac  30600
tttgggtaga taagtgggat gaaatcctat tttaattaat gcgatagcct tgtcctcgtg  30660
cagatatcca aacgcttttg tgatagtatg gcattcattg tctagaaacg ctctacgaat  30720
```

```
atctgtgaca gatatcatct ttagagaata tactagtcgc gttaatagta ctacaatttg  30780
tattttttaa tctatctcaa taaaaaaatt aatatgtatg attcaatgta taactaaact  30840
actaactgtt attgataact agaatcagaa tctaatgatg acgtaaccaa gaagtttatc  30900
tactgccaat ttagctgcat tatttttagc atctcgttta gattttccat cggccttatc  30960
gaatactctt ccgtcgatgt ctacacaggc ataaaatgta ggagagttac taggccccac  31020
tgattcaata cgaaaagacc aatctctctt agttatttgg cagtactcat taataacggt  31080
gacagggtta gcacctttcc aatcaataat ttttttagcc ggaataacat catcaaaaga  31140
cttatgatcc tctctcattg atttttcgcg ggatacatca tctattatga cgtcagccat  31200
agcatcagca tccggcttat ccgcctccgt tgtcataaac caacgaggag gaatatcgtc  31260
ggagctgtac accatagcac tacgttgaag atcgtacaga gctttattaa cttctcgctt  31320
ctccatatta agttgtctag ttagttgtgc agcagtagct ccttcgattc caatggtttt  31380
aatagcctca cacacaatct ctgcgtcaga acgctcgtca atatagatct tagacatttt  31440
tagagagaac taacacaacc agcaataaaa ctgaacctac tttatcattt ttttattcat  31500
catcctctgg tggttcgtcg ttcctatcga atgtggatct gattaacccg tcatctatag  31560
gtgatgctgg ttctggagat tctggaggag atggattatt atctggaaga atctctgtta  31620
tttccttgtt ttcatgtatc gattgcgttg taacattaag attgcgaaat gctctaaatt  31680
tgggaggctt aaagtgttgt ttgcaatctc tacacgcgtg tctaactagt ggaggttcgt  31740
cagcggctct agtttgaatc atcatcggtg tagtattcct acttttacag ttaggacacg  31800
gtgtattgta tttctcgtcg agaacgttaa aataatcgtt gtaactcaca tcctttattt  31860
tatctatatt gtattctact cctttcttaa tgcattttat accgaataag agatagcgaa  31920
ggaattcttt ttcggtgccg ctagtaccct taatcatatc acatagtgtt ttatattcca  31980
aatttgtggc aatagacggt ttatttctat acgatagttt gtttctggaa tcctttgagt  32040
attctatacc aatattattc tttgattcga atttagtttc ttcgatatta gattttgtat  32100
tacctatatt cttgatgtag tactttgatg atttttccat ggcccattct attaagtctt  32160
ccaagttggc atcatccaca tattgtgata gtaattctcg gatatcagta gcggttaccg  32220
ccattgatgt ttgttcattg gatgagtaac tactaatgta tacattttcc atttataaca  32280
cttatgtatt aactttgttc atttatattt tttcattatt atgttgatat taacaaaagt  32340
gaatatatat atgttaataa ttgtattgtg gttatacggc tacaatttta taatgagtga  32400
aagtcagtgt ccgatgatca atgacgatag ctttactctg aaaagaaagt atcaaatcga  32460
tagtgcggag tcaacaataa aaatggataa gaagaggata aagtttcaga atagagccaa  32520
aatggtaaaa gaaataaatc agacaataag agcagcacaa actcattacg agacattgaa  32580
actaggatac ataaaattta agagaatgat tatgactact actctagaag atatagcacc  32640
atctattcca aataatcaga aaacttataa actattctcg gacatttcag ccatcggcaa  32700
agcatcacag aatccgagta agatggtata tgctctgctg ctttacatgt ttcccaattt  32760
gtttggagat gaccatagat tcattcgtta tagaatgcat ccaatgagta aaatcaaaca  32820
caagatcttc tctcctttca aacttaatct tattagaata ttagtggaag aaagattcta  32880
taataatgaa tgcagatcta ataaatggag aataattgga acacaagttg ataaaatgtt  32940
gatagctgaa tctgataaat atacaataga tgcaaggtat aacctaaaac ccatgtatag  33000
aatcaaggga gaatctgaag aagataccct ctttatcaaa cagatggtag aacaatgtgt  33060
gacatcccag gaattggtgg aaaaagtgtt gaagatactg tttagagatt tgttcaagag  33120
```

```
tggagaatac aaagcgtaca gatacgatga tgatgtagaa aatggattca ttggattgga  33180
tacactaaaa ttaaacattg ttcatgatat agttgaacca tgtatgcctg ttcgtaggcc  33240
agtggctaag atactgtgta aagaaatggt aaataaatac tttgagaatc cgctacatat  33300
tattggtaaa aatcttcaag agtgcattga ctttgttagt gaataggcat ttcatctttc  33360
tccaatacta attcaaattg ttaaattaat aatggatagt ataaatagtt attagtgata  33420
aaatagtaaa aataattatt agaataagag tgtagtatca tagataactc tcttctataa  33480
aaatggattt tattcgtaga aagtatctta tatacacagt agaaaataat atagattttt  33540
taaaggatga tacattaagt aaagtaaaca attttaccct caatcatgta ctagctctca  33600
agtatctagt tagcaatttt cctcaacatg ttattactaa ggatgtatta gctaatacca  33660
atttttttgt tttcatacat atggtacgat gttgtaaagt gtacgaagcg gttttacgac  33720
acgcatttga tgcacccacg ttgtacgtta aagcattgac taagaattat ttatcgttta  33780
gtaacgcaat acaatcgtac aaggaaaccg tgcataaact aacacaagat gaaaaatttt  33840
tagaggttgc cgaatacatg gacgaattag gagaacttat aggcgtaaat tatgacttag  33900
ttcttaatcc attatttcac ggaggggaac ccatcaaaga tatggaaatc atttttttaa  33960
aactgtttaa gaaaacagac ttcaaagttg ttaaaaaatt aagtgttata agattactta  34020
tttgggcata cctaagcaag aaagatacag gcatagagtt tgcggataat gatagacaag  34080
atatatatac tctatttcaa caaactggta gaatcgtcca tagcaatcta acagaaacgt  34140
ttagagatta tatctttccc ggagataaga ctagctattg ggtgtggtta aacgaaagta  34200
tagctaatga tgcggatatc gttcttaata gacacgccat taccatgtat gataaaattc  34260
ttagttatat atactctgag ataaaacaag gacgcgttaa taaaaacatg cttaagttag  34320
tttatatctt tgagcctgaa aaagatatca gagaacttct gctagaaatc atatatgata  34380
ttcctggaga tatcctatct attattgatg caaaaaacga cgattggaaa aaatatttta  34440
ttagttttta taaagctaat tttattaacg gtaatacatt tattagtgat agaacgttta  34500
acgaggactt attcagagtt gttgttcaaa tagatcccga atatttcgat aatgaacgaa  34560
ttatgtcttt attctctacg agtgctgcgg acattaaacg atttgatgag ttagatatta  34620
ataacagtta tatatctaat ataatttatg aggtgaacga tatcacatta gatacaatgg  34680
atgatatgaa aaagtgtcaa atctttaacg aggatacgtc gtattatgtt aaggaataca  34740
atacatacct gtttttgcac gagtcggatc ccatggtcat agagaacgga atactaaaaa  34800
aactgtcatc tataaaatcc aagagtagac ggctgaactt gtttagcaaa aacattttaa  34860
aatattattt agacggacaa ttggctcgtc taggtcttgt gttagatgat tataaaggag  34920
acttgttagt taaaatgata aaccatctta agtctgtgga ggatgtatcc gcattcgttc  34980
gattttctac agataaaaac cctagtattc ttccatcgct aatcaaaact attttagcta  35040
gttataatat ttccatcatc gtcttatttc aaaggttttt gagagataat ctatatcatg  35100
tagaagaatt cttggataaa agcatccatc taaccaagac ggataagaaa tatatacttc  35160
aattgataag acacggtaga tcatagaaca gaccaaatat attattaata atttgtatat  35220
acatagatat aattatcaca catttttgat aaatgggaac tgctgcaaca attcagactc  35280
ccaccaaatt aatgaataaa gaaaatgcag aaatgatttt ggaaaaaatt gttgatcata  35340
tagttatgta tattagtgac gaatcaagtg attcagaaaa taatcctgaa tatattgatt  35400
ttcgtaacag atacgaagac tatagatctc tcattataaa aagtgatcac gagtttgtaa  35460
```

```
agctatgtaa aaatcatgcg gagaaaagtt ctccagaaac gcaacaaatg attatcaaac  35520
acatatacga acaatatctt attccagtat ctgaagtact attaaaacct ataatgtcca  35580
tgggtgacat aattacatat aacggatgta aagacaatga atggatgcta gaacaactct  35640
ctaccctaaa ctttaacaat ctccgcacat ggaactcatg tagcataggc aatgtaacgc  35700
gtctgtttta tacatttttt agttatctga tgaaagataa actaaatata taagtataat  35760
cccattctaa tactttaacc tgatgtatta gcatcttatt agaatattaa cctaactaaa  35820
agacataaca taaaaactca ttacatagtt gataaaaagc ggtaggatat aaatattatg  35880
gctgccaccg ttccgcgttt tgacgacgtg tacaaaaatg cacaaagaag aattctagat  35940
caagaaacat tttttagtag aggtctaagt agaccgttaa tgaaaaacac atatctattt  36000
gataattacg cgtatggatg gataccagaa actgcaattt ggagtagtag atacgcaaac  36060
ctagatgcta gtgactatta tcccatttcg ttgggattac ttaaaaagtt cgagtttctc  36120
atgtctctat ataaaggtcc tattcccgta tatgaagaaa aagtaaatac tgaattcatt  36180
gctaatggat cgttctctgg tagatacgta tcatatcttc gaaagttttc tgctcttcca  36240
acaaacgagt ttattagttt tttgttactg acttccattc caatctataa tatcttgttc  36300
tggtttaaaa atacacagtt tgatattact aaacacacat tattcagata cgtctataca  36360
gataatgcca aacacctggc gttggctagg tatatgcatc aaacaggaga ctataagcct  36420
ttgtttagtc gtctcaaaga gaattatata tttaccggtc ccgttccaat aagtatcaaa  36480
gatatagatc accctaatct tagtagagca agaagtccat ccgattatga gacattagct  36540
aatattagta ctatattgta ctttaccaag tatgatccgg tattaatgtt tttattgttt  36600
tacgtacctg ggtattcaat tactacaaaa attactccag ccgtagaata tctaatggat  36660
aaactgaatc taacaaagag cgacgtacaa ctgttgtaaa ttattttatg cttcgtaaaa  36720
tgtaggtttt gaaccaaaca ttctttcaaa gaatgagatg cataaaactt tattatccaa  36780
tagattgact atttcggacg tcaatcgttt aaagtaaact tcgtaaaata ttctttgatc  36840
actgccgagt ttaaaacttc tatcgataat tgtttcatat gttttaatat ttacaagttt  36900
tttggtccat ggtacattag gacaaatata tgcaaaataa tatcgttctc caagttctat  36960
agtctctgga ttatttttat tatattcagt aaccaaatac atattagggt tatctgcgga  37020
tttataattt gagtgatgca ttcgactcaa cataaataat tctaaaggag acgatctact  37080
atcaaattcg gatcgtaaat ctgtttctaa agaacggaga atatctatac atacctgatt  37140
agaattcatc cgtccttcag acaacatctc agacagtctg gtcttgtatg tcttaatcat  37200
attcttatga aacttggaaa catctcttct agtttcacta gtacctttat taattctctc  37260
aggtacagat tttgaattcg acgatgctga gtatttcatc gttgtatatt tcttcttcga  37320
ttgcataatc agattcttat ataccgcctc aaactctatt ttaaaattat taaacaatac  37380
tctattatta atcagtcgtt ctaactcctt tgctatttct atggacttat ctacatcttg  37440
actgtctatc tctgtaaaca cggagtcggt atctccatac acgctacgaa aacgaaatct  37500
gtaatctata ggcaacgatg ttttcacaat cggattaata tctctatcgt ccatataaaa  37560
tggattactt aatggattgg caaaccgtaa cataccgtta gataactctg ctccatttag  37620
taccgattct agatacaaga tcattctacg tcctatggat gtgcaactct tagccgaagc  37680
gtatgagtat agagcactat ttctaaatcc catcagacca tatactgagt tggctactat  37740
cttgtacgta tattgcatgg aatcataaat ggccttttca gttgaactgg tagcctgttt  37800
taacatcttt ttatatctgg ctctctctgc caaaaatgtt cttaatagtc taggaatggt  37860
```

```
tccttctatc gatctatcga aaattgctat ttcagagatg aggttcggta gtctaggttc  37920
acaatgaacc gtaatatatc taggaggtgg atatttctga agcaagagct gattatttat  37980
ttcttcttcc aatctattgg tactaacaac gacaccgact aatgtttccg gagatagatt  38040
tccaaagata cacacattag gatacagact gttataatca aagattaata cattattact  38100
aaacattttt tgttttggag caaatacctt accgccttca taaggaaact tttgttttgt  38160
ttctgatcta actaagatag ttttagtttc caacaatagc tttaacagtg gacccttgat  38220
gactgtactc gctctatatt cgaataccat ggattgagga agcacatatg ttgacgcacc  38280
cgcgtctgtt tttgtttcta ctccataata ctcccacaaa tactgacaca aacaagcatc  38340
atgaatacag tatctagcca tatctaaagc tatgtttaga ttataatcct tatacatctg  38400
agctaaatca acgtcatcct ttccgaaaga taatttatat gtatcattag gtaaagtagg  38460
acataatagt acgactttaa atccattttc ccaaatatct ttacgaatta ctttacatat  38520
aatatcctca tcaacagtca cataattacc tgtggttaaa acctttgcaa atgcagcggc  38580
tttgcctttc gcgtctgtag tatcgtcacc gatgaacgtc atttctctaa ctcctctatt  38640
taatacttta cccatgcaac tgaacgcgtt cttggatata gaatccaatt tgtacgaatc  38700
caatttttca aatttttgaa tgaatgaata tagatcgaaa aatatagttc cattattgtt  38760
attaacgtga aacgtagtat tggccatgcc gcctactccc ttatgactag actgatttct  38820
ctcataaata cagagatgta cagcttcctt tttgtccgga gatctaaaga taatcttctc  38880
tcctgttaat aactctagac gattagtaat atatctcaga tcaaagttat gtccgttaaa  38940
ggtaacgacg tagtcgaacg ttagttccaa caattgttta gctattcgta acaaaactat  39000
ttcagaacat aaaactagtt ctcgttcgta atccatttcc attagtgact gtatcctcaa  39060
acatcctcta tcgacggctt cttgtatttc ctgttccgtt aacatctctt cattaatgag  39120
cgtaaacaat aatcgtttac cacttaaatc gatataacag taacttgtat gcgagattgg  39180
gttaataaat acagaaggaa acttcttatc gaagtgacac tctatatcta gaaataagta  39240
cgatcttggg atatcgaatc taggtatttt tttagcgaaa cagttacgtg gatcgtcaca  39300
atgataacat ccattgttaa tctttgtcaa atattgctcg tccaacgagt aacatccgtc  39360
tggagatatc ccgttagaaa tataaaacca actaatattg agaaattcat ccatggtggc  39420
attttgtatg ctgcgtttct ttggctcttc tatcaaccac atatctgcga cggagcattt  39480
tctatcttta atatctagat tataacttat tgtctcgtca atgtctatag ttctcatctt  39540
tcccaacggc ctcgcattaa atggaggagg agacaatgac tgatatattt cgtccgtcac  39600
tacgtaataa aagtaatgag gaaatcgtat aaatacggtc tcaccatttc gacatctgga  39660
tttcagatat aaaaatctgt tttcaccgtg actttcaaac caattaatgc accgaacatc  39720
catttataga atttagaaat atattttcat ttaaatgaat cccaaacatt ggggaagagc  39780
cgtatggacc attattttta tagtactttc gcaagcgggt ttagacggca acatagaagc  39840
gtgtaaacga aaactatata ctatagttag cactcttcca tgtcctgcat gtagacggca  39900
cgcgactatc gctatagagg acaataatgt catgtctagc gatgatctga attatattta  39960
ttattttttc atcagattat ttaacaattt ggcatctgat cccaaatacg cgatcgatgt  40020
gacaaaggtt aaccctttat aaacttaacc cattataaaa cttatgatta gtcacaactg  40080
aaataaccgc gtgattattt tttggtataa ttctacacgg catggtttct gtgactatga  40140
attcaacccc cgttacatta gtgaaatctt taacaaacag caagggttcg tcaaagacat  40200
```

```
aaaactcatt gtttacaatc gaaatagacc ccctatcaca cttaaaataa aaaatatcct  40260
tatcctttac caccaaataa aattctgatt ggtcaatgtg aatgtattca cttaacagtt  40320
ccacaaattt atttattaac tccgaggcac atacatcgtc ggtatttttt atggcaaact  40380
ttactcttcc agcatccgtt tctaaaaaaa tattaacgag ttccatttat atcatccaat  40440
attattgaaa tgacgttgat ggacagatga tacaaataag aaggtacggt acctttgtcc  40500
accatctcct ccaattcatg ctctattttg tcattaactt taatgtatga aaacagtacg  40560
ccacatgctt ccatgacagt gtgtaacact ttggatacaa aatgtttgac attagtataa  40620
ttgttcaaga ctgtcaatct ataatagata gtagctataa tatattctat gatggtattg  40680
aagaagatga caaccttggc atattgatca tttaacacag acatggtatc aacagatagc  40740
ttgaatgaaa gagaatcagt aattggaata agcgtcttct cgatagagtg tccgtatacc  40800
aacatgtctg atattttgat gtattccatt aaattattta gttttttctt tttattctcg  40860
ttaaacagca tttctgtcaa cggaccccaa catcgttgac cgattaagtt ttgattgatt  40920
tttccgtgta atgcgtatct agtcagatcg tatagcctat ccaataatcc atcgtctgtg  40980
tgtagatcac atcgtacact ttttaattct ctatagaaga gcgacagaca tctggagcaa  41040
ttacagacag caatttcttt attctctaca gatgtaagat acttgaagac attcctatga  41100
tgatgcagaa ttttggataa cacggtattg atggtatctg ttaccataat tcctttgatg  41160
gctgatagtg tcagagcaca agatttccaa tctttgacaa tttttagcac cattatcttt  41220
gttttgatat ctatatcaga cagcatggtg cgtctgacaa cacagggatt aagacggaaa  41280
gatgaaatga ttctctcaac atcttcaatg gataccttgc tatttttttct ggcattatct  41340
atatgtgcga gaatatcctc tagagaatca gtatcctttt tgatgatagt ggatctcaat  41400
gacatgggac gtctaaacct tcttattcta tcaccagatt gcatggtgat ttgtcttctt  41460
tcttttatca taatgtaatc tctaaattca tcggcaaatt gtctatatct aaaatcataa  41520
tatgagatgt ttacctctac aaatatctgt tcgtccaatg ttagagtatt tacatcagtt  41580
ttgtattcca aattaaacat ggcaacggat ttaattttat attcctctat taagtcctcg  41640
tcgataataa cagaatgtag ataatcattt aatccatcgt acatggttgg aagatgcttg  41700
ttgacaaaat ctttaattgt cttgatgaag gtgggactat atctaacatc ttgattaata  41760
aaatttataa cattgtccat aggatacttt gtaactagtt ttatacacat ctcttcatcg  41820
gtaagtttag acagaatatc gtgaacaggt ggtatattat attcatcaga tatacgaaga  41880
acaatgtcca aatctatatt gtttaatata ttatatagat gtagcgtagc tcctacagga  41940
atatctttaa ctaagtcaat gatttcatca accgttagat ctattttaaa gttaatcata  42000
taggcattga tttttaaaag gtatgtagcc ttgactacat tctcattaat taaccattcc  42060
aagtcactgt gtgtaagaag attatattct atcataagct tgactacatt tggtcccgat  42120
accattaaag aattcttatg atataaggaa acagatttta ggtactcatc tactctacaa  42180
gaattttgga gagccttaac gatatcagtg acgtttatta tttcaggagg aaaaaaccta  42240
acattgagaa tgtcggagtt aatagcttcc agatacagtg attttggcaa tagtccgtgt  42300
aatccataat ccagtaacac gagctggtgc ttgctagaca ccttttcaat gtttaatttt  42360
tttgaaataa gctttgataa agccttcctc gcaaattccg gatacatgaa catgtcggcg  42420
acatgattaa gtattgtttt ttcattattt tctcaacaag ttctcaatac cccaatagat  42480
gatagaatat cacccaatgc gtccatgttg tctatttcca acaggtcgct atatccacca  42540
atagaagttt ttccaaaaaa gattctagga acagttctac caccagtaat ttgttcaaaa  42600
```

```
taatcccgca attcattttc gggtttaaat tctttaatat cgacaatttc atacgctcct  42660
cttttgaaac taaacttatt tagaatatcc agtgcatttc tacaaaaagg acatgtaaac  42720
ttgacaaaaa ttgtcacttt gttattggcc aacctttgtt gtacaaattc ctcggccatt  42780
ttaatattta agtgatataa aactatctcg acttatttaa ctctttagtc gagatatatg  42840
gacgcagata gctatatgat agccaactac agaaggcaaa cgctataaaa aacataatta  42900
cgacgagcat atttataaat atttttattc agcattactt gatatagtaa tattaggcac  42960
agtcaaacat tcaaccactc tcgatacatt aactctctca ttttctttaa caaattctgc  43020
aatatcttcg taaaaagatt cttgaaactt tttagaatat ctatcgactc tagatgaaat  43080
agcgttcgtc aacatactat gttttgtata cataaaggcg cctattttaa cagtttctag  43140
tgacaaaatg ctagcgatcc taggatcctt tagaatcaca tagattgacg attcgtctct  43200
cttagtaact ctagtaaaat aatcatacaa tctagtacgc gaaataatat tatccttgac  43260
ttgaggagat ctaaacaatc tagttttgag aacatcgata agttcatcgg gaatgacata  43320
catactatct ttaatagaac tcttttcatc cagttgaatg gattcgtcct taaccaactg  43380
attaatgaga tcttctattt tatcattttc cagatgatat gtatgtccat taaagttaaa  43440
ttgtgtagcg cttcttttta gtctagcagc caatacttta acatcactaa tatcgatata  43500
caaaggagat gatttatcta tggtattaag aattcgtttt tcgacatctg tcaaaaccaa  43560
ttccttttg cctgtatcat ccagttttcc atcctttgta aagaaattat tttctactag  43620
actattaata agactgataa ggattcctcc ataattgcac aatccaaact ttttcacaaa  43680
actagacttt acgagatcta caggaatgcg tacttcaggt tttttagctt gtgatttttt  43740
cttttgcgga cattttctag taaccaactc atctaccatt tcattgattt tagcagtgaa  43800
ataagctttc aatgcacggg cactgatact attgaaaacg agttgatctt caaattccgc  43860
catttaagtt caccaaacaa cttttaaata caaatatatc aatagtagta gaataagaac  43920
tataaaaaaa ataataatta accaatacca accccaacaa ccggtattat tagttgatgt  43980
gactgttttc tcatcactta gaacagattt aacaatttct ataaagtctg tcaaatcatc  44040
ttccggagac cccataaata caccaaatat agcggcgtac aacttatcca tttatacatt  44100
aaatattggc ttttctttat cgctatcttc atcatattca tcatcaatat caacaagtcc  44160
cagattacga gccagatttt cttctacatt ttcagtcatt gatacacgtt cactatctcc  44220
agagagtccg ataacgttag ccaccacttc tctatcaatg attagtttct tgagcgcgaa  44280
tgtaattttt gtttccgttc cggatctata gaagacgata ggtgtgataa ttgccttggc  44340
caattgtctt tctcttttac tgagtgattc tagttcacct tctatagatc tgagaatgga  44400
tgattctcca gtcgaaacat attctaccat ggatccgttt aatttgttga tgaagatgga  44460
ttcatcctta aatgttttct ctgtaatagt ttccaccgaa agactatgca aagaatttgg  44520
aatgcgttcc ttgtgcttaa tgtttccata gacggcttct agaagttgat acaacatagg  44580
actagccgcg gtaactttta tttttagaaa gtatccatcg cttctatctt gtttagattt  44640
atttttataa agtttagtct ctccttccaa cataataaaa gtggaagtca tttgactaga  44700
taaactatca gtaagtttta tagagataga cgaacaatta gcgtattgag aagcatttag  44760
tgtaacgtat tcgatacatt ttgcattaga tttactaatc gattttgcat actctataac  44820
acccgcacaa gtctgtagag aatcgctaga tgcagtaggt cttggtgaag tttcaactct  44880
cttcttgatt accttactca tgattaaacc taaataattg tactttgtaa tataatgata  44940
```

```
tatattttca ctttatctca tttgagaata aaaatgtttt tgtttaacca ctgcatgatg  45000
tacagatttc ggaatcgcaa accaccagtg gttttatttt atccttgtcc aatgtgaatt  45060
gaatgggagc ggatgcgggt ttcgtacgta gatagtacat tcccgttttt aaaccgagac  45120
tccatccgta aaaatgcata ctcgttagtt tggaataact cggatctgct atatggatat  45180
tcatagattg actttgatcg atgaaggctc ccctgtctgc agccattttt atgatcgtct  45240
tttgtggaat ttcccaaata gttttataaa ctcgcttaat atcttctgga aggtttgtat  45300
tctgaatgga tccaccatct gccataatcc tattcttgat ctcatcattc cataattttc  45360
tctcggttaa aactctaagg agatgcggat taactacttg aaattctcca gacaatactc  45420
tccgagtgta aatattactg gtatacggtt ccaccgactc attatttccc aaaatttgag  45480
cagttgatgc agtcggcata ggtgccacca ataaactatt tctaagaccg tatgttctga  45540
ttttatcttt tagaggttcc caattccaaa gatccgacgg tacaacattc caaagatcat  45600
attgtagaat accgttactg gcgtacgatc ctacatatgt atcgtatggt ccttccttct  45660
cagctagttc acaactcgcc tctaatgcac cgtaataaat ggtttcgaag atcttcttat  45720
ttagatcttg tgcttccagg ctatcaaatg gataatttaa gagaataaac gcgtccgcta  45780
atccttgaac accaataccg ataggtctat gtctcttatt agagatttca gcttctggaa  45840
taggataata attaatatct ataattttat tgagatttct gacaattact ttgaccacat  45900
ccttcagttt gagaaaatca aatcgcccat ctattacaaa catgttcaag gcaacagatg  45960
ccagattaca aacggctacc tcattagcat ccgcatattg tattatctca gtgcaaagat  46020
tactacactt gatagttcct aaattttgtt gattactctt tttgttacac gcatccttat  46080
aaagaatgaa tggagtacca gtttcaatct gagattctat aatcgctttc cagacgactc  46140
gagcctttat tatagatttg tatctccttt ctctttcgta tagtgtatac aatcgttcga  46200
actcgtctcc ccaaacattg tccaatccag gacattcatc cggacacatc aacgaccact  46260
ctccgtcatc cttcactcgt ttcataaaga gatcaggaat ccaaagagct ataaatagat  46320
ctctggttct atgttcctcg tttcctgtat tctttttaag atcgaggaac gccataatat  46380
cagaatgcca cggttccaag tatatggcca taactccagg ccgtttgttt cctccctgat  46440
ctatgtatct agcggtgtta ttataaactc tcaacattgg aataataccg tttgatatac  46500
cattggtacc ggagatatag cttccactgg cacgaatatt actaattgat agacctattc  46560
cccctgccat tttagagatt aatgcgcatc gttttaacgt gtcatagata ccctctatgc  46620
tatcatcgat catgttaagt agaaaacagc tagacatttg gtgacgacta gttcccgcat  46680
taaataaggt aggagaagcg tgcgtaaacc atttttcaga aagtagattg tacgtctcaa  46740
tagctgagtc tatatcccat tgatgaattc ctactgcgac acgcattaac atgtgctgag  46800
gtctttcaac gatcttgttg tttattttca acaagtagga tttttccaaa gttttaaaac  46860
caaaatagtt gtatgaaaag tctcgttcgt aaataataac cgagttgagt ttatccttat  46920
atttgttaac tatatccatg gtgatacttg aaataatcgg agaatgtttc ccatttttag  46980
gattaacata gttgaataaa tcctccatca cttcactaaa tagttttttt gtttccttgt  47040
gtagatttga tacggctatt ctggcggcta gaatggcata atccggatgt tgtgtagtac  47100
aagtggctgc tatttcggct gccagagtgt ccaattctac cgttgttact ccattatata  47160
ttccttgaat aaccttcata gctattttaa taggatctat atgatccgtg tttaagccat  47220
aacataattt tctaatacga gacgtgattt tatcaaacat gacattttcc ttgtatccat  47280
ttcgtttaat gacaaacatt tttgttggtg taataaaaaa attatttaac ttttcattaa  47340
```

```
tagggatttg acgtacgtag cgtacaaaat gattgttcct ggtatataga taaagagtcc  47400
tatatatttg aaaatcgtta cggctcgatt aaactttaat gattgcatag tgaatatatc  47460
attaggattt aactccttga ctatcatggc ggcgccagaa attaccatca aaagcattaa  47520
tacagttatg ccgatcgcag ttagaacggt tatagcatcc accatttata tctaaaaatt  47580
agatcaaaga atatgtgaca aagtcctagt tgtatactga gaattgacga aacaatgttt  47640
cttacatatt tttttcttat tagtaactga cttaatagta ggaactggaa aactagactt  47700
gattattcta taagtataga tacccttcca aataatattc tctttgataa aagttccaga  47760
aaatgtagaa ttttttaaaa agttatcttt tgctattacc aagattgtgt ttagacgctt  47820
attattaata tgagtgatga aatccacacc gcctctagat atcgccttta tttccacatt  47880
agatggtaaa tccaatagtg aaactatctt tttaggaatg tatggactcg cgtttagagg  47940
agtgaacgtc ttaggcgtcg gaaaggatga ttcgtcaaac gaataaacaa tttcacaaat  48000
ggatgttaat gtattagtag gaaatttttt gacgctagtg gaattgaaga ttctaatgga  48060
tgatgttcta cctatttcat ccgataacat gttaatttcc gacaccaacg gttttaatat  48120
ttcgatgata tacggtagtc tctctttcgg acttatatag cttattccac aatacgagtc  48180
attatatact ccaaaaaaca aaataactag tataaaatct gtatcgaatg ggaaaaacga  48240
aattatcgac ataggtatag aatccggaac attgaacgta ttaatactta attctttttc  48300
tgtggtaagt accgataggt tattgacatt gtatggtttt aaatattcta taacttgaga  48360
cttgatagat attagtgatg aattgaaaat tatttttatc accacgtgtg tttcaggatc  48420
atcgtcgacg cccgtcaacc aaccgaatgg agtaaaataa atatcattaa tatatgctct  48480
agatattagt atttttatca atcctttgat tatcatcttc tcgtaggcga atgattccat  48540
gatcaagagt gatttaagaa catcctccgg agtattaatg ggcttagtaa acagtccatc  48600
gttgcaataa taaaagttat ccaagttaaa ggatattatg cattcgttta aagatatcac  48660
ctcatctgac ggagacaatt ttttggtagg ttttagagac tttgaagcta cttgtttaac  48720
aaagttattc atcgtcgttt actattctat ttaattttgt agttaattta tcacatatca  48780
cattaattga ctttttggtc catttttcca tacgtttata ttcttttaat cctgcgttat  48840
ccgtttccgt tatatccagg gatagatctt gcaagttaaa tagaatgctc ttaaataatg  48900
tcattttctt atccgctaaa aatttaaaga atgtataaac ttttttcaaa gatttgaaac  48960
tcttaggtgg tgtcctagta cacaatatca taaacaaact aataaacatt ccacattcag  49020
attccaacag ctgattaact tccacattaa tacagcctat tttcgctcca aatgtacatt  49080
cgaaaaatct gaataaaaca tcaatgtcgc aatttgtatt atccaataca gaatgtttgt  49140
gattcgtgtt aaaaccatcg gagaaggaat agaaataaaa attattatag tggtggaatt  49200
cagttggaat attgcctccg gagtcataaa aggatactaa acattgtttt ttatcataaa  49260
ttacacattt ccaatgagac aaataacaaa atccaaacat tacaaatcta gaggtagaac  49320
ttttaatttt gtctttaagt atatacgata agatatgttt attcataaac gcgtcaaatt  49380
tttcatgaat cgctaaggag tttaagaatc tcatgtcaaa ttgtcctata taatccactt  49440
cggatccata agcaaactga gagactaagt tcttaatact tcgattgctc atccaggctc  49500
ctctctcagg ctctattttc atcttgacga cctttggatt ttcaccagta tgtattcctt  49560
tacgtgataa atcatcgatt ttcaaatcca tttgtgagaa gtctatcgcc ttagatactt  49620
tttcccgtag tcgaggttta aaaaaatacg ctaacggtat actagtaggt aactcaaaga  49680
```

-continued

```
catcatatat agaatggtaa cgcgtcttta actcgtcggt taactctttc ttttgatcga  49740
gttcgtcgct actattgggt ctgctcaggt gccccgactc tactagttcc aacatcatac  49800
cgataggaat acaagacact ttgccggcgg ttgtagattt atcatatttt tccactacat  49860
atccgttaca atttgttaaa aatttagata catctatatt gctacataat ccagctagtg  49920
aatatatatg acataataaa ttggtaaatc ctagttctgg tattttacta attactaaat  49980
ctgtatatct ttccatttat catggaaaag aatttaccag atatcttctt ttttccaaac  50040
tgcgttaatg tattctctta caaatattca caagatgaat tcagtaatat gagtaaaacg  50100
gaacgtgata gtttctcatt ggccgtgttt ccagttataa aacatagatg gcataacgca  50160
cacgttgtaa aacataaagg aatatacaaa gttagtacag aagcacgtgg aaaaaaagta  50220
tctcctccat cactaggaaa acccgcacac ataaacctaa ccgcgaagca atatatatac  50280
agtgaacaca caataagctt tgaatgttat agttttctaa aatgtataac aaatacagaa  50340
atcaattcgt tcgatgagta tatattaaga ggactattag aagctggtaa tagtttacag  50400
atattttcca attccgtagg taaacgaaca gatactatag gtgtactagg gaataagtat  50460
ccatttagca aaattccatt ggcctcatta actcctaaag cacaacgaga gatattttca  50520
gcgtggattt ctcatagacc tgtagtttta actggaggaa ccggagtggg taagacgtca  50580
caggtaccca agttattgct ttggtttaat tatttatttg gtggattctc tactctagat  50640
aaaatcactg actttcacga aagaccagtc attctatctc ttcctaggat agctttagtt  50700
agattgcata gcaataccat tttaaaatca ttgggattta aggtactaga tggatctcct  50760
atttctttac ggtacggatc tataccggaa gaattaataa acaaacaacc aaaaaaatat  50820
ggaattgtat tttctaccca taagttatct ctaacaaaac tatttagtta tggcactctt  50880
attatagacg aagttcatga gcatgatcaa ataggagata ttattatagc agtagcgaga  50940
aagcatcata cgaaaataga ttctatgttt ttaatgactg ccacgttaga ggatgacagg  51000
gaacggctaa aagtattttt acctaatccc gcatttatac atattcctgg agatacactg  51060
tttaaaatta gcgaggtatt tattcataat aagataaatc catcttccag aatggcatac  51120
atagaagaag aaaagagaaa tttagttact gctatacaga tgtatactcc tcctgatgga  51180
tcatccggta tagtctttgt ggcatccgtt gcacagtgtc acgaatataa atcatattta  51240
gaaaaaagat taccgtatga tatgtatatt attcatggta aggtcttaga tatagacgaa  51300
atattagaaa aagtgtattc atcacctaat gtatcgataa ttatttctac tccttatttg  51360
gaatccagcg ttactatacg caatgttaca cacatttatg atatgggtag agtttttgtc  51420
cccgctcctt ttggaggatc gcaacaattt atttctaaat ctatgagaga tcaacgaaaa  51480
ggaagagtag gaagagttaa tcctggtaca tacgtctatt tctatgatct gtcttatatg  51540
aagtctatac agcgaataga ttcagaattt ctacataatt atatattgta cgctaataag  51600
tttaatctaa cactccccga agatttgttt ataatcccta caaatttgga tattctatgg  51660
cgtacaaagg aatatataga ctcgttcgat attagtacag aaacatggaa taaattatta  51720
tccaattatt atatgaagat gatagagtat gctaaacttt atgtactaag tcctattctc  51780
gctgaggagt tggataactt tgagaggacg ggagaattaa ctagtattgt acgagaagcc  51840
attttatctc taaatttaca aattaagatt ttaaatttta aacataaaga tgatgatacg  51900
tatatacact tttgtaaaat attattcggt gtctataacg gaacaaacgc tactatatat  51960
tatcatagac ctctaacggg atatatgaat atgatttcag atactatatt tgttcctgta  52020
gataataact aaaaatcaaa ctctaatgac cacatctttt tttagagatg aaaaattttc  52080
```

```
cacatctcct tttgtagaca cgactaaaca ttttgcagaa aaaagtttat tagtgtttag  52140
ataatcgtat acttcatcag tgtagatagt aaatgtgaac agataaaagg tattcttgct  52200
caatagattg gtaaattcca tagaatatat taatcctttc ttcttgagat cccacatcat  52260
ttcaaccaga gacgttttat ccaatgattt acctcgtact ataccacata caaaactaga  52320
ttttgcagtg acgtcgtacc tggtattctt accaaacaaa attttacttt tagttctttt  52380
agaaaattct aaggtagaat ctctatttgc caatatgtca tctatggaat taccactagc  52440
aaaaaatgat agaaatatat attgatacat cgcagctggt tttgatctac tatactttaa  52500
aaacgaatca gattccataa ttgcctgtat atcatcagct gaaaaactat gttttacacg  52560
tattccttcg gcatttcttt ttaatgatat atcttgttta gacaatgata aagttatcat  52620
gtccatgaga gacgcgtctc cgtatcgtat aaatatttca ttagatgtta gacgcttcat  52680
taggggtata cttctataag gtttcttaat cagtccatca ttggttgcgt caagaactac  52740
tatcggatgt tgttgggtat ctctagtgtt acacatggcc ttactaaagt ttgggtaaat  52800
aactatgata tctctattaa ttatagatgc atatatttca ttcgtcaagg atattagtat  52860
cgacttgcta tcgtcattaa tacgtgtaat gtaatcatat aaatcatgcg atagccaagg  52920
aaaattcaaa tagatgttca tcatataatc gtcgctataa ttcatattaa tacgttgaca  52980
ttgactaatt tgtaatatag cctcgccacg aagaaagctc tcgtattcag tttcatcgat  53040
aaaggatacc gttaaatata actggttgcc gatagtctca tagtctatta agtggtaagt  53100
ttcgtacaaa tacagaatcc ctaaaatatt atctaatgtt ggattaatct ttaccataac  53160
tgtataaaat ggagacggag tcataactat tttaccgttt gtacttactg gaatagatga  53220
aggaataatc tccggacatg ctggtaaaga cccaaatgtc tgtttgaaga aatccaatgt  53280
tccaggtcct aatctcttaa caaaaattac gatattcgat cccgatatcc tttgcattct  53340
atttaccagc atatcacgaa ctatattaag attatctatc atgtctattc tcccaccgtt  53400
atataaatcg cctccgctaa gaaacgttag tatatccata caatggaata cttcatttct  53460
aaaatagtat tcgttttcta attctttaat gtgaaatcgt atactagaaa gggaaaaatt  53520
atctttgagt tttccgttag aaaagaacca cgaaactaat gttctgattg cgtccgattc  53580
cgttgctgaa ttaatggatt tacaccaaaa actcatataa cttctagatg tagaagcatt  53640
cgctaaaaaa ttagtagaat caaaggatat aagtagatgt tccaacaagt gagcaattcc  53700
caagatttca tctatatcat tctcgaatcc gaaattagaa attcccaagt agatatcctt  53760
tttcatccga tcgttgatga aaatacgaac tttattcggt aagacaatca tttactaagg  53820
agtaaaatag gaagtaatgt tcgtatgtcg ttatcatcgt ataaattaaa ggtgtgtttt  53880
ttaccattaa gtgacattat aattttacca atattggaat tataatatag gtgtatttgc  53940
gcactcgcga cggttgatgc atcggtaaat atagctgtat ctaatgttct agtcggtatt  54000
tcatcatttc gctgtctaat aatagcgttt tctctatctg tttccattac agctgcctga  54060
agtttattgg tcggataata tgtaaaataa taagaaatac atacgaataa caaaaataaa  54120
ataagatata ataaagatgc catttagaga tctaattttg ttcaacttgt ccaaattcct  54180
acttacagaa gatgaggaat cgttggagat agtgtcttcc ttatgtagag gatttgaaat  54240
atcttataat gacttgataa cttactttcc agataggaaa taccataaat atatttataa  54300
agtatttgaa catgtagatt tatcggagga attaagtatg gaattccatg atacaactct  54360
gagagattta gtctatctta gattgtacaa gtattccaag tgtatacggc cgtgttataa  54420
```

```
attaggagat aatctaaaag gcatagttgt tataaaggac aggaatattt atattaggga  54480
agcaaatgat gacttgatag aatatctcct caaggaatac actcctcaga tttatacata  54540
ttctaatgag cgcgtcccca taactggttc aaaattaatt ctttgtggat tttctcaagt  54600
tacatttatg gcgtatacaa cgtcgcatat aacaacaaat aaaaaggtag atgttctcgt  54660
ttccaaaaaa tgtatagatg aactagtcga tccaataaat tatcaaatac ttcaaaattt  54720
atttgataaa ggaagcggaa caataaacaa aatactcagg aagatatttt attcggtaac  54780
aggtggccaa actccatagg tagctttttc tatttcggat tttagaattt ccaaattcac  54840
cagcgattta tcggttttgg tgaaatccaa ggatttatta atgtccacaa atgccatttg  54900
ttttgtctgt ggattgtatt tgaaaatgga aacgatgtag ttagatagat gcgctgcaaa  54960
gtttcctatt agggttccgc gcttcacgtc acccagcata cttgaatcac catcctttaa  55020
aaaaaatgat aagatatcaa catggagtat atcatactcg gattttaatt cttctactgc  55080
atcactgaca ttttcacaaa tactacaata cggtttaccg aaaataatca gtacgttctt  55140
catttatggg tatcaaaaac ttaaaatcgt tactgctgga aaataaatca ctgacgatat  55200
tagatgataa tttatacaaa gtatacaatg gaatatttgt ggatacaatg agtatttata  55260
tagccgtcgc caattgtgtc agaaacttag aagagttaac tacggtattc ataaaatacg  55320
taaacggatg ggtaaaaaag ggagggcatg taaccctttt tatcgataga ggaagtataa  55380
aaattaaaca agacgttaga gacaagagac gtaaatattc taaattaacc aaggacagaa  55440
aaatgctaga attagaaaag tgtacatccg aaatacaaaa tgttaccgga tttatggaag  55500
aagaaataaa ggcagaaatg caattaaaaa tcgataaact cacatttcaa atatatttat  55560
ctgattctga taacataaaa atatcattga atgagatact aacacatttc aacaataatg  55620
agaatgttac attattttat tgtgatgaac gagacgcaga attcgttatg tgtctcgagg  55680
ctaaaacaca tttctctacc acaggagaat ggccgttgat aataagtacc gatcaggata  55740
ctatgctatt tgcatctgct gataatcatc ctaagatgat aaaaaactta actcaactgt  55800
ttaaatatgt tccatctgca gaggataact atttagcaaa attaacggcg ttagtgaatg  55860
gatgtgattt ctttcctgga ctctatgggg catctataac acccaccaac ttaaacaaaa  55920
tacaattgtt tagtgatttt acaatcgata atatagtcac tagtttggca attaaaaatt  55980
attatagaaa gactaactct accgtagacg tgcgtaatat tgttacgttt ataaacgatt  56040
acgctaattt agacgatgtc tactcgtata ttcctccttg tcaatgcact gttcaagaat  56100
ttatattttc cgcattagat gaaaaatgga atgaatttaa atcatcttat ttagagaccg  56160
ttccgttacc ctgccaatta atgtacgcgt tagaaccacg taaggagatt gatgtttcag  56220
aagttaaaac tttatcatct tatatagatt tcgaaaatac taaatcagat atcgatgtta  56280
taaaatctat atcctcgatc ttcggatatt ctaacgaaaa ctgtaacacg atagtattcg  56340
gcatctataa ggataattta ctactgagta taaatagttc attttacttt aacgatagtc  56400
tgttaataac caatactaaa agtgataata taataaatat aggttactag attaaaaatg  56460
gtgttccaac tcgtgtgctc tacgtgcggc aaagatattt ctcacgaacg atataaattg  56520
attatacgaa aaaaatcatt aaaggatgta ctcgtcagtg taaagaacga atgttgtagg  56580
ttaaaattat ctacacaaat agaacctcaa cgtaacttaa cagtgcaacc tctattggat  56640
ataaactaat atggatccgg ttaattttat caagacatat gcgcctagag gttctattat  56700
ttttattaat tataccatgt cattaacaag tcatttgaat ccatcgatag aaaaacatgt  56760
gggtatttat tatggtacgt tattatcgga acacttggta gttgaatcaa catatagaaa  56820
```

```
aggagttcga atagtcccat tggatagttt ttttgaagga tatcttagtg caaaagtata  56880
catgttagag aatattcaag ttatgaaaat agcagctgat acgtcattaa ctttattggg  56940
tattccgtat ggatttggtc atgatagaat gtattgtttt aaattggtag ctgactgtta  57000
taaaaatgcc ggtgttgaaa catcgtctaa acgaatatta ggtaaagata tttttctgag  57060
ccaaaacttc acagacgata atagatggat aaagatatat gattctaata atttaacatt  57120
ttggcaaatt gattacctta aagggtgagt taatatgcat aactactcct ccgttgtttt  57180
ttccctcgtt ctttttctta acgttgtttg ccatcactct cataatgtaa agatattcta  57240
aaatggtaaa cttttgcata tcggacgcag aaattggtat aaatgttgta attgtattat  57300
ttcccgtcaa tggactagtc acagctccat cagttttata tcctttagag tatttctcac  57360
tcgtgtctag cattctagag cattccatga tctgtttatc gttgatattg gccggaaaga  57420
tagatttttt atttttattt atattactat tggcaattgt agatataact tctggtaaat  57480
atttttctac cttttcaatc tcttctattt tcaagccggc tatatattct gctatattgt  57540
tgctagtatc aataccttttt ctggctaaga agtcatatgt ggtattcact atatcagttt  57600
taactggtag ttccattagc ctttccactt ctgcagaata atcagaaatt ggttctttac  57660
cagaaaatcc agctactata ataggctcac cgatgatcat tggcaaaatc ctatattgta  57720
ccagattaat gagagcatat ttcatttcca ataattctgc tagttcttga gacattgatt  57780
tatttgatga atctagttgg ttctctagat actctaccat ttctgccgca tacaataact  57840
tgttagataa aatcagggtt atcaaagtgt ttagcgtggc tagaatagtg ggcttgcatg  57900
tattaaagaa tgcggtagta tgagtaaacc gttttaacga attatatagt ctccagaaat  57960
ctgtggcgtt acatacatga gccgaatgac atcgaagatt gtccaatatt tttaatagct  58020
gctctttgtc cattatttct atatttgact cgcaacaatt gtagatacca ttaatcaccg  58080
attccttttt cgatgctgga caatagcaca attgtttagc tttggactct atgtattcag  58140
aattaataga tatatctctt aatacagatt gcactataca ttttgaaact atgtcaaaaa  58200
ttgtagaacg acgctgttct gcagccattt aactttaaat aatttacaaa aatttaaaat  58260
gagcatccgt ataaaaatcg ataaactgcg ccaaattgtg gcatattttt cagagttcag  58320
tgaagaagta tctataaatg tagactcgac ggatgagtta atgtatattt ttgccgcctt  58380
gggcggatct gtaaacattt gggcaattat acctctaagt gcatcagtgt tttaccgagg  58440
agccgaaaac attgtgttta atcttccggt gtccaaggta aaatcgtgtt tgtgtagttt  58500
tcacaatgat gccatcatag atatagaacc tgatctggaa aataatctag taaaactttc  58560
tagttatcat gtagtaagtg tcgattgtaa caaggaactg atgcctatta ggacagatac  58620
tactatttgt ctaagtatag atcaaaagaa atcttacgtg tttaattttc acaagtatga  58680
agaaaaatgt tgtggtagaa ccgtcattca tctagaatgg ttgttgggct ttatcaagtg  58740
tattagtcag catcagcatt tggctattat gtttaaagat gacaatatta ttatgaagac  58800
tcctggtaat actgatgcat tttccaggga atattctatg actgaatgtt ctcaagaact  58860
acaaaagttt tctttcaaaa tagctatctc gtctctcaac aaactacgag gattcaaaaa  58920
gagagtcaat gtttttgaaa ctagaatcgt aatggataat gacgataaca ttttaggaat  58980
gttgttttcg gatagagttc aatcctttaa gatcaacatc tttatggcgt ttttagatta  59040
atactttcaa tgagataaat atgggtagcg gagtaagtgt tgagctccct aaacgggatc  59100
cgcctccggg agtacccact gatgagatgt tattaaacgt ggataaaatg catgacgtga  59160
```

-continued

```
tagctcccgc taagctttta gaatatgtgc atataggacc actagcaaaa gataaagagg  59220
ataaagtaaa gaaaagatat ccagagttta gattagtcaa cacaggaccc ggtggtcttt  59280
cagcattgtt aagacaatcg tataatggaa ccgcacccaa ttgctgtcgc acttttaatc  59340
gtactcatta ttggaagaag gatggaaaga tatcagataa gtatgaagag ggtgcagtat  59400
tagaatcgtg ttggccagac gttcacgaca ctggaaaatg cgatgttgat ttattcgact  59460
ggtgtcaggg ggatacgttc gatagaaaca tatgccatca gtggatcggt tcagccttta  59520
ataggagtaa tagaactgta gagggtcaac aatcgttaat aaatctgtat aataagatgc  59580
aaacattatg tagtaaagat gctagtgtac caatatgcga atcatttttg cattatttac  59640
gcgcacacaa tacagaagat agcaaagaga tgatcgatta tattctaaga caacagtctg  59700
cggactttaa acagaaatat atgagatgta gttatcccac tagagataag ttagaagagt  59760
cattaaaata tgcggaacct cgagaatgtt gggatccaga gtgttcgaat gccaatgtta  59820
atttcttact aacacgtaat tataataatt taggactttg caatattgta cgatgtaata  59880
ctagcgtgaa caacttacag atggataaaa cttcctcatt aagattgtca tgtggattaa  59940
gcaatagtga tagattttct actgttcccg tcaatagagc aaaagtagtt caacataata  60000
ttaaacactc gttcgaccta aaattgcatt tgatcagttt attatctctc ttggtaatat  60060
ggatactaat tgtagctatt taaatgggtg ccgcggcaag catacagacg acggtgaata  60120
cactcagcga acgtatctcg tctaaattag aacaagaagc gaacgctagt gctcaaacaa  60180
aatgtgatat agaaatcgga aatttttata tccgacaaaa ccatggatgt aacctcactg  60240
ttaaaaatat gtgctctgcg gacgcggatg ctcagttgga tgctgtgtta tcagccgcta  60300
cagaaacata tagtggatta acaccggaac aaaaagcata cgtgccagct atgtttactg  60360
ctgcgttaaa cattcagacg agtgtaaaca ctgttgttag agattttgaa aattatgtga  60420
aacagacttg taattctagc gcggtcgtcg ataacaaatt aaagatacaa aacgtaatca  60480
tagatgaatg ttacggagcc ccaggatctc caacaaattt ggaatttatt aatacaggat  60540
ctagcaaagg aaattgtgcc attaaagcgt tgatgcaatt gacgactaag gccactactc  60600
aaatagcacc tagacaagtt gctggtacag gagttcagtt ttatatgatt gttatcggtg  60660
ttataatatt ggcagcgttg tttatgtact atgccaagcg tatgctgttc acatccacca  60720
atgataaaat caaacttatt ttagccaata aggaaaacgt ccattggact acttacatgg  60780
acacattctt tagaacttct ccgatggtta ttgctaccac ggatatgcaa aactgaaaat  60840
atattgataa tattttaata gattaacatg gaagttatcg ctgatcgtct agacgatata  60900
gtgaaacaaa atatagcgga tgaaaaattt gtagattttg ttatacacgg tctagagcat  60960
caatgtcctg ctatacttcg accattaatt aggttgttta ttgatatact attatttgtt  61020
atagtaattt atatttttac ggtacgtcta gtaagtagaa attatcaaat gttgttggcg  61080
ttggtggcgc tagtcatcac attaactatt ttttattact ttatactata atagtactag  61140
actgacttct aacaaacatc tcacctgcca taaataaatg cttgatatta aagtcttcta  61200
tttctaacac tattccatct gtggaaaata atactctgac attatcgcta attgacacat  61260
cggtgagtga tatgcctata aagtaataat cttctttggg cacatatacc agtgtaccag  61320
gttctaacaa cctatttact ggtgctcctg tagcatactt tttctttacc ttgagaatat  61380
ccatcgtttg cttggtcaat agcgatatgt gatttttat caaccactcg aaaaagtaat  61440
tggagtgttc atatcctcta cgggctattg tctcatggcc gtgtatgaaa tttaagtaac  61500
acgactgtgg tagatttgtt ctatagagcc ggttgccgca aatagataga actaccaata  61560
```

```
tgtctgtaca aatgttaaac attaattgat taacagaaaa aacaatgttt gttctgggaa  61620
tagaaaccag atcaaaacaa aattcgttag aatatatgcc acgtttatac atggaatata  61680
aaataactac agtttgaaaa ataacagtat catttaaaca tttaacttgc ggggttaatt  61740
tcacaacttt actgtttttg aactgttcaa aatatagcat agatccgtga gaaatacgtt  61800
tagccgcctt taatagagga aatcccaccg cctttctgga tctcaccaac gacgatagtt  61860
ctgaccagca actcatttct tcatcatcca cctgttttaa catataatag gcaggagata  61920
gatatccgtc attgcaatat tccttctcgt aggcacacaa tctaatattg ataaaatctc  61980
cattctcttc tctgcattta ttatcttgtt tcggtggctg attaggctgt agtcttggtt  62040
taggctttgg tatatcgttg ttgaatctat tttggtcatt aaatctttca tttcttcctg  62100
gtatattttt atcacctcgt ttggttggat ttttgtctat attatcgttt gtaacatcgg  62160
tacgggtatt catttatcac aaaaaaaact tctctaaatg agtctactgc tagaaaacct  62220
catcgaagaa gataccatat tttttgcagg aagtatatct gagtatgatg atttacaaat  62280
ggttattgcc ggcgcaaaat ccaaatttcc aagatctatg ctttctattt ttaatatagt  62340
acctagaacg atgtcaaaat atgagttgga gttgattcat aacgaaaata tcacaggagc  62400
aatgtttacc acaatgtata atataagaaa caatttgggt ctaggagatg ataaactaac  62460
tattgaagcc attgaaaact atttcttgga tcctaacaat gaagttatgc ctcttattat  62520
taataatacg gatatgactg ccgtcattcc taaaaaaagt ggtaggagaa agaataagaa  62580
catggttatc ttccgtcaag gatcatcacc tatcttgtgc attttcgaaa ctcgtaaaaa  62640
gattaatatt tataaagaaa atatggaatc cgcgtcgact gagtatacac ctatcggaga  62700
caacaaggct ttgatatcta aatatgcggg aattaatgtc ctgaatgtgt attctccttc  62760
cacatccata agattgaatg ccatttacgg attcaccaat aaaaataaac tagagaaact  62820
tagtactaat aaggaactag aatcgtatag ttctagccct cttcaagaac ccattaggtt  62880
aaatgatttt ctgggactat tggaatgtgt taaaaagaat attcctctaa cagatattcc  62940
gacaaaggat tgattactat aaatggagaa tgttcctaat gtatacttta atcctgtgtt  63000
tatagagccc acgtttaaac attctttatt aagtgtttat aaacacagat taatagtttt  63060
atttgaagta ttcgttgtat tcattctaat atatgtattt tttagatctg aattaaatat  63120
gttcttcatg cctaaacgaa aaatacccga tcctattgat agattacgac gtgctaatct  63180
agcgtgtgaa gacgataaat taatgatcta tggattacca tggatgacaa ctcaaacatc  63240
tgcgttatca ataaatagta aaccgatgtg tataaagatt gtgcaaagct tttgcgatca  63300
ataaatggat cacaaccagt atctcttaac gatgttcttc gcagatgatg attcattttt  63360
taagtatttg gctagtcaag atgatgaatc ttcattatct gatatattgc aaatcactca  63420
atatctagac tttctgttat tattattgat ccaatcaaaa aataaattag aagccgtggg  63480
tcattgttat gaatctcttt cagaggaata cagacaattg acaaaattca cagactctca  63540
agattttaaa aaactgttta acaaggtccc tattgttaca gatggaaggg tcaaacttaa  63600
taaaggatat ttgttcgact ttgtgattag tttgatgcga ttcaaaaaag aatcctctct  63660
agctaccacc gcaatagatc ctattagata catagatcct cgtcgtgata tcgcattttc  63720
taacgtgatg gatatattaa agtcgaataa agtgaacaat aattaattct ttattgtcat  63780
catgaacggc ggacatattc agttgataat cggccccatg ttttcaggta aaagtacaga  63840
attaattaga cgagttagac gttatcaaat agctcaatat aaatgcgtga ctataaaata  63900
```

```
ttctaacgat aatagatacg gaacgggact atggacgcat gataagaata attttgaagc  63960
attggaagca actaaactat gcgatgtctt ggaatcaatt acagatttct ccgtgatagg  64020
tatcgatgaa ggacagttct ttccagacat tgttgaattc tgtgagcgta tggcaaacga  64080
aggaaaaata gttatagtag ccgcactcga tgggacattt caacgtaaac cgtttaataa  64140
tattttgaat cttattccat tatctgaaat ggtggtaaaa ctaactgctg tgtgtatgaa  64200
atgctttaag gaggcttcct tttctaaacg attgggtgag gaaaccgaga tagaaataat  64260
aggaggtaat gatatgtatc aatcggtgtg tagaaagtgt tacatcgact cataatatta  64320
tatttttat ctaaaaaact aaaaataaac attgattaaa ttttaatata atacttaaaa  64380
atggatgttg tgtcgttaga taaaccgttt atgtattttg aggaaattga taatgagtta  64440
gattacgaac cagaaagtgc aaatgaggtc gcaaaaaaac taccgtatca aggacagtta  64500
aaactattac taggagaatt attttttctt agtaagttac agcgacacgg tatattagat  64560
ggtgccaccg tagtgtatat aggatcggct cctggtacac atatacgtta tttgagagat  64620
catttctata atttaggagt gatcatcaaa tggatgctaa ttgacggccg ccatcatgat  64680
cctattctaa atggattgcg tgatgtgact ctagtgactc ggttcgttga tgaggaatat  64740
ctacgatcca tcaaaaaaca actgcatcct tctaagatta ttttaatttc tgatgtgaga  64800
tccaaacgag gaggaaatga acctagtacg gcggatttac taagtaatta cgctctacaa  64860
aatgtcatga ttagtatttt aaaccccgtg gcgtctagtc ttaaatggag atgcccgttt  64920
ccagatcaat ggatcaagga cttttatatc ccacacggta ataaaatgtt acaacctttt  64980
gctccttcat attcagctga aatgagatta ttaagtattt ataccggtga gaacatgaga  65040
ctgactcgag ttaccaaatt agacgctgta aattatgaaa aaaagatgta ctaccttaat  65100
aagatcgtcc gtaacaaagt agttgttaac tttgattatc ctaatcagga atatgactat  65160
tttcacatgt actttatgct gaggaccgtg tactgcaata aaacatttcc tactactaaa  65220
gcaaaggtac tatttctaca acaatctata tttcgtttct taaatattcc aacaacatca  65280
actgaaaaag ttagtcatga accaatacaa cgtaaaatat ctagcaaaaa ttctatgtct  65340
aaaaacagaa atagcaagag atccgtacgc ggtaataaat agaaacgtac tactgagata  65400
tactaccgat atagagtata atgatttagt tactttaata accgttagac ataaaattga  65460
ttctatgaaa actgtgtttc aggtatttaa cgaatcatcc ataaattata ctccggttga  65520
tgatgattat ggagaaccaa tcattataac atcgtatctt caaaaaggtc ataacaagtt  65580
tcctgtaaat tttctataca tagatgtggt aatatctgac ttatttccta gctttgttag  65640
actagatact acagaaacta atatagttaa tagtgtacta caaacaggtg atggtaaaaa  65700
gactcttcgt cttcccaaaa tgttagagac ggaaatagtt gtcaagattc tctatcgccc  65760
taatatacca ttaaaaattg ttagattttt ccgcaataac atggtaactg gagtagagat  65820
agccgataga tctgttattt cagtcgctga ttaatcaatt agtagagatg agataagaac  65880
attataataa tcaataatat atcttatatc ttatatcttg tttagaaaaa tgctaatatt  65940
aaaatagcta acgctagtaa tccaatcgga agccatttga tatctataat agggtatcta  66000
atttcctgat ttaaatagcg gacagctata ttctcggtag ctactcgttt ggaatcacaa  66060
acattattta catctaattt actatctgta atggaaacgt ttcccaatga aatggtacaa  66120
tccgatacat tgcattttgt tatatttttt tttaaagagg ctggtaacaa cgcatcgctt  66180
cgtttacatg gctcgtacca acaataatag ggtaatcttg tatctattcc tatccgtact  66240
atgcttttat caggataaat acatttacat cgtatatcgt ctttgttagc atcacagaat  66300
```

```
gcataaattt gttcgtccgt catgataaaa atttaaagtg taaatataac tattattttt  66360
atagttgtaa taaaaaggga aatttgattg tatactttcg gttctttaaa agaaactgac  66420
ttgataaaaa tggctgtaat ctctaaggtt acgtatagtc tatatgatca aaaagagatt  66480
aatgctacag atattatcat tagtcatgtt aaaaatgacg acgatatcgg taccgttaaa  66540
gatggtagac taggtgctat ggatggggca ttatgtaaga cttgtgggaa aacggaattg  66600
gaatgtttcg gtcactgggg taaagtaagt atttataaaa ctcatatagt taagcctgaa  66660
tttatttcag aaattattcg tttactgaat catatatgta ttcactgcgg attattgcgt  66720
tcacgagaac cgtattccga cgatattaac ctaaaagagt tatcgggaca cgctcttagg  66780
agattaaagg ataaaatatt atccaagaaa aagtcatgtt ggaacagcga atgtatgcaa  66840
ccgtatcaaa aaattacttt ttcaaagaaa aaggtttgtt tcgtcaacaa gttggatgat  66900
attaacgttc ctaattctct catctatcaa aagttaattt ctattcatga aaagttttgg  66960
ccattattag aaattcatca atatccagct aacttatttt atacagacta ctttcccatc  67020
cctccgctga ttattagacc ggctattagt ttttggatag atagtatacc caaagagacc  67080
aatgaattaa cttacttatt aggtatgatc gttaagaatt gtaacttgaa tgctgatgaa  67140
caggttatcc agaaggcggt aatagaatac gatgatatta aaattatttc taataacact  67200
accagtatca atttatcata tattacatcc ggcaaaaata atatgattag aagttatatc  67260
gtcgcccggc gaaaagatca gaccgctaga tctgtaattg gtcccagtac atctatcacc  67320
gttaatgagg taggaatgcc cgcatatatt agaaatacac ttacagaaaa gatatttgtt  67380
aatgccttta cagtggataa agttaaacaa ctattagcgt caaaccaagt taaattttac  67440
tttaataaac gattaaacca attaacaaga atacgccaag gaaagtttat taaaaataaa  67500
atacatttat tgcctggtga ttgggtagaa gtagctgttc aagaatatac aagtattatt  67560
tttggaagac agccgtctct acatagatac aacgtcatcg cttcatctat cagagctacc  67620
gaaggagata ctatcaaaat atctcccgga attgctaact ctcaaaatgc tgatttcgac  67680
ggggatgagg aatggatgat attagaacaa aatcctaaag ctgtaattga acaaagtatt  67740
cttatgtatc cgacgacgtt actcaaacac gatattcatg gagcccctgt ttatggatct  67800
attcaagatg aaatcgtagc agcgtattca ttgtttagga tacaagatct ttgtttagat  67860
gaagtattga acatcttggg gaaatatgga agagagttcg atcctaaagg taaatgtaaa  67920
ttcagcggta aagatatcta tacttacttg ataggtgaaa agattaatta tccgggtctc  67980
ttaaaggatg gtgaaattat tgcaaacgac gtagatagta attttgttgt ggctatgagg  68040
catctgtcat tggctggact cttatccgat cataagtcga acgtggaagg tatcaacttt  68100
attatcaagt catcttatgt ttttaagaga tatctatcta tttacggttt tggggtgaca  68160
ttcaaagatc tgagaccaaa ttcgacgttc actaataaat tggaggccat caacgtagaa  68220
aaaatagaac ttatcaaaga agcatacgcc aaatatctca acgatgtaag agacgggaaa  68280
atagttccat tatctaaagc tttagaggcg gactatgtgg aatccatgtt atccaacttg  68340
acaaatctta atatccgaga gatagaagaa catatgagac aaacgctgat agatgatcca  68400
gataataacc tcctgaaaat ggccaaagcg ggttataaag taaatcccac agaactaatg  68460
tatattctag gtacttatgg acaacagagg attgatggtg aaccagcaga gactcgagta  68520
ttgggtagag ttttacctta ctatcttcca gactctaagg atccagaagg aagaggttac  68580
attcttaatt ctttaacaaa aggattaacg ggttctcaat attacttttc gatgctggtt  68640
```

```
gccagatctc aatctactga tatcgtctgt gaaacatcac gtaccggaac actggctaga  68700
aaaatcatta aaaagatgga ggatatggtg gtcgacggat acggacaagt agttataggt  68760
aatacgctca tcaagtacgc cgccaattat accaaaattc taggctcagt atgtaaacct  68820
gtagatctta tctatccaga tgagtccatg acttggtatt tggaaattag tgctctgtgg  68880
aataaaataa aacagggatt cgtttactct cagaaacaga aacttgcaaa gaagacattg  68940
gcgccgttta atttcctagt attcgtcaaa cccaccactg aggataatgc tattaaggtt  69000
aaggatctgt acgatatgat tcataacgtc attgatgatg tgagagagaa atacttcttt  69060
acggtatcta atatagattt tatggagtat atattcttga cgcatcttaa tccttctaga  69120
attagaatta caaaagaaac ggctatcact atctttgaaa agttctatga aaaactcaat  69180
tatactctag gtggtggaac tcctattgga attatttctg cacaggtatt gtctgagaag  69240
tttacacaac aagccctgtc cagttttcac actactgaaa aaagtggtgc cgtcaaacaa  69300
aaacttggtt tcaacgagtt taataacttg actaatttga gtaagaataa gaccgaaatt  69360
atcactctgg tatccgatga tatctctaaa cttcaatctg ttaagattaa tttcgaattt  69420
gtatgtttgg gagaattaaa tccaaacatc actcttcgaa aagaaacaga taggtatgta  69480
gtagatataa tagtcaatag attatacatc aagagagcag aaataaccga attagtcgtc  69540
gaatatatga ttgaacgatt catctccttt agcgtcattg taaaggaatg ggtatggaa   69600
acattcattg aggatgagga taatattaga tttactgtct acctaaattt cgttgaaccg  69660
gaagaattga atcttagtaa gtttatgatg gttcttccgg gtgccgccaa caagggcaag  69720
attagtaaat tcaagattcc tatctttgac tatacgggat atgacgactt caatcaaaca  69780
aaaaagctca ataagatgac tgtagaactc atgaatctaa aagaattggg ttctttcgat  69840
ttggaaaacg tcaacgtgta tcctggagta tggaatacat acgatatctt cggtatcgag  69900
gccgctcgtg aatacttgtg cgaagccatg ttaaacacct atggagaagg gttcgattat  69960
ctgtatcagc cttgtgatct tctcgctagt ttactatgtg ctagttacga accagaatca  70020
gtgaataaat tcaagttcgg cgcagctagt actcttaaga gagctacgtt cggagacaat  70080
aaagcattgt taaacgcggc tcttcataaa aagtcagaac ctattaacga taatagtagc  70140
tgccactttt ttagcaaggt ccctaatata ggaactggat attacaaata ctttatcgac  70200
ttgggtcttc tcatgagaat ggaaaggaaa ctatctgata agatatcttc tcaaaagatc  70260
aaggaaatgg aagaaacaga agacttttaa ttcttatcaa taacatattt ttctatgatc  70320
tgtcttttaa acgatggatt ttccacaaat gcgcctctca agtccctcat agaatgatac  70380
acgtataaaa aatatagcat aggcaatgac tccttatttt tagacattag atatgccaaa  70440
atcatagccc cgcttctatt tactcccgca gcacaatgaa ccaacacggg ctcgtttcgt  70500
tgatcacatt tagataaaaa ggcggttacg tcgtcaaaat atttactaat atcggtagtt  70560
gtatcatcta ccaacggtat atgaataata ttaatattag agttaggtaa tgtatattta  70620
tccatcgtca aatttaaaac atatttgaac ttaacttcag atgatggtgc atccatagca  70680
tttttataat ttcccaaata cacattattg gttactcttg tcattatagt gggagatttg  70740
gctttgtgca tatctccagt tgaacgtagt agtaagtatt tatacaaact tttcttatcc  70800
atttataacg tacaaatgga taaaactact ttatcggtaa acgcgtgtaa tttagaatac  70860
gttagagaaa aggctatagt aggcgtacaa gcagccaaaa catcaacact tatattcttt  70920
gttattatat tggcaattag tgcgctatta ctctggtttc agacgtctga taatccagtc  70980
tttaatgaat taacgagata tatgcgaatt aaaaatacgg ttaacgattg gaaatcatta  71040
```

```
acggatagca aaacaaaatt agaaagtgat agaggtaaac ttctagccgc tggtaaggat  71100
gatatattcg acttcaaatg tgtggatttc ggcgcctatt ttatagctat gcgattggat  71160
aagaaaacat atctgccgca agctattagg cgaggtactg gagacgcgtg gatggttaaa  71220
aaggcggcaa aggtcgatcc atctgctcaa caattttgtc agtatttgat aaaacacaag  71280
tctaataatg ttattacttg tggtaatgag atgttaaatg aattaggtta tagcggttat  71340
tttatgtcac cgcattggtg ttccgatttt agtaatatgg aatagtgtta gataaatgcg  71400
gtaacgaatg ttcctgtaag gaaccataac agcttagatt taacgttaaa gatgagcata  71460
aacataataa acaaaattac aatcaaacct ataacattaa tatcaaacaa tccaaaaaat  71520
gaaatcagtg gagtagtaaa cgcgtacata actcctggat aacgtttagc agctgccgtt  71580
cctattctag accaaaaatt cggtttcatg ttttcgaaac ggtattctgc aacaagtcga  71640
ggatcgtgtt ctacatattt ggcggcgtta tccagtatct gcctattgat cttcatttcg  71700
ttttcgattc tggctatttc aaaataaaat cccgatgata gacctccaga ctttataatt  71760
tcatctacga tgttcagcgc cgtagtaact ctaataatat aggctgataa gctaacatca  71820
taccctcctg tatatgtgaa tatggcatga tttttgtcca ttacaagctc ggttttaact  71880
ttattgcctg taataatttc tctcatctgt aggatatcta tttttttgtc atgcattgcc  71940
ttcaagacgg gacgaagaaa cgtaatatcc tcaataacgt tatcgttttc tacaataact  72000
acatattcta ccttttttatt ttctaactca gtaaaaaaat tagaatccca tagggctaaa  72060
tgtctagcga tatttctttt cgtttcctct gtacacatag tgttacaaaa ccctgaaaag  72120
aagtgagtat acttgtcatc atttctaatg tttcctccag tccactgtat aaacgcataa  72180
tccttgtaat gatctggatc atccttgact accacaacat ttcttttttc tggcataact  72240
tcgttgtcct ttacatcatc gaacttctga tcattaatat gctcatgaac attaggaaat  72300
gtttctgatg gaggtctatc aataactggc acaacaataa caggagtttt caccgccgcc  72360
atttagttat tgaaattaat catatacaac tctttaatac gagttatatt ttcgtctatc  72420
cattgtttca catttacata tttcgacaaa aagatataaa atgcgtattc caatgcttct  72480
ctgtttaatg aattactaaa atatacaaac acgtcactgt ctggcaataa atgatatctt  72540
agaatattgt aacaatttat tttgtattgc acatgttcgt gatctatgag ttcttcttcg  72600
aatggcatag gatctccgaa tctgaaaacg tataaatagg agttagaata ataatatttg  72660
agagtattgg taatatataa actctttagc ggtataatta gttttttttct ctcaatttct  72720
atttttagat gtgatggaaa aatgactaat tttgtagcat tagtatcatg aactctaatc  72780
aaaatcttaa tatcttcgtc acacgttagc tctttgaagt ttttaagaga tgcatcagtt  72840
ggttctacag atggagtagg tgcaacaatt ttttgttcta cacatgtatg tactggagcc  72900
attgttttaa ctataatggt gcttgtatcg aaaaacttta atgcagatag cggaagctct  72960
tcgccgcgac tttctacgtc gtaattgggt tctaacgccg atctctgaat ggatactagt  73020
tttctaagtt ctaatgtgat tctctgaaaa tgtaaatcca attcctccgg cattatagat  73080
gtgtatacat cggtaaataa aactatagta tccaacgatc ccttctcgca aattctagtc  73140
ttaaccaaaa aatcgtatat aaccacggag atggcgtatt taagagtgga ttcttctacc  73200
gttttgttct tggatgtcat ataggaaact ataaagtccg cactactgtt aagaatgatt  73260
actaacgcaa ctatatagtt caaattaagc attttggaaa cataaaataa ctctgtagac  73320
gatacttgac tttcgaataa gtttgcagac aaacgaagaa agaacagacc tctcttaatt  73380
```

```
tcagaagaaa actttttttc gtattcctga cgtctagagt ttatatcaat aagaaagtta  73440
agaattagtc ggttaatgtt gtatttcatt acccaagttt gagatttcat aatattatca  73500
aaagacatga taatattaaa gataaagcgc tgactatgaa cgaaatagct atatggttcg  73560
ctcaagaata tagtcttgtt aaacgtggaa acgataactg tatttttaat cacgtcagcg  73620
gcatctaaat taaatatagg tatatttatt ccacacactc tacaatatgc cacaccatct  73680
tcataataaa taaattcgtt agcaaaatta ttaattttag tgaaatagtt agcgtcaact  73740
ttcatagctt ccttcaatct aatttgatgc tcacacggtg cgaattccac tctaacatcc  73800
cttttccatg cctcaggttc atcgatctct ataatatcta gtttttgcg tttcacaaac  73860
acaggctcgt ctctcgcgat gagatctgta tagtaactat gtaaatgata actagataga  73920
aagatgtagc tatatagatg acgatccttt aagagaggta taataacttt accccaatca  73980
gatagactgt tgttatggtc ttcggaaaaa gaatttttat aaatttttcc agtattttcc  74040
aaatatacgt acttaacatc taaaaaatcc ttaatgataa taggaatgga taatccgtct  74100
attttataaa gaaatacata tcgcacatta tacttttttt tggaaatggg aataccgatg  74160
tgtctacata aatatgcaaa gtctaaatat tttttagaga atcttagttg gtccaaattc  74220
ttttccaagt acggtaatag atttttcata ttgaacggta tcttcttaat ctctggttct  74280
agttccgcat taaatgatga aactaagtca ctatttttat aactaacgat tacatcacct  74340
ctaacatcat catttaccag aatactgatc ttcttttgtc gtaaatacat gtctaatgtg  74400
ttaaaaaaaa gatcatacaa gttatacgtc atttcatctg tggtattctt gtcattgaag  74460
gataaactcg tactaatctc ttctttaaca gcctgttcaa atttatatcc tatatacgaa  74520
aaaatagcaa ccagtgtttg atcatccgcg tcaatattct gttctatcgt agtgtataac  74580
aatcgtatat cttcttctgt gatagtcgat acgttataaa ggttgataac gaaaatattt  74640
ttatttcgtg aaataaagtc atcgtaggat tttggactta tattcgcgtc tagtagatat  74700
gcttttattt ttggaatgat ctcaattaga atagtctctt tagagtccat ttaaagttac  74760
aaacaactag gaaattggtt tatgatgtat aatttttta gtttttatag attctttatt  74820
ctatacttaa aaaatgaaaa taaatacaaa ggttcttgag ggttgtgtta aattgaaagc  74880
gagaaataat cataaattat ttcattatcg cgatatccgt taagtttgta tcgtaatggc  74940
gtggtcaatt acaaataaag cggatactag tagcttcaca aagatggctg aaatcagagc  75000
tcatctaaaa aatagcgctg aaaataaaga taaaaacgag gatattttcc cggaagatgt  75060
aataattcca tctactaagc ccaaaaccaa acgagccact actcctcgta aaccagcggc  75120
tactaaaaga tcaaccaaaa aggaggaagt ggaagaagaa gtagttatag aggaatatca  75180
tcaaacaact gaaaaaaatt ctccatctcc tggagtcagc gacattgtag aaagcgtggc  75240
tgctgtagag ctcgatgata gcgacgggga tgatgaacct atggtacaag ttgaagctgg  75300
taaagtaaat catagtgcta gaagcgatct ctctgaccta aaggtggcta ccgacaatat  75360
cgttaaagat cttaagaaaa ttattactag aatctctgca gtatcgacgg ttctagagga  75420
tgttcaagca gctggtatct ctagacaatt tacttctatg actaaagcta ttacaacact  75480
atctgatcta gtcaccgagg gaaaatctaa agttgttcgt aaaaaagtta aaacttgtaa  75540
gaagtaaatg cgtgcacttt tttataaaga tggtaaactc tttaccgata ataatttttt  75600
aaatcctgta tcagacgata atccagcgta tgaggttttg caacatgtta aaattcctac  75660
tcatttaaca gatgtagtag tatatgaaca aacgtgggag gaggcgttaa ctagattaat  75720
ttttgtggga agcgattcaa aaggacgtag acaatacttt tacggaaaaa tgcatgtaca  75780
```

```
gaatcgcaac gctaaaagag atcgtatttt tgttagagta tataacgtta tgaaacgaat  75840
taattgtttt ataaacaaaa atataaagaa atcgtccaca gattccaatt atcagttggc  75900
ggtttttatg ttaatggaaa ctatgttttt tattagattt ggtaaaatga aatatcttaa  75960
ggagaatgaa acagtagggt tattaacact aaaaaataaa cacatagaaa taagtcccga  76020
tgaaatagtt atcaagtttg taggaaagga caaagtttca catgaatttg ttgttcataa  76080
gtctaataga ctatataaac cgctattgaa actgacggat gattctagtc ccgaagaatt  76140
tctgttcaac aaactaagtg aacgaaaggt atacgaatgt atcaaacagt ttggtattag  76200
aatcaaggat ctccgaacgt atggagtcaa ttatacgttt ttatataatt tttggacaaa  76260
tgtaaagtcc atatctcctc ttccgtcacc aaaaaagtta atagcgttaa ctatcaaaca  76320
aactgctgaa gtggtaggtc atactccatc aatttcaaaa agagcttata tggcaacgac  76380
tattttagaa atggtaaagg ataaaaattt tttagatgta gtatctaaaa ctacgttcga  76440
tgaattccta tctatagtcg tagatcacgt taaatcatct acggatggat gatatagatc  76500
tttacacaaa taattacaag accgataaat ggaaatggat aagcgtatga aatctctcgc  76560
aatgacagct ttcttcggag agctaaacac attagatatt atggcattga taatgtctat  76620
atttaaacgc catccaaaca ataccatttt ttcagtggat aaggatggtc agtttatgat  76680
tgatttcgaa tacgataatt ataaggcttc tcaatatttg gatctgaccc tcactccgat  76740
atttggagat gaatgcaaga ctcacgcatc gagtatagcc gaacaattgg cgtgtgtgga  76800
tattattaaa gaggatatta gcgaatatat caaaactact ccccgtctta aacgatttat  76860
aaaaaaatac cgcaatagat cagatactcg catcagtcga gatacagaaa agcttaaaat  76920
agctctagct aaaggcatag attacgaata tataaaagac gcttgttaat aagtaaatga  76980
aaaaaaacta gtcgtttata ataaaacacg atatggatgc caacgtagta tcatcttcta  77040
ctattgcgac gtatatagac gctttagcga agaatgcttc agaattagaa cagaggtcta  77100
ccgcatacga aataaataat gaattggaac tagtatttat taagccgcca ttgattactt  77160
tgacaaatgt agtgaatatc tctacgattc aggaatcgtt tattcgattt accgttacta  77220
ataaggaagg tgttaaaatt agaactaaga ttccattatc taaggtacat ggtctagatg  77280
taaaaaatgt acagttagta gatgctatag ataacatagt ttgggaaaag aaatcattag  77340
tgacggaaaa tcgtcttcac aaagaatgct tgttgagact atcgacagag gaacgtcata  77400
tatttttgga ttacaagaaa tatggatcct ctatccgact agaattagtc aatcttattc  77460
aagcaaaaac aaaaaacttt acgatagact ttaagctaaa atattttcta ggatccggtg  77520
cccagtctaa aagttcttta ttacacgcta ttaatcatcc aaagtcaagg cctaatacat  77580
ctctggaaat agaattcaca cctagagaca atgaaacagt tccatatgat gaactaataa  77640
aggaattgac gactctatca cgtcatatat ttatggcttc tccagagaat gtaattcttt  77700
ctccgcctat taacgcgcct ataaaaacct ttatgttgcc taaacaagat atagtaggtt  77760
tggatctgga aaatctatat gccgtaacta agactgacgg cattcctata actatcagag  77820
ttacatcaaa cgggttgtat tgttatttta cacatcttgg ttatattatt agatatcctg  77880
ttaagagaat aatagattcc gaagtagtag tctttggtga ggcagttaag gataagaact  77940
ggaccgtata tctcattaag ctaatagagc ctgtgaatgc aatcaatgat agactagaag  78000
aaagtaagta tgttgaatct aaactagtgg atatttgtga tcggatagta ttcaagtcaa  78060
agaaatacga aggtccgttt actacaacta gtgaagtcgt cgatatgtta tctacatatt  78120
```

```
taccaaagca accagaaggt gttattctgt tctattcaaa gggacctaaa tctaacattg  78180
attttaaaat taaaaaggaa aatactatag accaaactgc aaatgtagta tttaggtaca  78240
tgtccagtga accaattatc tttggagaat cgtctatctt tgtagagtat aagaaattta  78300
gcaacgataa aggctttcct aaagaatatg gttctggtaa gattgtgtta tataacggcg  78360
ttaattatct aaataatatc tattgtttgg aatatattaa tacacataat gaagtgggta  78420
ttaagtccgt ggttgtacct attaagttta tagcagaatt cttagttaat ggagaaatac  78480
ttaaacctag aattgataaa accatgaaat atattaactc agaagattat tatggaaatc  78540
aacataatat catagtcgaa catttaagag atcaaagcat caaaatagga gatatcttta  78600
acgaggataa actatcggat gtgggacatc aatacgccaa taatgataaa tttagattaa  78660
atccagaagt tagttatttt acgaataaac gaactagagg accgttggga attttatcaa  78720
actacgtcaa gactcttctt atttctatgt attgttccaa aacattttta gacgattcca  78780
acaaacgaaa ggtattggcg attgattttg gaaacggtgc tgacctggaa aaatactttt  78840
atggagagat tgcgttattg gtagcgacgg atccggatgc tgatgctata gctagaggaa  78900
atgaaagata caacaaatta aactctggaa ttaaaaccaa gtactacaaa tttgactaca  78960
ttcaggaaac tattcgatcc gatacatttg tctctagtgt cagagaagta ttttattttg  79020
gaaagtttaa tatcatcgac tggcagtttg ctatccatta ttcttttcat ccgagacatt  79080
atgctaccgt catgaataac ttatccgaac taactgcttc tggaggcaag gtattaatca  79140
ctaccatgga cggagacaaa ttatcaaaat taacagataa aaagactttt ataattcata  79200
agaatttacc tagtagcgaa aactatatgt ctgtagaaaa aatagctgat gatagaatag  79260
tggtatataa tccatcaaca atgtctactc caatgactga atacattatc aaaaagaacg  79320
atatagtcag agtgtttaac gaatacggat ttgttcttgt agataacgtt gatttcgcta  79380
caattataga acgaagtaaa aagtttatta atggcgcatc tacaatggaa gatagaccgt  79440
ctacaaaaaa ctttttcgaa ctaaatagag gagccattaa atgtgaaggt ttagatgtcg  79500
aagacttact tagttactat gttgtttatg tcttttctaa gcggtaaata ataatatggt  79560
atgggttctg atatccccgt tctaaatgca ttaaataatt ccaatagagc gatttttgtt  79620
cctataggac cttccaactg tggatactct gtattgttaa tagatatatt aatacttttg  79680
tcgggtaaca gaggttctac gtcttctaaa aataaaagtt ttataacatc tggcctgttc  79740
ataaataaaa acttggcgat tctatatata ctcttattat caaatctagc cattgtctta  79800
tagatgtgag ctactgtagg tgtaccattt gattttcttt ctaatactat atatttctct  79860
cgaagaagtt cttgcacatc atctgggaat aaaatactac tgttgagtaa atcagttatt  79920
tttttatat cgatattgat ggacattttt atagttaagg ataataagta tcccaaagtc  79980
gataacgacg ataacgaagt atttatactt ttaggaaatc acaatgactt tatcagatta  80040
aaattaacaa aattaaagga gcatgtattt ttttctgaat atattgtgac tccagataca  80100
tatggatctt tatgcgtcga attaaatggg tctagttttc agcacggcgg tagatatata  80160
gaggtggagg aatttataga tgctggaaga caagttagat ggtgttctac atccaatcat  80220
atatctaaag atatacccga agatatgcac actgataaat ttgtcattta tgatatatac  80280
acttttgacg ctttcaagaa taaacgattg gtatttgtac aggtacctcc gtcgttagga  80340
gatgatagtc atttgactaa tccgttattg tctccgtatt atcgtaattc agtagccaga  80400
caaatggtca ataatatgat ttttaatcaa gattcatttt taaaatattt attagaacat  80460
ctgattagaa gccactatag agtttctaaa catataacaa tagttagata caaggatacc  80520
```

gaagaattaa atctaacgag aatatgttat aatagagata agtttaaggc gtttgtattc 80580
gcttggttta acggcgtttc ggaaaatgaa aaggtactag atacgtataa aaaggtatct 80640
aatttgatat aatgaattca gtgactgtat cacacgcgcc atatactatt acttatcacg 80700
atgattggga accagtaatg agtcaattgg tagagtttta taacgaagta gccagttggc 80760
tgctacgaga cgagacgtcg cctattcctg ataagttctt tatacagttg aaacaaccgc 80820
ttagaaataa acgagtatgt gtgtgcggta tagatccgta tccgaaagat ggaactggtg 80880
taccgttcga atcaccaaat tttacaaaaa aatcaattaa ggagatagct tcatctatat 80940
ctagattaac cggagtaatt gattataaag gttataacct taatataata gacggggtta 81000
taccctggaa ttattactta agttgtaaat taggagaaac aaaaagtcac gcgatttact 81060
gggataagat ttccaagtta ctgctgcagc atataactaa acacgttagt gttctttatt 81120
gtttgggtaa aacagatttc tcgaatatac gggccaagtt agaatccccg gtaactacca 81180
tagtcggata tcatccagcg gctagagacc gccaattcga gaaagataga tcatttgaaa 81240
ttatcaacgt tttactggaa ttagacaaca aggcacctat aaattgggct caagggttta 81300
tttattaatg ctttagtgaa attttaactt gtgttctaaa tggatgcggc tattagaggt 81360
aatgatgtta tctttgttct taagactata ggtgtcccgt cagcgtgcag acaaaatgaa 81420
gatccaagat ttgtagaagc atttaaatgc gacgagttag aaagatatat tgagaataat 81480
ccagaatgta cactattcga aagtcttagg gatgaggaag catactctat agtcagaatt 81540
ttcatggatg tagatttaga cgcgtgtcta gacgaaatag attatttaac ggccattcaa 81600
gattttatta tcgaggtgtc aaactgtgta gctagattcg cgtttacaga atgcggcgcc 81660
attcatgaaa atgtaataaa atccatgaga tctaattttt cattgactaa gtctacaaat 81720
agagataaaa caagttttca tattatcttt ttagatacgt ataccactat ggatacattg 81780
atagctatga aacgaacact attagaatta agtagatcat ctgaaaatcc actaaccaga 81840
tcgatagaca ctgccgtata taggagaaaa acaactcttc gggttgtagg tactaggaaa 81900
aatccaaatt gcgacactat tcatgtaatg caaccaccgc atgataatat agaagattac 81960
ctattcactt acgtggatat gaacaacaat agttattact tttctctaca acaacgattg 82020
gaggatttag ttcctgataa gttatgggaa ccagggttta tttcattcga agacgctata 82080
aaaagagttt caaaaatatt cattaattct ataataaact ttaatgatct cgatgaaaat 82140
aattttacaa cggtaccact ggtcatagat tacgtaacac cttgtgcatt atgtaaaaaa 82200
cgatcgcata aacatccgca tcaactatcg ttggaaaatg gtgctattag aatttacaaa 82260
actggtaatc cacatagttg taaagttaaa attgttccgt tggatggtaa taaactgttt 82320
aatattgcac aaagaatttt agacactaac tctgttttat taaccgaacg aggagaccat 82380
atagtttgga ttaataattc atggaaattt aacagcgaag aacccttgat aacaaaacta 82440
attttgtcaa taagacatca actacctaag gaatattcaa gcgaattact ctgtccaaga 82500
aaacgaaaga ctgtagaagc taacatacga gacatgttag tagattcagt agagaccgat 82560
acctatccgg ataaacttcc gtttaaaaat ggtgtattgg acctggtaga cggaatgttt 82620
tactctggag atgatgctaa aaaatatacg tgtactgtat caaccggatt taaatttgac 82680
gatacaaagt tcgtcgaaga cagtccagaa atggaagagt taatgaatat cattaacgat 82740
atccaaccat taacggatga aaataagaaa aatagagagc tatatgaaaa aacattatct 82800
agttgtttat gtggtgctac caaaggatgt ttaacattct tttttggaga aactgcaact 82860

```
ggaaagtcga caaccaaacg tttgttaaag tctgctatcg gtgacctgtt tgttgagacg  82920
ggtcaaacaa ttttaacaga tgtattggat aaaggaccta atccatttat cgctaacatg  82980
catttgaaaa gatctgtatt ctgtagcgaa ctacctgatt ttgcctgtag tggatcaaag  83040
aaaattagat ctgacaatat taaaaagttg acagaacctt gtgtcattgg aagaccgtgt  83100
ttctccaata aaattaataa tagaaaccat gcgacaatca ttatcgatac taattacaaa  83160
cctgtttttg ataggataga taacgcatta atgagaagaa ttgccgtcgt gcgattcaga  83220
acacactttt ctcaaccttc tggtagagag gctgctgaaa ataatgacgc gtacgataaa  83280
gtcaaactat tagacgaggg gttagatggt aaaatacaaa ataatagata tagatttgca  83340
tttctatact tgttggtgaa atggtacaga aaatatcatg ttcctattat gaaactatat  83400
cctacacccg aagagattcc tgactttgca ttctatctca aaataggtac tctgttagta  83460
tctagctctg taaagcatat tccattaatg acggacctct ccaaaaaggg atatatattg  83520
tacgataatg tggttactct tccgttgact actttccaac agaaaatatc caagtatttt  83580
aattctagac tatttggaca cgatatagag agcttcatca atagacataa gaaatttgcc  83640
aatgttagtg atgaatatct gcaatatata ttcatagagg atatttcatc tccgtaaata  83700
tatgctcata tatttataga agatatcaca tatctaaatg aataccggaa ttatagattt  83760
atttgataat catgttgata gtataccaac tatattacct catcagttag ctactctaga  83820
ttatctagtt agaactatca tagatgagaa cagaagcgtg ttattgttcc atattatggg  83880
atcaggtaaa acaataatcg ctttgttgtt cgccttggta gcttccagat ttaaaaaggt  83940
ttacattcta gtgccgaaca tcaacatctt aaaaattttc aattataata tgggtgtagc  84000
tatgaacttg tttaatgacg aattcatagc tgagaatatc tttattcatt ccacaacaag  84060
tttttattct cttaattata acgataacgt cattaattat aacggattat ctcgctacaa  84120
taactctatt tttatcgttg atgaggcaca taatatcttt gggaataata ctggagaact  84180
tatgaccgtg ataaaaaata aaaacaagat tccttttcta ctattgtctg gatctcccat  84240
tactaacaca cctaatactc tgggtcatat tatagattta atgtccgaag agacgataga  84300
ttttggtgaa attattagtc gtggtaagaa agtaattcag acacttctta acgaacgcgg  84360
tgtgaatgta cttaaggatt tgcttaaagg aagaatatca tattacgaaa tgcctgataa  84420
agatctacca acgataagat atcacggacg taagtttcta gatactagag tagtatattg  84480
tcacatgtct aaacttcaag agagagatta tatgattact agacgacagc tatgttatca  84540
tgaaatgttt gataaaaata tgtataacgt gtcaatggca gtattgggac aacttaatct  84600
gatgaataat ttagatactt tatttcagga acaggataag gaattgtacc caaatctgaa  84660
aataaataat ggcgtgttat acggagaaga attggtaacg ttaaacatta gttccaaatt  84720
taaatacttt attaatcgga tacagacact caacggaaaa cattttatat acttttctaa  84780
ttctacatat ggcggattgg taattaaata tatcatgctc agtaatggat attctgaata  84840
taatggttct cagggaacta atccacatat aataaacggc aaaccaaaaa catttgctat  84900
cgttactagt aaaatgaaat cgtctttaga ggatctatta gatgtgtata attctcctga  84960
aaacgatgat ggtagtcaat tgatgttttt gttttcatca aacattatgt ccgaatccta  85020
tactctaaaa gaggtaaggc atatttggtt tatgactatc ccagatactt tttctcaata  85080
caaccaaatt cttggacgat ctattagaaa attctcttac gccgatattt ctgaaccagt  85140
taatgtatat cttttagccg ccgtatattc cgatttcaat gacgaagtga cgtcattaaa  85200
cgattacaca caggatgaat taattaatgt tttaccattt gacatcaaaa agctgttata  85260
```

```
tctaaaattt aagacgaaag aaacgaatag aatatactct attcttcaag agatgtctga  85320
aacgtattct cttccaccac atccatcaat tgtaaaagtt ttattgggag aattggtcag  85380
acaatttttt tataataatt ctcgtattaa gtataacgat accaagttac ttaaaatggt  85440
tacatcagtt ataaaaaata aagaagacgc taggaattac atagatgata ttgtaaacgg  85500
tcacttcttt gtatcgaata aagtatttga taaatctctt ttatacaaat acgaaaacga  85560
tattattaca gtaccgttta gactttccta cgaaccattt gtttggggag ttaactttcg  85620
taaagaatat aacgtggtat cttctccata aaactgatga gatatataaa gaaataaatg  85680
tcgagctttg ttaccaatgg atacctttcc gttacattgg aacctcatga gctgacgtta  85740
gacataaaaa ctaatattag gaatgccgta tataagacgt atctccatag agaaattagt  85800
ggtaaaatgg ccaagaaaat agaaattcgt gaagacgtgg aattacctct cggcgaaata  85860
gttaataatt ctgtagttat aaacgttccg tgtgtaataa cctacgcgta ttatcacgtt  85920
ggggatatag tcagaggaac attaaacatc gaagatgaat caaatgtaac tattcaatgt  85980
ggagatttaa tctgtaaact aagtagagat tcgggtactg tatcatttag cgattcaaag  86040
tactgctttt ttcgaaatgg taatgcgtat gacaatggca gcgaagtcac tgccgttcta  86100
atggaggctc aacaaggtat cgaatctagt tttgtttttc tcgcgaatat cgtcgactca  86160
taagaaagag aatagcggta agtataaaca cgaatactat ggcaataatt gcgaatgttt  86220
tattctcttc gatatatttt tgataaatatg aaaaacatgt ctctctcaaa tcggacaacc  86280
atctcataaa atagttctcg cgcgctggag aggtagttgc tgctcgtata atctctccag  86340
aataatatac ttgcgtgtcg tcgttcaatt tatacggatt tctatagttc tctgttatat  86400
aatgcggttt tccatcatga ttagacgacg acaatagtgt tctgaattta gatagttgat  86460
cagaatgaat gtttattggc gttggaaaaa ttatccatac agcgtctgca gagtgcttga  86520
tagttgttcc tagatatgta aaataatcca acttactagg cagcaaattg tctagataaa  86580
atactgaatc aaacggtgca gacgtattgg cggatctaat ggaatccaat tgattaacta  86640
tcttttgaaa atatacattt ttatgatcca atacttgtaa gaatatagaa ataatgataa  86700
gtccatcatc gtgttttttt gcctcttcat aagaactata ttttttctta ttccaatgaa  86760
caagattaat ctctccagag tatttgtaca catctatcaa gtgattggat ccataatcgt  86820
cttcctttcc ccaatatata tgtagtgatg ataacacata ttcattgggg agaaaccctc  86880
cacttatata tcctccttta aaattaatcc ttactagttt tccagtgttc tggatagtgg  86940
ttggtttcga ctcattataa tgtatgtcta acggcttcaa tcgcgcgtta gaaattgctt  87000
ttttagtttc tatattaata ggagatagtt gttgcggcat agtaaaaatg aaatgataac  87060
tgtttaaaaa tagctcttag tatgggaatt acaatggatg aggaagtgat atttgaaact  87120
cctagagaat taatatctat taaacgaata aaagatattc caagatcaaa agacacgcat  87180
gtgtttgctg cgtgtataac aagtgacgga tatccgttaa taggagctag aagaacttca  87240
ttcgcgttcc aggcgatatt atctcaacaa aattcagatt ctatctttag agtatccact  87300
aaactattac ggtttatgta ctacaatgaa ctaagagaaa tctttagacg gttgagaaaa  87360
ggttctatca acaatatcga tcctcacttt gaagagttaa tattattggg tggtaaacta  87420
gataaaaagg aatctattaa agattgttta agaagagaat taaaagagga aagtgatgaa  87480
cgtataacag taaaagaatt tggaaatgta attctaaaac ttacaacacg ggataaatta  87540
tttaataaag tatatataag ttattgcatg gcgtgtttta ttaatcaatc gttggaggat  87600
```

ttatcgcata ctagtattta caatgtagaa attagaaaga ttaaatcatt aaatgattgt 87660
attaacgacg ataaatacga atatctgtct tatatttata atatgctagt taatagtaaa 87720
tgaactttta cagatctagt ataattagtc agattattaa gtataataga cgactagcta 87780
agtctattat ttgcgaggat gactctcaaa ttattacact cacggcattc gttaaccaat 87840
gcctatggtg tcataaacga gtatccgtgt ccgctatttt attaactact gataacaaaa 87900
tattagtatg taacagacga gatagttttc tctattctga aataattaga actagaaaca 87960
tgtttagaaa gaaacgatta tttctgaatt attccaatta tttgaacaaa caggaaagaa 88020
gtatactatc gtcatttttt tctctagatc cagctactac tgataatgat agaatagacg 88080
ctatttatcc gggtggcata cccaaaaggg gtgagaatgt tccagagtgt ttatccaggg 88140
aaattaaaga agaagttaat atagacaatt cttttgtatt catagacact cggtttttta 88200
ttcatggcat catagaagat accattatta ataaattttt tgaggtaatc ttctttgtcg 88260
gaagaatatc tctaacgagt gatcaaatca ttgatacatt taaaagtaat catgaaatca 88320
aggatctaat atttttagat ccgaattcag gtaatggact ccaatacgaa attgcaaaat 88380
atgctctaga tactgcaaaa cttaaatgtt acggccatag aggatgttat tatgaatcat 88440
taaaaaaatt aactgaggat gattgattag aaaatataaa ttaatttacc atcgtgtatt 88500
tttataacgg gattgtccgg catatcatgt agatagttac cgtctacatc gtatactcga 88560
ccatctacgc ctttaaatcc tctatttatt gacattaatc tattagaatt ggaataccaa 88620
atattagtac cctcaattag tttattggta atattttttt tagacgatag atcgatggct 88680
cttgaaacca aggttttcca accggactca ttgtcgatcg gtgagaagtc tttttcatta 88740
gcatgaatcc attctaatga tgtatgttta aacactctaa acaattggac aaattctttt 88800
gatttgcttt gaatgatttc aaataggtct tcgtctacag taggcatacc attagataat 88860
ctagccatta taaagtgcac gtttacatat ctacgttctg gaggagtaag aacgtgacta 88920
ttgagacgaa tggctcttcc tactatctga cgaagagacg cctcgttcca tgtcatatct 88980
aaaatgaaga tatcattaat tgagaaaaaa ctaataccct cgcctccact agaagagaat 89040
acgcatgttt taatgcattc tccgttagtg tttgattctt ggttaaactc agccaccgcc 89100
ttgattctag tatcttttgt tctagatgag aactctatat tagagatacc aaagactttg 89160
aaatatagta ataagatttc tattcctgac tgattaacaa atggttcaaa gactagacat 89220
ttaccatggg atgctaatat tcccaaacat acatctataa atttgacgct tttctctttt 89280
aattcagtaa atagagagat atcagccgca ctagcatccc ctttcaatag ttctcccttt 89340
ttaaaggtat ctaatgcgga tttagaaaac tttctatctc ttaatgaatt tttaaaatca 89400
ttatatagtg ttgctatctc ttgcgcgtat tcgcccggat cacgattttg tctttcagga 89460
aagctatcga acgtaaacgt agtagccata cgtctcagaa ttctaaatga tgatatacct 89520
gtttttattt cagcgagttt agccttttga taaatttctt cttgcttttt cgacatatta 89580
acgtatcgca ttaatactgt tttcttagcg aatgatgcag acccttctac gtcatcaaaa 89640
atagaaaact cgttattaac tatatacgaa cataggcctc ctagtttgga gactaattct 89700
ttttcatcga ctagacgttt attctcaaat agcgattggt gttgtaagga tcctggtcgt 89760
agtaagttaa ccaacatggt gaattcttgc acactattga cgataggtgt agccgataaa 89820
caaatcatct tatggttttt taacgcaatg gtcttagata aaaaattata tactgaacga 89880
gtaggacgga tcttaccatc ttctttgatt aatgatttag aaatgaagtt atgacattca 89940
tcaatgatga cgcatattct actcttggaa ttaatagttt tgatattagt aaaaaattta 90000

```
tttctaaaat tttgatcatc gtaattaata aaaatacaat ccttcgttat ctctggagcg  90060
tatctgagta tagtgttcat ccaaggatct tctatcaaag cctttttcac caataagata  90120
atagcccaat tcgtataaat atccttaaga tgtttgagaa tatatacagt agtcattgtt  90180
ttaccgacac ccgtttcatg gaacaataaa agagaatgca tactgtctaa tcctaagaaa  90240
actcttgcta caaaatgttg ataatccttg aggcgtacta cgtccgaccc catcatttca  90300
acgggcatat tagtagttct gcgtaaggca taatcgatat aggccgcgtg tgatttactc  90360
atttatgagt gataagtaat aactatgttt taaaaatcac agcagtagtt taactagtct  90420
tctctgatgt ttgttttcga tactttttga atcagaagtc atactagaat aaagcaacga  90480
gtgaacgtaa tagagagctt cgtatactct attcgaaaac tctaagaact tattaatgaa  90540
ttccgtatcc actggattgt ttaaaatact aaattgaaca ctgttcacat ccttccaaga  90600
agaagactta gtgacggact taacatgaga cataaataaa tccaaatttt ttttacaaac  90660
atcactagcc accataatgg cgctatcttt caaccagcta tcgcttacgc attttagcag  90720
tctaacattt ttaaagagac tacaatatat tctcatagta tcgattacac ctctaccgaa  90780
taaagttgga agtttaataa tacaatattt ttcgtttaca aaatcaaata atggtcgaaa  90840
cacgtcgaag gttaacatct tataatcgct aatgtataga ttgttttcag tgagatgatt  90900
attagattta atagcatctc gttcacgttt gaacagttta ttgcgtgcgc tgaggtcggc  90960
aactacggcg tccgctttag tactcctccc ataatacttt acgctattaa tctttaaaat  91020
ttcatagact ttatctagat cgctttctgg taacatgata tcatgtgtaa aaagttttaa  91080
catgtcggtc ggcattctat ttagatcatt aactctagaa atctgaagaa agtaattagc  91140
tccgtattcc agactaggta atgggctttt acctagagac agattaagtt ctggcaatgt  91200
ttcataaaat ggaagaagga catgcgttcc ctcccggata ttttttacaa tttcatccat  91260
ttacaactct atagtttgtt ttcattatta ttagttatta tctcccataa tcttggtaat  91320
acttacccct tgatcgtaag ataccttata caggtcatta catacaacta ccaattgttt  91380
ttgtacataa tagattggat ggttgacatc catggtggaa taaactactc gaacagatag  91440
tttatctttc cccctagata cattagccgt aatagttgtc ggcctaaaga atatctttgg  91500
tgtaaagtta aaagttaggg ttcttgttcc attattgctt tttgtcagta gttcattata  91560
aattctcgag atgggtccgt tctctgaata tagaacatca tttccaaatc taacttctag  91620
tctagaaata atatcggtct tattcttaaa atctattccc ttgatgaagg gatcgttaat  91680
gaacaaatcc ttggcctttg attcggctga tctattatct ccgttataga cgttacgttg  91740
actagtccaa agacttacag gaatagatgt atcgatgatg ttgatactat gtgatatgtg  91800
agcaaagatt gttctcttag tggcatcact atatgttcca gtaatggcgg aaaacttttt  91860
agaaatgtta tatataaaag aattttttcg tgttccaaac attagcagat tagtatgaag  91920
ataaacactc atattatcag gaacattatc aatttttaca tacacatcag catcttgaat  91980
agaaacgata ccatcttctg gaacctctac gatctcggca gactccggat aaccagtcgg  92040
tggaccatcg ctaacaataa ctagatcatc caacaatcta ctcacatatg catctatata  92100
atctttttca tcttgtgagt accctggata cgaaataaat ttattatccg tatttccata  92160
ataaggttta gtataaacag agagagatgt tgccgcatga acttcagtta cagtcgccgt  92220
tggttggttt atttgaccta ttactctcct aggtttctct ataaatgatg gtttaatttg  92280
tacattctta accatatatc caataaagct caattcagga acataaacaa attctttgtt  92340
```

```
gaacgtttca aagtcgaacg aagagtcacg aataacgata tcggatactg gattgaaggt  92400
caccgttacg gtaatttttg aatcggatag tttaagactg ctgaatgtat cttccacatc  92460
aaacggagtt ttaatataaa cgtatactgt agatggttct ttaatagtgt cattaggagt  92520
taggccaata gaaatatcat taagttcact agaatatcca gagtgtttca aagcaattgt  92580
attattgata caattattat ataattcttc gccctcaatt tcccaaataa caccgttaca  92640
cgaagagata gatacgtgat taatacattt atatccaaca tatggtacgt aactgaatct  92700
tcccatacct ttaacttctg gaagttccaa actcagaacc aaatgattaa gcgcagtaat  92760
atactgatcc ctaatttcga agctagcgat agcctgattg tctggaccat cgtttgtcat  92820
aactccggat agagaaatat attgcggcat atataaagtt ggaatttgac tatcgactgc  92880
gaagacatta gaccgtttaa tagagtcatc cccaccgatc aaagaattaa tgatagtatt  92940
attcattttc tatttaaaat ggaaaaagct tacaataaac tccgtagaga aatatctata  93000
atttgtgagt tttccttaaa gtaacagctt ccgtaaacgc cgtctttatc tcttagtagg  93060
tttattgtat ttatgacctt ttccttatct tcatagaata ctaaaggcaa caaagaaatt  93120
tttggttctt ctctaagagc tacgtgagac ttaaccatag aagccaacga atccctacat  93180
attttagaac agaaataccc tacttcacca cccttgtatg tctcaatact aataggtcta  93240
aaaaccaaat cttgattaca aaaccaacac ttatcaatta cactatttgt cttaatagac  93300
acatctgcca tagatttata atactttggt agtatacaag cgagtgcttc ttctttagcg  93360
ggcttaaaga ctgctttagg tgctgaaata accacatctg gaaggcttac tcgcttagcc  93420
atttaattac ggaactattt ttttatactt ctaatgagca agtagaaaac ctctcatcta  93480
caaaaacgta ctcgtgtcca taatcctcta ccatagttac acgtttttta gatctcatat  93540
gtgctaaaaa gttttcccat actaattggt tactattatt tttcgtataa tttttaacag  93600
tttgaggttt tagattttta gttacagaag tgatatcgaa tattttatcc aaaaagaatg  93660
aataattaat tgtcttagaa ggagtgtttt cttggcaaaa gaataccaag tgcttaaata  93720
tttctactac ttcattaatc ttttctgtac tcagattcag tttctcatct tttacttgat  93780
tgattatttc aaagactaac ttataatcct ttttatttat tctctcgtta gccttaagaa  93840
aactagatac aaaatttgca tctacatcat ccgtggatat ttgatttttt tccatgatat  93900
ccaagagttc cgagataatt tctccagaac attgatgaga caataatctc cgcaatacat  93960
ttctcaaatg aataagttta ttagacacgt ggaagtttga cttttttttgt acctttgtac  94020
atttttgaaa taccgactcg caaaaaatac aatattcata tccttgttca gatactatac  94080
cgttgtgtct acaaccgcta cataatcgta gattcatgtt aacactctac gtatctcgtc  94140
gtccaatatt ttatataaaa acattttatt tctagacgtt gccagaaaat cctgtaatat  94200
ttttagtttt ttgggctgtg aataaagtat cgccctaata tggttaccgt cttccgccaa  94260
tatagtagtt aaattatccg cacatgcaga agaacaccgc ttaggcggat tcagtacaat  94320
gttatatttt tcgtaccaac tcatttaaat atcataatct aaaatagttc tgtaatatgt  94380
ctagcgctaa tatattgatc ataatcctgt gcataaatta agatacaaca atgtctcgaa  94440
atcatcgaca tggcttcttc catagttaga agatcgtcgt caaagttagc aacgtgattc  94500
atcaacattt gctgttttga ggcagcaaat actgaaccgt cgccattcaa ccattcataa  94560
aaaccatcgt ctgaatccat tgataatttc ttgtactggt ttttgagagc tcgcatcaat  94620
ctagcatttc tagctcccgg attgaaaaca gaaagaggat cgtacatcca gggtccattt  94680
tctgtaaata gaatcgtata atgtcccttc aagaagatat cagacgatcc acaatcaaag  94740
```

```
aattggtctc cgagtttgta acaaactgcg gactttaacc tatacatgat accgtttagc  94800
ataatttctg gtgatacgtc aatcggagta tcatctatta gagatctaaa gccggtgtaa  94860
cattctccac caaacatatt cttattctga cgtcgttcta cataaaacat cattgctcca  94920
ttaacgataa caggggaatg aacagcacta cccatcacat tagttcccaa tggatcaatg  94980
tgtgtaactc cagaacatct tccatagcct atgttaggag gagcgaacac cactcttcca  95040
ctattgccat cgaatgccat agaataaata tccttggaat tgatagaaat cggactgtcg  95100
gatgttgtga tcatcttcat aggattaaca actatgtatg gtgccgcctg aagtttcata  95160
tcgtaactga tgccgtttat aggtctagcc acagaaacca acgtaggtct aaatccaact  95220
atagacaaaa tagaagccaa tatctgttcc tcatctgtca taacttgaga gcatccagta  95280
tgaataatct tcattagatg gggatctacc gcatcatcat cgttacaata aaaaattccc  95340
attctaatgt tcataattgc ttttctaatc atggtatgca tgtttgctct ctgaatctct  95400
gtggaaatta gatctgatac acctgtaatc actatcggat tatcctccgt aagacgatta  95460
accaacaaca tataattata agactttact tttctaaatt cataaagttg ctggattagg  95520
ctataggtgt ctccatgtac atacgcgttc tcgagcgcag gaagtttaat accgaatagt  95580
gccatcagaa taggatgaat atagtaatta gtttctggtt ttctataaat aaaagacaaa  95640
tcttgtgaac tagacatatc ggtaaaatgc atggattgga atcgtgtagt cgacagaaga  95700
atatgatgat tagatggaga gtatatttta tctaactctt tgagttggtc accgattcta  95760
ggactagctc gagaatgaat aagtactaaa ggatgagtac atttcacaga aacactagca  95820
ttgttcaatg tgctctttac atgggtaagg agttgaaata gctcgtttct atttgttctg  95880
acaatattta gtttattcat aatgttaagc atatcctgaa tagtaaagtt agatgtgtca  95940
tacttgttag tagttagata tttagcaatt gcattcccat catttctcaa tctcgtactc  96000
caatcatgtg tagatgctac ttcatctata gaaaccatac aatccttttt gataggctgt  96060
tgagattgat tatttcctgc acgtttaggt ttggtacgtt gatttctagc ccctgcggat  96120
ataaagtcat cgtctacaat ttgggacaat gaattgcata cactacaaga caaagattta  96180
tcagaagtgt gaatatgatc ttcatctacc aaagaaagag tttgattagt ataactagat  96240
tttagtcctg cgttagatgt taaaaaaaca tcgctattga ccacggcttc cattatttat  96300
attcgtagtt tttactcgaa agcgtgattt taatatccaa tcttattact tttggaatcg  96360
ttcaaaacct ttgactaatt gtagaatttg atctattgcc ctacgcgtat actcccttgc  96420
atcatatacg ttcgtcacca gatcgtttgt ttcggcctga agttggtgca tatctctttc  96480
aacattcgac atgagatcct taagggccat atcgtctaga ttttgttgag atgttgctcc  96540
tggatttgga ttttgttgtg ctgttgtaca tactgtacca ccagtaggtg taggagtaca  96600
tacagtggcc acaataggag gttgaggagg tgtaaccgtt ggagtagtac aagaaatact  96660
tccatccgat tgttgtgtac atgtagttgt tggtaacgtc tgagaaggtt gggtagatgg  96720
cggtgtcgtc gtcttttgat ctttattaaa tttagagata atatcctgaa cagcattgct  96780
cggcgtcaac gctggaagga gtgaactcgc cggcgcatca gtatctgcag acagccaatc  96840
aaaaagatta gacatatcag atgatgtatt agtttgttgt cgtggttttg gtgtaggagc  96900
agtactacta ggtagaagaa taggagccgg tgtagctgtt ggaaccggct gtggagttat  96960
atgaatagtt ggttgtagcg gttggatagg ctgtctgctg gcggccatca tattatctct  97020
agctagttgt tctcgcaact gtctttgata atacgactct tgagacttta gtcctatttc  97080
```

```
aatcgcttca tcctttttcg tatccggatc cttttcttca gaataataga ttgacgactt  97140
tggtgtagag gattctgcca gcctctgtga gaacttgtta aagaagtcca tttaaggctt  97200
taaaattgaa ttgcgattat aagattaaat ggcagacaca gacgatatta tcgactatga  97260
atccgatgat ctcaccgaat acgaggatga tgaagaagag gaagaagatg gagagtcact  97320
agaaactagt gatatagatc ccaaatcttc ttataagatt gtagaatcag catccactca  97380
tatagaagat gcgcattcca atcttaaaca tatagggaat catatatctg ctcttaaacg  97440
acgctatact agacgtataa gtctatttga aatagcgggt ataatagcag aaagctataa  97500
cttgcttcaa cgaggaagat tacctctagt ttcagaattt tctgacgaaa cgatgaagca  97560
aaatatgcta catgtaatta tacaagagat agaggagggt tcttgtccta tagtcatcga  97620
aaagaacgga gaattgttgt cggtaaacga ttttgacaaa gatggtctaa aattccatct  97680
agactatatt atcaaaattt ggaaacttca aaaacgatat tagaatttat acgaatatcg  97740
ttctctaaat gtcacaatca agtctcgcat gttcagcaat ttattgtcgt actttatatc  97800
gtgttcatta acgatatctt gcaaaatagt aatgattcta tcttccttcg atagatattc  97860
ttcagagatt attgtcttat attctttctt gttatccgat atgaatttga taagactttg  97920
aacattattg atacccgtct gtttaatttt ttctacagat attttagttt tggcagattc  97980
tatcgtatct gtcaatagac atccaacatc gacattcgac gtcaattgtc tataaatcaa  98040
cgtataaatt ttagaaataa cattagcgaa ttgttgtgcg ttgatgtcgt tattctgaaa  98100
cagtatgatt ttaggtagca ttttcttaac aaagagaacg tatttattgt tactcagttg  98160
aacagatgat atatccagat tactaacgca tctgattccg tataccaaac tttcagaaga  98220
aatggtatac aattgtttgt attcattcaa tgtctctttt tcagaaatta gtttagagtc  98280
gaatactgca ataattttca agagatagtt ttcatcagat aagattttat ttagtgtaga  98340
tatgataaaa ctattgtttt gttggagaac tgatacgccg cgttctcgtg tcgacgctct  98400
caaatgggaa acaatctcca ttattttttt ggaatcggat acaatatctt cggtatcttg  98460
acgcagtcta gtatacatag agttaagaga gattagagtt tgtacattaa gcaacatgtc  98520
tctaaatgtg gctacaaact tttccttttc cacatcatct agtttattat ataccgattt  98580
cacaacggca ccagatttaa ggaaccagaa tgaaaaactc tgataactac aatatttcat  98640
catagttacg attttatcat cttctatagt tggtgtaata gcgcatacct ttttctccaa  98700
gactggaacc aacgtcataa aaatgtttaa atcaaaatcc atatcaacat ctgatgcgct  98760
aagaccagtc tcgcgttcaa gattatcttt actaatggtg acgaactcat cgtatagaac  98820
tctaagtttg tccattattt atttacagat ttagttgttt aatttatttg tgctcttcca  98880
gagttgggat agtatttttc taacgtcggt attatattat taggatctac gttcatatgt  98940
atcataatat taatcatcca cgttttgata aatctatctt tagcttctga aataacgtat  99000
ttaaacaaag gagaaaaata tttagctacg gcatcagacg caataacatt ttttgtaaat  99060
gtaacgtatt tagacgacag atcttcgtta aaaagttttc catctatgta gaatccatcg  99120
gttgttaaca ccattcccgc gtcagattga ataggagttt gaatagtttg ttttggaaat  99180
agatccttca ataacttata gttgggtggg aaaaaatcga ttttatcact agactctttc  99240
ttttttacta tcattacctc atgaactatt tcttgaatga gtatatgtat tttctttcct  99300
atatcggacg cgttcattgg aaaatatacc atgtcgttaa ctataagaat atttttatcc  99360
tcgtttacaa actgaataat atcagatgta gttcgtaaac gaactatatc atcaccagca  99420
caacatctaa ctatatgata tccactagtt tcctttagtc gtttattatc ttgttccata  99480
```

```
ttagcagtca ttccatcatt taagaaggcg tcaaaaataa tagggagaaa tgacattttg  99540
gattctgtta caactttacc aaaattaagg atatacggac ttactatctt tttctcaacg  99600
tcgatttgat gaacacacga tgaaaatgtg cttcgatgag attgatcatg tagaaaacaa  99660
caagggatac aatatttccg catatcatga aatatattaa gaaatcccac cttattatat  99720
ttccccaaag gatccatgca cgtaaacatt atgccgttat cattaataaa gacttctttc  99780
tcatcggatc tgtaaaagtt gttactgatt tttttcattc caggatctag ataattaata  99840
atgatgggtt ttctattctt attctttgta ttttggcata tcctagacca gtaaacagtt  99900
tccactttgg taaaatcagc agacttttga acgctattaa acatggcatt aatggcaata  99960
actaaaaatg taaaatattt ttctatgtta ggaatatggt ttttcacttt aatagatata 100020
tggtttttgg ccaaaatgat agatattttt ttatccgagg atagtaaaat attattagtc 100080
gccgtctcta taaaaatgaa gctagtctcg atatccaatt ttattctaga attgatagga 100140
gtcgccaaat gtaccttata cgttatatct cccttgatgc gttccatttg tgtatctata 100200
tcggacacaa gatctgtaaa tagttttacg ttattaatca tcacggtatc gccgtcgcta 100260
gataacgcta atgtaccatc caagtcccaa atggagagat ttaactgttc atcgtttaga 100320
ataaaatgat taccggtcat attaataaag tgttcatcgt atctagataa caacgactta 100380
taattaatgt ccaagtcttg aactcgctga atgatctttt ttaacccagt tagttttaga 100440
ttggtacgaa atatattgtt aaactttgat tctacagtaa tgtccaaatc tagttgtgga 100500
aatacttcca tcaacattgt ttcaaacttg ataatattat tatctacatc ttcgtacgat 100560
ccaaattccg gaatagatgt atcgcacgct ctggccaccc agataaccaa aaagtcacac 100620
gctccaggat atacattgta taaaaagcta tcgtttttta gtagggtttt tttctgcgtg 100680
tatacgaagg gattaaaaat agtattatca acgtaactat attccaaatt attcttatga 100740
gaatagataa taatatcgtc cttaatatct aacaaatttc ctaaatatcc ctttaattga 100800
gtcattcgaa gcgtcaatag aatatgtctc ttaactattt ccggctgttg tatatttaaa 100860
tgacttcgta aaaaataata tatgggcgac ttctcatcta tgtaatcata tggagtgaga 100920
tatagggctc gttctacctc ctgcccctta cccacctgta ataccaattg cggacttact 100980
atatatcgca tatttatatc gtggggtaaa gtgaaaatct actaccgatg atgtaagtct 101040
tacaatgttc gaaccagtac cagatcttaa tttggaggcc tccgtagaac taggggaggt 101100
aaatatagat caaacaacac ctatgataaa ggagaatagc ggttttatat cccgtagtag 101160
acgtctattc gcccatagat ctaaggatga tgagagaaaa ctagcactac gattcttttt 101220
acaaagactt tattttttag atcatagaga gattcattat ttgttcagat gcgttgacgc 101280
tgtaaaagac gtcactatta ccaaaaaaaa taacattatc gtggcgcctt atatagcact 101340
tttaactatc gcatcaaaag gatgcaaact tacagaaaca atgattgaag cattctttcc 101400
agaactatat aatgaacata gtaagaaatt taaattcaac tctcaagtat ccatcatcca 101460
agaaaaactc ggataccagt ttggaaacta tcacgtttat gattttgaac cgtattactc 101520
tacagtagct ctggctattc gagatgaaca ttcatctggc atttttaata tccgtcaaga 101580
gagttatctg gtaagttcat tatctgaaat aacatataga ttttatctaa ttaatctaaa 101640
atctgatctt gttcaatgga gtgctagtac gggcgctgta attaatcaaa tggtaaatac 101700
tgtattgatt acagtgtatg aaaagttaca actggtcata gaaaatgatt cacaatttac 101760
atgttcattg gctgtggaat caaaacttcc aataaaatta cttaaagata gaaatgaatt 101820
```

atttacaaaa ttcattaacg agttaaaaaa gaccagttca ttcaagataa gcaaacgcga 101880
taaggatacg ctactaaaat attttactta ggactggagt tagaatttat agacgactca 101940
tttcgtttat cattgttact attattacta ttactatcat tattagtgtt ggcattatta 102000
gtattcttct tgtcatcttg ttcagaaata tacagcaatg ctatacctaa tactaaatac 102060
attatcatgc tcgcaatggc tctaacaaca acgaaccaaa atgaatttgg tcgtagcttt 102120
tgttcacaaa aatacataaa gaaatgtcta cataaatcta tggcgccatt ggctacttga 102180
aatagcgcca gtcctcctac agattttaat atagctgtat aacatgacat ttattcatca 102240
tcaaaagaga cagagtcacc atctgtcata tttagatttt ttttcatgtg ttcaaagtat 102300
cctctactca tttcattata atagtttatc atacttagaa ttttaggacg gatcaatgag 102360
taagacttga ctagatcgtc agtagtaatt tgtgcatcgt ctattctgca tccgcttcgt 102420
cgaataatgt atagcatcgc tttgagattc tccatagcta tcaagtcttt atacaatgac 102480
atggaaatat ctgtgaatac tttatacttc tccaacatcg atgccttaac atcatcgcct 102540
actttagcat tgaaaatacg ttctattgtg tagatggatg tagcaagatt tttaaacaat 102600
aatgccatct tacacgatga ttgcctcaag tctccaatcg tttgtttaga acgattagct 102660
acagagtcca atgcttggct gactagcata ttattatctt tagaaattgt attcttcaat 102720
gaggcgttta tcatatctgt gatttcgtta gtcatattac agtctgactg ggttgtaatg 102780
ttatccaaca tatcacctat ggatacggta cacgtaccag catttgtaat aatcctatct 102840
aagatgttgt atggcattgc gcagaaaata tcttctcctg taatatctcc actctcgata 102900
aatctactca gattattctt aaatgcctta ttctctggag aaaagatatc agtgtccatc 102960
atttcattaa tagtatacgc agaaaagata ccacgagtat caattctatc caagatactt 103020
atcggttccg agtcacagat aatggtttcc tctccttcgg gagatcctgc atagaaatat 103080
ctaggacaat agtttctata ctgtctgtaa ctctgataat ctctaaagtc actaactgat 103140
accatgaaat tgagaagatc aaacgctgaa gtaattaatt tttctgcctc gtttttacta 103200
caactagttt tcatcaatgt agtgacgatg tattgtttag ttacttttgg tctaatactg 103260
atgatagaga tattattgct tcccataatg gatcttctag tagtcacctt aaagcccatt 103320
gatgcgaata gcagatagat aaagtcttgg tatgactcct ttctaatata gtacggacta 103380
cctttgtcac ccaactttat acccacataa gccataacaa cctctttaat agccgtttca 103440
tgaggtttat cagccatgag cctgagtagt tggaagaatc tcatgaatcc cgtctcagaa 103500
agtcctatat gcatgataga tttatctttc ctgggaaact ctcgtatagt catagatgaa 103560
atactcttca aagtttctga aataagatta gtaacagtct tacctccgac tactctaggt 103620
aacaaacaaa ctctaatagg tgttttctct gcggagataa tatcagaaag gatagagcaa 103680
taagtagtat tattgtgatt ataaagaccg aatacataac aggtagaatt tataaacatc 103740
atgtcctgaa ggtttttaga cttgtattcc tcgtaatcca taccgtccca aaacatggat 103800
ttggtaactt tgatagccgt agatctttgt tccttcgcca acaggttaaa gaaattaata 103860
aagaatttgt tgtttctatt tatgtccaca aattgcacgt ttggaagcgc cacggttaca 103920
ttcactgcag cattttgagg atcgcgagta tgaagtacga tgttattgtt tactggtata 103980
tctggaaaga aatctaccag tctaggaata agagattgat atcgcataga aatagtaaag 104040
tttataatct catcatcgaa gagcattttg ttaccattgt aataaatatc cactctgtca 104100
tatgtataaa tgaagtactg ttcaaacatg atgagatgtt tatatgttgg catagtagtg 104160
agatcgacgt ttggtaatgg caatgtatta agattaactc cataatgtct agcagcatct 104220

```
gcgatgttat aagcgtcgtc aaagcggggt cgatcttgta ttgttatata ttgtctaaca 104280
cctataagat tatcaaaatc ttgtctgctt aatacaccgt taacaatttt tgccttgaat 104340
tcttttattg gtgcattaat aacatcctta tagaggatgt taaacaaata agtgttatca 104400
aagttaagat ctggatattt cttttctgct agaacatcca ttgagtcgga gccatctggt 104460
ttaatataac caccgataaa tctagctctg tattctgtat ccgtcaatct aatattaaga 104520
aggtgttgag tgaaaggtgg aagatcgtaa aagctgtgag tattaatgat aggattagtt 104580
tccgaactaa tgttaattgg ggtattaata atatctatat ttccagcgtt aagtgtaaca 104640
ttaaacagtt ttaattcacg tgacgtggta tcaattaaat aattaatgcc caatttggat 104700
atagcagcct gaagctcatc ttgtttagtt acggatccta atgagttatt aagcaatata 104760
tcgaacggat gaacgaaggt tgttttaagt tggtcgcata ctttgtaatc tagacataga 104820
tgcggaagaa cggtagaaac tatacgaaat aaatattcag agtcctctaa ttgatcaaga 104880
gtaactattg acttaatagg catcatttat ttagtattaa atgacgaccg taccagtgac 104940
ggatatacaa aacgatttaa ttacagagtt ttcagaagat aattatccat ctaacaaaaa 105000
ttatgaaata actcttcgtc aaatgtctat tctaactcac gttaacaacg tggtagatag 105060
agaacataat gccgccgtag tgtcatctcc agaggaaata tcctcacaac ttaatgaaga 105120
tctatttcca gatgatgatt caccggccac tattatcgaa cgagtacaac ctcatactac 105180
tattattgac gatactccac ctcctacgtt tcgtagagag ttattaatat cggaacaacg 105240
tcaacaacga gaaaaaagat ttaatattac agtatcgaaa aatgctgaag caataatgga 105300
atctagatct ataataactt ctatgccaac acaaacacca tccttgggag tagtttatga 105360
taaagataaa agaattcaga tgttagagga tgaagtggtt aatcttagaa atcaacgatc 105420
taatacaaaa tcatctgata atttagataa ttttaccaaa atactatttg gtaagactcc 105480
gtataaatca acagaagtta ataagcgtat agccatcgtt aattatgcaa atttgaacgg 105540
gtctccctta tcagtcgagg acttggatgt ttgttcggag gatgaaatag atagaatcta 105600
taaaacgatt aaacaatatc acgaaagtag aaaacgaaaa attatcgtca ctaacgtgat 105660
tattattgtc ataaatatta tcgagcaggc attgctaaaa ctcggatttg aagaaatcaa 105720
aggactgagt accgatatca cttcagaaat tatcgatgtg gagatcggag atgactgcga 105780
tgctgtagca tcaaaactag gaatcggtaa cagtccggtt cttaatattg tattgtttat 105840
actcaagata ttcgttaaac gaattaaaat tatttaattt aatacattcc catatccaga 105900
caacaatcgt ctggattaat ctgttcctgt cgtctcatac cggacgacat attaatcttt 105960
ttattagtgg gcatcttttt agatggtttc tttttcccag cattaactga gtcgatacct 106020
agaagatcgt gattgatctc tccgaccatt ccacgaactt ctaattggcc gtctctgacg 106080
gtaccataaa ctattttacc agcattagta acagcttgga caatctgacc atccatcgca 106140
ttgtacgatg tagttgctgt tgttctacgt ctaggagcac cagaagtatt tttggagccc 106200
ttggatgttg atgtagaaga agacgaggat tttgattttg gtttacatgt aatacatttt 106260
gaactctttg attttgtatc acatgcgccg gcagtcacat ctgtttgaga attaagatta 106320
ttgttgcctc ctttgacggc tgcatctcca ccgatttgcg ctagtagatt tttaagctgt 106380
ggtgtaatct tattaactgt ttcgatataa tcatcgtaac tgcttctaac ggctaaattt 106440
tttttatccg ccatttagaa gctaaaaata tttttattta tgcagaagat ttaactagat 106500
tatacaatga actaatatga tccttttcca gattatttac aaacttggta ttttttggtt 106560
```

```
ctggaggagg cgaatttaaa ttcggacttg gattcggatt ttgtaagttc ttgatcttat 106620
tatacatcga gtataggatg gcgacagtaa ctgctacaca aataccgatc aaaagaagaa 106680
taccaatcat ttattgacaa taacttcact attgatcaag tatgcaatat atcatctttt 106740
cactaaataa gtagtaataa tgattcaaca atgtcgagat atatggacga taataattta 106800
gttcatggaa atatcgctat gattggtgtg aatgactccg ctaactctgt ggggtgcgca 106860
gtgctttccc cacatagaat aaattagcat tccgactgtg ataataatac caagtataaa 106920
cgccataata ctcaatactt tccatgtacg agtgggactg gtagacttac taaagtcaat 106980
aaaggcgaag atacacgaaa gaatcaaaag aatgattcca gcgattagca cgccggaaaa 107040
ataatttcca atcataagca tcatgtccat ttaactaata aaaattttaa atcgccgaat 107100
gaacaaagtg gaatataaac catataaaaa caatagtttg tactgcaaaa ataatatcta 107160
tttttgtttt cgaagatatg gtaaaattaa atagtagtac acagcaggtt ataactaaca 107220
gcagcaacgg ctcgtaatta cttatcattt actagacgaa aaggtggtgg gatattttct 107280
tgctcaaata atacgaatat atcacccatc cattttatgc gatgtttata tactctaatc 107340
tttaatagat ctatagacga cgggtttacc aacaatatag attttatcga ttcatctaat 107400
ttaaaccctt ccttaaacgt gaatgatcta ttatctggca taacgatgac cctacctgat 107460
gaatcggaca atgtactggg ccatgtagaa taaattatca acgaattatc gtctacgaac 107520
atttatatca tttgttttaa ttttaggacg cgaataaatg gatataaaat agaaaataac 107580
agatattaca accagtgtta tggccgcgcc caaccaggta ggcagtttta ttttatcttt 107640
tactacaggt tctcctggat gtacgtcacc aacggcggac gtagttctag tacaattaga 107700
cgtaagttcc gcttgggaat tttttaacgc taaagagtta acgttaatcg tacacccaac 107760
gtatttacat ctagttcttt gaacatcttg attataatat aaccattttc tatctctaga 107820
ttcgtcggtg cactcatgta accaacatac cctaggtcct aaatatttat ctccggaatt 107880
agattttgga taattcgcgc accaacaatt tctatttcct ttatgatcgt tacaaaagac 107940
gtataatgcc gtatccccaa aagtaaaata atcaggacga ataattctaa taaactcaga 108000
acaatatctc gcatccatat gtttggagca aatatcggaa taagtagaca tagccggttt 108060
ccgttttgca cgtaaccatt ctaaacaatt ggggtttcca ggatcgtttc tacaaaatcc 108120
agtcatgaaa tcatcacaat gttctgtctt gtaattatta ttaaatattt ttggacagtg 108180
tttggtattt gtcttagaac aacattttgc tacgctatca ctatcgccca ggagataatc 108240
ctttttttata aaatgacatc gttgcccgga tgctatataa tcagtagcgt gttttaaatc 108300
cttaatatat tcaggagtta cctcgttctg ataatagatt aatgatccag gacgaaattt 108360
gaaagaacta catggttctc catgaattaa tacatattgt ttagcaaatt caggaactat 108420
aaaactacta caatgatcta tcgacatacc atctatcaaa caaaacttgg gtttaatttc 108480
tcccggagat gtttcataat agtacgtata actttcttct gcaaacttaa cagctctatt 108540
atattcagga taattaaaac ctaattccat atatttgtct cgtatatctg ctattcctgg 108600
tgctattttg attctattaa gagtaacagc tgccccccatt cttaataatc gtcagtattt 108660
aaactgttaa atgttggtat atcaacatct accttatttc ccgcagtata aggtttgttg 108720
caggtatact gttcaggaat ggttacattt atacttcttc tatagtcctg tctttcgatg 108780
ttcatcacat atgcaaagaa cagaataaac aaaataatgt aagaaataat attaaatatc 108840
tgtgaattcg taaatacatt gattgccata ataattacag cagctacaat acacacaata 108900
gacattccca cagtgttgcc attacctcca cgatacattt gagttactaa gcaataggta 108960
```

ataactaagc tagtaagagg caatagaaaa gatgagataa atatcatcaa tatagagatt 109020
agaggagggc tatatagagc caagacgaac aaaatcaaac cgagtaacgt tctaacatca 109080
ttatttttga agattcccaa ataatcattc attcctccat aatcgttttg catcatacct 109140
ccatctttag gcataaacga ttgctgctgt tcctctgtaa ataaatcttt atcaagcact 109200
ccagcacccg cagagaagtc gtcaagcata ttgtaatatc ttaaataact catttatata 109260
ttaaaaaatg tcactattaa agatggagta taatctttat gccgaactaa aaaaaatgac 109320
ttgtggtcaa cccctaagtc tttttaacga agacggggat ttcgtagaag ttgaaccggg 109380
atcatccttt aagtttctga tacctaaggg attttacgcc tctccttccg taaagacgag 109440
tctagtattc gagacattaa caacgaccga taataaaatc actagtatca atccaacaaa 109500
tgcgccaaag ttatatcctc ttcaacgcaa agtcgtatct gaagtagttt ctaatatgag 109560
gaaaatgatc gaatcaaaac gtcctctata cattactctt cacttggcgt gtggatttgg 109620
taagactatt accacgtgtt atcttatggc tacacacggt agaaaaaccg tcatttgcgt 109680
acccaataaa atgttaatac atcaatggaa gacacaggta gaggcagtcg gattggaaca 109740
taagatatcc atagatggag taagtagtct attaaaggaa ctaaagactc aaagtccgga 109800
tgtattaata gtagtcagta gacatctgac aaacgatgcc ttttgtaaat atatcaataa 109860
gcattatgat ttgttcatct tggatgaatc acatacgtat aatctgatga acaatacagc 109920
agttacaaga tttttagcgt attatcctcc gatgatgtgt tattttttaa ctgctacacc 109980
tagaccagct aaccgaattt attgtaacag tattattaat attgccaagt tatccgatct 110040
aaaaaaaact atctatgcag tagatagttt ttttgagcca tattccacag acaatattag 110100
acatatgata aaacgattag atggaccatc taataaatat catatatata ctgagaagtt 110160
attatctgta gacgagccta gaaatcaact tattcttaat accctggtag aagaattcaa 110220
gtcaggaact attaatcgca ttttagttat tactaaacta cgtgaacata tggtattctt 110280
ctacaaacga ttattagatc ttttcggacc agaggttgta tttataggag acgcccaaaa 110340
tagacgtact ccagatatgg tcaaatcaat caaggaacta aatagattta tattcgtatc 110400
caccttattt tattccggta ctggtttaga tattcctagt ttggattcgt tgttcatttg 110460
ctcggcagta atcaacaata tgcaaataga gcaattacta gggagggtat gtcgagaaac 110520
agaactatta gataggacgg tatatgtatt tcctaacaca tccatcaaag aaataaagta 110580
catgatagga aatttcatgc aacgaattat tagtctgtct gtagataaac taggatttaa 110640
acaaaaaagt tatcggaaac atcaagaatc cgatcccact tttgtatgta caacatcctc 110700
cagagaagaa cgtgtattaa atagaatatt taactcgcaa aatcgttaag aagtttaagc 110760
gacgatccgc atgctgcgca ggccagtgta ttacccctca tagtattaat ataatccaat 110820
gatacttttg tgatgtcgga aatcttaacc aatttagact gacaggcaga acacgtcatg 110880
caatcatcat cgtcatcgat aactgtagtc ttgggcttct ttttgcggct cttcattccg 110940
gaacgcacat tggtgctatc catttaggta gtaaaaaata agtcagaata tgccctatag 111000
cacgatcgtg caaaacctgg tatatcgtct ctatctttat cacaatatag tgtatcgaca 111060
tttttattat tattgacctc gtttatcttg gaacatggaa tgggaacatt tttgttatca 111120
acggccatct ttgccttaat tccagatgtt gtaaaattat aactaaacag tctatcatcg 111180
acacaaatga aattcttgtt tagacgtttg tagtttacgt atgcggctcg ttcgcgtctc 111240
attttttcag atattgcagg tactataata ttaaaaataa gaatgaaata acataggatt 111300

```
aaaaataaag ttatcatgac ttctagcgct gatttaacta acttaaaaga attacttagt 111360
ctgtacaaaa gtttgagatt ttcagattct gcggctatag aaaagtataa ttctttggta 111420
gaatggggaa catctactta ctggaaaata ggcgtgcaaa aggtagctaa tgtcgagacg 111480
tcaatatctg attattatga tgaggtaaaa aataaaccgt ttaatattga tccgggctat 111540
tacattttct taccggtata ttttgggagc gtctttattt attcgaaggg taaaaatatg 111600
gtagaacttg gatctggaaa ctcttttcaa ataccagatg atatgcgaag tgcgtgtaac 111660
aaagtattag acagcgataa cggaatagac tttctgagat ttgttttgtt aaacaataga 111720
tggataatgg aagatgctat atcaaaatat cagtctccag ttaatatatt taaactagct 111780
agtgagtacg gattaaacat acccaaatat ttagaaattg aaatagagga agacacatta 111840
tttgacgaca agttatactc tattatagaa cgctctttcg atgataaatt tccaaaaata 111900
tccatatcgt atattaagtt gggagaactt agacggcaag ttgtagactt tttcaaattc 111960
tcattcatgt atattgagtc catcaaggta gatcgtatag gagataatat ttttattcct 112020
agcgttataa caaaatcagg aaaaaagata ttagtaaaag atgtagacca tttaatacga 112080
tccaaggtta gagaacatac atttgtaaaa gtaaaaaaga aaaacacatt ttccatttta 112140
tacgactatg atggaaacgg aacagaaact agaggagaag taataaaacg aattatagac 112200
actataggac gagactatta tgttaacgga aagtatttct ctaaggttgg tagtgcaggc 112260
ttaaagcaat tgactaataa attagatatt aatgagtgcg caactgtcga tgagttagtt 112320
gatgagatta ataaatccgg aactgtaaaa cgaaaaataa aaaaccaatc agcatttgat 112380
ttaagcagag aatgtttggg atatccagaa gcggatttta taacgttagt taataacatg 112440
cggttcaaaa tagaaaattg taaggttgta aatttcaata ttgaaaatac taattgttta 112500
aataacccga gtattgaaac tatatatgga aactttaacc agttcgtctc aatctttaag 112560
tcgtcaccga tgtcaaaaaa agattattcg agtgaaataa tatgcgcctt tgatataggt 112620
gcaaaaaatc ctgccagaac tgttttagaa gtcaaggata actccgttag ggtatggata 112680
tatcaaaaat tagactggag ttctgattgg gaaaggcgca tagctaaaga tttgtcacaa 112740
tatgaataca ctacagttct tctagaacgt cagcctagaa ggtcgccgta tgttaaattt 112800
atctatttta ttaaaggctt tttatatcat acatcggctg ccaaagttat ttgcgtctcg 112860
cctgtcatgt ctggtaattc atatagagat cgaaaaaaga gatcggtcga agcatttctt 112920
gattggatgg acacattcgg attgcgagac tccgttccgg atagacgcaa attagacgat 112980
gtagcggata gtttcaattt ggctatgaga tacgtattag ataaatggaa tactaattat 113040
acaccttata ataggtgtaa atctagaaat tacataaaaa aaatgtaata acgttagtaa 113100
cgccattatg gataatctat ttacctttct acatgaaata gaagatagat atgccagaac 113160
tatttttaac tttcatctaa taagttgcga tgaaatagga gatatatatg gtcttatgaa 113220
agaacgcatt tcctcagagg atatgtttga taatatagtg tataataaag atatacatcc 113280
tgccattaag aaactagtgt attgcgacat ccaacttact aaacacatta ttaatcagaa 113340
tacgtatccg gtatttaacg attcttcaca agtgaaatgt tgtcattatt tcgacataaa 113400
ctcagataat agcaatatta gctctcgtac agtagagata tttgagaggg aaaagtcatc 113460
tcttgtatca tatattaaaa ctaccaataa gaagagaaag gtcaattacg gcgaaataaa 113520
gaaaactgtt catggaggca ctaatgcaaa ttacttttcc ggtaaaaagt ctgacgagta 113580
tctgagtact acagttagat ccaacattaa tcaaccttgg atcaaaacca tttctaagag 113640
aatgagagta gatatcatta atcactctat agtaacgcgt ggaaaaagct ctatattaca 113700
```

aactatagaa attattttta ctaatagaac atgtgtgaaa atattcaagg attctactat 113760
gcacattatt ctatccaagg acaaggatga aaaggggtgt atacacatga ttgacaaatt 113820
attctatgtc tattataatt tatttctgtt gttcgaagat atcatccaaa acgagtactt 113880
taaagaagta gctaatgttg taaaccacgt actcacggct acggcattag atgagaaatt 113940
attcctaatt aagaaaatgg ctgaacacga tgtttatgga gttagcaatt tcaaaatagg 114000
gatgtttaac ctgacattta ttaagtcgtt ggatcatacc gttttcccct ctctgttaga 114060
tgaggatagc aaaataaagt tttttaaggg gaaaaagctc aatattgtag cattacgatc 114120
tctggaggat tgtataaatt acgtgactaa atccgagaat atgatagaaa tgatgaagga 114180
aagatcgact attttaaata gcatagatat agaaacggaa tcggtagatc gtctaaaaga 114240
attgcttcta aaatgaaaaa aaacactgat tcagaaatgg atcaacgact cggatataag 114300
tttttggtgc ctgatcctaa agccggagtt ttttatagac cgttacattt ccaatatgta 114360
tcgtattcta attttatatt gcatcgattg catgaaatct tgaccgtcaa gcggccactc 114420
ttatcgttta agaataatac agaacgaatt atgatagaaa ttagcaatgt taaagtgact 114480
cctccagatt actcacctat aatcgcgagt attaaaggta agagttatga cgcattagcc 114540
acgttcactg taaatatctt taaagaggta atgaccaaag agggtatatc catcactaaa 114600
ataagtagtt atgagggaaa agattctcat ttgataaaaa ttccgctact aataggatac 114660
gggaataaaa atccacttga tacagccaag tatcttgttc ctaatgtcat aggtggagtc 114720
tttatcaata aacaatctgt cgaaaaagta ggaattaatc tagtagaaaa gattacaaca 114780
tggccaaaat ttagggttgt taagccaaac tcattcactt tctcgttttc ctccgtatcc 114840
cctcctaatg tattaccgac aagatatcgc cattacaaga tatctctgga tatatcacaa 114900
ttggaagcgt tgaatatatc atcgacaaag acatttataa cggtcaatat tgttttgctg 114960
tctcaatatt tatctagagt gagtctagaa ttcattagac gtagtttatc atacgatatg 115020
cctccagaag ttgtctatct agtaaacgca ataatagata gtgctaaacg aattactgaa 115080
tctattactg actttaatat tgatacatac attaatgacc tggtggaagc tgaacacatt 115140
aaacaaaaat ctcagttaac gataaacgag ttcaaatatg aaatgctgca taacttttta 115200
cctcatatga actatacacc cgatcaacta aagggatttt atatgatatc tttactaaga 115260
aagtttctct actgtatctt ccacacttct agatatccag atagagattc gatggtttgt 115320
catcgcatcc taacgtacgg caaatatttt gagacgttgg cacatgatga attagagaat 115380
tacataggca acatccgaaa cgatatcatg aacaatcaca agaacagagg cacttacgcg 115440
gtaaacattc atgtactaac aactcccgga cttaatcatg cattttctag tctattgagt 115500
ggaaagttca aaaagtcaga cggtagttat cgaacacatc ctcactattc atggatgcag 115560
aatatttcta ttcctaggag tgttggattt tatccggatc aagtaaagat ttcaaagatg 115620
ttttctgtca gaaaatacca tccaagtcaa tatctttact tttgttcatc agacgttccg 115680
gaaagaggtc ctcaggtagg tttagtatct caattgtctg tcttgagttc cattacaaat 115740
atactaacgt ctgagtattt ggatttggaa aagaaaattt gtgagtatat cagatcatat 115800
tataaagatg atataagtta ctttgaaaca ggatttccaa tcactataga aaatgctcta 115860
gtcgcatctc ttaatccaaa tatgatatgt gattttgtaa ctgactttag acgtagaaaa 115920
cggatgggat tcttcggtaa cttggaggta ggtattactt tagttaggga tcacatgaat 115980
gaaattcgca ttaatattgg agcgggaaga ttagtcagac cattcttggt tgtggataac 116040
ggagagctca tgatggatgt gtgtccggag ttagaaagca gattagacga catgacattc 116100
tctgacattc agaaagagtt tccgcatgtc atcgaaatgg tagatataga acaatttact 116160
tttagtaacg tatgtgaatc ggttcaaaaa tttagaatga tgtcaaagga tgaaagaaag 116220
caatacgatt tatgtgactt tcctgccgaa tttagagatg gatatgtagc atcttcacta 116280
gtgggaatca atcacaattc tggacccaga gctattcttg gatgtgctca agctaaacaa 116340
gctatctctt gtctgagctc ggatatacga aataaaatag acaatggaat tcatttgatg 116400
tatccagaga ggccaatcgt gattagtaag gctttagaaa cttcaaagat tgcggctaat 116460
tgcttcggcc aacatgttac tatagcatta atgtcgtaca aaggtatcaa tcaagaggat 116520
ggaattatca tcaaaaaaca atttattcag agaggcggtc tcgatatagt taccgccaag 116580
aaacatcaag tagaaattcc attggaaaac tttaataaca aagaaagaga taggtctaac 116640
gcctattcaa aattagaaag taatggatta gttagactga atgctttctt ggaatccgga 116700
gacgctatgg cacgaaatat ctcatcaaga actcttgaag atgattttgc tagagataat 116760
cagattagct tcgatgtttc cgagaaatat accgatatgt acaaatctcg cgttgaacga 116820
gtacaagtag aacttactga caaagttaag gtacgagtat taaccatgaa agaaagaaga 116880
cccattctag gagacaaatt taccactaga acgagtcaaa agggaacagt cgcgtatgtc 116940
gcggatgaaa cggaacttcc atacgacgaa aatggtatca caccagatgt cattattaat 117000
tctacatcca tcttctctag aaaaactata tctatgttga tagaagttat tttaacagcc 117060
gcatattctg ctaagccgta caacaataag ggagaaaacc gacctgtctg ttttcctagt 117120
agtaacgaaa catccatcga tacatatatg caattcgcta aacaatgtta tgagcattca 117180
aatccgaaat tgtctgatga agaattatcg gataaaatct tttgtgaaaa gattctctat 117240
gatcctgaaa cggataagcc ttatgcatcc aaagtatttt ttggaccaat ttattacttg 117300
cgtctgaggc atttaactca ggacaaggca accgttagat gtagaggtaa aaagacgaag 117360
ctcattagac aggcgaatga gggacgaaaa cgtggaggag gtatcaagtt cggagaaatg 117420
gagagagact gtttaatagc gcatggcgca gccaatacta ttacagaagt tttgaaagat 117480
ttggaagaag attatcaaga tgtgtatgtt tgtgaaaatt gtggagacat agcagcacaa 117540
atcaagggta ttaatacatg tcttagatgt tcaaaactta atctctctcc tctcttaaca 117600
aaaattgata ccacacacgt atctaaagta tttcttactc aaatgaacgc cagaggcgta 117660
aaagtcaaat tagatttcga acgaaggcct ccttcgtttt ataaaccatt agataaagtt 117720
gatctcaaac cgtcttttct ggtgtaatat tctagtttag tagtagatac atatcaatat 117780
catcaaattc gagatccgaa ttataaaatg ggcgtggatt gttaactata gaatcggacg 117840
tctgatattc gaaaatctgt ggagtttcag gttttggtgg aggtgtaact gctacttggg 117900
atactgaagt ctgatattca gaaagctgtg gatgttctgg ttcgacatcc accgatggtg 117960
tcacaccact actaattggt tcagtaacgt ctgtggacga tggaggtgct acttctacag 118020
aacctgtagc ctcagttgtc aacggagata catttttaat gcgaggaaat gtataatttg 118080
gtaatggttt ctcatgtgga tctgaagaag aggtaagata tctactagaa agataccgat 118140
cacgttctag ttctcttttg tagaacttaa ctttttcttt ctccgcatct agttgatatt 118200
ccaacctctt cacgttacta cgttcagatt ccaattcacg ttcgcatggg ttacctccgc 118260
agtttttacg agcgatttca cgttcagcct tcatgcgtct ctccttctct ctatcgagtt 118320
tatcagagca gtctttctga aggcgatcga actccataaa tttctccaac gctttgattg 118380
tttccataga tttccgaagt tcagctttta ggactgtgat tctttttctt tcgaattcac 118440
agctggatgt acaaccgttt ccattaccgc catctctaag tttcttttct agatcggcaa 118500
catttcatcc ccatgccttt tacattcctc gagtctactg tcgtcgaaat atcgttccag 118560
ctccttttcg acatcaataa ctttagcacg ttgtctctca agctctcttt tgtagttatc 118620
tgattccctg gcacgtttaa gatcttcatg caattgagtc agctcttaac ttcctctctt 118680
gcttcttcgt catagtactt acaatcacta tgggatccat tgttaccacg tctacactcg 118740
gcgagctcgc gtttaagaga ttcaatttcc cgtttgtatt ggtccatgtt tccattgcta 118800
ccaccattag atttacaggc tgctagttgt cgttcgagat cagaaatacg ggttttcttg 118860
gaattgattt cgtcgatgta cttggcatcg aaacacttat taagttcttt ttccaattct 118920
acgattttat ttctttcgcg agtcaattcc ctcctgtagt aactatctgt tttgtcagat 118980
tcacgctctc tacgtagact ttcttgcaag ttactaattt gttccctagc acgtccgagt 119040
ttagttttat atgctgaata gagttctgat tcatcctttg agcagatctc tagcgatcgt 119100
ttaagattcc tgattctagt ctttagccta tttacctcct cagaagatgt tccgttaccg 119160
ttgcgtttac actcgttaag ctgtctatca agatccatga ttctatctct aagacgttgc 119220
atctctcttt ccatatcagc attgctttca ttattacgtc tgcagtcact caactgtctt 119280
tcaatatctg agattctatc tctaagacgt cgcatctctc tctgtttcgg cattggtttc 119340
attattacgt ctacagtcgt tcaactgtct ttcaagatct gatattctag attggagtct 119400
gctaatctct gtagcatttt cacggcattc actcagttgt ctttcaagat ctgaaatttt 119460
agattggagt ctgctaatct ctgtaagatt tcctcctccg ctctcgatgc agtcggtcaa 119520
cttattctct agttctctaa tacgcgaacg cagtgcatca acttcttgcg tgtcttcctg 119580
gttgcgtgta cattcatcga gtctagattc gagatctcta acgcgtcgtc gttcttcctc 119640
aagttctctg cgtactacag aaagcgtgtc cctatcttgt tgatatttag caatttctga 119700
ttctagagta ctgattttgc ttacgtagtt actaatagtt gtcttggcct tatcaagatc 119760
ctccttgtat ttgtcgcatt ccttgatatc cctacgaagt ctggacagtt cccattcgac 119820
attacgacgt ttatcgattt cagctcggag atcgtcatcg cgttgtttta gccacatacg 119880
actgagttca agttctcgtt gacaagatcc atctactttt ccattcctaa tagtatccag 119940
ttccttttct agttctgaac gcatttctcg ttccctatca agcgattctc tcaattctcg 120000
gatagtcttc ttatcaattt ctaataaatc tgaaccatca tctgtcccat tttgaatatc 120060
cctgtgttct ttgatctctt ttgtaagtcg gtcgattctt tcggttttat aaacagaatc 120120
cctttccaaa gtcctaatct tactgagttt atcactaagt tctgcattca attcggtgag 120180
ttttctcttg gcttcttcca actctgtttt aaactctcca ctatttccgc attcttcctc 120240
gcatttatct aaccattcaa ttagtttatt aataactagt tggtaatcag cgattcctat 120300
agccgttctt gtaattgtgg gaacataatt aggatcttct aatggattgt atggcttgat 120360
aacttcgtga ataatgtttc tatgttttct actgatgcat gtatttgctt cgattttttt 120420
atcccatgtt tcatctatca tagatttaaa cgcagtaatg ctcgcaacat taacatcttg 120480
aaccgttggt acaattccgt tccataaatt tataatgttc gccatttata taactcattt 120540
tttgaatata cttttaatta acaaaagagt taagttactc atatggacgc cgtccagtct 120600
gaacatcaat ctttttagcc agagatatca tagccgctct tagagtttca gcgtgatttt 120660
ccaacctaaa tagaacttca tcgttgcgtt tacaacactt ttctatttgt tcaaactttg 120720
ttgttacatt agtaatcttt ttttccaaat tagttagccg ttgtttgaga gtttcctcat 120780
tgtcgtcttc atcggcttta acaattgctt cgcgtttagc ctctggcttt ttagcagcct 120840
ttgtagaaaa aaattcagtc gctggaattg caagatcgtc atctccgggg aaaagagttc 120900
cgtccattta aagtacagat tttagaaact gacactctgc gttatttata tttggtacaa 120960
cacatggatt ataaatattg atgttaataa catcagaaaa tgtaaagtct atacattgtt 121020
gcatcgtgtt aaattttcta atggatctag tattattggg tccaacttct gcctgaaatc 121080
caaatatgga agcggataca aaaccgtttc ctggataaac cacacatctc cacttttgct 121140
ttacatcaga aattgtgtcg ttgacatctt gaactctcct atctaatgcc ggtgttccac 121200
ctatagattt tgaatattcg aatgctgcat gagtagcatt aaattcctta atattgccat 121260
aattttcata tattgagtaa ccctggataa aaagtaaaca caccgcagcc gtcgctacca 121320
caataaaaaa aattgataga gagttcattt ataatctatt agaagctgac aaaatttttt 121380
tacacgcatc agacaatgct ttaataaata gttcaacatc tacttttgtc atatcgaacc 121440
gatggtatga ttctaaccta gaattacatc cgaaaaagtt gactatgttc atagtcatta 121500
agtcattaac aaacaacatt ccagactctg gattataaga cgatactgtt tcgtcacaat 121560
tacctacctt aatcatgtga ttatgaatat tggctattag agcaccttct aagaaatcta 121620
taatatcttt gaaacacgat ttaaaatcaa accacgaata tacttctacg aagaaagtta 121680
gtttacccat aggagaaata actataaatg gagatctaaa tacaaaatcc ggatctatga 121740
tagttttaac attattatat tctctattaa atacctccac atctaaaaat gttaattttg 121800
aaactatgtc ttcgtttatt accgtacctg aactaaacgc tataagctct attgtttgag 121860
aactctttaa acgatattct tgaaatacat gtaacaaagt ttcctttaac tcggtcggtt 121920
tatctaccat agttacagaa tttgtatcct tatctataat ataataatca aaatcgtata 121980
aagttatata attatcgcgt tcagattggg atcttttcaa atagactaaa aaccccattt 122040
ctctagtaag tatcttatgt atatgtttgt aaaatatctt catggtggga atatgctcta 122100
ccgcagttag ccattcctca ttgacagcgg tagatgtatt agacaaaact attccaatgt 122160
ttaacaaggg ccattttacg agattattaa atccttgttt gataaatgta gccaatgagg 122220
gttcgagttc aacgacgatt gaattctctt cccgcggatg ctgcatgatg aacgacggga 122280
tgttgttcga ttgatttgga attctttttc gactttttgt ttatattaaa tattttaaaa 122340
tttatagcgg atagcaattc atgtaccacg gataatgtag acgcgtattg cgcatcgata 122400
tctttattat tagataaatt tatcaataaa tgtgagaagt ttgcctcgtt aaggtcttcc 122460
atttaaatat tatataaaca tttgtgtttg tatcttattc gtcttttatg gaatagtttt 122520
ttactagtaa agctgcaatt acacactttg tccgtaaaac ataaatataa acaccagctt 122580
ttatcaatcg ttccaaaaag tcgacggcgg acatttttaa catggcatct attttaaata 122640
cacttaggtt tttggaaaaa acatcatttt ataattgtaa cgattcaata actaaagaaa 122700
agattaagat taaacataag ggaatgtcat ttgtatttta taagccaaag cattctaccg 122760
ttgttaaata cttgtctgga ggaggtatat atcatgatga tttggttgta ttggggaagg 122820
taacaattaa tgatctaaag atgatgctat tttacatgga tttatcatat catggagtga 122880
caagtagtgg agcaatttac aaattgggat cgtctatcga tagactttct ctaaatagga 122940
ctattgttac aaaagttaat aattatgatg atacattttt tgacgacgat gattgatcgc 123000
tattgcacaa ttttgttttt gtactttcta atatagtgtt taggttcttt ttcatatgag 123060
aatattgatt tactaaaata tcgatgttta acttttgttc tataacgtcc ttatcggcgg 123120
tatcggtaca tatacgtaat tcaccttcac aaaatacgga gtcttcgata ataatagcca 123180
atcgattatt ggatctagct gtctgtatca tattcaacat gtttaatata tcctttcgtt 123240
ttccctttac aggcatcgat cgtagcatat tttccgcgtc tgagatggaa atgttaaaac 123300
tacaaaaatg cgtaatgtta gcccgtccta atattggtac gtgtctataa gtttggcata 123360
gtagaataat agacgtgttc aaatgccttc cgaagtttaa gaattctatt agagtattgc 123420
attttgatag tttatcgcct acatcatcaa aaataagtaa aaagtgtgct gattttttat 123480
gattttgtgc gacagcaata catttttcta tgttactttt agttcgtatc agattatatt 123540
ctagagattc ctgactacta acgaaattaa tatgatttgg ccaaatgtat ccatcataat 123600
ctgggttata aacgggtgta aacaagaata tatgtttata ttttttaact agtgtagaaa 123660
acagagatag taaatagata gtttttccag atccagatcc tcccgttaaa accattctaa 123720
acggcatttt taataaattt tctcttgaaa attgttttc ttggaaacaa ttcataatta 123780
tatttacagt tactaaatta atttgataat aaatcaaaat atggaaaact aaggttgtta 123840
gtagggagga gaacaaagaa ggcacatcgt gacataaata acatttatta tcatgatgac 123900
accagaaaac gacgaagagc agacatctgt gttctccgct actgtttacg gagacaaaat 123960
tcagggaaag aataaacgca aacgcgtgat tggtctatgt attagaatat ctatggttat 124020
ttcactacta tctatgatta ccatgtcagc gtttctcata gtgcgcctaa atcaatgcat 124080
gtctgctaac gaggctgcta ttactgacgc cgctgttgcc gttgctgctg catcatctac 124140
tcatagaaag gttgcgtcta gcactacaca atatgatcac aaagaaagct gtaatggttt 124200
atattaccag ggttcttgtt atatattaca ttcagactac cagttattct cggatgctaa 124260
agcaaattgc actgcggaat catcaacact acccaataaa tccgatgtct tgattacctg 124320
gctcattgat tatgttgagg atacatgggg atctgatggt aatccaatta caaaaactac 124380
atccgattat caagattctg atgtatcaca agaagttaga aagtattttt gtgttaaaac 124440
aatgaactaa tatttatttt tgtacattaa taaatgaaat cgcttaatag acaaactgta 124500
agtaggttta agaagttgtc ggtgccggcc gctataatga tgatactctc aaccattatt 124560
agtggcatag gaacatttct gcattacaaa gaagaactga tgcctagtgc ttgcgccaat 124620
ggatggatac aatacgataa acattgttat ttagatacta acattaaaat gtctacagat 124680
aatgcggttt atcagtgtcg taaattacga gccagattgc ctagaccgga tactagacat 124740
ctgagagtat tgtttagtat tttttataaa gattattggg taagtttaaa aaagaccaat 124800
aataaatggt tagatattaa taatgataaa gatatagata ttagtaaatt aacaaatttt 124860
aaacaactaa acagtacgac ggatgctgaa gcgtgttata tatacaagtc tggaaaactg 124920
gttaaaacag tatgtaaaag tactcaatct gtactatgtg ttaaaaaatt ctacaagtga 124980
caacaaaaaa tgaattaata ataagtcgtt aacgtacgcc gccatggacg ccgcgtttgt 125040
tattactcca atgggtgtgt tgactataac agatacattg tatgatgatc tcgatatctc 125100
aatcatggac tttataggac catacattat aggtaacata aaaactgtcc aaatagatgt 125160
acgggatata aaatattccg acatgcaaaa atgctacttt agctataagg gtaaaatagt 125220
tcctcaggat tctaatgatt tggctagatt caacatttat agcatttgtg ccgcatacag 125280
atcaaaaaat accatcatca tagcatgcga ctatgatatc atgttagata tagaagataa 125340
acatcagcca ttttatctat tcccatctat tgatgttttt aacgctacaa tcatagaagc 125400
gtataacctg tatacagctg gagattatca tctaatcatc aatccttcag ataatctgaa 125460
aatgaaattg tcgtttaatt cttcattctg catatcagac ggcaatggat ggatcataat 125520
tgatgggaaa tgcaatagta attttttatc ataaaagttg taaagtaaat aataaaacaa 125580
taaatattga actagtagta cgtatattga gcaatcagaa atgatgctgg tacctcttat 125640
cacggtgacc gtagttgcgg gaacaatatt agtatgttat atattatata tttgtaggaa 125700
aaagatacgt actgtctata atgacaataa aattatcatg acaaaattaa aaaagataaa 125760
gagttctaat tccagcaaat ctagtaaatc aactgatagc gaatcagact gggaggatca 125820
ctgtagtgct atggaacaaa acaatgacgt agataatatt tctaggaatg agatattgga 125880
cgatgatagc ttcgctggta gtttaatatg ggataacgaa tccaatgtta tggcgcctag 125940
cacagaacac atttacgata gtgttgctgg aagcacgctg ctaataaata atgatcgtaa 126000
tgaacagact atttatcaga acactacagt agtaattaat gaaacggaga ctgttaaagt 126060
acttaatgaa gataccaaac agaatcctaa ctattcatcc aatcctttcg taaattataa 126120
taaaaccagt atttgtagca agtcaaatcc gtttattaca gaacttaaca ataaatttag 126180
tgagaataat ccgtttagac gagcacatag cgatgattat cttaataagc aagaacaaga 126240
tcatgaacac gatgatatag aatcatcagt cgtatcattg gtgtgattag tttccttttt 126300
ataaaattga agtaatattt agtattattg ctgccgtcac gttgtacaaa tggagatatt 126360
ccctgtattc ggcatttcta aaattagcaa ttttattgct aataatgact gtagatatta 126420
tatagataca gaacatcaaa aaattatatc tgatgagatc aatagacaga tggatgaaac 126480
ggtacttctt accaacatct taagcgtaga agttgtaaat gacaatgaga tgtaccatct 126540
tattcctcat agattatcga cgattatact ctgtattagt tctgtcggag gatgtgttat 126600
ctctatagat aatgacatca atgacaaaaa tattctaacc tttcccattg atcatgctgt 126660
aatcatatcc ccactgagta aatgtgtcgt agttagcaag ggccctacaa ccatattggt 126720
tgttaaagcg gatataccta gcaaacgatt ggtaacatcg tttacaaacg acatactata 126780
tgtaaacaat ctgtcactga ttaattattt gccgttgtct gtattcatta ttagacgagt 126840
caccgactat ttggatagac acatatgcga tcagatattt gctaataata agtggtattc 126900
ccttataacc atcgacgata agcaatatcc tattccatca aactgtatag gtatgtcctc 126960
tgccaagtac ataaattcta gcatcgagca agatacttta atccatgttt gtaacctcga 127020
gcatccgttc gactcagtat acaaaaaaat gcagtcgtac aattctctac ctatcaagga 127080
acaaatattg tacggtagaa ttgataatat aaatatgagc attagtattt ctgtggatta 127140
atagatttct agtatgggga tcattaatca tctctaatct ctaaatacct cataaaacga 127200
aaaaaaaagc tattatcaaa tactgtacgg aatggattca ttctcttctc tttttatgaa 127260
actctgttgt atatctactg ataaaactgg aagcaaaaaa tctgataaaa agaataagaa 127320
taagatcaag gattatatgg aacacgatta ttataaaata acaatagttc ctggttcctc 127380
ttccacgtct actagctcgt ggtattatac acatgcctag taatagtctc tttgcgttga 127440
cggaaagcag actagaaata acaggctaaa atgttcagac accataatag ttcccaaccc 127500
agataataac agagtaccat caacacattc ctttaaactc aatcccaaac ccaaaaccgt 127560
taaaatgtat ccggccaatt gatagtagat aatgaggtgt acagcgcatg ataatttaca 127620
cagtaaccaa aatgaaaaca ctttagtaat tataagaaat atagacggta atgtcatcat 127680
caacaatcca ataatatgcc tgagagtaaa cattgacgga taaaacaaaa atgctccgca 127740
taactctatc atggcaataa cacaaccaaa tacttgtaaa attcctaaat tagtagaaaa 127800
tacaacggat atcgatgtat aagtgatctc gagaaataat aagaataaag taatgcccgt 127860
aaagataaac atcaacattg tttggtaatc attaaaccaa ttagtatgaa gttgaactaa 127920
tttcacagta gattttattc cagtgttatc ctcgcatgta taagtacctg gtaagatatc 127980
tttatattcc ataatcaatg agacatcact atccgataac gaatgaagtc tagcactagt 128040
atgccattta cttaatattg tcgtcttgga agttttatta taagttaaaa tatcatggtt 128100
atccaatttc catctaatat actttgtcgg attatctata gtacacggaa taatgatggt 128160
atcattacat gctgtatact ctatggtctt tgtagttgtt ataacaacca acgtatagag 128220
gtatatcaac gatattctaa ctcttgacat tttttattta tttaaaatga tacctttgtt 128280
atttatttta ttctattttg ctaacggtat tgaatggcat aagtttgaaa cgagtgaaga 128340
aataatttct acttacttat tagacgacgt attatacacg ggtgttaatg gggcggtata 128400
cacattttca aataataaac taaacaaaac tggtttaact aataataatt atatcacaac 128460
atctataaaa gtagaggatg cggataagga tacattagta tgcggaacca ataacggaaa 128520
tcccaaatgt tggaaaatag acggttcaga cgacccaaaa catagaggta gaggatacgc 128580
tccttatcaa aatagcaaag taacgataat cagtcacaac ggatgtgtac tatctgacat 128640
aaacatatca aaagaaggaa ttaaacgatg gagaagattt gacggaccat gtggttatga 128700
tttattcacg gcggataacg taattccaaa agatggttta cgaggagcat tcgtcgataa 128760
agatggtact tatgacaaag tttacattct tttcactgat actatcggct caaagagaat 128820
tgttaaaatt ccgtatatag cacaaatgtg cttaaacgac gaaggtggtc catcatcatt 128880
gtctagtcat agatggtcga cgtttctcaa agtcgaatta gaatgtgata tcgacggaag 128940
aagttataga caaattattc attctagaac tataaaaaca gataatgata cgatactata 129000
tgtattcttc gatagtcctt attccaagtc cgcattatgt acctattcta tgaataccat 129060
taaacaatct tttctacgt caaaattgga aggatataca aagcaattgc cgtctccagc 129120
tcctggtata tgtttaccag ctggaaaagt tgttccacat accacgtttg aagtcataga 129180
acaatataat gtactagatg atattataaa gcctttatct aaccaaccta tcttcgaagg 129240
accgtctggt gttaaatggt tcgatataaa ggagaaggaa aatgaacatc gggaatatag 129300
aatatacttc ataaaagaaa attctatata ttcgttcgat acaaaatcta aacaaactcg 129360
tagctcgcaa gtcgatgcgc gactattttc agtaatggta actgcgaaac cgttatttat 129420
agcagatata gggataggag taggaatgcc acaaatgaaa aaaatactta aaatgtaatc 129480
ttaatcgagt acaccacacg acaatgaaca aacataagac agattatgct ggttatgctt 129540
gctgcgtaat atgcggtcta attgttggaa ttatttttac agcgacacta ttaaaagttg 129600
tagaacgtaa attagttcat acaccatcaa tagataaaac gataaaagat gcatatatta 129660
gagaagattg tcctactgac tggataagct ataataataa atgtatccat ttatctactg 129720
atcgaaaaac ctgggaggaa ggacgtaatg catgcaaagc tctaaatcca aattcggatc 129780
taattaagat agagactcca aacgagttaa gtttttttaag aagcattaga cgcggatatt 129840
gggtaggaga atccgaaata ttaaaccaga caaccccata taattttata gctaagaatg 129900
ccacgaagaa tggaactaaa aaacggaaat atatttgtag cacaacgaat actcccaaac 129960
tgcattcgtg ttacactata taacaattac actacatttt tattcatacc actacttcgg 130020
ttagatgttt tagaaaaaaa taaatatcgc cgtaccgttc ttgtttttat aaaaataaca 130080
attaacaatt atcaaatttt ttctttaata ttttacgtgg ttgaccattc ttggtggtaa 130140
aataatctct tagtgttgga atggaatgct gtttaatgtt tccgcactca tcgtatattt 130200
tgacgtatgc agtcacatcg tttacgcaat agtcagactg tagttctatc atgcttccta 130260
catcagaagg aggaacagtt ttaaagtctc ttggttttaa tctattgccg ttagttttca 130320
tgaaatcctt tgttttatcc acttcacatt ttaaataaat gtccactata cattcttttg 130380
ttaattttac tagatcgtca tgggtcatag aatttatagg ttccgtagtc catggatcca 130440
aactagcaaa cttcgcgtat acggtatcgc gattagtgta tacaccaact gtatgaaaat 130500
taagaaaaca gtttaataaa tcaacagaaa tatttaatcc tccgtttgat acagatgcgc 130560
catatttatg gatttcggat tcacacgttg tttgtctgag gtgttcgtct agtgttgctt 130620
ctacgtaaac ttcgattccc atatattctt tattgtcaga atcgcatacc gatttatcat 130680
catacactgt ttgaaaacta aatggtatac acatcaaaat aacaaatact aacgagtaca 130740
ttctgcaata ttgttatcgt aattggaaaa atagtgttcg agtgagttgg attatgtgag 130800
tattggattg tatattttat tttatatttt gtaataagaa taaaatgcta atgtcaagtt 130860
tattccaata gatgtcttat taaaaacata tataataaat aacaatggct gaatggcata 130920
aaattatcga ggatatctca aaaaataata agttcgagga tgccgccatc gttgattaca 130980
agactacaaa gaatgttcta gctgctattc ctaacagaac atttgccaag attaatccgg 131040
gtgaaattat tcctctcatc actaatcgta atattctaaa acctcttatt ggtcagaaat 131100
attgtattgt atatactaac tctctaatgg atgagaacac gtatgctatg gagttgctta 131160
ctgggtacgc ccctgtatct ccgatcgtta tagcgagaac tcataccgca cttatatttt 131220
tgatgggtaa gccaacaaca tccagacgtg acgtgtatag aacgtgtaga gatcacgcta 131280
cccgtgtacg tgcaactggt aattaaaata aaaagtaata ttcatatgta gtgtcaattt 131340
taaatgatga tgatgaaatg gataatatcc atattgacga tgtcaataat gccggtattg 131400
gcatacagtt catcgatttt tagatttcat tcagaggatg tggaattatg ttatgggcat 131460
ttgtattttg ataggatcta taatgtagta aatataaaat ataatccgca tattccatat 131520
agatataatt ttattaatcg cacgttaacc gtagatgaac tagacgataa tgtctttttt 131580
acacatggtt attttttaaa acacaaatat ggttcactta atcctagttt gattgtctca 131640
ttatcaggaa acttaaaata taatgatata caatgctcag taaatgtatc gtgtctcatt 131700
aaaaatttgg caacgagtac atctactata ttaacatcta aacataagac ttattctcta 131760
catcggtcca cgtgtattac tataatagga tacgattcta ttatatggta taaagatata 131820
aatgacaagt ataatgacat ctatgatttt actgcaatat gtatgctaat agcgtctaca 131880
ttgatagtga ccatatacgt gtttaaaaaa ataaaaatga actcttaatt atgctatgct 131940
attagaaatg gataaaatca aaattacggt tgattcaaaa attggtaatg ttgttaccat 132000
atcgtataac ttggaaaaga taactattga tgtcacacct aaaaagaaaa aagaaaagga 132060
tgtattatta gcgcaatcag ttgctgtcga agaggcaaaa gatgtcaagg tagaagaaaa 132120
aaatattatc gatattgaag atgacgatga tatggatgta gaaagcgcgt aatacgatct 132180
ataaaaataa gtatataata aatacttttt atttactgta ctcttactgt gtagtggtga 132240
taccctactc gattattttt ttaaaaaaaa atacttattc tgattcttct aaccatttcc 132300
gtgttcgttc gaatgccaca tcgacgtcaa agatagggga gtagttgaaa tctagttctg 132360
cattgttggt acgcacctca aatgtagtgt tggatatctt caacgtatag ttgttgagta 132420
gtgatggttt tctaaataga attctcttca tatcattctt gcacgcgtac atttttagca 132480
tccatcttgg aattctagat ccttgttcta ttcccaatgg tttcatcaat agaagattaa 132540
acatatcgta cgaacacgat ggagagtaat cgtagcaaaa gtaagcattt cctttaatct 132600
cagatcccgg atactggata tattttgcag ccaacacgtg catccatgca acatttccta 132660

```
catatacccg gctatgcacc gcgtcatcat cgactgtacg atacataatg ttaccgtgtt 132720
gcttacattg ctcgtaaaag actttcgtca atttgtctcc ttctccgtaa attccagtgg 132780
gtcttaggca acaagtatac aattttgctc cattcatgat tacggaatta ttggctttca 132840
taaccagttg ctcggccata cgtttacttt ttgcgtatac atgtcctggt gatatatcat 132900
aaagggtatg ctcatggccg atgaatggat caccgtgttt attgggtcct attgcttcca 132960
tgctactagt atagatcaaa tacttgattc ctaggtccac acaagctgcc aaaatagtct 133020
gtgttccata atagtttact ttcatgattt cattatcggt gtattttcca aatacatcca 133080
ctagagcagc cgtatgaata atcagattta ccccatctag cgcttctctc accttatcaa 133140
agtcgtttat atcacattgt atatagttta taaccttaac tttcgaggtt attggttgtg 133200
gatcttctac aatatctatg actctgattt cttgaacatc atctgcacta attaacagtt 133260
ttactatata cctgcctaga aatccggcac caccagtaac cgcgtacacg gccattgctg 133320
ccactcataa tatcagacta cttattctat tttactaaat aatggctgtt tgtataatag 133380
accacgataa tatcagagga gttatttact ttgaaccagt ccatggaaaa gataaagttt 133440
taggatcagt tattggatta aaatccggaa cgtatagttt aataattcat cgttacggag 133500
atattagtca aggatgtgat tccataggca gtccagaaat atttatcggt aacatctttg 133560
taaacagata tggtgtagca tatgtttatt tagatacaga tgtaaatata tctacaatta 133620
ttggaaaggc gttatctatt tcaaaaaatg atcagagatt agcgtgtgga gttattggta 133680
tttcttacat aaatgaaaag ataatacatt ttcttacaat taacgagaat ggcgtttgat 133740
atatcagtta atgcgtctaa aacaataaat gcattagttt acttttctac tcagcaaaat 133800
aaattagtca tacgtaatga agttaatgat acacactaca ctgtcgaatt tgatagggac 133860
aaagtagttg acacgtttat ttcatataat agacataatg acaccataga gataagaggg 133920
gtgcttccag aggaaactaa tattggttgc gcggttaata cgccggttag tatgacttac 133980
ttgtataata agtatagttt taaactgatt ttagcagaat atataagaca cagaaatact 134040
atatccggca atatttattc ggcattgatg acactagatg atttggctat taaacagtat 134100
ggagacattg atctattatt taatgagaaa cttaaagtag actccgattc gggactattt 134160
gactttgtca actttgtaaa ggatatgata tgttgtgatt ctagaatagt agtagctcta 134220
tctagtctag tatctaaaca ttgggaattg acaaataaaa agtataggtg tatggcatta 134280
gccgaacata tatctgatag tattccaata tctgagctat ctagactacg atacaatcta 134340
tgtaagtatc tacgcggaca cactgagagc atagaggata aatttgatta ttttgaagac 134400
gatgattcgt ctacatgttc tgccgtaacc gacagggaaa cggatgtata atttttttat 134460
agtgtgaagg atatgataaa aaatataatt gttgtattta tcccattcca atcaccttat 134520
atgattctgt aacacaataa aggagtctca tagatgtata gaggtcagat actggtttga 134580
taaactgttt attccacata agtatgtttg actttatggt tagacccgca tactttaaca 134640
aatcactgaa aattggagtt aggtattgac ctctcagaat cagttgccgt tctggaacat 134700
taaatgtatt ttttatgata tactccaacg catttatgtg ggcatacaac aagtcattac 134760
taatggagta ttccaagagt tttagttgtc tagtatttaa caagagaaga gatttcaaca 134820
gactgtttat gaactcgaat gccgcctcat tgtcgcttat attgatgatg tcgaattctc 134880
ccaatatcat caccgatgag tagctcatct tgttatcggg atccaagttt tctaaagatg 134940
tcattaaacc ctcgatcatg aatggattta tcatcatcgt ttttatgttg gacatgagct 135000
```

```
tagtccgttt gtccacatct atagacgacg atttctgaat tatttcatat atccctctct 135060
ttaactccag gaacttgtca ggatggtcta ctttaatatg ttctcgtcta agagatgaaa 135120
atctttggat ggttgcacgc gacttttctc taaaggatga cgttgcccaa gatcctctct 135180
taaatgaatc catcttatcc ttggacaaga tggacagtct attttcctta gatggtttaa 135240
tatttttgtt acccatgatc tataaaggta gacctaatcg tctcggatga cctatatatt 135300
tattttcagt tttattatac gcataaattg taaaaaatat gttaggttta caaaaatgtc 135360
tcgtggggca ttaatcgttt ttgaaggatt ggacaaatct ggaaaaacaa cacaatgtat 135420
gaacatcatg gaatcaatac cttcaaacac aataaaatac cttaactttc ctcagagatc 135480
cactgtcact ggaaagatga tagatgacta tctaactcgt aaaaaaacct ataatgatca 135540
tatagttaat ctattatttt gtgcaaatag atgggagttt gcatctttta tacaagaaca 135600
actagaacag ggaattactt taatagttga tagatacgca ttttctggag tagcgtatgc 135660
cgccgctaaa ggcgcgtcaa tgactctcag taagagttat gaatctggat tgcctaaacc 135720
cgacttagtt atattcttgg aatctggtag caaagaaatt aatagaaacg tcggcgagga 135780
aatttatgaa gatgttacat tccaacaaaa ggtattacaa gaatataaaa aaatgattga 135840
agaaggagat attcattggc aaattatttc ttctgaattc gaggaagatg taaagaagga 135900
gttgattaag aatatagtta tagaggctat acacacggtt actggaccag tggggcaact 135960
gtggatgtaa taaagtgaaa ttacattttt tataaataga tgttagtaca gtgttataaa 136020
tggatgaagc atattactct ggcaacttgg aatcagtact cggatacgtg tccgatatgc 136080
ataccgaact cgcatcaata tctcaattag ttattgccaa gatagaaact atagataatg 136140
atatattaaa caaggacatt gtaaatttta tcatgtgtag atcaaacttg gataatccat 136200
ttatctcttt cctagatact gtatatacta ttatagatca agagaactat cagactgagt 136260
tgattaattc attagacgac aatgaaatta tcgattgtat agttaataag tttatgagct 136320
tttataagga taacctagaa aatatagtag atgctatcat tactctaaaa tatataatga 136380
ataatccaga ttttaaaact acgtatgccg aagtactcgg ttccagaata gccgatatag 136440
atattaaaca agtgatacgt aagaatatac tacaattgtc taatgatatc cgcgaacgat 136500
atttgtgaaa aatattaaaa aaaaatactt tttttattaa atgacgtcgc ttcgcgaatt 136560
tagaaaatta tgctgtgata tatatcacgc atcaggatat aaagaaaaat ctaaattaat 136620
tagagacttt ataacagata gggatgataa atatttgatc attaagctat tgctttccgg 136680
attagacgat agaatttata acatgaacga taaacaaatt ataaaattat atagtataat 136740
atttaaacaa tctcaggaag atatgctaca agatttagga tacggatata taggagacac 136800
tattaggact ttcttcaaag agaacacaga aatccgtcca cgagataaaa gcattttaac 136860
tttagaagaa gtggatagtt ttttaactac gttatcatcc gtaactaaag aatcgcatca 136920
aataaaatta ttgactgatg tagcatctgt ttgtacatgt aatgatttaa aatgtgtagt 136980
catgcttatt gataaagatc taaaaattaa agcgggtcct cggtacgtac ttaacgctat 137040
tagtcctcat gcctatgatg tgtttagaaa atctaataac ttgaaagaga taatagaaaa 137100
ttcatctaaa caaaatctag actctatatc tatttctgtt atgactccaa ttaatcccat 137160
gttagcggaa tcgtgtgatt ctgtcaataa agcgtttaaa aaatttccat caggaatgtt 137220
tgcggaagtc aaatacgatg gtgaaagagt acaagttcat aaaaataata acgagtttgc 137280
cttctttagt agaaacatga aaccagtact ctctcataaa gtggattatc tcaaagaata 137340
cataccgaaa gcatttaaaa aagctacgtc tatcgtattg gattctgaaa ttgttcttgt 137400
```

agacgaacat aatgtaccgc taccgtttgg aagtttagga atacacaaaa agaaagaata 137460
taaaaactct aacatgtgtt tgttcgtgtt tgactgtttg tactttgatg gattcgatat 137520
gacggacatt ccattgtacg aacgaagatc ttttctcaaa gatgttatgg ttgaaatacc 137580
caatagaata gtattctcag agttgacgaa tattagtaac gagtctcagt taactgacgt 137640
attggatgat gcactaacga gaaaattaga aggattggtc ttaaaagata ttaatggagt 137700
atacgaaccg ggaaagagaa gatggttaaa aataaagcga gactatttga acgagggttc 137760
catggcagat tctgccgatt tagtagtact aggtgcttac tatggtaaag gagcaaaggg 137820
tggtatcatg gcagtctttc taatgggttg ttacgacgat gaatccggta aatggaagac 137880
ggttaccaag tgttcaggac acgatgataa tacgttaagg gagttgcaag accaattaaa 137940
gatgattaaa attaacaagg atcccaaaaa aattccagag tggttagtag ttaataaaat 138000
ctatattccc gattttgtag tagaggatcc aaaacaatct cagatatggg aaatttcagg 138060
agcagagttt acatcttcca agtcccatac cgcaaatgga atatccatta gatttcctag 138120
atttactagg ataagagagg ataaaacgtg gaaagaatct actcatctaa acgatttagt 138180
aaacttgact aaatcttaat agttacatac aaactgaaaa ttaaaataac actatttagt 138240
tggtggtcgc catggatggt gttattgtat actgtctaaa cgcgctagta aaacatggcg 138300
aggaaataaa tcatataaaa aatgatttca tgattaaacc atgttgtgaa agagtttgtg 138360
aaaaagttaa gaacgttcac atcgacggac aatctaaaaa caatacagtg attgcagatt 138420
tgccatatct ggataatgct gtatcggatg tatgcaattc actgtataaa aagaatgtat 138480
caagaatatc cagatttgct aatttgataa agatagatga cgatgacaag actcctactg 138540
gtgtatataa ttattttaaa cctaaagatg ccattcctgt tattatatcc ataggaaagg 138600
atagagatgt ttgtgaacta ttaatctcat ctgataaagc gtgtgcgtgt atagagttaa 138660
attcatatca cgtagccatt cttcccatgg atgtttcctt ttttaccaaa ggaaatgcat 138720
cattgattat tctcctgttt gatttctcta tcgatgcggc acctctctta agaagtgtaa 138780
ccgataataa tgttattata tctagacacc agcgtctaca tgacgagctt ccgagttcca 138840
attggttcaa gttttacata agtataaagt ccgactattg ttctatatta tatatggttg 138900
ttgatggatc tgtgatgcat gcgatagctg ataatagaac tcacgcaatt attagcaaaa 138960
atatattaga caatactacg attaacgatg agtgtagatg ctgttatttt gaaccacaga 139020
ttaggattct tgatagagat gagatgctca atggatcatc gtgtgatatg aacagacatt 139080
gtattatgat gaatttacct gatgtaggcg aatttggatc tagtatgttg ggaaatatg 139140 aacctgacat gattaagatt gctctttcgg tggctggtaa tttaataaga aatcgagact 139200
acattcccgg gagacgagga tatagctact acgtttacgg tatagcctct agataatttt 139260
tttaagcacg aaataaaaaa cataatttta aaccaatcta tttcatacta ttttgtgtga 139320
tcaccatgga cataaagata gatattagta tttctggtga taaatttacg gtgactacta 139380
ggagggaaaa tgaagaaaga aaaaaatatc tacctctcca aaaagaaaaa actactgatg 139440
ttatcaaacc tgattatctt gagtacgatg acttgttaga tagagatgag atgtttacta 139500
ttctagagga atattttatg tacagaggtc tattaggcct cagaataaaa tatggacgac 139560
tctttaacga aattaaaaaa ttcgacaatg atgcggaaga acaattcggt actatagaag 139620
aactcaagca gaaacttaga ttaaattttg aagagggagc agataacttt atagattata 139680
taaaggtaca aaaacaggat atcgtcaaac ttactgtata cattgcatat cttgatagga 139740
ttgtgtgcat gcgtggtaga tgtttggaga aatgagaaac tgttttctag atggaaatat 139800
tgtttacgag cgattaaact gtttattgat gatcacatgc ttgataagat aaaatctata 139860
ctgcagaata gactagtata tgtggaaatg tcatagaaag ttaaaagtta atgagagcaa 139920
aaatatataa ggttgtattc catatttgtt atttttttct gtaatagtta gaaaaataca 139980
ttcgatggtc tatctatcag attattatgt gttataaggt actttttctc ataataaact 140040
agagtatgag taagatagtg tttttcaaaa catataaatc taaaattgat ggatgagata 140100
tacagctatt aatttcgaaa atatatttta atctgataac tttaaacatg gatttttgat 140160
ggtggtttaa cgttttaaaa aaagattttg ttattgtagt atatgataat attaaaagat 140220
ggatataaag aatttgctga ctgtatgtac tattttttac attactacat tggctacggc 140280
agatatacct actccgccac tgccacacgc tccggtaaac ggggcatgtg acgagggaga 140340
atatcttgat aagaggcata atcaatgttg taatcagtgt ccacctggag aatttgccaa 140400
ggttagatgt aatggtaacg ataacacaaa atgtgaacgc tgcccacctc atacatatac 140460
cgcaatcccc aattactcta atggatgtca tcaatgtaga aaatgcccaa caggatcatt 140520
tgataaggta aagtgtaccg gaacacagaa cagtaaatgt tcgtgtcttc ctggttggta 140580
ttgcgctact gattcttcac agactgaaga ttgtcgagat tgtataccaa aaaggagatg 140640
tccatgcgga tactttggtg gaatagatga acaaggaaat cctatttgta aatcgtgttg 140700
tgttggtgaa tattgcgact acctacgtaa ttatagactt gatccatttc ctccatgcaa 140760
actatctaaa tgtaattaat tatgattttg atgataatgt taccatacat tatatcgcta 140820
cttggttagt gtattattca gtatgaagac ctattaataa ttacttatct tttgacgatc 140880
ttgttataat tataatataa aaacttatgg catagtaact cataattgct gacgcgataa 140940
attcgtaata atctgttttg ttcaaatttt tataaggaat ctacaggcat aaaaataaaa 141000
atataattta taatatactc ttacagcgcg ccatcatgaa taacagcagt aaattaattg 141060
ctgttattaa tggatttaga aatagtggac gattttgtga tattagtata gttattaatg 141120
atgaaatgat aaacgctcac agactcatcc tatctggagc ctccgaatat ttttccattc 141180
tgttttccaa taattttatc gattctaatg aatacgaagt taatctaagt catttagatt 141240
atcaaagtgt taacgatttg atcgattaca tttatgggat acctttgagc ctaactaacg 141300
ataacgtgaa atatattctt tcaaccgctg atttttttaca aattggatct gctattacgg 141360
agtgcgaaaa atacatactt aaaaatcttt gttctagaaa ctgtatcgat ttctacatat 141420
acgctgataa atataataac aagaaaatag aatcagcgtc gtttaacaca atattacaaa 141480
atattttgag actcatcaac gatgaaaact ttaaatactt aacagaggaa tcaatgataa 141540
aaattttaag cgatgatatg ttaaatataa aaaatgagga tttcgcccca ctaattctca 141600
ttaaatggtt agagagtact caacaaccat gcaccgtcga gttacttaaa tgcctcagaa 141660
tatcattgct ttccccacaa gttataaaat cactttatag tcatcgactg gttagttcaa 141720
tctacgaatg tataacattc ttaaacaata tagcattctt ggatgaatca tttcctagat 141780
accatagcat cgagttgata tctatcggta taagtaattc gcatgataag atttccataa 141840
actgctacaa tcataaaaaa aatacatggg aaatgatatc ttcacgtaga tataggtgta 141900
gtttcgcagt ggccgtcctg gataatatta tctatatgat gggtggatat gatcagtccc 141960
cgtatagaag ttcaaaggtt atagcgtaca atacatgtac aaattcttgg atatatgata 142020
taccagagct aaaatatcct cgttctaatt gtgggggact ggctgatgac gaatacattt 142080
attgtatagg cggcatacgc gatcaggatt catcgttgac atctagtatt gataaatgga 142140
agccatcaaa accatattgg cagaagtatg ctaaaatgcg cgaaccaaaa tgtgatatgg 142200
gggttgcgat gttaaacgga ttaatatatg tcatgggtgg aatcgttaaa ggtgacacgt 142260
gtaccgacgc actagagagt ttatcagaag atggatggat gaagcatcaa cgtcttccaa 142320
taaaaatgtc caatatgtcg acgattgttc atgatggcaa gatttatata tctggaggtt 142380
acaacaatag tagtgtagtt aatgtaatat cgaatctagt ccttagctat aattcgatat 142440
atgatgaatg gaccaaatta tcatcattaa acattcctag aattaatccc gctctatggt 142500
cagcgcataa taaattatat gtaggaggag gaatatctga tgatgttcga actaatacat 142560
ctgaaacata cgataaagaa aaagattgtt ggacattgga taatggtcac gtgttaccac 142620
gcaattatat aatgtataaa tgcgaaccga ttaaacataa atatccattg gaaaaaacac 142680
agtacacgaa tgattttcta aagtatttgg aaagttttat aggtagttga tagaacaaaa 142740
tacataattt tgtaaaaata aatcactttt tatactaata tgacacgatt accaatactt 142800
ttgttactaa tatcattagt atactctaca ccttctcctc agacatctaa aaaaataggt 142860
gatgatgcaa ctctatcatg taatcgaaat aatacaaatg actacgttgt tatgagtgct 142920
tggtataagg agcccaattc cattattctt ttagctgcta aaagcgacgt cttgtatttt 142980
gataattata ccaaggataa aatatcttac gactctccat acgatgatct agttacaact 143040
atcacaatta aatcattgac tgctagagat gccggtactt atgtatgtgc attctttatg 143100
acatcgccta caaatgacac tgataaagta gattatgaag aatactccac agagttgatt 143160
gtaaatacag atagtgaatc gactatagac ataatactat ctggatctac acattcaccg 143220
gaaactagtt ctgagaaacc tgattatata gataattcta attgctcgtc ggtattcgaa 143280
atcgcgactc cggaaccaat tactgataat gtagaagatc atacagacac cgtcacatac 143340
actagtgata gcattaatac agtaagtgca tcatctggag aatccacaac agacgagact 143400
ccggaaccaa ttactgataa agaagaagat catacagtca cagacactgt ctcatacact 143460
acagtaagta catcatctgg aattgtcact actaaatcaa ccaccgatga tgcggatctt 143520
tatgatacgt acaatgatac agtaccacca actactgtag gcggtagtac aacctctatt 143580
agcaattata aaaccaagga ctttgtagaa atatttggta ttaccgcatt aattatattg 143640
tcggccgtgg caattttctg tattacatat tatatatata ataaacgttc acgtaaatac 143700
aaaacagaga acaaagtcta gatttttgac ttacataaat gtctgggata gtaaaatcta 143760
tcatattgag cgggccatct ggtttaggaa agacagccat agccaaaaga ctatgggaat 143820
atatttggat ttgtggtgtc ccataccact agatttcctc gtcctatgga acgagaaggt 143880
gtcgattacc attacgttaa cagagaggcc atctggaagg gaatagccgc cggaaacttt 143940
ctagaacata ctgagttttt aggaaatatt tacggaactt ctaaaactgc tgtgaataca 144000
gcggctatta ataatcgtat ttgtgtgatg gatctaaaca tcgatggcgt tagaagtctt 144060
aaaaatacgt acctaatgcc ttactcggtg tatataagac ctacctctct taaaatggtt 144120
gagaccaagc ttcgtcgtag aaacactgaa gcggatgatg agattcatcg tcgtgtgatg 144180
ttggcaaaaa ctgacatgga tgaggcaggt gaagccggtc tattcgacac tattatcatt 144240
gaagatgatg tgaatttagc atatagtaag ttaattcaga tactacagga ccgtattaga 144300
atgtatttta acactaatta gagacttaag acttaaaact tgataattaa taatataact 144360
cgtttttata tgtgtctatt tcaacgtcta atgtattagt taaatattaa aacttaccac 144420
gtaaaactta aaatttaaaa tgatatttca ttgacagata gatcacacat tatgaacttt 144480
caaggacttg tgttaactga caattgcaaa aatcaatggg tcgttggacc attaatagga 144540
aaaggtggat tcggtagtat ttatactact aatgacaata attatgtagt aaaaatagag 144600
cccaaagcta acggatcatt atttaccgaa caggcatttt atactagagt acttaaacca 144660
tccgttatcg aagaatggaa aaaatctcac aatataaagc acgtaggtct tatcacgtgc 144720
aaggcatttg gtctatacaa atccattaat gtggaatatc gattcttggt aattaataga 144780
ttaggtgcag atctagatgc ggtgatcaga gccaataata atagactacc aaaaaggtcg 144840
gtgatgttga tcggaatcga aatcttaaat accatacaat ttatgcacga gcaaggatat 144900
tctcacggag atattaaagc gagtaatata gtcttggatc aaatagataa gaataaatta 144960
tatctagtgg attacggatt ggtttctaaa ttcatgtcta atggcgaaca tgttccattt 145020
ataagaaatc caaataaaat ggataacggt actctagaat ttacacctat agattcgcat 145080
aaaggatacg ttgtatctag acgtggagat ctagaaacac ttggatattg tatgattaga 145140
tggttgggag gtatcttgcc atggactaag atatctgaaa caaagaattg tgcattagta 145200
agtgccacaa aacagaaata tgttaacaat actgcgactt tgttaatgac cagtttgcaa 145260
tatgaaccta gagaattgct gcaatatatt accatggtaa actctttgac atattttgag 145320
gaacccaatt acgacaagtt tcggcacata ttaatgcagg gtgtatatta ttaagtgtgg 145380
tgtttggtcg ataaaaatta aaaaataact taatttatta ttgatctcgt gtgtacaacc 145440
gaaatcatgg cgatgtttta cgcacacgct ctcggtgggt acgacgagaa tcttcatgcc 145500
tttcctggaa tatcatcgac tgttgccaat gatgtcagga aatattctgt tgtgtcagtt 145560
tataataaca agtatgacat tgtaaaagac aaatatatgt ggtgttacag tcaggtgaac 145620
aagagatata ttggagcact gctgcctatg tttgagtgca atgaatatct acaaattgga 145680
gatccgatcc atgatcaaga aggaaatcaa atctctatca tcacatatcg ccacaaaaac 145740
tactatgctc taagcggaat cgggtacgag agtctagact tgtgtttgga aggagtaggg 145800
attcatcatc acgtacttga aacaggaaac gctgtatatg gaaaagttca acatgattat 145860
tctactatca aagagaaggc caaagaaatg agtacactta gtccaggacc tatcatcgat 145920
taccacgtct ggataggaga ttgtatctgt caagttactg ctgtggacgt acatggaaag 145980
gaaattatga gaatgagatt caaaaagggt gcggtgcttc cgatcccaaa tctggtaaaa 146040
gttaaacttg gggagaatga tacagaaaat ctttcttcta ctatatcggc ggcaccatcg 146100
aggtaaccac ctctctggaa gacagcgtga ataatgtact catgaaacgt ttggaatcta 146160
tacgccatat gtggtctgtt gtatatgatc attttgatat tgtgaatggt aaagaatgct 146220
gttatgtgca tacgcatttg tctaatcaaa atcttatacc gagtactgta aaaacaaatt 146280
tgtacatgaa gactatggga tcatgcattc aaatggattc catggaagct ctagagtatc 146340
ttagcgaact gaaggaatca ggtggatgga gtcccagacc agaaatgcag gaatttgaat 146400
atccagatgg agtggaagac actgaatcaa ttgagagatt ggtagaggag ttcttcaata 146460
gatcagaact tcaggctggt gaatcagtca aatttggtaa ttctattaat tgttaaacat 146520
acatctgttt cagctaagca actaagaaca cgtatacggc agcagcttcc ttctatactc 146580
tcatctttta ccaacacaaa gggtggatat ttgttcattg gagttgataa taatacacac 146640
aaagtatttg gattcacggt gggttacgac tacctcagac tggtagagaa tgatatagaa 146700
aagcatatca aaagactttg tgttgtgtat ttctgtgaga agaaagagga catcaagtac 146760
gcgtgtcgat tcatcaaggt atataaacct ggggatgagg ctacctcgac atacgtgtgc 146820
gctatcaaag tggaaagatg ctgttgtgct gtgtttgcag attggccaga atcatggtat 146880

```
atggatacta atggtatcaa gaagtattct ccagatgaat gggtgtcaca tataaaattt 146940
taattaatgt aatagagaac aaataataag gttgtaatat catatagaca ataactaaca 147000
attaattagt aactgttatc tctttttaac taaccaacta actatatacc tattaataca 147060
tcgtaattat agtttcttaa catctattaa tcattaattc gcttctttaa ttttttataa 147120
actaacattg ttaattgaaa agggataaca tgttacagaa tataaattat atatggattt 147180
ttttaaaaag gaaatacttg actggagtat atatttatct cttcattata tagcacgcgt 147240
gttttccaat ttttccacat cccatataat acaggattat aatctcgttc gaacatacga 147300
gaaagtggat aaaacaatag ttgatttttt atctaggttg ccaaatttat tccatatttt 147360
agaatatggg gaaaatattc tacatattta ttctatggat gatgctaata cgaatattat 147420
aatttttttt ctagatagag tattaaatat taataagaac gggtcattta tacacaatct 147480
cgggttatca tcatccatta atataaaaga atatgtatat caattagtta ataatgatca 147540
tccagataat aggataagac taatgcttga aaatggacgt agaacaagac atttttttgtc 147600
ttatatatca gatacagtta atatctatat atgtatttta ataaatcatg gattttatat 147660
agatgccgaa gacagttacg gttgtacatt attacataga tgtatatatc actataagaa 147720
atcagaatca gaatcataca atgaattaat taagatattg ttaaataatg gatccgatgt 147780
agataaaaaa gatacgtacg gaaacacacc ttttatccta ttatgtaaac acgatatcaa 147840
caacgtggaa ttgtttgaga tatgtttaga gaatgctaat atagactctg tagactttaa 147900
tagatataca cctcttcatt atgtctcatg tcgtaataaa tatgattttg taaagttatt 147960
aatttctaaa ggagcaaatg ttaatgcgcg taataaattc ggaactactc cattttattg 148020
tggaattata cacggtatct cgcttataaa actatatttg gaatcagaca cagagttaga 148080
aatagataat gaacatatag ttcgtcattt aataattttt gatgctgttg aatctttaga 148140
ttatctatta tccagaggag ttattgatat taactatcgt actatataca acgaaacatc 148200
tatttacgac gctgtcagtt ataatgcgta taatacgttg gtctatctat taaacaaaaa 148260
tggtgatttt gagacgatta ctactagtgg atgtacatgt atttcggaag cagtcgcaaa 148320
caacaacaaa ataataatgg aagtactatt gtctaaacga ccatctttga aaattatgat 148380
acagtctatg atagcaatta ctaaacataa acagcataat gcagatttat tgaaaatgtg 148440
tataaaatat actgcgtgta tgaccgatta tgatactctt atagatgtac agtcgctaca 148500
gcaatataaa tggtatattt taaaatgttt cgatgaaata gatatcatga agagatgtta 148560
tataaaaaat aaaactgtat tccaattagt tttttgtatc aaagacatta atactttaat 148620
gagatacggt aaacatcctt ctttcgtgaa gtgcactagt ctcgacgtat acggaagtcg 148680
tgtacgtaat atcatagcat ctattagata tcgtcagaga ttaattagtc tattatccaa 148740
gaagctggat cctggagata aatggtcgtg ttttcctaac gaaataaaat ataaaatatt 148800
ggaaaacttt aacgataacg aactatccac atatctaaaa atcttataaa cactattaaa 148860
atataaaatc taagtaggat aaaatcacac tacatcattg tttcctttta gtgctcgaca 148920
gtgtatacta tttttaacgc tcataaataa aaatgaaaac gatttccgtt gttacgttgt 148980
tatgcgtact acctgctgtt gtttattcaa catgtactgt acccactatg aataacgcta 149040
aattaacgtc taccgaaaca tcgtttaatg ataaacagaa agttacattt acatgtgatc 149100
agggatatca ttctttggat ccaaatgctg tctgcgaaac agataaatgg aaatacgaaa 149160
atccatgcaa gaaaatgtgc acagtttctg attatgtctc tgaattatat gataagccat 149220
```

```
tatacgaagt gaattccacc atgacactaa gttgcaacgg cgaaacaaaa tattttcgtt 149280
gcgaagaaaa aaatggaaat acttcttgga atgatactgt tacgtgtcct aatgcggaat 149340
gtcaacctct tcaattagaa cacggatcgt gtcaaccagt taaagaaaaa tactcatttg 149400
gggaatatat gactatcaac tgtgatgttg gatatgaggt tattggtgct tcgtacataa 149460
gttgtacagc taattcttgg aatgttattc catcatgtca acaaaaatgt gatatgccgt 149520
ctctatctaa cggattaatt tccggatcta cattttctat cggtggcgtt atacatctta 149580
gttgtaaaag tggttttaca ctaacggggt ctccatcatc cacatgtatc gacggtaaat 149640
ggaatcccgt actcccaata tgtgtacgaa ctaacgaaaa atttgatcca gtggatgatg 149700
gtcccgacga tgagacagat ttgagcaaac tctcgaaaga cgttgtacaa tatgaacaag 149760
aaatagaatc gttagaagca acttatcata taatcatagt ggcgttaaca attatgggcg 149820
tcatattttt aatctccgtt atagtattag tttgttcctg tgacaaaaat aatgaccaat 149880
ataagttcca taaattgcta ccgtaaatat aaatccgtta aaataattaa taatttaata 149940
acaaacaagt atcaaaagat taaagactta tagctagaat caattgagat gtcttcttca 150000
gtggatgttg atatctacga tgccgttaga gcatttttac tcaggcacta ttataacaag 150060
agatttattg tgtatggaag aagtaacgcc atattacata atatatacag gctatttaca 150120
agatgcgccg ttataccgtt cgatgatata gtacgtacta tgccaaatga atcacgtgtt 150180
aaacaatggg tgatggatac acttaatggt ataatgatga atgaacgcaa tgtttctgta 150240
agcgttggca ccggaatact attcatggaa atgtttttcg attacaataa aaatagtatc 150300
aacaatcaac taatgtatga tataattaat agcgtatcta taattctagc taatgagaga 150360
tatagaagcg cttttaacga cgatggtata tacatccgta gaaatatgat taacaagttg 150420
tacggatacg catctctaac tactattggc acgatcgctg gaggtgtttg ttattatctg 150480
ttgatgcatc tagttagttt gtataaataa ttatttcaat atactagtta aaattttaag 150540
attttaaatg tataaaaaac taataacgtt tttatttgta ataggtgcat tagcatccta 150600
ttcgaataat gagtacactc cgtttaataa actgagtgta aaactctata tagatggagt 150660
agataatata gaaaattcat atactgatga taataatgaa ttggtgttaa attttaaaga 150720
gtacacaatt tctattatta cagagtcatg cgacgtcgga tttgattcca tagatataga 150780
tgttataaac gactataaaa ttattgatat gtataccatt gactcgtcta ctattcaacg 150840
cagaggtcac acgtgtagaa tatctaccaa attatcatgc cattatgata agtaccctta 150900
tattcacaaa tatgatggtg atgagcgaca atattctatt actgcagagg gaaaatgcta 150960
taaaggaata aaatatgaaa taagtatgat caacgatgat actctattga gaaaacatac 151020
tcttaaaatt ggatctactt atatatttga tcgtcatgga catagtaata catattattc 151080
aaaatatgat ttttaaaaat ttaaaatata ttatcacttc agtgacagta gtcaaataac 151140
aaacaacacc atgagatata ttataattct cgcagttttg ttcattaata gtatacatgc 151200
taaaataact agttataagt ttgaatccgt caattttgat tccaaaattg aatggactgg 151260
ggatggtcta tacaatatat cccttaaaaa ttatggcatc aagacgtggc aaacaatgta 151320
tacaaatgta ccagaaggaa catacgacat atccgcattt ccaaagaatg atttcgtatc 151380
tttctgggtt aaatttgaac aaggcgatta taaagtgaaa gagtattgta cgggactatg 151440
cgtcgaagta aaaattggac caccgactgt aacattaact gaatacgacg accatatcaa 151500
tttgtacatc gagcatccgt atgctactag aggtagcaaa aagattccta tttacaaacg 151560
cggtgacatg tgtgatatct acttgttgta tacggctaac ttcacattcg gagattctaa 151620
```

```
agaaccagta ccatatgata tcgatgacta cgattgcacg tctacaggtt gcagcataga 151680
ctttgtcaca acagaaaaag tgtgcgtgac agcacaggga gccacagaag ggtttctcga 151740
aaaaattact ccatggagtt cgaaagtatg tctgacacct aaaaagagtg tatatacatg 151800
cgcaattaga tccaaagaag atgttcccaa tttcaaggac aaaatggcca gagttatcaa 151860
gagaaaattt aataaacagt ctcaatctta tttaactaaa tttctcggta gcacattaaa 151920
tgatgttacc acttttctta gcatgcttaa cttgactaaa tattcataac taatttttat 151980
taatgataca aaaacgaaat aaaactgcat attatacact ggttaacgcc cttataggct 152040
ctaaccattt tcaagatgag gtccctgatt atagtccttc tgttcccctc tatcatctac 152100
tccatgtcta ttagacgatg tgagaagact gaagaggaaa catggggatt gaaaataggg 152160
ttgtgtataa ttgccaaaga tttctatccc gaaagaactg attgcagtgt tcatctccca 152220
actgcaagtg aaggattgat aactgaaggc aatggattca gggatatacg aaacaccgat 152280
aaattataaa aaaagcaatg tgtccgctgt ttccgttaat aatactattt tcgtaactgg 152340
cggattattc ataaataact ctaatagcac gatcgtggtt aacaatatgg aaaaacttga 152400
catttataaa gacaaacaat ggtcgattat agaaatgcct atggctaggg tatatcacgg 152460
catcgactcg acatttggaa tgttatattt tgccggaggt ctatccgtta ccgaacaata 152520
tggtaattta gagaaaaaca acgagatatc ttgttacaat cctagaacga ataagtggtt 152580
tgatatttca tatactattt ataagatatc catatcatca ttgtgtaaac taaataacgt 152640
cttctatgta tttagtaagg acattggata tgtggaaaag tatgatggtg catggaagtt 152700
agtacatgat cgtctccccg ctataaaggc attatcaact tctccttatt gattgaaaat 152760
gaaaatataa atagttttta tgtatagcag tattacccta tagttttatt gcttactact 152820
aacatggata cagatgttac aaatgtagaa gatatcataa atgaaataga tagagagaaa 152880
gaagaaatac taaaaaatgt agaaattgaa aataataaaa acattaacaa gaatcatccc 152940
aatgaatata ttagagaagc actcgttatt aataccagta gtaatagtga ttccattgat 153000
aaagaagtta tagaatgtat ctgtcacgat gtaggaatat agatcatatc tactaatttt 153060
tataatcgat acaaaacata aaaaacaact cgttattaca tagcaggcat ggaatccttc 153120
aagtattgtt ttgataacga tggcaagaaa tggattatcg gaaatacttt atattctggt 153180
aattcaatac tctataaggt cagaaaaaat ttcactagtt cgttctacaa ttacgtaatg 153240
aagatagatc acaaatcaca caagccattg ttgtctgaaa tacgattcta tatatctgta 153300
ttggatcctt tgactatcga caactggaca cgggaacgtg gtataaagta tttggctatt 153360
ccagatctgt atggaattgg agaaaccgat gattatatgt tcttcgttat aaagaatttg 153420
ggaagagtat tcgccccaaa ggatactgaa tcagtcttcg aagcatgtgt cactatgata 153480
aacacgttag agtttataca ctctcaagga tttacccatg gaaaaataga accgaggaat 153540
atactgatta gaaataaacg tctttcacta attgactatt ctagaactaa caaactatac 153600
aagagtggaa actcacatat agattacaac gaggacatga taacttcagg aaatatcaat 153660
tatatgtgtg tagacaatca tcttggagca acagtttcaa gacgaggaga tttagaaatg 153720
ttgggatatt gcatgataga atggttcggt ggcaaacttc catggaaaaa cgaaagtagt 153780
ataaaagtaa taaaacaaaa aaaagaatat aaaaaattta tagctacttt ctttgaggac 153840
tgttttcctg aaggaaatga acctctggaa ttagttagat atatagaatt agtatacacg 153900
ttagattatt ctcaaactcc taattatgac agactacgta gactgtttat acaagattga 153960
```

aattatattc tttttttttat agagtgtggt agtgttacgg atatctaata ttaatattag 154020
actatctcta tcgcgctaca cgaccaatat cgattactat ggatatcttc tatgaaagga 154080
gagaatgtat tcatttctcc agcgtcaatc tcgtcagtat tgacaatact gtattatgga 154140
gctaatggat ccactgctga acagctatca aaatatgtag aaacggagga gaacacggat 154200
aaggttagcg ctcaaaatat ctcattcaaa tccataaata aagtatatgg gcgatattct 154260
gccgtgttta aagattcctt tttgagaaaa attggcgata agtttcaaac tgttgacttc 154320
actgattgtc gcactataga tgcaatcaac aagtgtgtag atatctttac tgaggggaaa 154380
atcaatccac tattggatga accattgtct cctagcaatt agtgccgtat actttaaagc 154440
aaaatggttg acgccattcg aaaaggaatt taccagtgat tatccctttt acgtatctcc 154500
gacggaaatg gtagacgtaa gtatgatgtc tatgtacggc gagctattta atcacgcatc 154560
tgtaaaagaa tcattcggca acttttcaat catagaactg ccatatgttg gagatactag 154620
tatgatggtc attcttccag acaagattga tggattagaa tccatagaac aaaatctaac 154680
agatacaaat tttaagaaat ggtgtaactc tctggaagct acgtttatcg atgttcacat 154740
tcccaagttt aaggtaacag gctcgtataa tctggtggat actctagtaa agtcaggact 154800
gacagaggtg ttcggttcaa ctggagatta tagcaatatg tgtaatttag atgtgagtgt 154860
cgacgctatg atccacaaaa cgtatataga tgtcaatgaa gagtatacag aagcagctgc 154920
agcaacttct gtactagtgg cagactgtgc atcaacagtt acaaatgagt tctgtgcaga 154980
tcatccgttc atctatgtga ttaggcatgt tgatggcaaa attcttttcg ttggtagata 155040
ttgctctcca acaactaatt gttaaccatt tttttaaaa aaaatagaaa aaacatgtgg 155100
tattagtgca ggtcgttgtt cttccaattg caattggtaa gatgacggcc aactttagta 155160
cccacgtctt ttcaccacag cactgtggat gtgacagact gaccagtatt gatgacgtca 155220
aacaatgttt gactgaatat atttattggt cgtcctatgc ataccgcaac aggcaatgcg 155280
ctggacaatt gtattccaca ctcctctctt ttagagatga tgcggaatta gtgttcatcg 155340
acattcgcga gctggtaaaa aatatgccgt gggatgatgt caaagattgt acagaaatca 155400
tccgttgtta tataccggat gagcaaaaaa ccatcagaga gatttcggcc atcatcggac 155460
tttgtgcata tgctgctact tactggggag gtgaagacca tcccactagt aacagtctga 155520
acgcattgtt tgtgatgctt gagatgctaa attacgtgga ttataacatc atattccggc 155580
gtatgaattg atgagttgta catcttggac attttctttc ttctcttctc cctttcttct 155640
cttctccctt tcttctcttc tcccttcctc cctcttctcc ctttcccaga aacaaacttt 155700
tttacccact ataaaataaa atgagtatac tacctattat atttcttcct atattttttt 155760
attcttcatt cgttcagact tttaacgcgc ctgaatgtat cgacaaaggg caatattttg 155820
catcattcat ggagttagaa aacgagccag taatcttacc atgtcctcaa ataaatacgc 155880
tatcatccgg atataatata ttagatattt tatgggaaaa acgaggagcg gataataata 155940
gaattatacc gatagataat ggtagcaata tgctaattct gaacccgaca caatcagact 156000
ctggtattta tatatgcatt accacgaacg aaacctactg tgacatgatg tcgttaaatt 156060
tgacaatcgt gtctgtctca gaatcaaata tagatcttat ctcgtatcca caaatagtaa 156120
atgagagatc tactggcgaa atggtatgtc ccaatattaa tgcatttatt gctagtaacg 156180
taaacgcaga tattatatgg agcggacatc gacgccttag aaataagaga cttaaacaac 156240
ggacacctgg aattattacc atagaagatg ttagaaaaaa tgatgctggt tattatacat 156300
gtgttttaga atatatatac ggtggcaaaa catataacgt aaccagaatt gtaaaattag 156360

```
aggtacggga taaaataata ccttctacta tgcaattacc agatggcatt gtaacttcaa 156420
taggtagtaa tttgactatt gcgtgtagag tatcgttgag acctcccaca acggatgcag 156480
acgtcttttg gataagtaat ggtatgtatt acgaagaaga tgatggggac ggaaacggta 156540
gaataagtgt agcaaataaa atctatatga ccgataagag acgtgttatt acatcccggt 156600
taaacattaa tcctgtcaag gaagaagatg ctacaacgtt tacgtgtatg gcgtttacta 156660
ttcctagcat cagcaaaaca gttactgtta gtataacgtg aatgtatgtt gttacatttc 156720
catgtcaatt gagtttataa gaatttttta tacattatct tccaacaaac aattgacgaa 156780
cgtattgcta tgattaaact cccacgaata ctatgcatat tattaatcat taacttgcag 156840
actataccta gtgctatttt gacatactca tgttcttgtg taattgcggt atctatatta 156900
ttaaagtacg taaatctagc tatagtttta ttatttaatt ttagataata taccgtctcc 156960
ttatttttaa aaattgccac atcctttatt aaatcatgaa tgggaatttc tatgtcatcg 157020
ttagtatatt gtgaacaaca agagcagata tctataggaa agggtggaat gcgatacatt 157080
gatctatgta gttttaaaac acacgcaaac tttgaagaat ttatataaat cattccatcg 157140
atacatcctt ctatgttgac atgtatatat ccaggaattc ttttattaat gtcaggaaat 157200
gtataaacta aaacattgcc cgaaagcggt gcctctatct gcgttatatc cgttcttaac 157260
ttacaaaatg taaccaatac ctttgcatga cttgttttgt tcggcaacgt tagtttaaac 157320
ttgacgaatg gattaattac aatagcatga tccgcgcatc tattaagttt ttttacttta 157380
acgcccttgt atgtttttac agagacttta tctaaatttc tagtgcttgt atgtgttata 157440
aatataacgg gatatagaac cgaatcacct accttagata cccaattaca ttttatcaga 157500
tccagataat aaacaaattt tgtcgcccta actaattcta tattgttata tattttacaa 157560
ttggttatga tatcatgtaa taacttggag tctaacgcgc atcgtcgtac gtttatacaa 157620
ttgtgattta gtgtagtata tctacacatg tatttttccg cactatagta ttctggacta 157680
gtgataaaac tatcgttata tctatcttca atgaactcat cgagatattg ctctctgtca 157740
tattcataca cctgcataaa ctttctagac atcttacaat ccgtgttatt ttaggatcat 157800
atttacatat ttacgggtat atcaaagatg ttagattagt taatgggaat cgtctataat 157860
aatgaatatt aaacaattat atgaggactt ttaccacaaa gcatcataaa aatgagtcgt 157920
cgtctgattt atgttttaaa tatcaaccgc gaatcaactc ataaaataca agagaatgaa 157980
atatatacat attttagtca ttgcaatata gaccatactt ctacagaact tgattttgta 158040
gttaaaaact atgatctaaa cagacgacaa cctgtaactg ggtatactgc actacactgc 158100
tatttgtata ataattactt tacaaacgat gtactgaaga tattattaaa tcatggagtg 158160
gatgtaacga tgaaaaccag tagcggacgt atgcctgttt atatattgct tactagatgt 158220
tgtaatattt cacatgatgt agtgatagat atgatagaca aagataaaaa ccacttatcg 158280
catagagact attccaacct attactagag tatataaaat ctcgttacat gttattaaag 158340
gaagaggata tcgatgagaa catagtatcc actttattag ataagggaat cgatcctaac 158400
tttaaacaag acggatatac agcgttacat tattattatt tgtgtctcgc acacgtttat 158460
aaaccaggtg agtgtagaaa accgataacg ataaaaaagg ccaagcgaat tatttctttg 158520
tttatacaac atggagctaa tctaaacgcg ttagataatt gtggtaatac accattccat 158580
ttgtatctta gtattgaaat gtgtaataat attcatatga ctaaaatgct gttgactttt 158640
aatccgaatt tcgaaatatg taataatcat ggattaacgc ctatactatg ttatataact 158700
```

```
tccgactaca tacaacacga tattcttgtt atgttaatac atcactatga aacaaatgtt 158760
ggagaaatgc cgatagatga gcgtcgtatg atcgtattcg agtttatcaa aacatattct 158820
acacgtccgg cagattcgat aacttatttg atgaataggt ttaaaaatat aaatatttat 158880
acccgctatg aaggaaagac attattacac gtagcatgtg aatataataa tacacaagta 158940
atagattatc ttatacgtat caacggagat ataaatgcgt taaccgacaa taacaaacac 159000
gctacacaac tcattataga taacaaagaa aattccccat ataccattaa ttgtttactg 159060
tatatactta gatatattgt agataagaat gtgataagat cgttggtgga tcaacttcca 159120
tctctaccta tctttcgtcg cttatcatac tagtcatatc ctaaatgttg atcatattcc 159180
accaaatgat tgtgaaagag attgagatta aatcgtctaa caaacaatta gtttttatga 159240
cattaacata taataaataa attaatcatt attgacttaa cgatgacgaa agttatcatc 159300
atcttaggat tcttgattat taatacaaat tcattgtcta tgaaatgtga acaaggtgtc 159360
tcatattata attcacaaga attaaagtgt tgtaaactat gtaagccagg aacatattca 159420
gatcatcgat gtgataaata cagcgatacc atttgtggac attgtccgag tgacacattc 159480
acgtcaatat ataatcgttc tccttggtgt catagttgta gaggtccatg tggtactaat 159540
cgagtagagg tcacaccttg tacacctacc acaaatagaa tctgtcattg tgactcgaat 159600
agttattgtc tccttaaagc ttctgatggt aactgtgtta catgtgctcc taaaacaaaa 159660
tgtggtcgtg ggtatggaaa gaaaggagaa gatgaaatgg gtaataccat ttgtaagaaa 159720
tgtcggaagg gtacttattc agatattgta tctgactctg atcaatgtaa accaatgaca 159780
agataagact tactcgcatc tactggatag acataaaata tcctcctcgt aataatgaaa 159840
tataaatata cactaattat taatatcaat aacaatcgag tattaatata taggtcattt 159900
ttaaatccct tttgggttcc gtcccaaacg gcgtttcggt ctgcgtcgcc gccatggcca 159960
tgccgagcct ctccgcgtgc tcctccatcg aggacgactt caactatggc agctcggtgg 160020
cgtctgccag cgtgcacata cgaatggcat ttctaagaaa agtctacggt atcctttgtc 160080
tacaatttct tttaacaacg gcaacaactg cagtattttt atactttgac tgcatgcgga 160140
catttataca agggagtcct gttctaatat tggcatcaat gttcggatct ataggcttga 160200
ttttcgcatt gactttacac agacataaac atcccctgaa tctgtacctg ctttgtggat 160260
ttacactgtc ggaatctcta acgctggcct ctgttgttac tttctatgat gtgcatgtcg 160320
ttatgcaagc tttcatgctg actactgcag cgtttcttgc tctgactaca tatactctac 160380
aatcaaagag agatttcagt aaacttggag caggattgtt tgctgctttg tggattttaa 160440
ttttgtcagg actcttgggg atatttgtgc aaaatgagac agtggagctg gtcctgtctg 160500
cttttggggc ccttgtattc tgtggattca ttatctatga cacgcactca ctaatacata 160560
agctctcgcc tgaagagtat gtgttagcct ctatcaatct ctacttggat atcatcaatc 160620
tgttcttgca tctgttgcag cttttggaag tatctaataa gaaataaagt ttaaaataga 160680
attaataaaa acatataggt catttttttaa acatggattg gaaaccaagg tagttagtta 160740
atacacacaa gatatatttt tttcacatca tccacccatg ggtaacacca aggttgttag 160800
ttaataatat acaagatatt ttttctcact ctgatccatg taaaccaagg acgagataag 160860
acactctcat tcctcatcca caacccatta aaaaaatgga aattaaagcc ctctattagc 160920
ataaacggct acaggtctac cttcacaatg gcctttcctt gtgcccagtt cagaccctgt 160980
cattgccacg ctactaagga ctccctgaat accgtggccg acgtcagaca ttgtctgact 161040
gaatacatcc tgtgggtttc tcatagatgg acccatagag aaagcgcagg gtctctctac 161100
```

aggcttctca tctctttcag aactgatgca acggagctct ttggtggtga gttgaaggat 161160
tcacttccgt gggacaattg cgtggagatc attaaatgtt tcatcagaaa tgactccatg 161220
aaaaccgccg aagaacttcg tgcaatcatt ggactttgta ctcaatcagc tatcgtctct 161280
ggaagagtct tcaacgataa gtatatcgac atactactta tgctgcgaaa gattctgaac 161340
gagaacgact atctcaccct cttggatcat atccgcactg ctaaatacta aatctccttc 161400
atgctctctc actacacttt ttatcatctt atgaggaatg attgccttcg tgaaatagga 161460
ataattagca ccagaatagc tatggattat tgtggtagag agtgcactat tctatgtcgt 161520
ctactggatg aagatgtgac gtacaaaaaa ataaaaccag agattgaaac gtgtcacaac 161580
ttatcaaaac atatagatag acgaggaaac aatgcgctac attgttacgt ctccaataaa 161640
tgcgatacag acattaagat tgttcggctg ttactctctc gcggagtcga gagactttgt 161700
agaaacaacg aaggattaac tccgctagga gcatacagta agcatagata cgtcaaatct 161760
cagattgtgc atctactgat atccagctat tcgaattcct ctaacgaact caagtcgaat 161820
ataaatgatt tcgatctgta ttcgtataat atcgacttac gtctgctaaa atacctaatt 161880
gtggataaac ggatacgtcc gtccaagaat acgaattatg caatcaatgg tctcggattg 161940
gtggatatat acgtaacgac gcctaatccg agaccagaag tattgctatg gcttcttaaa 162000
tcagaatgtt acagcaccgg ttacgtattt cgtacctgta tgtacgacag tgatatgtgt 162060
aagaactctc ttcattacta tatatcgtct catagagaat ctcaatctct atccaaggat 162120
gtaattaaat gtttgatcaa taacaatgtt tccattcatg gcagagacga aggaggatct 162180
ttacccatcc aatactactg gtctttctca accatagata tagagattgt taaattatta 162240
ataaaggatg tggacacgtg tagagtatac gacgtcagcc ctatattaga ggcgtattat 162300
ctaaacaagc gatttagagt aaccccatat aatgtagaca tggaaatcgt taatcttctt 162360
attgagagac gtcatactct tgtcgacgta atgcgtagta ttacttcgta cgattccaga 162420
gaatataacc actacatcat cgataacatt ctaaagagat ttagacaaca ggatgaatcc 162480
atcgtacaag ccatgttgat aaactactta cattacggcg atatggtaag tatacctatc 162540
attcaatgca tgttggataa cggacaacaa ctatcctctg cacgactact ttgttaataa 162600
taatctcgtc gatgtaaacg tcgtaaggtt tatcgtggaa aatatggaca cgcggctgta 162660
aatcacgtat cgaacaatgg ccgtctatgt atgtacggtc tgatattatc gagatttaat 162720
aattgcgggt atcactgtta tgaaaccata ctgatagatg tatttgatat actaagcaag 162780
tacatggata atatagatat gatcgataac tctactatat tacgcggtcg atgtcaataa 162840
tatacaattt gcaaagcggt tattggaata tggagcgagt gttacaacat cacacgctcg 162900
ataatcaata cggccatcca gaaaagcagt taccaaagag aaaacaaaac gaggatagtt 162960
gatttattac tgagttacca tcccactcta gagactatga ttgacgcatt taatagagat 163020
atacgctatc tatatcctga accattattc gcctgtatca gatacgcctt aatcctagat 163080
gatgattttc cttctaaagt aaatatgata tcttccggtc gtcataagga actaaagcgc 163140
tatagagtag acattaatag aatgaagaat gtctacatat caggcgtctc catgtttgat 163200
atattcttta aacggaacag acgccacaga ttgagatacg caaagaatcc gacatcaaat 163260
ggtacaaaaa agaactaacg tccatcatta cagaaactgt aaagaacaat gagaggatcg 163320
actccatagt ggacaacatt aatacagacg ataacttgat ttcgaaatta cccatggaga 163380
tactttatta ctccattaaa taatttatca tggagcgata atgtcctgtt tcatttgttt 163440

```
ccatgacata ttacaaaatc gattccgtcc aagatgataa aaacatttac cggcatcata 163500
aacacggagt ttattttata tgtctcgcat aaacattact aaaaaaatat attgttctgt 163560
ttttctttca catctttaat tatgaaaaag taaatcatta tgagatggac gagattgtac 163620
gcatcgttcg cgacagtatg tggtacatac ctaacgtatt tatggacgac ggtaagaatg 163680
aaggtcacgt ttctgtcaac aatgtctgtc atatgtattt tacgttcttt gatgtagata 163740
catcgtctca tctgtttaag ctagttatta aacactgcga tctgaataaa cgaggtaact 163800
ctccattaca ttgctatacg atgaatacac gatttaatcc atctgtatta aagatattgt 163860
tacaccacgg catgcgtaac tttgatagca aggatgacca ctatcaatcg ataacaagat 163920
ctttgatata ctaacggaca ccattgatga ctttagtaaa tcatccgatc tattgctgtg 163980
ttatcttaga tataaattca atgggagctt aaactattac gttctgtaca aaggatccga 164040
ccctaattgc gccgacgagg atgaactcac ttctcttcat tactactgta aacacatatc 164100
cacgttctac gaaagcaatt attacaagtt aagtcacact aagatgcgag ccgagaagcg 164160
attcatctac gcgataatag attatggagc aaacattaac gcggttacac acttaccttc 164220
aacagtatac caaacatagt cctcgtgtgg tgtatgctct tttatctcga ggatacgtaa 164280
taatcttgat tgtacaccca tcatggaacg attgtgcaac aggtcatatt ctcataatgt 164340
tactcaattg gcacgaacaa aaggaagaag gacaacatct actttatcta ttcataaaac 164400
ataatcaagg atacactctc aatatactac ggtatctatt agataggttc gacattcaga 164460
aagacgaata ctataatacc gcctttcaaa attgtaacaa caatgttgcc tcatacatcg 164520
gatacgacat caaccttccg actaaagacg gtattcgact tggtgtttga aaacagaaac 164580
atcatataca aggcggatgt tgtgaatgac atcatccacc acagactgaa agtatctcta 164640
cctatgatta aatcgttgtt ctacaagatg tctctcccta cgacgattac tacgtaaaaa 164700
agatactagc ctactgccta ttaagggacg agtcattcgc ggaactacat agtaaattct 164760
gtttaaacga ggactataaa agtgtattta tgaaaaatat atcattcgat aagatagatt 164820
ccatcatcgt gacataagtc gccttaaaga gattcgaatc tccgacaccg acctgtatac 164880
ggtatcacag ctatcttaaa gccatacatt cagacagtca catttcattt cccatgtacg 164940
acgatctcat agaacagtgc catctatcga tggagcgtaa aagtaaactc gtcgacaaag 165000
cactcaataa attagagtct accatcggtc aatctagact atcgtatttg cctccggaaa 165060
ttatgcgcaa tatcatctaa acagtatgtt gtacggaaag aaccattaca aatattatcc 165120
atgatagaaa gaaaatatct atatgattgg agaagtagga aacaggaaca agacgacgat 165180
tactacatta ttaaatcatg aagtccgtat tatactcgta tatattgttt ctctcatgta 165240
taataataaa cggaagagat atagcaccgc atgcaccatc cgatggaaag tgtaaagaca 165300
acgaatacaa acgccataat ttgtgtccgg gaacatacgc ttccagatta tgcgatagca 165360
agactaacac acaatgtacg ccgtgtggtt cgggtacctt cacatctcgc aataatcatt 165420
tacccgcttg tctaagttgt aacggaagac gcgatcgtgt aacacgactc acaatagaat 165480
ctgtgaatgc tctcccggat attattgtct tctcaaagga tcatccggat gcaaggcatg 165540
tgtttcccaa acaaaatgtg gaataggata cggagtatcc ggagacgtca tctgttctcc 165600
gtgtggtctc ggaacatatt ctcacaccgt ctcttccgca gataaatgcg aacccgtacc 165660
cagtaatacc tttaactata tcgatgtgga aattaatctg tatcccgtta acgacacatc 165720
gtgtactcgg acgaccacta ccggtctcag cgaatccatc tcaacgtcgg aactaactat 165780
tactatgaat cataaagact gtaatcccgt ctttcgtgat ggatacttct ccgttcttaa 165840
```

```
taaggtagcg acttcaggtt tctttacagg agaaaggtgt gcactctgaa tttcgagatt 165900

aaatgcaata acaaagattc ttcctccaaa cagttaacga aagcaaagaa tgatactatc 165960

atgccgcatt cggagactgt aactctagtg ggcgacatct atatactata tagtaatacc 166020

aatactcaag actacgaaac tgatacaatc tcttatcatg tgggtaatgt tctcgatgtc 166080

gatagccata tgcccggtag ttgcgatata cataaactga tcactaattc caaacccacc 166140

cactttttat agtaagtttt tcacccataa ataataaata caataattaa tttctcgtaa 166200

aagtagaaaa tatattctaa tttattgcac ggtaaggaag tagaatcata aagaacagta 166260

ctcaatcaat agcaattatg aaacaatata tcgtcctggc atgcatgtgc ctggcggcag 166320

ctgctatgcc tgccagtttt cagcaatcat cctcatcctc ctcctcgtgt acggaagaag 166380

aaaacaaaca tcatatggga atcgatgtta ttatcaaagt cacaaagcaa gaccaaacac 166440

cgaccaatga taagatttgc caatccgtaa cggaaattac agagtccgag tcagatccag 166500

atcccgaggt ggaatcagaa gatgattcca catcagtcga ggatgtagat cctcctacca 166560

cttattactc catcatcggt ggaggtctga gaatgaactt tggattcacc aaatgtcctc 166620

agattaaatc catctcagaa tccgctgatg gaaacacagt gaatgctaga ttgtccagcg 166680

tgtccccagg acaaggtaag gactctcccg cgatcactcg tgaagaagct cttgctatga 166740

tcaaagactg tgaggtgtct atcgacatca gatgtagcga agaagagaaa gacagcgaca 166800

tcaagaccca tccagtactc gggtctaaca tctctcataa gaaagtgagt tacgaagata 166860

tcatcggttc aacgatcgtc aatacaaaat gtgtcaagaa tctagagttt agcgttcgta 166920

tcggagacat gtgcaaggaa tcatctgaac ttgaggtcaa ggatggattc aagtatgtcg 166980

acggatcggc atctgaaggt gcaaccgatg atacttcact catcgattca acaaaactca 167040

aagcgtgtgt ctgaatcgat aactctattc atctgaaatt ggatgagtag ggttaatcga 167100

acgattcagg cacaccacga at                                         167122
```

<210> SEQ ID NO 2
<211> LENGTH: 24
<212> TYPE: DNA
<213> ORGANISM: Artificial Sequence
<220> FEATURE:
<223> OTHER INFORMATION: forward primer

<400> SEQUENCE: 2

```
aggaacagga tcattgtcat taca                                       24
```

<210> SEQ ID NO 3
<211> LENGTH: 24
<212> TYPE: DNA
<213> ORGANISM: Artificial Sequence
<220> FEATURE:
<223> OTHER INFORMATION: reverse primer

<400> SEQUENCE: 3

```
tgaactaaat gttccagatg agga                                       24
```

<210> SEQ ID NO 4
<211> LENGTH: 24
<212> TYPE: DNA
<213> ORGANISM: Artificial Sequence
<220> FEATURE:
<223> OTHER INFORMATION: foward primer

<400> SEQUENCE: 4
agttctgcat tcaattcggt gagt 24

<210> SEQ ID NO 5
<211> LENGTH: 24
<212> TYPE: DNA
<213> ORGANISM: Artificial Sequence
<220> FEATURE:
<223> OTHER INFORMATION: reverse primer

<400> SEQUENCE: 5
aattgtacca acggttcaag atgt 24

<210> SEQ ID NO 6
<211> LENGTH: 24
<212> TYPE: DNA
<213> ORGANISM: Artificial Sequence
<220> FEATURE:
<223> OTHER INFORMATION: reverse primer

<400> SEQUENCE: 6
tcgtttatca acactaccgt taga 24

<210> SEQ ID NO 7
<211> LENGTH: 189421
<212> TYPE: DNA
<213> ORGANISM: Vaccinia virus

<400> SEQUENCE: 7
ctgaaaggaa ataggaatag gaataggaat agtgtcataa tcgtatcaca ctattgagac 60
agaaaaagaa gaagtcgcga gaggtaactt tttgtgaatg tagttaagaa catttttgtt 120
ttgcaaaccg gaatatagtg tccggtacac ttttttaatt cgtggtgtgc ctgaatcgtt 180
cgattaaccc tactcatcca atttcagatg aatagagtta tcgattcaga cacacgcttt 240
gagttttgtt gaatcgatga gtgaagtatc atcggttgca ccttcagatg ccgatccgtc 300
gacatacttg aatccatcct tgacctcaag ttcagatgat tccttgcaca tgtctccgat 360
acgaacgcta aactctagat ttttgacgca ttttgtatcg acgatcgttg aaccgatgat 420
atcttcgtaa ctcactttct tatgagagat gttagacccg agtactggat gggtcttgat 480
gtcgctgtct ttctcttctt cgctacatct gatgtcgata gacacctcac agtctttgat 540
catagcaaga gcttcttcat gagtgatcgc gggagagtcc ttaccttgtc ctggggacac 600
gctggacaat ctagcattca ctgtgtttcc atcagcggat tctgagatgg atttaatctg 660
aggacatttg gtgaatccaa agttcattct cagacctcca ccgatgatgg agtaataagt 720
ggtaggagga tctacatcct cgactgatgt ggaatcatct tctgattcca cctcgggatc 780
tggatctgac tcggactctg taatttccgt tacggattgg caaatcttat cattggtcgg 840
tgtttggtct tgctttgtga ctttgataat aacatcgatt cccatatgat gtttgttttc 900
ttcttccgta cacgaggagg aggatgagga tgattgctga agactggcag gcatagcagc 960
tgccgccagg cacatgcatg ccaggacgat atattgtttc ataattgcta ttgattgagt 1020
actgttcttt atgattctac ttccttaccg tgcaataaat tagaatatat tttctacttt 1080
tacgagaaat taattattgt atttattatt tatgggtgaa aaacttacta taaaaagtgg 1140
gtgggtttgg aattagtgat cagtttatgt atatcgcaac taccgggcat atggctatcg 1200
acatcgagaa cattacccac atgataagag attgtatcag tttcgtagtc ttgagtattg 1260
gtattactat atagtatata gatgtcgccc actagagtta ctgtctccga atgcggcatg 1320
atagtatcat tctttgcttt cgttaactgt ttggaggaag aatctttgtt attgcattta 1380

```
atctcgaaat tcagagtgca cacctttctc ctgtaaagaa acctgaagtt gctaccttat   1440
taaggacgga gaagtattcc tcacgaaaga cgggattaca gtctttatga ttcatagtaa   1500
tagttagttc cgacgttgag atggattcgc tgagaccggt agtggtcgtc cgagtacacg   1560
atgtgtcgtt aactggatac aggttaattt ccacatcgat atagttaaag gtatttctgg   1620
gtacgggttc gcatttatct gcggaagaga cggtgtgaga atatgttccg agaccacacg   1680
gagaacagat gacgtctccg gatactccgt atcctattcc acattttgtt tgggaaacac   1740
atgccttgca tccggatgat cctttgagaa gacaataata tccgggagag cattcacaga   1800
ttctattgtg agtcgtgtta cacgatcgcg tcttccgtta caacttagac aagcgggtaa   1860
atgattattg cgagatgtga aggtacccga accacacggc gtacattgtg tgttagtctt   1920
gctatcgcat aatctggaag cgtatgttcc cggacacaaa ttatggcgtt tgtattcgtt   1980
gtctttacac tttccatcgg atggtgcatg cggtgctata tctcttccgt ttattattat   2040
acatgagaga aacaatatat acgagtataa tacggacttc atgatttaat aatgtagtaa   2100
tcgtcgtctt gttcctgttt cctacttctc caatcatata gatattttct ttctatcatg   2160
gataatattt gtaatggttc tttccgtaca acatactgtt tagatgatat tgcgcataat   2220
ttccggaggc aaatacgata gtctagattg accgatggta gactctaatt tattgagtgc   2280
tttgtcgacg agtttacttt tacgctccat cgatagatgg cactgttcta tgagatcgtc   2340
gtacatggga aatgaaatgt gtctgtccga atgtatggct ttaagatagc tgtgataccg   2400
tatacaggtc ggtgtcggag attcgaatct ctttaaggcg acttatgtca cgatgatgga   2460
atctatctta tcgaatgata tatttttcat aaatacactt ttatagtcct cgtttaaaca   2520
gaatttacta tgtagttccg cgaatgactc gtcccttaat aggcagtagg ctagtatctt   2580
ttttacgtag taatcgtcgt agggagagac atcttgtaga acaacgattt aatcataggt   2640
agagatactt tcagtctgtg gtggatgatg tcattcacaa catccgcctt gtatatgatg   2700
tttctgtttt caaacaccaa gtcgaatacc gtctttagtc ggaaggttga tgtcgtatcc   2760
gatgtatgag gcaacattgt tgttacaatt ttgaaaggcg gtattatagt attcgtcttt   2820
ctgaatgtcg aacctatcta gtagataccg tagtatattg agagtgtatc cttgattatg   2880
ttttatgaat agataaagta gatgttgtcc ttcttccttt tgttcgtgcc aagtgagtaa   2940
cattatgaga atatgacctg ttgcacaatc gttccatgat gggtgtacaa tcaagattat   3000
tacgtatcct cgagataaaa gagcatacac cacacgagga ctatgtttgg tatactgttg   3060
aaggtaagtg tgtaaccgcg ttaatgtttg ctccataatc tattatcgcg tagatgaatc   3120
gcttctcggc tcgcatctta gtgtgactta acttgtaata attgctttcg tagaacgtgg   3180
atatgtgttt acagtagtaa tgaagagaag tgagttcatc ctcgtcggcg caattagggt   3240
cggatccttt gtacagaacg taatagttta agctcccatt gaatttatat ctaagataac   3300
acagcaatag atcggatgat ttactaaagt catcaatggt gtccgttagt atatcaaaga   3360
tcttgttatc gattgatagt ggtcatcctt gctatcaaag ttacgcatgc cgtggtgtaa   3420
caatatcttt aatacagatg gattaaatcg tgtattcatc gtatagcaat gtaatggaga   3480
gttacctcgt ttattcagat cgcagtgttt aataactagc ttaaacagat gagacgatgt   3540
atccacatca aagaacgtga aatacatatg acagacattg ttgacagaaa cgtgaccttc   3600
attcttaccg tcgtccataa atacgttagg tataaaccac atactatcgc gaacgatgcg   3660
tacaatctcg tccatctcat aatgatttac tttttcataa ttagagatgt acgaaagaaa   3720
```

```
aagaaaaaga aaaagaaaaa cagaacaata tatttttta gtaatgttta tgcgagacat   3780
ataaaataaa ctccgtgttt atgatgccgg taaatgtttt tatcatcttg gacggaatcg   3840
attttgtaat atgtcatgga aacaaatgaa acaggacatt atcgctccat gataaattat   3900
ttaatggagt aataaagtat ctccatgggt aatttcgaaa tcaagttatc gtctgtatta   3960
atgttgtcca ctatggagtc gatcctctca ttgttcttta cagtttctgt aatgatggac   4020
gttagttctt ttttgtacca tttgatgtcg gattctttgc gtatctcaat ctgtggcgtt   4080
tgcttcgttt aaataatata tcaaacatgg agacgcctga tatgtagaca ttcttcattc   4140
tattaatgtc tgctctatag cgctttagtt ccttatgacg accggcgata tcatacttta   4200
ctttagaagg aaaatcatca tctaggatta aggcgtatct gatacaggcg aataatggtt   4260
caggatatag atagcgtata tctctattaa atgcgtcaat catagtctct agagtgggat   4320
ggtaactcag taataaatca actagcttcg ttttgttttc tcttctgtaa ctgcttttct   4380
ggatggccgt attgattatc gagcgtgaca ctcgctccat attccaataa ccgctttgca   4440
aattgtatat tattgacatc gaccgcgtaa tatagtagag ttatcgatca tatctatatc   4500
atccatgtac ttgcttagta tatcaaatac atctatcagt atggtttcat aacagtgata   4560
cccgcaatta ttaaatctcg ataatatcag accgtacata catagacggc cattgttcga   4620
tatgtgattt acagccgcgt gtccatattt tccacgataa accttacgac gtttacatcg   4680
acgagattat tattaacaaa gtagtcgtgc agaggatagt tgttgtccgt cgtcttatcc   4740
atggttgctc cgttatccaa catgcattga atgataggta tacttaccat atcgccgtaa   4800
tgtaagtagt ttatcaacat ggcttgtaca tcctgttgtc taaatctctt tagaatgtta   4860
tcgatgatgt agtggttata ttctctggaa tcgtacgaag taatactacg cattacgtcg   4920
acaagagtat gacgtctctc aataagaaga ttaacgattt ccatgtctac attatatggg   4980
gttactctaa atcgcttgtt tagataatac gcctctaata tagggctgac gtcgtatact   5040
ctacacgtgt ccacatcctt tattaataat ttaacaatct ctatatctat ggttgagcaa   5100
gaccagtagt attggatggg taaagatcct ccttcgtctc tgccatggat ggaaacattg   5160
ttatcgatca aacatttaat tacatccttg gatagagatt gagattctct atgagacgat   5220
atatagtaat gaagagagtt cttacacata tcactgtcgt acatacaggt acgaaatacg   5280
taaccggtgc tgtaacattc tgatttaaga agccatagca atacttctgg tctcggatta   5340
ggcgtcgtta cgtatatatc caccaatccg agaccattga ttgcataatt cgtattcttg   5400
gacggacgta tccgtttatc cacaattagg tattttagca gacgtaagtc gatattatcc   5460
gaatacagat cgaaatcatt tatattcgac ttgagttcgt tagaggaatt cgaatagctg   5520
gatatcagta gatgcacaat ctgagatttg acgtatctat gcttactgta tgctcctagc   5580
ggagttaatc cttcgttgtt tctacaaagt ctctcgactc cgcgagagag taacagccga   5640
acaatcttaa tgtctgtatc gcatttattg aagacgtaac aatgtagcgc attgtttcct   5700
cgtctatcta tatgttttga taagttgtga cacgtttcaa tctctggttt tattttttg   5760
tacgtcacat cttcatccag tagacgacat aaaatagtgc actctctacc acaataatcc   5820
atagctattc tggtgctaat tattcctatt tcacgaaggc aatcattcct cataagatga   5880
taaaaagtgt agtgagagag catgaaggag atttagtatt tagcagtgcg gatatgatcc   5940
aagagggtga gatagtcgtt ctcgttcaga atctttcgca gcataagtag tatgtcgata   6000
tacttatcgt tgaagactct tccagagacg atagctgatt gagtacaaag tccaatgatt   6060
gcacgaagtt cttcggcggt tttcatggag tcatttctga tgaaacattt aatgatctcc   6120
```

```
acgcaattgt cccacggaag tgaatccttc aactcaccac caaagagctc cgttgcatca   6180
gttctgaaag agatgagaag cctgtagaga gaccctgcgc tttctctatg ggtccatcta   6240
tgagaaaccc acaggatgta ttcagtcaga caatgtctga cgtcggccac ggtattcagg   6300
gagtccttag tagcgtggca atgacagggt ctgaacttgg cacaaggaga ggccattgtg   6360
aaggtagacc tgtagccgtc tatgctaata gagggcttta atttccattt ttttaatggg   6420
gttgtggatg aggaatgaga gtgatatcat attgagatac gtagttatgt agaggtgtat   6480
ttcctatatt atttactttc ggtttcatat tttaccaact ctttaataaa tttcttttca   6540
cgatgcatct tattaaatga cgttttctca taagtggaca tatagatgca aaagtaatga   6600
agaaaagtat tacctctatc atctacataa ttagggtctg ctcctttttt taacaactta   6660
tacagtacgt agtagtagtt tatcggtttt aaatcaagtc tagaatatat agtggattaa   6720
tatattttta tattcgctaa agctatctat actatcagaa agcatatcat tctcaacttc   6780
atcatgagtt aaatatttgt gtaatggaat gtgaccatca ctgtcatgac atactccttt   6840
aataggtttt ttaaaacaga tgattcaaat ccttcattca ttagataaca gtgtaacgga   6900
gtcgtacctt ctactagttt gtttatatca cagcattcta caaacagtct aaacaataga   6960
gaagacggac agactttaac gtataaatga cacatgttat cgatattcgt tgatgaatta   7020
ttattaaacg tagttatgat aaatgattct aacgacatct ctcgctagag ataaaatcta   7080
gtatcgtatc atactcgcat agcatagttt ttcataatta atacaatatt taaaagactt   7140
attcggaaag tattttaata catgtatcat cgatggagat ccatatgagg agtcacttgt   7200
agttcttcag tagtaataac agtgctatca tcgatagtat aattatatgt tgttgtaatt   7260
ggagtaactg ttggtagttc ttccgtggaa tcaataatta tactaacagc aatagtataa   7320
ttatataaat atgttccgtt gatatcacat attttaatga actcatttct aacaccctca   7380
gctatatctg tccaattaaa tgtagccaac aatctactac gttctctttg attgactact   7440
tgtacggtag cgacgctaca ctatctttat tgtcttctac atgctccaat tgaatgtcat   7500
gatacaacgc agtttttctt atgcatgttt cataacacca cgaacatgtc gcagtaagat   7560
aatttctgta aattcatgat tgccggtcat aaacaagccc gtcaataatt gtggctatat   7620
attcagttta tagagcaaaa taattaagca caatagcgct taatctcaaa atatgttatg   7680
tttatttttt tcatattaaa catactggtt aaaatcctct aaaggctgat cttcatctat   7740
aaatcaagat cataattaca tttagacagt ggtttcatgt ttataaaaat gttctttttg   7800
tgtgaataag gaatatacta atcaataatc aaccatcgac cccattacga tagtatgcag   7860
gcaacccccc attagagagg tacgtgtaat cagtctctcc agttttagta tttttataag   7920
tcattgttac ataaacggct tttaaacagt ctcctcgata ataagccata tctggaaatt   7980
tattaaatac tcgagtcatt ttacgcacgg tcaaaaaagt aagtaatgtc gacgacttct   8040
tacattctat agaaacacct agaatactca ttttcttttg gaaaatatcc tcagactctg   8100
atttgaacaa tgcacgacct atagtaaacc gtgaccaata agttatatta gtcaatggta   8160
tatccaaacc atcaggtgtg gatagtacgc cgatagtcca gtctttggta tcgatagtgt   8220
agttattgaa ctgagaagtt accgtatagt ctttttggtc atctctaaac aaggaaacta   8280
atacctctac actattgaac gatttatctt ccgtaatggg tggaataacg ggaatataaa   8340
gtggactagc gatggatgaa gtcacgaata taagacacgc tattaatccg tatatcatca   8400
ttttgatatt acttataata acgatttgtt taatttttag tttatactat taattgtaaa   8460
```

```
tgatattatt atttttttt aagtattatc agctttagtt tatactatta ctatttgtaa   8520
tatttagaca tagataaacg tgataaaagt ctatttgttt atatttattg cggatagcag   8580
tatttcccta taaaaagtat acgtcctgtg ttgtctttaa tcatgtacat gaatggatgg   8640
tttatgtaga ccttcgtacg atataccatc gaaaagttag tcataaatac tcctgtaacg   8700
gccgatgctt ctgtatactc ctcattaaca tctataaacg tcgtatgtag aaatttttct   8760
acagtgatag tttcattaca catcttgcta aaatctgcat aatatccgaa tatattagta   8820
agtcctaaat tttctaaaat cggtaccaga ttatacggtt ctgtcatttc cactttaaac   8880
tttggcatat acaagtctat acttttagta gataacatac cacaccattt tttaaatttt   8940
tcatctgtta tatttttttc tatgttatat ataccttcta tgtcgtccgg tagtataatt   9000
accatactag agtttccctc gtatggaata tcgataatag agaatcctcc gaataattca   9060
ttaatatgta catattgcaa gttattctcg gtacccacca tcatatcaac gctggtaact   9120
atattcttag aaatataaaa cttgtctgta tatgtaagat gtttagaaaa tggatatttc   9180
cacattgctt taaaatggac ggcgctaaca actgtcatac gagtattaat ggatagcgga   9240
ctagtcaata aggaattaat tttaccattt gtcattgtct taacccattc gttgattagt   9300
tcctttgttt ggttagcatt attaaagttt acagtttgaa aatcgtcttt tattttttgt   9360
aggaaggagg catggaactc gatactatcg ctaccgtata ttttatttgc ggtagctagt   9420
gtcgcacaat acggaatatc tacgtccatg tcattattgt catcgggtgt attctcattc   9480
atattctcta tatattttga tagttgttca gctgtagaac cagctgctcc atgatttaga   9540
atagataaag tagataaaat agaaactgga gaaatcaaaa cattttcatc agggtgtttt   9600
acgattagtt ctttaaagat atccatggta tagaccaaac aataacgata acgatatata   9660
tcataaataa ataatgttaa atttcagttt atgtttgtac cccgtattca tacttaacaa   9720
attggtattg cgtacacaat caatcatatt acataccatt aataatgcaa gcataaaaaa   9780
tcgttagtag atgtttctaa atataggttc cgtaagcaaa gaatataaga atgaagcggt   9840
aatgataaaa tcaattgtta tctaaaatga tcatactcat ttattttatt ctattatatt   9900
aacacataca tttttaacag caacacattc aatattgtat tgttattttt atattattta   9960
cacaattaac aatatattat tagtttatat tactgaatta ataatataaa attcccaatc  10020
ttgtcataaa cacacactga gaaacagcat aaacacaaaa tccatcaaaa atgttgataa  10080
attatctgat gttgttgttc gctgctatga taatcagatc attcgccgat agtggtaacg  10140
ctatcgaaac gacatcgcca gaaattacaa acgctacaac agatattcca gctatcagat  10200
tatgcggtcc agagggagat ggatattgtt tacacggtga ctgtatccac gctagagata  10260
ttgacggtat gtattgtaga tgctctcatg gttatacagg cattagatgt cagcatgtag  10320
tattagtaga ctatcaacgt tcagaaaacc caaacactac aacgtcatat atcccatctc  10380
ccggtattat gcttgtatta gtaggcatta ttattattac gtgttgtcta ttatctgttt  10440
ataggttcac tcgacgaact aaactactta tacaagatat ggttgtgcca taatttttat  10500
aaattttttt tatgagtatt tttacaaaaa tgtataaagt gtatgtctta tgtatattta  10560
taaaaatgct aaatatgcga tgtatctatg ttatttgtat ttatctaaac aatacctcta  10620
cctctagata ttatacaaaa atttttttatt tcggcatatt aaagtaaaat ctagttacct  10680
tgaaaatgaa tacagtgggt ggttccgtat caccagtaag aacataatag tcgaatacag  10740
tatccgattg agattttgca tacaatacta gtctagaaag aaatttgtaa tcattttctg  10800
tgacgggagt ccatatatct gtatcatcgt ctagtttatc agtgtcccat gctatattcc  10860
```

```
tgttatcatc attagttaat gaaaataact ctcgtgcttc agaaaagtca aatattgtat  10920
ccatacatac atctccaaaa ctatcgctta tacgtttatc tttaacgata cctataccta  10980
gatggttatt tactaacaga cattttccag atctattgac tataactcct atagtttcca  11040
catcaaccaa gtaatgatca tctattgtta tataacaata acataactct tttccatttt  11100
tatcagtatg tatatctata tcaacgtcgt cgttgtagtg aatagtagtc attgatctat  11160
tatatgaaac ggatatgtct agaacggcaa ttgttttacg tccagttaac actttctttg  11220
atttaaagtc tagagtcttt gcaaacataa tatccttatc cgactttata tttcctgtag  11280
ggtggtataa ttttatttg cctccacata tcggtgtttc caaatatatt actagacaat  11340
attccatata gttattagtt aagggtaccc aattagaaca cgtacgctta ttatcatcat  11400
ttggatcgta tttcataaaa gttattgtac tatcgatgtc aacacattct acatttttta  11460
atcgtctata tagtattttt ctgatatttt ctataatatc agaattgtct tccatcggaa  11520
gttgtatact atcggaatca gttacatgtt taaataattc tctgatgtca ttccttatac  11580
aatcaaattc attattaaac agtttaatag tctgtagacc tttattgtcg taaatatcca  11640
ttgtcttatt agttacgctt atttttatgt gttttacgtt gctttattat attttataag  11700
aatgattgtt tgacgaatca cgagaactat taagacacat tattaggtat atattataaa  11760
aaagtttttg attacgatgt tataagagga aagaggacac attaacatca tacatcaatt  11820
aactacattc ttataacatc gtaatcaaaa gaattgcaat tttgatgtat aacaactgtc  11880
aatgggttat ggaattgtat attacatatt atacggtatg ttggtaacga caaataccgg  11940
tcggtaattg tctgccggtg taatagaatt atatatatct atctattaca ccggccttgt  12000
atacataata ataagttgtg gtagtatgat ctccatattt ataatttagg actttgtatt  12060
cagtattttt ggaatcataa aaaataaaaa aaagttttac taatttaaaa tttaaaaagt  12120
atttacattt ttttcactgt ttagtcgcgg atatggaatt cgatcctgcc aaaatcaata  12180
catcatctat agatcatgta acaatattac aatacataga tgaaccaaat gatataagac  12240
taacagtatg cattatccga aatattaata acattacata ttatatcaat atcacaaaaa  12300
taaatacaca tttggctaat caatttcggg cttggaaaaa acgtatcgcc ggaagggact  12360
atatgactaa cttatctaga gatacaggaa tacaacaatc aaaacttact gaaactatac  12420
gtaactgtca aaaaaataga aacatatatg gtctatatat acactacaat ttagttatta  12480
attggataac cgatgtgatt gttcaatcaa tattaagagg gttggtaaat tggtacatag  12540
ctaataatac ctatactcca aatacaccca ataatacaac aaccatttct gagttggata  12600
tcatcaaaat actggataaa tacgaggacg tgtatagagt aagtaaagaa aaagaatgtg  12660
gaatttgcta tgaagttgtt tactcaaaac gatagatact ttggtttatt ggattcgtgt  12720
aatcatatat tttgcataac atgtatcaat atatggcata gaacacgaag agaaaccggt  12780
gcgtcggata attgtcctat atgccgtacc cgttttagaa acataacaat gagcaagttc  12840
tataagctag ttaactaata aataaaaagt ttaatttgtt gacgacgtat gtcgttattt  12900
tttctcgtat aaaagattaa tttgattcta atataatctt tagtattgga taaatatcaa  12960
ttcaaattaa ttccattaga ttatatcata aataaaaata gtagcacgca ctacttcagc  13020
caaatattct tttttgaaac gccatctatc gtagtgagga cacaagtgaa cctataatta  13080
tcaaatttat tagtatcagt cacatgaagg actttctgta gagtgacgat tccactatct  13140
gtggtacgaa cggtttcatc ttctttgatg ccatcaccca gatgttctat aaacttggta  13200
```

```
tcctcgtccg atttcatatc ctttgctaac caatacatat agctaaactc aggcatatgt  13260
tccacacatc ctgaacaatg aaattctcca gaagatgtta caatgtctag atttggacat  13320
ttggtttcaa ccgcgttaac atatgagtga acacacccat acatgaaagc gatgagaaat  13380
aggattctca tcttgccaaa atatcactag aaaaaattta tttatcaatt ttaaaggtat  13440
aaaaaatact tattgttgct cgaatatttt gtatttgatg gtatacggaa gattagaaat  13500
gtaggtatta tcatcaactg attctatggt tttatgtatt ctatcatgtt tcactattgc  13560
gttggaaata atatcatatg cttccacata tattttattt tgttttaact cataatactc  13620
acgtaattct ggattattgg catatctatg aataatttta gctccatgat cagtaaatat  13680
taatgagaac atagtattac cacctaccat tatttttttc atctcattca attcttaatt  13740
gcaaagatct atataatcat tatagcgttg acttatggac tctggaatct tagacgatgt  13800
acagtcatct ataatcatgg catatttaat acattgtttt atagcatagt cgttatctac  13860
gatgttagat atttctctca atgaatcaat cacataatct aatgtaggtt tatgacataa  13920
tagcattttc agcagttcaa tgtttttaga ttcgttgatg gcaatggcta tacatgtata  13980
tccgttattt gatctaatgt tgacatctga accggattct agcagtaaag atactagaga  14040
ttgtttatta tatctaacag ccttgtgaag aagtgtttct cctcgtttgt caatcatgtt  14100
aatgtcttta agataaggta ggcaaatgtt tatagtacta agaattgggc aagcataaga  14160
catgtcacaa agaccctttt tgtatgtata agtgtaaaaa ttataacatc catagttgga  14220
tttacatagg tgtccaatcg ggatctctcc atcatcgaga taattgatgg catctccctt  14280
cctttttag tagatatttc atcgtgtaag aatcaatatt aatatttcta aagtatccgt  14340
gtatagcctc tttatttacc acagttccat attccactag agggatatcg ccgaatgtca  14400
tatactcaat tagtatatgt tggaggacat ccgagttcat tgttttcaat atcaaagaga  14460
tggtttcctt atcatttctc catagtggta caatactaca cattatttcg tgcggctttc  14520
cattttccaa aaacaatttg accaaatcta aatctacatc tttattgtat ctataatcac  14580
tatttagata atcagccata attactcgag tgcaacatgt tagatcgtct atatatgaat  14640
aagccgtgtt atctattcct ttcattaaca atttaacgat gtctatatct atatgagatg  14700
acttaatata atattgaaga gctgtacaat agtttttatc tataaaagac ggcttgattc  14760
cgtgattaat tagacattta acaacttccg gacgcacata tgctctcgta tccgactctg  14820
aatacagatg agagatgata tacagatgca atacggtacc gcaatttcgt agttgataat  14880
catcatacgc gtatcagtac tcgtcctcat aaagaacact gcagccattt tctatgaaca  14940
aatcaataat tttaggaaca ggatcattgt cattacataa ttttctataa ctgaacgatg  15000
gttttcacat ttaacactca agtcaaatcc atgttctacc aacaccttta ttaagtcaac  15060
gtctacattt ttggatttca tatagctgaa tatattaaag tcatttatgt tgctaaatcc  15120
agtggcttct agtagagcca tcgctatatc ctttaacttt aacatgtcta ctatttgtgt  15180
attcttctaa tggggtagct gtctccaatt tttgcgtaat ggattagtgc cactgtctag  15240
tagtagtttg acgacctcga cattattaca atgctcatta aaaaggtatg cgtgtaaagc  15300
attattcttg aattggttcc tggtatcatt aggatctctg tctttcaaca tctgtttaag  15360
ttcatcgaga gccacctcct cattttccaa atagtcaaac attttgactg aatgagctac  15420
tgtgaactct atacacccac acaactaatg tcattaaata tcatgtcaaa aacttgtaca  15480
attattaata aaaataattt agtgtttaaa ttttaccagt tccagatttt acacctccgt  15540
taatacctcc attaacccca ctggacgatc ctcctcccca cattccaccg ccaccagatg  15600
```

```
tataagtttt agatccttta ttactaccat catgtccatg gataaagaca ctccacatgc  15660
cgccactacc ccctttagaa gacatattaa taagacttaa ggacaagttt aacaataaaa  15720
ttaatcacga gtaccctact accaacctac actattatat gattatagtt tctattttta  15780
cagtaccttg actaaagttt ctagtcacaa gagcaatact accaacctac actattatat  15840
gattatagtt tctattttta taggaacgcg tacgagaaaa tcaaatgtct aatttctaac  15900
ggtagtgttg ataaacgatt atcgtcaatg gatacctcct ctatcatgtc gtctattttc  15960
ttactttgtt ctattaactt attagcatta tatattattt gattataaaa cttatattgc  16020
ttattagccc aatctgtaaa tatcggatta ttaacatatc gtttctttgt aggtttattt  16080
aacttgtaca tcactgtaag catgtcctta ccatttattt taatttgacg catatccgca  16140
atttcttttt cgcagtcggt tataaattct atatatgatg gatacatgct acatgtgtac  16200
ttataatcga ctaatatgaa gtacttgata catatttcca gtaacgattt attattacca  16260
cctatgaata agtacctgtg atcgtctagg taatcaactg ttttcttaat acattcgatg  16320
gttggtaatt tactcagaat aatttccaat atcttaatat ataattctgc tatttctggg  16380
atatatttat ctgccagtat aacacaaata gtaatacatg taaacccata ttttgttatt  16440
atattaatgt ctgcgccatt atctattaac cattctacta ggctgacact atgcgactca  16500
atacaatgat aaagtatact acatccatgt ttatctattt tgtttatatc atcaatatac  16560
ggcttacaaa gttttagtat cgataacaca tccaactcac gcatagagaa ggtagggaat  16620
aatggcataa tatttattag gttatcatca ttgtcattat ctacaactaa gtttccattt  16680
tttaaaatat actcgacaac tttaggatct ctattgccaa atttttgaaa atatttattt  16740
atatgcttaa atctatataa tgtagctcct tcatcaatca tacatttaat aacattgatg  16800
tatactgtat gataagatac atattctaac aatagatctt gtatagaatc tgtatatctt  16860
ttaagaattg tggatattag gatattatta cgtaaactat tacacaattc taaaatataa  16920
aacgtatcac ggtcgaataa tagttgatca actatataat tatcgatttt gtgatttttc  16980
ttcctaaact gtttacgtaa atagttagat agaatattca ttagttcata accactatag  17040
ttactatcga ataacgcgtc aaatatttcc cgtttaatat cgcatttgtc aagataataa  17100
tagagtgtgg tatgttcacg ataagtataa taacgcatct ctttttcgtg tgaaattaaa  17160
tagtttatca cgtccaaaga tgtagcataa ccatcttgtg acctagtaat aatataataa  17220
tagagaactg ttttacccat tctatcatca taatcagtgg tgtaatcgta atcgtaatcg  17280
tctaattcat catcccaatt ataatattca ccagcacgtc taatctgttc tattttgatc  17340
ttgtatccat actgtatgtt gctacatgta ggtattcctt tatccaataa tagtttaaac  17400
acatctacat tgggatttga tgttgtagcg tatttttcta caatattaat accatttttg  17460
atactattta tttctatacc tttcgaaatt agtaatttca ataagtctat atcgatgtta  17520
ttagaacata gatattcgaa tatatcaaaa tcattgatat ttttatagtc gactgacgac  17580
aataacaaaa tcacaacatc gtttttgata ttattatttt tcttggtaac gtatgccttt  17640
aatggagttt caccatcata ctcatataat ggatttgcac cactttctat caatgattgt  17700
gcactgctgg catcgatgtt aaatgtttta caactatcat agagtatctt atcgttaacc  17760
atgattggtt gttgatgcta tcgcattttt tggtttcttt catttcagtt atgtatggat  17820
ttagcacgtt tgggaagcat gagctcatat gatttcagta ctgtagtgtc agtactatta  17880
gtttcgatca gatcaatgtc tagatctata gaatcaaaac acgataggtc agaagataat  17940
```

```
gaatatctgt acgcttcttt ttgtactgta acttctggtt ttgttagatg gttgcatcgt  18000
gctttaacgt caatggtaca aattttatcc tcgctttgtg tatcatattc gtctctacta  18060
taaaattgta tattcagatt atcatgagat gtgtatacgc taacggtatc aataaacgga  18120
gcacaccatt tagtcataac cgtaatccaa aaatttttaa agtatatctt aacgaaagaa  18180
gttgtgtcat tgtctacggt gtatggtact agatcctcat aagtgtatat atctagagta  18240
atgtttaatt tatcaaatgg ttgataatat ggatcgtcgt ggcaatttcc taagacgaaa  18300
ataagacata aacacgcaat aaatctaatc gaagacatgg ttactcctta aaaaaatacg  18360
aataatcacc ttggctattt agtaagtgtc atttaacact atactcatat taatccatgg  18420
actcataatc tctatacggg attaacggat gttctatata cggggatgag tagttctctt  18480
ctttaacttt atacttttta ctaatcatat ttagactgat gtatgggtaa tagtgtttga  18540
agagctcgtt ctcatcatca gaataaatca atatctctgt ttttttgtta tacagatgta  18600
ttacagcctc atatattacg taatagaacg tgtcatctac cttattaact ttcaccgcat  18660
agttgtttgc aaatacggtt aatcctttga cctcgtcgat ttccgaccaa tctgggcgta  18720
taatgaatct aaactttaat ttcttgtaat cattcgaaat aatttttagt ttgcatccgt  18780
agttatcccc tttatgtaac tgtaaatttc tcaacgcgat atctccatta ataatgatgt  18840
cgaattcgtg ttgtataccc atactgaatg gatgaacgaa tatcaacggc gttaatagta  18900
atttactttt tcatctttac atattgggta ctagttttac tatcataagt ttataaattc  18960
cacaagctac tatggaataa gccaaccatc ttagtataac acacatgtct taaagtttat  19020
taattaatta catgttgttt tatatatcgc tacgaattta aacagagaaa tcagtttagg  19080
aaaaaaaatt atctatctac atcatcacgt ctctgtattc tacgatagag tgctacttta  19140
agatgagaca tatccgtgtc atcaaaaata tactccatta aaatgattat tccggcagcg  19200
aacttgatat tggatatatc acaacctttg ttaatatcta cgacaataga cagcagtccc  19260
atggttccat aaacagtgag tttatctttc tttgaagaga tattttgtag agatcttata  19320
aaactgtcga atgacatcgc atttatattt ttagctaaat cgtatatgtt accatcgtaa  19380
tatctaaccg cgtctatctt aaacgtttcc atcgctttaa agacgtttcc gatagatggt  19440
ctcatttcat cagtcatact gagccaacaa atataatcgt gtataacatc tttgatagaa  19500
tcagactcta aagaaaacga atcggcttta ttatacgcat tcatgataaa cttaatgaaa  19560
aatgtttttc gttgtttaag ttggatgaat agtatgtctt aataattgtt attatttcat  19620
taattaatat ttagtaacga gtacactcta taaaaacgag aatgacataa ctagttatca  19680
aagtgtctag gacgcgtaat tttcatatgg tatagatcct gtaagcattg tctgtattct  19740
ggagctattt tctctatcgc attagtgagt tcagaatatg ttataaattt aaatcgaata  19800
acgaacataa ctttagtaaa gtcgtctata ttaactcttt tattttctag ccatcgtaat  19860
accatgttta agatagtata ttctctagtt actacgatct catcgttgtc tagaatatca  19920
catactgaat ctacatccaa ttttagaaat tggtctgtgt tacatatctc ttctatatta  19980
ttgttgatgt attgtcgtag aaaactatta cgtagaccat tttctttata aaacgaatat  20040
atagtactcc aattatcttt accgatatat ttgcacacat aatccattct ctcaatcact  20100
acatctttaa gattttcgtt gttaagatat ttggctaaac tatataattc tattagatca  20160
tcaacagaat cagtatatat ttttctagat ccaaagacga actctttggc gtcctctata  20220
atattcccag aaaagatatt ttcgtgtttt agtttatcga gatctgatct gttcatatac  20280
gccatgattg tacggtacgt tatgataacc gcataaaata aaaatccatt ttcattttta  20340
```

accaatacta ttcataattg agattgatgt aatactttgt tactttgaac gtaaagacag 20400
tacacggatc cgtatctcca acaagcacgt agtaatcaaa tttggtgttg ttaaacttcg 20460
caatattcat caatttagat agaaacttat actcatcatc tgttttagga atccatgtat 20520
tattaccact ttccaactta tcattatccc aggctatgtt tcgtccatca tcgttgcgca 20580
gagtgaataa ttcttttgta ttcggtagtt caaatatatg atccatgcat agatcggcaa 20640
agctattgta gatgtgattt ttcctaaatc taatataaaa ctcgtttact agcaaacact 20700
ttcctgattt atcaaccaag acacatatgg tttctaaatc tatcaagtgg tggggatcca 20760
tagttatgac gcagtaacat atattattac attcttgact gtcgctaata tctaaatatt 20820
tattgttatc gtattggatt ctgcatatag atggcttgta tgtcaaagat atagaacaca 20880
taaccaattt atagtcgcgc tttacattct cgaatctaaa gttaagagat ttagaaaaca 20940
ttatatcctc ggatgatgtt atcactgttt ctggagtagg atatattaaa gtctttacag 21000
atttcgtccg attcaaataa atcactaaat aatatcccac attatcatct gttagagtag 21060
tatcattaaa tctattatat tttatgaaag atatatcact gctcacctct atatttcgta 21120
catttttaaa ctgtttgtat aatatctctc tgatacaatc agatatatct attgtgtcgg 21180
tagacgatac cgttacattt gaattaatgg tgttccattt tacaactttt aacaagttga 21240
ccaattcatt tctaatagta tcaaactctc catgattaaa tattttaata gtatccattt 21300
tatatcacta cggacacaaa gtagctgaca taaaccattg tataattttt atgttttatg 21360
tttattagcg tacacatttt ggaagttccg gcttccatgt atttcctgga gagcaagtag 21420
atgatgagga accagatagt ttatatccgt acttgcactt aaagtctaca ttgtcgttgt 21480
atgagtatga tcttttaaac ccgctagaca agtatccgtt tgatattgta ggatgtggac 21540
atttaacaat ctgacacgtg ggtggatcgg accattctcc tcctgaacac aggacaccag 21600
agttaccaat caacgaatat ccactattgc aactataagt tacaacgctc ccatcggtat 21660
aaaaatcctc gtatccgtta tgtcttccgt tggatataga tggaggggat tggcatttaa 21720
cagattcaca aataggtgcc tcgggattcc ataccataga tccagtagat cctaattcac 21780
aatacgattt agattcaccg atcaaatgat atccgctatt acaagagtac gttatactag 21840
agccaaagtc tactccacca atatcaagtt ggccattatc gatatctcga ggcgatgggc 21900
atctccgttt aatacattga ttaaagagtg tccatccagt acctgtacat ttagcatata 21960
taggtcccat tttttgcttt ctgtatccag gtagacatag atattctata gtgtctccta 22020
tgttgtaatt agcattagca tcagtctcca cactattctt aaatttcata ttaatgggtc 22080
gtgacggaat agtacagcat gatagaacgc atcctattcc caacaatgtc aggaacgtca 22140
cgctctccac cttcatattt atttatccgt aaaaatgtta tcctggacat cgtacaaata 22200
ataaaaagcc catatatgtt cgctattgta gaaattgttt ttcacagttg ctcaaaaacg 22260
atggcagtga cttatgagtt acgttacact ttggagtctc atctttagta aacatatcat 22320
aatattcgat attacgagtt gacatatcga acaaattcca agtatttgat tttggataat 22380
attcgtattt tgcatctgct ataattaaga tataatcacc gcaagaacac acgaacatct 22440
ttcctacatg gttaaagtac atgtacaatt ctatccattt gtcttcctta actatatatt 22500
tgtatagata attacgagtc tcgtgagtaa ttccagtaat tacatagatg tcgccgtcgt 22560
actctacagc ataaactata ctatgatgtc taggcatggg agactttttt atccaacgat 22620
ttttagtgaa acattccaca tcgtttaata ctacatattt ctcatacgtg gtataaactc 22680

```
cacccattac atatatatca tcgtttacga ataccgacgc gcctgaatat ctaggagtaa  22740
ttaagtttgg aagtcttatc catttcgaag tgccgtgttt caaatattct gccacacccg  22800
ttgaaataga aaattctaat cctcctatta catataactt tccatcgtta acacaagtac  22860
taacttctga ttttaacgac gacatattag taaccgtttt ccattttttc gttttaagat  22920
ctacccgcga tacggaataa acatgtctat tgttaatcat gccgccaata atgtatagac  22980
aattatgtaa aacatttgca ttatagaatt gtctatctgt attaccgact atcgtccaat  23040
attctgttct aggagagtaa tgggttattg tggatatata atcagagttt ttaatgacta  23100
ctatattatg ttttatacca tttcgtgtca ctggctttgt agatttggat atagttaatc  23160
ccaacaatga tatagcattg cgcatagtat tagtcataaa cttgggatgt aaaatgttga  23220
tgatatctac atcgtttgga tttttatgta tccactttaa taatatcata gctgtaacat  23280
cctcatgatt tacgttaacg tcttcgtggg ataagatagt tgtcagttca tcctttgata  23340
attttccaaa ttctggatcg gatgtcaccg cagtaatatt gttgattatt tctgacatcg  23400
acgcattata tagtttttta attccatatc ttttagaaaa gttaaacatc cttatacaat  23460
ttgtgaaatt aatattatga atcatagttt ttacacatag atctactaca ggcggaacat  23520
caattattat ggcagcaact agtatcattt ctacattgtt tatggtgatg tttatcttct  23580
tccagcgcat atagtctaat agcgattcaa acgcgtgata gtttatacca ttcaatataa  23640
tcgcttcatc ctttagatgg tgatcctgaa tgcgtttaaa aaaattatac ggagacgccg  23700
taataatttc cttattcact tgtataattt ccccattgat agaaaatatc acgctttcca  23760
ttcttaaagt actataagta attatagtat aatgtaaacg tttatatatt caatattttt  23820
ataaaaatca ttttgacatt aattcctttt taaatttccg tctatcatct atagaaacat  23880
attctatgaa tttataaaat gcttttacgt gtcctatcgt aggcgataga accgctaaaa  23940
agcctattga atttctacaa aagaatctgt tatatggtat agggagagta taaaacatta  24000
aatgtccgta cttattaaag tattcagtag ccaatcctaa ctctttcgaa tacttattaa  24060
tggctcttgt tctgtacgaa tctatttttt tgaacaacgg acctagtggt atatcttgtt  24120
ctatgtatct aaaataatgt ctgactagat ccgttagttt aatatccgca gtcatcttgt  24180
ctagaatggc aaatctaact gcgggtttag gctttagttt agtttctata tctacatcta  24240
tgtctttatc taacaccaaa aatataatag ctaatatttt attacaatca tccggatatt  24300
cttctacgat ctcactaact aatgtttctt tggttatact agtatagtca ctatcggaca  24360
aataaagaaa atcagatgat cgatgaataa tacatttaaa ttcatcatct gtaagatttt  24420
tgagatgtct cattagaata ttattagggt tagtactcat tatcattcgg cagctattac  24480
ttattttatt atttttcacc atatagatca atcattagat catcaaaata tgtttcaatc  24540
atcctaaaga gtatggtgaa tgactcttcc catctaattt ctgaacgttc accaatgtct  24600
ctagccactt tggcactaat agcgatcatt cgcttagcgt cttctatatt attaactggt  24660
tgattcaatc tatctagcaa tggaccgtcg gacagcgtca ttctcatgtt cttaatcaat  24720
gtacatacat cgccgtcatc taccaattca tccaacaaca taagcttttt aaaatcatca  24780
ttataatagg tttgatcgtt gtcatttctc caaagaatat atctaataag tagagtcctc  24840
atgcttagtt aacaactatt ttttatgtta aatcaattag tacaccgcta tgtttaatac  24900
ttattcatat tttagttttt aggattgaga atcaatacaa aaaattaatg catcattaat  24960
tttagaaata cttagtttcc acgtagtcaa tgaaacattt gaactcatcg tacaggacgt  25020
tctcgtacag gacgtaacta taaaccggtt tatatttgtt caagatagat acaaatccga  25080
```

```
taactttttt tacgaattct acgggatcca ctttaaaagt gtcataccgg gttcttttta  25140
ttttttaaa cagatcaatg gtgtgatgtt gattaggtct tttacgaatt tgatatagaa  25200
tagcgtttac atattctcca taatggtcaa tcgccatttg ttcgtatgtc ataaattctt  25260
taattatatg acactgtgta ttgtttagtt catccttgtt cattgttagg aatctatcca  25320
aaatggcaat tatactagaa ctataggtgc gttgtataca catattgatg tgtctgttta  25380
tacaatccat gatatttgga tccatgctac taccttcggg taaaattgta gcatcatata  25440
ccatttctag tactttaggt tcattattat ccattgcaga ggacgtcatg atcgaatcat  25500
aaaaaaatat attattttta tgttattttg ttaaaaataa tcatcgaata cttcgtaaga  25560
tactccttca tgaacataat cagttacaaa acgtttatat gaagtaaagt atctacgatt  25620
tttacaaaag tccggatgca taagtacaaa gtacgcgata aacggaataa taatagattt  25680
atctagtcta tctttttcta tagctttcat agttagatac atggtctcag aagtaggatt  25740
atgtaacatc agcttcgata aaatgactgg gttatttagt cttacacatt cgctcataca  25800
tgtatgaccg ttaactacag agtctacact aaaatgattg aacaatagat agtctaccat  25860
tgtttcgtat tcagatagta cagcgtagta catggcatct tcacaaatta tatcattgtc  25920
taatagatat ttgacgcatc ttatggatcc cacttcaaca gccatcttaa aatcggtaga  25980
atcatattgc tttcctttat cattaataat ttctagaaca tcatctctat cataaaagat  26040
acaaatatta actgtttgat ccgtaataac attgctagtc gatagcaatt tgttaataag  26100
atgcgctggg ctcaatgtct taataagaag tgtaagagga ctatctccga atttgttttg  26160
tttattaaca tccgttgatg gaagtaaaag atctataatg tctacattct tgactgtttt  26220
agagcataca atatggagag gtgtatttcc atcatgatct ggttttgagg gactaattcc  26280
tagtttcatc atccatgaga ttgtagaagc ttttggattg tctgacataa gatgtctatg  26340
aatatgattt ttgccaaatt tatccactat cctggcttcg aatccgatgg acattatttt  26400
tttaaacact ctttctgaag gatctgtaca cgccaacaac ggaccacatc cttcttcatc  26460
aaccgagttg ttaatcttgg ctccatactg taccaataaa tttattctct ctatgacttc  26520
atcatctgtt cccgagagat aatatagagg cgttttatgc tgtttatcac acgcgtttgg  26580
atctgcgccg tgcgtcagca gcatcgcgac tattctatta ttattaattt tagaagctat  26640
atgcaatgga taatttccat catcatccgt ctcatttgga gagtatcctc tatgaagaag  26700
ttcttcgaca aatcgttcat ctagtccttt aattccacaa tacgcatgta gaatgtgata  26760
attatttcca gaaggttcga tagcttgtag catattccta aatacatcta aatttttact  26820
attatatttg gcataaagag atagataata ctcggccgac ataatgttgt ccattgtagt  26880
ataaaaatta atatttctat ttctgtatat ttgcaacaat ttactctcta taacaaatat  26940
cataacttag ttcttttatg tcaagaaggc actggtttag ttcatctata aatgtcacgc  27000
cataactacc acgcatgcca tactcagaat tatgataaag atatttatcc ttggggtgta  27060
ggtaatgggg attaatcttt gttggatcag tctctaagtt aacacatgtc acacatgatc  27120
catttatagt tatatcacac gatgatgatt tatgaattga ttccggaaga tcgctatcgt  27180
attttgtggt tccacaattc atttccatac atgttattgt cacactaata ttatgatgaa  27240
ctttatctag ccgctgagtg gtaaacaaca gaacagatag tttattatct ttaccaacac  27300
cctcagccgc tgccacaaat ctctgatccg tatccatgat ggtcatgttt atttctagtc  27360
cgtatccagt caacactatg ttagcatttc tgtcgatata gctttcactc atatgacact  27420
```

```
caccaataat agtagaatta atgtcgtaat ttacaccaat agtgagttcg gcggcaaagt  27480
accaataccg gtaatcttgt cgaggaggac atatagtatt cttgtattct actgaatacc  27540
cgagagatgc gatacaaaag agtaagacta atttgtaaac catcttactc aaaatatgta  27600
acaatagtac gatgcaatga gtaagacaat aggaaatcta tcttatatac acataattat  27660
tctatcaatt ttaccaatta gttagtgtaa tgttaacaaa aatgtgggag aatctaatta  27720
gtttttcttt acacaattga cgtacatgag tttgagttcc ttgtttttgc taattatttc  27780
atccaattta ttattcttga ctatatcgag atcttttgta taggagtcag acttgtattc  27840
aacatgcttt tctataatca ttttagctat ttcggcatca tccaatagta cattttccag  27900
attagcagaa tagatattaa tgtcgtattt gaacagagcc tgtaacatct caatgtcttt  27960
attatctata gccaatttaa tgtccggaat gaagagaagg gaattattgg tgtttgtcga  28020
cgtcatatag tcgagcaaga gaatcatcat atccacgtgt ccattttttta tagtgatgtg  28080
aatacaacta aggagaatag ccagatcaaa agtagatggt atctctgaaa gaaagtagga  28140
aacaatactt acatcattaa gcatgacggc atgataaaat gaagttttcc atccagtttt  28200
cccatagaac atcagtctcc aatttttctt aacaaacagt tttaccgttt gcatgttacc  28260
actatcaacc gcataataca atgcagtgtt tcccttgtca tcaaattgtg aatcatccag  28320
tccactgaat agcaaaatct ttactatttt ggtatcttcc aatgtggctg cctgatgtaa  28380
tggaaattca ttctctagaa gatttttcaa tgctccagcg ttcaacaacg tacatactag  28440
acgcacgtta ttatcagcta ttgcataata caaggcacta tgaccgttga tatccgcctt  28500
aaatgcatct ttgctagaga gaaagctttt cagctgctta gacttccaag tattaattcg  28560
tgacagatcc atgtctgaaa cgagacgcta attagtgtat atttttttcat tttttataat  28620
tttgtcatat tgcaccagaa ttaataatat ctctaataga tctgattagt agatacatgg  28680
ctatcgcaaa acaacatata cacatttaat aaaaataata tttattaaga aaattcagat  28740
ttcacgtacc catcaatata aataaaataa tgattcctta caccgtaccc atattaagga  28800
gattccacct tacccataaa caatataaat ccagtaatat catgtctgat gatgaacaca  28860
aatggtgtat taaattccag tttttcagga gatgatctcg ccgtagctac catgatagta  28920
gatgcctctg ctacagttcc ttgttcgtcg acatctatct ttgcattctg aaacatttta  28980
taaatatata atgggtccct agtcatatgt ttaaacgacg cattatctgg attaaacata  29040
ctaggagcca tcatttcggc tatcgactta atatccctct tattttcgat agaaaattta  29100
gggagtttaa gattgtacac tttattccct aattgagacg accaatagtc taattttgca  29160
gccgtgatag aatctgtgaa atgggtcata ttatcaccta ttgccaggta catactaata  29220
ttagcatcct tatacggaag gcgtaccatg tcatattctt cgtcatcgat tgtgattgta  29280
tttccttgca atttagtaac tacgttcatc atgggaaccg ttttcgtacc gtacttatta  29340
gtaaaactag cattgcgtgt tttagtgata tcaaacggat attgccatat acctttaaaa  29400
tatatagtat taatgattgc ccatagagta ttattgtcga gcatattaga atctactaca  29460
ttagacatac cggatctacg ttctactata gaattaattt tattaaccgc atctcgtcta  29520
aagtttaatc tatataggcc gaatctatga tattgttgat aatacgacgg tttaatgcac  29580
acagtattat ctacgaaact ttgataagtt agatcagtgt acgtatattt agatgttttc  29640
agcttagcta atcctgatat taattctgta aatgctggac ccagatctct ttttctcaaa  29700
tccatagtct tcaataattc tattctagta ttacctgatg caggcaatag cgacataaac  29760
atagaaaacg aatagccaaa cggcgagaag acaatattat catcttgaat atttttatac  29820
```

```
gctactatac cggcattggt aaatccttgc agacgatagg tagacgctga acacgctaac  29880
gatagtatca ataacgcaat catgatttta tggtattaat aattaacctt atttttatgt  29940
tcggtataaa aaaattattg atgtctacac atccttttgt aattgacatc tatatatcct  30000
tttgtataat caactctaat cactttaact tttacagttt tccctaccag tttatcccta  30060
tattcaacat atctatccat atgcatctta acactctctg ccaagatagc ttcagagtga  30120
ggatagtcaa aaagataaat atatagagca taatcattct cgtatactct gccctttatt  30180
acatcacccg cattgggcaa cgaataacaa aatgcaagca tcttgttaac gggctcgtaa  30240
attgggataa aaattatgtt tttattgatt ttatatctat tttattcaag agaatattca  30300
ggaatttctt tttccggttg tatctcgtcg cagtatatat catttgtaca ttgtttcata  30360
tttttaata gtttacacct tttagtagga ctagtatcgt acaattcata gctgtatttt  30420
gaattccaat cacgcataaa aatatcttcc aattgttgac gaagacctaa tccatcatcc  30480
ggtgtaatat taatagatgc tccacatgta tccgtaaagt aatttcctgt ccaatttgag  30540
gtacctatat aggccgtttt atcggttacc atatatttgg catggtttac cctagaatac  30600
ggaatgggag gatcagcatc tggtacaata aatagcttta cttctatatt tatgttttta  30660
gattttagca tagcgataga tcttaaaaag tttctcatga taaacgaaga tcgttgccag  30720
caactaatca atagcttaac ggatacttgt ctgtctatag cggatcttct taattcatct  30780
tctatataag gccaaaacaa aattttaccc gccttcgaat aaataatagg gataaagttc  30840
ataacagata cataaacgaa tttactcgca tttctaatac atgacaataa agcggttaaa  30900
tcattggttc tttccatagt acatagttgt tgcggcgcag aagcaataaa tacagagtgt  30960
ggaacgccgc ttacgttaat actaagagga tgatctgtat tataatacga cggataaaag  31020
tttttccaat tatatggtag attgttaact ccaagatacc agtatacctc aaaaatttga  31080
gtgagatccg ctgccaagtt cctattattg aagatcgcaa tacccaattc tttgacctga  31140
gttagtgatc tccaatccat gttagcgctt cctaaataaa tatgtgtatt atcagatatc  31200
caaaattttg tatgaagaac tcctcctagg atatttgtaa tatctatgta tcgtacttca  31260
actccggcca tttgtagtct ttcaacatcc tttaatggtt tgttagattt attgacggct  31320
actctaactc gtactcctct tttgggtaat tgtacaatct cgtttaatat tatcgtgccg  31380
aaattcgtac ccacttcatc cgataaactc caataaaaag atgatatatc tagtgttttt  31440
gtggtattgg atagaatttc cctccacatg ttaaatgtag acaaatatac tttatcaaat  31500
tgcataccta taggaatagt ctctgtaatc actgcgattg tattatccgg attcatttta  31560
tttgttaaaa aataatccta tatcacttca ctctattaaa aatccaagtt tctatttctt  31620
tcatgactga ttttttaact tcatccgttt ccttatgaag atgatgtttg gcaccttcat  31680
aaatttttat ttctctatta caatttgcat gttgcatgaa ataatatgca cctaaaacat  31740
cgctaatctt attgtttgtt ccctggagta tgagagtcgg gggggtgtta atcttggaaa  31800
ttatttttct aaccttgttg gtagccttca agacctgact agcaaatcca gccttaattt  31860
tttcatgatt gattaatggg tcgtattggt atttataaac tttatccata tctctagata  31920
ctgattctgg acatagcttt ccgactggcg catttggtgt gatggttccc ataagtttgg  31980
cagctagcag attcagtctt gaaacagcat ctgcattaac tagaggagac attagaatca  32040
ttgctgtaaa caagtttgga ttatcgtaag aggctagtat agaaattgtt gctcccatgg  32100
aatgacccaa taagtagatt taatagttac cacgtgctgt accaaagtca tcaatcatca  32160
```

```
ttttttcacc attacttctt ccatgtccaa tatgatcatg tgagaatact aaaattccta  32220
acgatgatat gttttcagct agttcgtcat aacgtccaga atgtttacca gctccatgac  32280
ttatgaatac taatgcctta ggatatgtaa taggtttcca atatatgtaa tcattgtcca  32340
gattgaacat acagtttgca ctcatgattc acgttatata actatcaata ttaacagttc  32400
gtttgatgat catattattt ttatgtttta ttgataattg taaaaacata caattaaatc  32460
aatatagagg aaggagacgg ctactgtctt ttgtgagata gtcatggcga ctaaattaga  32520
ttatgaggat gctgtttttt actttgtgga tgatgataaa atatgtagtc gcgactccat  32580
catcgatcta atagatgaat atattacgtg gagaaatcat gttatagtgt ttaacaaaga  32640
tattaccagt tgtggaagac tgtacaagga attgatgaag ttcgatgatg tcgctatacg  32700
gtactatggt attgataaaa ttaatgagat tgtcgaagct atgagcgaag gagaccacta  32760
catcaatttt acaaaagtcc atgatcagga aagtttattc gctaccatag gaatatgtgc  32820
taaaatcact gaacattggg gatacaaaaa gatttcagaa tctagattcc aatcattggg  32880
aaacattaca gatctgatga ccgacgataa tataaacatc ttgatacttt ttctagaaaa  32940
aaaattgaat tgatgatata ggggtcttca taacgcataa ttattacgtt agcattctat  33000
atccgtgtta aaaaaaatta tcctatcatg tatttgagag ttttatatgt agcaaacatg  33060
atagctgtga tgccaataag ctttagatat tcacgcgtgc tagtgttagg gatggtatta  33120
tctggtggtg aaatgtccgt tatataatct acaaaacaat catcgcatat agtatgcgat  33180
agtagagtaa acatttttat agtttttact ggattcatac atcgtctacc caattcggtt  33240
ataaatgaaa ttgtcgccaa tcttacaccc aacccttgt tatccattag tatagtatta  33300
acttcgttat ttatgtcata aactgtaaat gattttgtag atgccatatc atacatgata  33360
ttcatgtccc tattataatc attactaact ttatcacaat atatgttgat aatatctata  33420
tatgatctag tctttgtggg caactgtcta tacaagtcgt ctaaacgttg tttactcata  33480
tagtatcgaa cagccatcat tacatggtcc cgttccgttg atagataatc gagtatgtta  33540
gtggacttgt caaatctata taccatattt tctggaagtg gatatacata gtcgtgatca  33600
acattattgc tagcctcatc ttctatatcc tgtactatac cattatctat atcatctaca  33660
taatctacga tattattaca cataaacatc gacaacatac tattgtttat tatctaagtc  33720
ctgttgatcc aaacccttga tctcctctat ttgtactatc tagagattgt acttcttcca  33780
gttctggata atatatacgt tgatagatta gctgagctat tctatctcca gtatttacat  33840
taaacgtaca ttttccatta ttaataagaa tgactcctat gtttccccta taatcttcgt  33900
ctattacacc gcctcctata tcaatgcctt ttagtgacag accagaccta ggagctattc  33960
taccatagca gaacttaggc atggacatac taatatctgt cttaattaac tgtctttctc  34020
ctggagggat agtataatcg taagcgctat acaaatcata tccggcagca cccggcgatt  34080
gcctagtagg agatttagct ctgttagttt ccttaacaaa tctaactggt gagttaatat  34140
tcatgttgaa cataaaacta atattttatt tcaaaattat ttaccatccc atatattcca  34200
tgaataagtg tgatgattgt acacttctat agtatctata tacgattcac gataaaatcc  34260
tcctatcaat agcagtttat tatccactat gatcaattct ggattatccc tcggataaat  34320
aggatcatct atcagagtcc atgtattgct ggattcacaa taaaattccg catttctacc  34380
aaccaagaat aaccttctac cgaacactaa cgcgcatgat ttataatgag gataataagt  34440
ggatggtcca aactgccact gatcatgatt gggtagcaaa tattctgtag ttgtatcagt  34500
ttcagaatgt cctcccatta cgtatataac attgtttata gatgccactg ctggattaca  34560
```

```
tctaggtttc agaagactcg gcatattaac ccaagcagca tccccgtgga accaacgctc  34620
aacagatgtg ggatttggta gacctcctac tacgtataat ttattgttag cgggtatccc  34680
gctagcatac agtctggggc tattcatcgg aggaattgga atccaattgt ttgatatata  34740
atttacagct atagcattgt tatgtatttc attgttcatc catccaccga tgagatatac  34800
tacttctcca acatgagtac ttgtacacat atggaatata tctataattt gatccatgtt  34860
cataggatac tctatgaatg gatacttgta tgatttgcgt ggttgtttat cacaatgaaa  34920
tattttggta cagtctagta tccattttac attatttata cctctgggag aaagataatt  34980
tgacctgatt acatttttga taaggagtag cagatttcct aatttatttc ttcgctttat  35040
ataccactta atgacaaaat caactacata atcctcatct ggaacattta gttcatcgct  35100
ttctagaata agttttatag atagataatc aaaattgtct atgatgtcat cttccagttc  35160
caaaaagtgt ttggcaataa agtttttagt atgacataag agattggata gtccgtattc  35220
tatacccatc atgtaacact cgacacaata ttcctttcta aaatctcgta agataaagtt  35280
tatacaagtg tagatgataa attctacaga ggttaatata gaagcacgta ataaattgac  35340
gacgttatga ctatctatat atacctttcc agtatacgag taaataacta tagaagttaa  35400
actgtgaatg tcaaggtcta gacaaaccct tgtaactgga tctttatttt tcgtgtattt  35460
ttgacgtaaa tgtgtgcgaa agtaaggaga taactttttc aatatcgtag aattgactat  35520
tatattgcca cctatagcat caataattgt tttgaatttc ttagtcatag acaatgctaa  35580
tatattctta cagtacacag tattgacaaa tatcggcatt tatgtttctt taaaagtcaa  35640
catctagaga aaaatgatta tctttttgag acataactcc catttttttgg tattcaccca  35700
cacgtttttc gaaaaaatta gtttttcctt ccaatgatat attttccatg aaatcaaacg  35760
gattggtaac attataaatt tttttaaatc ccaattcaga aatcaatcta tccgcgacga  35820
attctatata tgttttcatc atttcacaat tcattcctat aagtttaact ggaagagccg  35880
cagtaagaaa ttcttgttca atggataccg catctgttat aatagatcta acggtttctt  35940
cactcggtgg atgcaataaa tgtttaaaca tcaaacatgc gaagtcgcag tgtagaccct  36000
cgtctctact aattagttcg ttggaaaacg tgagtccggg cattaggcca cgctttttaa  36060
gccaaaatat ggaagcgaat gatccagaaa agaaaattcc ttctactgca gcaaaggcaa  36120
taagtctctc tccataaccg gcgctgtcat gtatccactt ttgagcccaa tcggccttct  36180
tttttacaca aggcatcgtt tctatggcat taaagagata gttttttttca ttactatctt  36240
taacataagt atcgatcaaa agactataca tttccgaatg aatgttttca atggccatct  36300
gaaatccgta gaaacatcta gcctcggtaa tctgtacttc tgtacaaaat cgttccgcca  36360
aattttcatt cactattccg tcactggctg caaaaaacgc caatacatgt tttataaaat  36420
atttttcgtc tggtgttagt ttattccaat cattgatatc tttagatata tctacttctt  36480
ccactgtcca aaatgatgcc tctgcctttt tatacatgtt ccagatgtca tgatattgga  36540
ttgggaaaat aacaaatcta tttggatttg gtgcaaggat gggttccata actaaattaa  36600
caataacaat aaattttttt tcagttatct atatgcctgt acttggatct tttgtacatc  36660
gatatcgccg caatcactac aataattaca agtattattg atagcattgt tattagtact  36720
atcataatta aattatcgac attcatgggt gctgaataat cgttattatc atcattatca  36780
ttttgtaatt gtgacatcat actagataaa tcgtttgcga gattgttgtg ggaagcgggc  36840
atggaggatg cattatcatt attatttaac gccttccatt tggattcaca aatgttacgc  36900
```

```
acattcaaca ttttatggaa actataattt tgtgaaaaca gataacaaga aaactcgtca  36960
tcgttcaaat ttttaacgat agtaaaccga ttaaacgtcg agctaatttc taacgctagc  37020
gactctgttg gatatgggtt tccagatata tatcttttca gttcccctac gtatctataa  37080
tcatctgtag gaaatggaag atatttccat ttatctactg ttcctaatat catatgtggt  37140
ggtgtagtag aaccattaag cgcgaaagat gttatttcgc atcgtatttt aacttcgcaa  37200
taatttctgg ttagataacg cactctacca gtcaagtcaa tgatattagc ctttacagat  37260
atattcatag tagtcgtaac gatgactcca tcttttagat gcgatactcc tttgtatgta  37320
ccagaatctt cgtacctcaa actcgatata tttaaacaag ttaatgagat attaacgcgt  37380
tttatgaatg atgatatata accagaagtt ttatcctcgg tggctagcgc tataacctta  37440
tcattataat accaactagt gtgattaata tgtgacacgt tagtgtgggt acaaatatgt  37500
acattatcgt ctacgtcgta ttcgatacat ccgcatacag ccaacaaata taaaatgaca  37560
aatactctaa cgccgttcgt acccatcttg atgcggttta ataaatgttt tgatttcaat  37620
ttattgtaaa aaaagattcg gttttatact gttcgatatt ctcattgctt atattttcat  37680
ctatcatctc cacacagtca aatccgtggt tagcatgcac ctcatcaacc ggtaaaagac  37740
tatcggactc ttctatcatt ataactctag aatatttaat ttggtcatta ttaatcaagt  37800
caattatctt atttttaaca aacgtgagta ttttactcat tttttataaa aacttttaga  37860
aatatacaga ctctatcgtg tgtctatatc ttctttttat atccaatgta tttatgtctg  37920
atttttcttc atttatcata tataatggtc caaattctac acgtgcttcg gattcatcca  37980
gatcattaag gttcttataa ttgtaacatc cttctcttcc ctcttctaca tcttccttct  38040
tattcttatt cttagcgtca cagaatctac cacagcagga tcccatgacg agcgtcatat  38100
taaactaatc cattttcaat tataatatat gattagtaat gaccattaaa ataaaaaata  38160
ttcttcataa ccggcaagaa agtgaaaagt tcacattgaa actatgtcag tagtatacat  38220
catgaaatga gatgaaatga gatgaaatga tgatatatat attctctatt ttggtggagg  38280
attatatgat ataattcgtg gataatcatt tttaagacac atttctttat tcgtaaatct  38340
tttcacgtta aatgagtgtc catattttgc aatttcttca tatgatggcg gtgtacgtgg  38400
acgaggctgc tcctgttctt gttgtagtcg ccgactgtcg tgtctgcgtt tagatccctc  38460
cattatcgcg attgcgtaga tggagtacta ttttatacct tgtaattaaa ttttttttatt  38520
aattaaacgt ataaaaacgt tccgtatctg tatttaagag ccagatttcg tctaatagaa  38580
caaatagcta cagtaaaaat aactagaata attgctacac ccactagaaa ccacggatcg  38640
taatacggca atcggttttc gataataggt ggaacgtata ttttatttaa ggacttaaca  38700
attgtctgta aaccacaatt tgcttccgcg gatcctgtat taactatctg taaaagcata  38760
tgttgaccgg gcggagccga acattctccg atatctaatt tctgtatatc tataatatta  38820
ttaacctccg catacgcatt acagttcttt tctagcttgg ataccgcact aggtacatcg  38880
tctagatcta ttcctatttc ctcagcgata gctcttctat ccttttccgg aagcaatgaa  38940
atcacttcaa taaatgattc aaccatgagt gtgaaactaa gtcgagaatt actcatgcat  39000
ttgttagtta ttcggagcgc gcaattttta aactgtccta taacctctcc tatatgaata  39060
gcacaagtga cattagtagg gatagaatgt tgagctaatt tttgtaaata actatctata  39120
aaaagattat acaaagtttt aaactcttta gtttccgcca tttatccagt ctgagaaaat  39180
gtctctcata ataaattttt ccaagaaact aattgggtga agaatggaaa cctttaatct  39240
atatttatca cagtctgtct tggtacacat gatgaattct tctaatgctg tactaaattc  39300
```

```
gatatctttt tcgatttctg gatatgtttt taataaagta tgaacaaaga aatggaaatc  39360
gtaataccag ttatgttcaa ctttgaaatt gtttttttatt ttcttgttaa tgattccagc  39420
cacttgggaa aagtcaaagt cgtttaatgc cgatttaata cgttcattaa aaacaaactt  39480
tttatccttt agatgaatta ttattggttc attggaatca aaaagtaaga tattatcggg  39540
tttaagatct gcgtgtaaaa agttgtcgca acagggtagt tcgtagattt taatgtataa  39600
cagagccatc tgtaaaaaga taaactttat gtattgtacc aaagatttaa atcctaattt  39660
gatagctaac tcggtatcta ctttatctgc cgaatacagt gctaggggaa aaattataat  39720
gtttcctctt tcatattcgt agttagttct cttttcatgt tcgaaaaagt gaaacatgcg  39780
gttaaaatag tttataacat taatattact gttaataact gccggataaa agtgggatag  39840
taatttcacg aatttgatac tgtcctttct ctcgttaaac gcctttaaaa aaactttaga  39900
agaatatctc aatgagagtt cctgaccatc catagtttgt atcaataaata gcaacatatg  39960
aagaacccgt ttatacagag tatgtaaaaa tgttaattta tagtttaatc ccatggccca  40020
cgcacacacg attaattttt tttcatctcc ctttagattg ttgtatagaa atttgggtac  40080
tgtgaactcc gccgtagttt ccatgggact atataatttt gtggcctcga atacaaattt  40140
tactacatag ttatctatct taaagactat accatatcct cctgtagata tgtgataaaa  40200
atcgtcgttt ataggataaa atcgtttatc cttttgttgg aaaaaggatg aattaatgta  40260
atcattctct tctatcttta gtagtgtttc cttattaaaa ttcttaaaat aatttaacaa  40320
tctaactgac ggagcccaat tttggtgtaa atctaattgg gacattatat tgttaaaata  40380
caaacagtct cctaatataa cagtatctga taatctatgg ggagacatcc attgatattc  40440
aggggatgaa tcattggcaa cacccattta ttgtacaaaa agccccaatt tacaaacgaa  40500
agtccaggtt tgatagagac aaacaattaa ctattttgtc tctgttttta acacctccac  40560
agtttttaat ttctttagta atgaaattat tcacaatatc agtatcttct ttatctacca  40620
gagattttac taacttgata accttggctg tctcattcaa tagggtagta atatttgtat  40680
gtgtgatatt gatatctttt tgaattgttt cttttagaag tgattctttg atggtgccag  40740
catacgaatt acaataatgc agaaactcgg ttaacatgca ggaattatag taagccaatt  40800
ccaattgttg cctgtgttgt attagagtgt caatatgagc aatggtgtcc ttgcgtttct  40860
ctgatagaat gcgagcagcg attttggcgt tatcatttga cgatatttct ggaatgacga  40920
atcctgtttc tactaacttt ttggtaggac aaagtgaaac aatcaagaag atagcttctc  40980
ctcctatttg tggaagaaat tgaactcctc tagatgatct actgacgata gtatctcctt  41040
gacagatatt ggaccgaatt acagaagtac ctggaatgta aagccctgaa accccctcat  41100
tttttaagca gattgttgcc gtaaatcctg cactgtgacc aagatagaga gctcctttgg  41160
tgaatccatc tctatgtttc agtttaacca agaaacagtc agctggtcta aaatttccat  41220
ctctatctaa tacagcatct aacttgatgt caggaactat gaccggttta atgttatatg  41280
taacattgag taaatcctta agttcataat catcactgtc atcagttatg tacgatccaa  41340
acaatgtttc taccggcata gtggatacga agatgctatc catcagaatg tttccctgat  41400
tagtattttc tatatagcta ttcttcttta aacgattttc caaatcagta actatgttca  41460
tttttttagg agtaggacgc ctagccagta tggaagagga ttttctagat cctctcttca  41520
acatctttga tctcgatgga atgcaaaacc ccatagtgaa acaaccaacg ataaaaataa  41580
tattgttttt cactttttat aattttacca tctgactcat ggattcatta atatctttat  41640
```

-continued

```
aagagctact aacgtataat tctttataac tgaactgaga tatatacacc ggatctatgg  41700
tttccataat tgagtaaatg aatgctcggc aataactaat ggcaaatgta taaaacaacg  41760
aaattatact agagttgtta aagttaatat tttctatgag ctgttccaat aaattatttg  41820
ttgtgactgc gttcaagtca taaatcatct tgatactatc cagtaaaccg tttttaagtt  41880
ctggaatatt attatcccat tgtaaagccc ctaattcgac tatcgaatat cctgctctga  41940
tagcagtttc aatatcgacg gacgtcaata ctgtaataaa ggtggtagta ttgtcatcat  42000
cgtgataaac tactggaata tggtcgttag taggtacggt aactttacac aacgcgatat  42060
ataactttcc ttttgtacca tttttaacgt agttgggacg tcctgcaggg tattgttttg  42120
aagaaatgat atcgagaaca gatttgatac gatatttgtt ggattcctga ttattcacta  42180
taatataatc tagacagata gatgattcga taaatagaga aggtatatcg ttggtaggat  42240
aatacatccc cattccagta ttctcggata ctctattgat gacactagtt aagaacatgt  42300
cttctattct agaaaacgaa aacatcctac atggactcat taaaacttct aacgctcctg  42360
attgtgtctc gaatgcctcg tacaaggatt tcaaggatgc catagattct ttgaccaacg  42420
atttagaatt gcgtttagca tctgattttt ttattaaatc gaatggtcgg ctctctggtt  42480
tgctacccca atgataacaa tagtcttgta aagataaacc gcaagaaaat ttatacgcat  42540
ccatccaaat aaccctagca ccatcggatg atattaatgt attattatag attttccatc  42600
cacagttatt gggccagtat actgttagca acggtatatc gaatagatta ctcatgtaac  42660
ctactagaat gatagttcgt gtactagtca taatatcttt aatccaatct aagaaattta  42720
aaattagatt ttttacactg ttaaagttaa caaaagtatt acccggatac gtggatatca  42780
tatatggcat tggtccatta tcagtaatag ctccataaac tgatacggcg atggttttta  42840
tatgtgtttg atctaacgag gaagaaattc gcgcccacaa ttcatctcta gatatgtatt  42900
taatatcaaa cggtaacaca tcaatttcgg gacgcgtata tgtttctaaa tttttaatcc  42960
aaatataatg atgacctata tgccctatta tcatactgtc aactatagta cacctaggga  43020
acttacgata catctgtttc ctgtaatcgt taaattttac aaatctataa catgctaaac  43080
cttttgacga caaccattca ttaatttctg atatggaatc tgtattctca ataccgtatc  43140
gttctaaagc cagtgctata tctccctgtt cgtgggaacg ctttcgtata atatcgatca  43200
acggataatc tgaagttttt ggagaataat atgactcatg atctatttcg tccataaaca  43260
atctagacat aggaattgga ggcgatgatc ttaattttgt gcaatgagtc gtcaatccta  43320
taacttctaa tcttgtaata ttcatcatcg acataatact atctatgtta tcatcgtata  43380
ttagtatacc atgaccttct tcatttcgtg ccaaaatgat atacagtctt aaataattac  43440
gcaatatctc aatagtttca taattgttag ctgttttcat caaggtttgt atcctgttta  43500
acatgatggc gttctataac gtctctattt tctattttta attttttaaa tttttaacga  43560
tttactgtgg ctagataccc aatctctctc aaatattttt ttagcctcgc ttacaagctg  43620
tttatctata ctattaaaac tgacgaatcc gtgattttgg taatgggttc cgtcgaaatt  43680
tgccgaagtg atatgaacat attcgtcgtc gactatcaac aattttgtat tattctgaat  43740
agtgaaaacc ttcacagata gatcattttg aacacacaac gcatctagac ttttggcggt  43800
tgccatagaa tatacgtcgt tcttatccca attaccaact agaagtctga tcttaactcc  43860
tctattaatg gctgcttcta taatggagtt gtaaatgtcg ggccaatagt agctattacc  43920
gtcgacacgt gtagtgggaa ctatggccaa atgttcaata tctatactag tcttagccga  43980
cttgagttta tcaataacta catcggtatc tagatctcta gaatatccca ataggtgttc  44040
```

```
cggagaatca gtaaagaaca ctccacctat aggattctta atatgatacg cagtgctaac  44100
tggcaaacaa caagccgcag agcataaatt caaccatgaa ttttttgcgc tattaaaggc  44160
tttaaaagta tcaaatcttc tacgaagatc tgtggccagc gggggataat cagaatatac  44220
acctaacgtt ttaatcgtat gtatagatcc tccagtaaat gacgcgtttc ctacataaca  44280
tctttcatca tctgacaccc aaaaacaacc gagtagtagt cccacattat tttttttatc  44340
tatattaacg gttataaaat ttatatccgg gcagtgactt tgtagctctc ccagatttct  44400
tttccctcgt tcatctagca aaactattat tttaatccct ttttcagatg cctcttttag  44460
tttatcaaaa ataagcgctc ccctagtcgt actcagagga ttacaacaaa aagatgctat  44520
gtatatatat ttcttagcta gagtgataat ttcgttaaaa cattcaaatg ttgtcaaatg  44580
atcggatcta aaatccatat tttctggtag tgtttctacc agcctacatt ttgctcccgc  44640
aggtaccggt gcaaatggcc acatttagtt aacataaaaa cttatacatc ctgttctatc  44700
aacgattcta gaatatcatc ggctatatcg ctaaaatttt catcaaagtc gacatcacaa  44760
cctaactcag tcaatatatt aagaagttcc atgatgtcat cttcgtctat ttctatatcc  44820
gtatccattg tagattgttg accgattatc gagtttaaat cattactaat actcaatcct  44880
tcagaataca atctgtgttt cattgtaaat ttataggcgg tgtatttaag ttggtagatt  44940
ttcaattatg tattaatata gcaacagtag tttttgctcc tccttgattc tagcatcctc  45000
ttcattattt tcttctacgt acataaacat gtccaatacg ttagacaaca caccgacgat  45060
ggcggccgcc acagacacga atatgactaa accgatgacc atttaaaaac ccctctctag  45120
ctttcactta aactgtatcg atcattcttt tagcacatgt ataatataaa aaaacattat  45180
tctatttcga atttaggctt ccaaaaattt ttcatccgta aaccgataat aatatatata  45240
gacttgttaa tagtcggaat aaatagatta atgcttaaac tatcatcatc tccacgatta  45300
gagatacaat atttacattc tttttgctgt ttcgaaactt tatcaataca cgttaataca  45360
aacccaggaa ggagatattg aaactgaggc tgttgaaaat gaaacggtga atacaataat  45420
tcagataatg taaaatcatg attccgtatt ctgatgatat tagaactgct aatggatgtc  45480
gatggtatgt atctaggagt atctatttta acaaagcatc gatttgctaa tatacaatta  45540
tccttttgat taattgttat tttattcata ttcttaaaag gtttcatatt tatcaattct  45600
tctacattaa aaatttccat ttttaattta tgtagccccg caatactcct cattacgttt  45660
catttttgt ctataatatc cattttgttc atctcggtac atagattatc caattgagaa  45720
gcgcatttag tagttttgta cattttaagt ttattgacga atcgtcgaaa actagttata  45780
gttaacattt tattatttga taccctgata ttaatacccc tgccgttact attatttata  45840
actgatgtaa tccacgtaac attagaatta attatcgata gtaatgcatc gacgcttcca  45900
aaattgtcta ttataaactc accgataatt tttttattgc atgttttcat attcattagg  45960
attatcaaat ctttaatctt attacgattg tatgcgttga tattgcaaga cgtcattcta  46020
aaagacggag gatctccatc aaatgccaaa caatcacgta caaagtacat ggaaataggt  46080
tttgttctat tgcgcatcat agatttatat agaacacccg tagaaatact aatttgtttt  46140
actctataaa atactaatgc atctatttca tcgttttgta taacgtcttt ccaagtgtca  46200
aattccaaat ttttttcatt gatagtacca aattcttcta tctctttaac tacttgcata  46260
gataggtaat tacagtgatg cctacatgcc gttttttgaa actgaataga tgcgtctaga  46320
agcgatgcta cgctagtcac aatcaccact ttcatattta gaatatatgt atgtaaaaat  46380
```

atagtagaat ttcattttgt ttttttctat gctataaatg aattctcatt ttgcatctgc 46440
tcatactccg ttttatatca ataccaaaga aggaagatat ctggttctaa aagccgttaa 46500
agtatgcgat gttagaactg tagaatgcga aggaagtaaa gcttcctgcg tactcaaagt 46560
agataaaccc tcatcgcccg cgtgtgagag aagaccttcg tccccgtcca gatgcgagag 46620
aatgaataac cctggaaaac aagttccgtt tatgaggacg gacatgctac aaaatatgtt 46680
cgcggctaat cgcgataatg tagcttctag acttttgtcc taaaatacta ttatatcctt 46740
ttcgatatta ataaatccgt gtcgtccagg ttttttatct ctttcagtat gtgaatagat 46800
aggtatttta tctctattca tcatcgaatt taagagatcc gataaacatt gtttgtattc 46860
tccagatgtc agcatctgat acaacaatat atgtgcacat aaacctctgg cacttatttc 46920
atgtaccttc cccttatcac taaggagaat agtatttgag aaatatgtat acatgatatt 46980
atcatgaatt agatatacag aatttgtaac actctcgaaa tcacacgatg tgtcggcgtt 47040
aagatctaat atatcactcg ataacacatt ttcatctaga tacactagac attttttaaa 47100
gctaaaatag tctttagtag taacagtaac tatgcgatta ttttcatcga tgatacattt 47160
catcggcata ttattacgct taccatcaaa gactatacca tgtgtatatc taacgtattc 47220
tagcatagtt gccatacgcg cattaaactt ttcaggatct ttggatagat cttccaatct 47280
atctatttga gaaaacattt ttatcatgtt caatagttga aacgtcggat ccactatata 47340
gatattatct ataaagattt taggaactac gttcatggta tcctggcgaa tattaaaact 47400
atcaatgata tgattatcgt tttcatcttt tatcaccata tagtttctaa gatatgggat 47460
tttacttaat ataatattat ttcccgtgat aaattttatt agaaaggcca aatctataag 47520
aaaagtccta gaattagtct gaagaatatc tatatcgccg tatagtatat ttggattaat 47580
tagatataga gaatatgatc cgtaacatat acaactttta ttatggcgtc taagatattc 47640
ttccatcaac ttattaacat ttttgactag ggaagataca ttatgacgtc ccattacttt 47700
tgccttgtct attactgcga cgttcataga atttagcata tctcttgcca attcttccat 47760
tgatgttaca ttataagaaa ttttagatga aattacattt ggagctttaa tagtaagaac 47820
tcctaatatg tccgtgtatg tggtcactaa tacagattgt agttctataa tcgtaaataa 47880
tttacctata ttatatgttt gagtctgttt agaaaagtag ctaagtatac gatcttttat 47940
ttctgatgca gatgtatcaa catcggaaaa aaatcttttt ttattctttt ttactaaaga 48000
tacaaatatg tctttgttaa aaacagttat tttctgaata tttctagctt gtaattttaa 48060
catatgatat tcgttcacac taggtactct gcctaaatag gtttctataa tctttaatgt 48120
aatattagga aaagtattct gatcaggatt cctattcatt ttgaggattt aaaactctga 48180
ttattgtcta atatggtctc tacgcaaact ttttcacaga gcgatagagt ttttgataac 48240
tcgtttttct taagaaatat aaaactactg tctccagagc tcgctctatc ttttatttta 48300
tctaattcga tacaaactcc tgatactggt tcagaaagta attcattaat tttcagtcct 48360
ttatagaaga tatttaatat agataataca aaatcttcag tttttgatat cgatctgatt 48420
gatcctagaa ctagatatat taataacgtg ctcattaggc agtttatggc agcttgataa 48480
ttagatatag tatattccag ttcatattta ttagataccg cattgcccag attttgatat 48540
tctatgaatt cctctgaaaa taaatccaaa ataactagac attctatttt ttgtggatta 48600
gtgtactctc ttccctctat catgttcact actggtgtcc acgatgataa atatctagag 48660
ggaatataat atagtccata ggatgccaat ctagcaatgt cgaataactg taatttgatt 48720
cttcgttctt cattatgaat tgattcttga ggtataaacc taacacaaat tatattatta 48780

```
gacttttcgt atgtaatgtc tttcatgtta taagttttta atcctggaat agaatctatt  48840
ttaatgaggc ttttaaacgc agagttctcc aacgagtcaa agcataatac tctgttgttt  48900
ttcttatata cgatgttacg attttcttct ttgaatggaa taggtttttg aattagttta  48960
taattacaac ataatagata aggaagtgtg caaatagtac gcggaaaaaa cataatagct  49020
cccctgtttt catccatggt tttaagtaaa tgatcactgg cttctttagt caatggatat  49080
tcgaacatta accgtttcat catcattgga cagaatccat atttcttaat gtaaagagtg  49140
atcaaatcat tgtgtttatt gtaccatctt gttgtaaatg tgtattcggt tatcggatct  49200
gctccttttt ctattaaagt atcgatgtcg atctcgtcta agaattcaac tatatcgaca  49260
tatttcattt gtatacacat aaccattact aacgtagaat gtataggaag agatgtaacg  49320
ggaacagggt ttgttgattc gcaaactatt ctaatacata attcttctgt taatacgtct  49380
tgcacgtaat ctattataga tgccaagata tctatataat tattttgtaa gatgatgtta  49440
actatgtgat ctatataagt agtgtaataa ttcatgtatt ttgatatatg ttccaactct  49500
gtctttgtga tgtctagttt cgtaatatct atagcatcct caaaaaatat attcgcatat  49560
attcccaagt cttcagttct atcttctaaa aaatcttcaa cgtatggaat ataataatct  49620
atttacctc ttctgatatc attaatgata taatttttga cactatcttc tgtcaattga  49680
ttcttattca ctatatctaa gaaacggata gcgtccctag gacgaactac tgccattaat  49740
atctctatta tagcttctgg acataattca tctattatac cagaattaat gggaactatt  49800
ccgtatctat ctaacatagt tttaagaaag tcagaatcta agacctgatg ttcatatatt  49860
ggttcataca tgaaatgatc tctattgatg atagtgacta tttcattctc tgaaaattgg  49920
taactcattc tatatatgct ttccttgttg atgaaggata gaatatactc aatagaattt  49980
gtaccaacaa actgttctct tatgaatcgt atatcatcat ctgaaataat catgtaaggc  50040
atacatttaa caattagaga cttgtctcct gttatcaata tactattctt gtgataattt  50100
atgtgtgagg caaatttgtc cacgttcttt aattttgtta tagtagatat caaatccaat  50160
ggagctacag ttcttggctt aaacagatat agtttttctg gaacaaattc tacaacatta  50220
ttataaagga ctttgggtag ataagtggga tgaaatccta ttttaattaa tgcgatagcc  50280
ttgtcctcgt gcagatatcc aaacgctttt gtgatagtat ggcattcatt gtctagaaac  50340
gctctacgaa tatctgtgac agatatcatc tttagagaat atactagtcg cgttaatagt  50400
actacaattt gtatttttta atctatctca ataaaaaaat taatatgtat gattcaatgt  50460
ataactaaac tactaactgt tattgataac tagaatcaga atctaatgat gacgtaacca  50520
agaagtttat ctactgccaa tttagctgca ttatttttag catctcgttt agattttcca  50580
tcggccttat cgaatactct tccgtcgata tctacacagg cataaaatgt aggagagtta  50640
ctaggcccaa ctgattcaat acgaaaagac caatctctcc tagtaatttg gcagtactca  50700
ttaataacgg tgacagggtt agcatctttc caatcaataa tttttttagc cggaataaca  50760
tcatcaaaag acttatgatc ctctctcatt gatttttcgc gggatacatc atctattatg  50820
gcgtcagcca taacatcagc atccggctta tccgcctccg ttgtcataaa ccaacgagga  50880
ggaatatcgt cggagctgta caccatagca ctacgttgaa gatcgtacag agctttatta  50940
acttctcgct tctccatatt aagttgtcta gttagttgtg cagcagtagc tccttcgatt  51000
ccaatggttt taatagcctc acacacaatc tctgcgttag aacgttcgtc gatatagatt  51060
ttagacattt ttagagagaa ctaacgcaat cagtaataaa actaatttat tttatcattt  51120
```

```
ttttattcat catcctctgg tggttcgtcg ttcctatcga atgtggatct gattaacccg  51180
tcatctatag gtgatgctgg ttctggagat tctggaggag atggattatt atctggaaga  51240
atctctgtta tttccttgtt ttcatgtatc gattgcgttg taacattaag attgcgaaat  51300
gctctaaatt tgggaggctt aaagtgttgt ttgcaatctc tacacgcgtg tctaactagt  51360
ggaggttcgt cagctgctct agtttgaatc atcatcggtg tagtattcct acttttacag  51420
ttaggacacg gtgtattgta tttctcgtcg agaacgttaa aataatcgtt gtaactcaca  51480
tcctttattt tatctatatt gtattctact cctttcttaa tgcattttat accgaataag  51540
agatagcgaa ggaattcttt ttcggtgccg ctagtaccct taatcatatc acatagtgtt  51600
ttatattcca aatttgtggc aatagacggt ttatttctat acgatagttt gtttctggaa  51660
tcctttgagt attctatacc aatattattc tttgattcga atttagtttc ttcgatatta  51720
gattttgtat tacctatatt cttgatgtag tactttgatg atttttccat ggcccattct  51780
attaagtctt ccaagttggc atcatccaca tattgtgata gtaattctcg gatatcagta  51840
gcggttaccg ccattgatgt ttgttcattg gatgagtaac tactaatgta tacattttcc  51900
atttataaca cttatgtatt aactttgttc atttatattt tttcattatt atgttgatat  51960
taacaaaagt gaatatatat gttaataatt gtattgtggt tatacggcta caattttata  52020
atgagtgaaa gtcagtgtcc gatgatcaat gacgatagct ttactctgaa aagaaagtat  52080
caaatcgata gtgcggagtc aacaataaaa atggataaga agaggacaaa gtttcagaat  52140
agagccaaaa tggtaaaaga aataaatcag acaataagag cagcacaaac tcattacgag  52200
acattgaaac taggatacat aaaatttaag agaatgatta ggactactac tctagaagat  52260
atagcaccat ctattccaaa taatcagaaa acttataaac tattctcgga catttcagcc  52320
atcggcaaag catcacagaa tccgagtaag atggtatatg ctctgctgct ttacatgttt  52380
cccaatttgt ttggagatga ccatagattc attcgttata gaatgcatcc aatgagtaaa  52440
atcaaacaca agatcttctc tcctttcaaa cttaatctta ttagaatatt agtggaagaa  52500
agattctata ataatgaatg cagatctaat aaatggaaaa taattggaac acaagttgat  52560
aaaatgttga tagctgaatc tgataaatat acaatagatg caaggtataa cctaaaaccc  52620
atgtatagaa tcaagggaga atctgaagaa gataccctct tcatcaaaca gatggtagaa  52680
caatgtgtga catcccagga attggtggaa aaagtgttga agatactgtt tagagatttg  52740
ttcaagagtg gagaatacaa agcgtacaga tacgatgatg atgtagaaaa tggattcatt  52800
ggattggata cactaaaatt aaacattgtt catgatatag ttgaaccatg tatgcctgtt  52860
cgtaggccag tggctaagat actgtgtaaa gaaatggtaa ataaatactt tgagaatccg  52920
ctacatatta ttggtaaaaa tcttcaagag tgcattgact ttgttagtga ataggcattt  52980
catctttctc caatactaat tcaaattgtt aaattaataa tggatagtat aaatagttat  53040
tagtgataaa atagtaaaaa taattattag aataagagtg tagtatcata gataactctc  53100
ttctataaaa atggatttta ttcgtagaaa gtatcttata tacacagtag aaaataatat  53160
agatttttta aaggatgata cattaagtaa agtaaacaat tttaccctca atcatgtact  53220
agctctcaag tatctagtta gcaattttcc tcaacatgtt attactaagg atgtattagc  53280
taataccaat ttttttgttt tcatacatat ggtacgatgt tgtaaagtgt acgaagcggt  53340
tttacgacac gcatttgatg cacccacgtt gtacgttaaa gcattgacta agaattattt  53400
atcgtttagt aacgcaatac aatcgtacaa ggaaaccgtg cataaactaa cacaagatga  53460
aaaattttta gaggttgccg aatacatgga cgaattagga gaacttatag gcgtaaatta  53520
```

```
tgacttagtt cttaatccat tatttcacgg aggggaaccc atcaaagata tggaaatcat  53580
ttttttaaaa ctgtttaaga aaacagactt caaagttgtt aaaaaattaa gtgttataag  53640
attacttatt tgggcatacc taagcaagaa agatacaggc atagagtttg cggataatga  53700
tagacaagat atatacactt tatttcaaca aactggtaga atcgtccata gcaatctaac  53760
agaaacgttt agagattata tctttcccgg agataagact agctattggg tgtggttaaa  53820
cgaaagtata gctaatgatg cggatattgt tcttaataga cacgccatta ccatgtatga  53880
taaaattctt agttatatat actctgagat aaaacaagga cgcgttaata aaaacatgct  53940
taagttagtt tatatctttg agcctgaaaa agatatcaga gaacttctgc tagaaatcat  54000
atatgatatt cctggagata tcctatctat tattgatgca aaaaacgacg attggaaaaa  54060
atattttatt agtttttata aagctaattt tattaacggt aatacattta ttagtgatag  54120
aacgtttaac gaggacttat tcagagttgt tgttcaaata gatcccgaat atttcgataa  54180
tgaacgaatt atgtctttat tctctacgag tgctgcggac attaaacgat ttgatgagtt  54240
agatattaat aacagttata tatctaatat aatttatgag gtgaacgata tcacattaga  54300
tacaatggat gatatgaaga agtgtcaaat ctttaacgag gatacgtcgt attatgttaa  54360
ggaatacaat acatacctgt ttttgcacga gtcggatccc atggtcatag agaacggaat  54420
actaaagaaa ctgtcatcta taaaatccaa gagtagacgg ctgaacttgt ttagcaaaaa  54480
cattttaaaa tattatttag acggacaatt ggctcgtcta ggtcttgtgt tagatgatta  54540
taaaggagac ttgttagtta aaatgataaa ccatcttaag tctgtggagg atgtatccgc  54600
attcgttcga ttttctacag ataaaaaccc tagtattctt ccatcgctaa tcaaaactat  54660
tttagctagt tataatattt ccatcatcgt cttatttcaa aggtttttga gagataatct  54720
atatcatgta gaagaattct tggataaaag catccatcta accaagacgg ataagaaata  54780
tatacttcaa ttgataagac acggtagatc atagaacaga ccaaatatat tattaataat  54840
ttgtatatac atagatataa ttatcacaca tttttgataa atgggaactg ctgcaacaat  54900
tcagactccc accaaattaa tgaataaaga aaatgcagaa atgattttgg aaaaaattgt  54960
tgatcatata gttatgtata ttagtgacga atcaagtgat tcagaaaata atcctgaata  55020
tattgatttt cgtaacagat acgaagacta tagatctctc attataaaaa gtgatcacga  55080
gtttgtaaag ctatgtaaaa atcatgcaga gaaaagttct ccagaaacgc aacaaatgat  55140
tatcaaacac atatacgaac aatatcttat tccagtatct gaagtactat taaaacctat  55200
aatgtccatg ggtgacataa ttacatataa cggatgtaaa gacaatgaat ggatgctaga  55260
acaactctct accctaaact ttaacaatct ccgcacatgg aactcatgta gcataggcaa  55320
tgtaacgcgt ctgttttata catttttag ttatctgatg aaagataaac taaatatata  55380
agtataatcc cattctaata ctttaacctg atgtattagc atcttattag aatattaacc  55440
taactaaaag acataacata aaaactcatt acatagttga taaaaagcgg taggatataa  55500
atattatggc tgccaccgtt ccgcgttttg acgacgtgta caaaaatgca caaagaagaa  55560
ttctagatca agaaacattt tttagtagag gtctaagtag accgttaatg aaaaacacat  55620
atctatttga taattacgcg tatggatgga taccagaaac tgcaatttgg agtagtagat  55680
acgcaaacct agatgctagt gactattatc ccatttcgtt gggattactt aaaaagttcg  55740
agtttctcat gtctctatat aaaggtccta ttccagtata cgaagaaaaa gtaaatactg  55800
aattcattgc taatggatcg ttctctggta gatacgtatc atatcttaga aagttttctg  55860
```

```
ctcttccaac aaacgagttt attagttttt tgttactgac ttccattcca atctataata  55920
tcttgttctg gtttaaaaat acacagtttg atattactaa acacacatta ttcagatacg  55980
tctatacaga taatgccaaa cacctggcgt tggctaggta tatgcatcaa acaggagact  56040
ataagccttt gtttagtcgt ctcaaagaga attatatatt taccggtccc gttccaataa  56100
gtatcaaaga tatagatcac cctaatctta gtagagcaag aagtccatcc gattatgaga  56160
cattagctaa tattagtact atattgtact ttaccaagta tgatccggta ttaatgtttt  56220
tattgtttta cgtacctggg tattcaatta ctacaaaaat tactccagcc gtagaatatc  56280
taatggataa actgaatcta acaaagagcg acgtacaact gttgtaaatt attttatgct  56340
tcgtaaaatg taggttttga accaaacatt ctttcaaaga atgagatgca taaaacttta  56400
ttatccaata gattgactat ttcggacgtc aatcgtttaa agtaaacttc gtaaaatatt  56460
ctttgatcac tgccgagttt aaaacttcta tcgataattg tttcatatgt tttaatattt  56520
acaagttttt tggtccatgg tacattagcc ggacaaatat atgcaaaata atatcgttct  56580
ccaagttcta tagtttctgg attattttta ttatattcag taaccaaata catattaggg  56640
ttatctgcgg atttataatt tgagtgatgc attcgactca acataaataa ttctagagga  56700
gacgatctac tatcaaattc ggatcgtaaa tctgtttcta aagaacggag aatatctata  56760
catacctgat tagaattcat ccgtccttca gacaacatct cagacagtct ggtcttgtat  56820
gtcttaatca tattcttatg aaacttggaa acatctcttc tagtttcact agtaccttta  56880
ttaattctct caggtacaga ttttgaattc gacgatgctg agtatttcat cgttgtatat  56940
ttcttcttcg attgcataat cagattctta tataccgcct caaactctat tttaaaatta  57000
ttaaacaata ctctactatt aatcagtcgt tctaactcct ttgctatttc tatggactta  57060
tctacatctt gactgtctat ctctgtaaac acggagtcgg tatctccata cacgctacga  57120
aaacgaaatc tgtaatctat aggcaacgat gttttcacaa tcggattaat atctctatcg  57180
tccatataaa atggattact taatggattg gcaaaccgta acataccgtt agataactct  57240
gctccattta gtaccgattc tagatacaag atcattctac gtcctatgga tgtgcaactc  57300
ttagccgaag cgtatgagta tagagcacta tttctaaatc ccatcagacc atatactgag  57360
ttggctacta tcttgtacgt atattgcatg gaatcataaa tggccttttc agttgaactg  57420
gtagcctgtt ttagcatctt tttatatctg gctctctctg ccaaaaatgt tcttaatagt  57480
ctaggaatgg ttccttctat cgatctatcg aaaattgcta tttcagagat gaggttcggt  57540
agtctaggtt cacaatgaac cgtaatatat ctaggaggtg gatatttctg aagcaagagc  57600
tgattattta tttcttcttc caatctattg gtactaacaa cgacaccgac taatgtttcc  57660
ggagatagat ttccaaagat acacacatta ggatacagac tgttataatc aaagattaat  57720
acattattac taaacatttt ttgttttgga gcaaatacct taccgccttc ataaggaaac  57780
ttttgttttg tttctgatct aactaagata gttttagttt ccaacaatag ctttaacagt  57840
ggacccttga tgactgtact cgctctatat tcgaatacca tggattgagg aagcacatat  57900
gttgacgcac ccgcgtctgt ttttgtttct actccataat actcccacaa atactgacac  57960
aaacaagcat catgaataca gtatctagcc atatctaaag ctatgtttag attataatcc  58020
ttatacatct gagctaaatc aacgtcatcc tttccgaaag ataatttata tgtatcatta  58080
ggtaaagtag gacataatag tacgacttta aatccatttt cccaaatatc tttacgaatt  58140
actttacata taatatcctc atcaacagtc acataattac ctgtggttaa aacctttgca  58200
aatgcagcgg ctttgccttt cgcgtccgta gtatcgtcac cgatgaacgt catttctcta  58260
```

```
actcctctat ttaatacttt acccatgcaa ctgaacgcgt tcttggatat agaatccaat  58320
ttgtacgaat ccaatttttc aaatttttga atgaatgaat atagatcgaa aaatatagtt  58380
ccattattgt tattaacgtg aaacgtagta ttggccatgc cgcctactcc cttatgacta  58440
gactgatttc tctcataaat acagagatgt acagcttcct ttttgtccgg agatctaaag  58500
ataatcttct ctcctgttaa taactctaga cgattagtaa tatatctcag atcaaagtta  58560
tgtccgttaa aggtaacgac gtagtcgaac gttagttcca acaattgttt agctattcgt  58620
aacaaaacta tttcagaaca tagaactagt tctcgttcgt aatccatttc cattagtgac  58680
tgtatcctca aacatcctct atcgacggct tcttgtattt cctgttccgt taacatctct  58740
tcattaatga gcgtaaacaa taatcgttta ccacttaaat cgatataaca gtaacttgta  58800
tgcgagattg ggttaataaa tacagaagga aacttcttat cgaagtgaca ctctatatct  58860
agaaataagt acgatcttgg gatatcgaat ctaggtattt ttttagcgaa acagttacgt  58920
ggatcgtcac aatgataaca tccattgtta atctttgtca aatattgctc gtccaacgag  58980
taacatccgt ctggagatat cccgttagaa atataaaacc aactaatatt gagaaattca  59040
tccatggtgg cattttgtat gctgcgtttc tttggctctt ctatcaacca catatctgcg  59100
acggagcatt ttctatcttt aatatctaga ttataactta ttgtctcgtc aatgtctata  59160
gttctcatct ttcccaacgg cctcgcatta aatggaggag gagacaatga ctgatatatt  59220
tcgtccgtca ctacgtaata aaagtaatga ggaaatcgta taaatacggt ctcaccattt  59280
cgacatctgg atttcagata taaaaatctg ttttcaccgt gactttcaaa ccaattaatg  59340
caccgaacat ccatttatag aatttagaaa tatattttca tttaaatgaa tcccaaacat  59400
tggggaagag ccgtatggac cattattttt atagtacttt cgcaagcggg tttagacggc  59460
aacatagaag cgtgtaaacg aaaactatat actatagtta gcactcttcc atgtcctgca  59520
tgtagacggc acgcgactat tgctatagag gacaataatg tcatgtctag cgatgatctg  59580
aattatattt attatttttt catcagatta tttaacaatt tggcatctga tcccaaatac  59640
gcgatcgatg tgacaaaggt taacccttta taaacttaac ccattataaa acttatgatt  59700
agtcacgact gaaataaccg cgtgattatt ttttggtata attctacacg gcatggtttc  59760
tgtgactatg aattcaaccc ccgttacatt agtgaaatct ttaacaaaca gcaagggttc  59820
gtcaaagaca taaaactcat tgtttacaat cgaaatagac cccctatcac acttaaaata  59880
aaaaatatcc ttatccttta ccaccaaata aaattctgat tggtcaatgt gaatgtattc  59940
acttaacagt tccacaaatt tatttattaa ctccgaggca catacatcgt cggtattttt  60000
tatggcaaac tttactcttc cagcatccgt ttctaaaaaa atattaacga gttccattta  60060
tatcatccaa tattattgaa atgacgttga tggacagatg atacaaataa gaaggtacgg  60120
tacctttgtc caccatctcc tccaattcat gctctatttt gtcattaact ttaatgtatg  60180
aaaacagtac gccacatgct tccatgacag tgtgtaacac tttggataca aaatgtttga  60240
cattagtata attgtccaag actgtcaatc tataatagat agtagctata atatattcta  60300
tgatggtatt gaagaagatg acaaccttgg catattgatc atttaacaca gacatggtat  60360
caacagatag cttgaatgaa agagaatcag taattggaat aagcgtcttc tcgatagagt  60420
gtccgtatac caacatgtct gatattttga tgtattccat taaattattt agtttttttct  60480
ttttattttc gttaaacagc atttctgtca acggacccca acatcgttga ccgattaagt  60540
tttgattgat ttttccgtgt aatgcgtatc tagtcagatc gtatagccta tccaataatc  60600
```

```
catcatctgt gcgtagatca catcgtacac tttttaattc tctatagaag agcgacagac  60660
atctggagca attacagaca gcaatttctt tattctctac agatgtaaga tacttgaaga  60720
cattcctatg atgatgcaga attttggata acacggtatt gatggtatct gttaccataa  60780
ttcctttgat ggctgatagt gtcagagcac aagatttcca atctttgaca atttttagca  60840
ccattatctt tgttttgata tctatatcag acagcatggt gcgtctgaca acacagggat  60900
taagacggaa agatgaaatg attctctcaa catcttcaat agataccttg ctattttttc  60960
tggcattatc tatatgtgcg agaatatcct ctagagaatc agtatccttt ttgatgatag  61020
tggatctcaa tgacatggga cgtctaaacc ttcttattct atcaccagat tgcatggtga  61080
tttgtcttct ttcttttatc ataatgtaat ctctaaattc atcggcaaat tgtctatatc  61140
taaaatcata atatgagatg tttacctcta caaatatctg ttcgtccaat gttagagtat  61200
ttacatcagt tttgtattcc aaattaaaca tggcaacgga tttaatttta tattcctcta  61260
ttaagtcctc gtcgataata acagaatgta gataatcatt taatccatcg tacatggttg  61320
gaagatgctt gttgacaaaa tctttaattg tcttgatgaa ggtgggacta tatctaacat  61380
cttgattaat aaaatttata acattgtcca taggatactt tgtaactagt tttatacaca  61440
tctcttcatc ggtaagttta gacagaatat cgtgaacagg tggtatatta tattcatcag  61500
atatacgaag aacaatgtcc aaatctatat tgtttaatat attatataga tgtagcgtag  61560
ctcctacagg aatatcttta actaagtcaa tgatttcatc aaccgttaga tctattttaa  61620
agttaatcat ataggcattg atttttaaaa ggtatgtagc cttgactaca ttctcattaa  61680
ttaaccattc caagtcactg tgtgtaagaa gattatattc tatcataagc ttgactacat  61740
ttggtcccga taccattaaa gaattcttat gatataagga aacagatttt aggtactcat  61800
ctactctaca agaattttgg agagccttaa cgatatcagt gacgtttatt atttcaggag  61860
gaaaaaacct aacattgaga atatcggaat taatagcttc cagatacagt gattttggca  61920
atagtccgtg taatccataa tccagtaaca cgagctggtg cttgctagac accttttcaa  61980
tgtttaattt ttttgaaata agctttgata aagccttcct cgcaaattcc ggatacatga  62040
acatgtcggc gacatgatta agtattgttt tttcattatt tttatatttt ctcaacaagt  62100
tctcaatacc ccaatagatg atagaatatc acccaatgcg tccatgttgt ctatttccaa  62160
caggtcgcta tatccaccaa tagaagtttt cccaaaaaag attctaggaa cagttctacc  62220
accagtaatt tgttcaaaat aatcccgcaa ttcattttcg ggtttaaatt ctttaatatc  62280
gacaatttca tacgctcctc ttttgaaact aaacttattt agaatatcca gtgcatttct  62340
acaaaaagga catgtatact tgacaaaaat tgtcactttg ttattggcca acctttgttg  62400
tacaaattcc tcggccattt taatatttaa gtgatataaa actatctcga cttatttaac  62460
tctttagtcg agatatatgg acgcagatag ctatatgata gccaactaca gaaggcaaac  62520
gctataaaaa acataattac aacgagcata tttataaata tttttattca gcattacttg  62580
atatagtaat attaggcaca gtcaaacatt caaccactct cgatacatta actctctcat  62640
tttctttaac aaattctgca atatcttcgt aaaaagattc ttgaaacttt ttagaatatc  62700
tatcgactct agatgaaata gcgttcgtca acatactatg ttttgtatac ataaaggcgc  62760
ccattttaac agtttctagt gacaaaatgc tagcgatcct aggatccttt agaatcacat  62820
agattgacga ttcgtctctc ttagtaactc tagtaaaata atcatacaat ctagtacgcg  62880
aaataatatt atccttgact tgaggagatc taaacaatct agttttgaga acatcgataa  62940
gttcatcggg aatgacatac atactatctt taatagaact cttttcatcc agttgaatgg  63000
```

```
attcgtcctt aaccaactga ttaatgagat cttctatttt atcattttcc agatgatatg  63060
tatgtccatt aaagttaaat tgtgtagcgc ttctttttag tctagcagcc aatactttaa  63120
catcactaat atcgatatac aaaggagatg atttatctat ggtattaaga attcgttttt  63180
cgacatctgt caaaaccaat tcctttttgc ctgtatcatc cagttttcca tcctttgtaa  63240
agaaattatt ttctactaga ctattaataa gactgataag gattcctcca taattgcaca  63300
atccaaactt tttaacaaaa ctagacttta caagatctac aggaatgcgt acttcaggtt  63360
tcttagcttg tgatttttttc ttttgcggac attttctagt aaccaactca tctaccattt  63420
cattgatttt agcagtgaaa taagctttca atgcacgggc actgatacta ttgaaaacga  63480
gttgatcttc aaattccgcc atttaagttc accaaacaac ttttaaatac aaatatatca  63540
atagtagtag aataagaact ataaaaaaaa taataattaa ccaataccaa ccccaacaac  63600
cggtattatt agttgatgtg actgttttct catcacttag aacagattta acaatttcta  63660
taaagtctgt caaatcatct tccggagacc ccataaatac accaaatata gcggcgtaca  63720
acttatccat ttatacattg aatattggct tttctttatc gctatcttca tcatattcat  63780
catcaatatc aacaagtccc agattacgag ccagatcttc ttctacattt tcagtcattg  63840
atacacgttc actatctcca gagagtccga taacgttagc caccacttct ctatcaatga  63900
ttagtttctt gagcgcgaat gtaatttttg tttccgttcc ggatctatag aagacgatag  63960
gtgtgataat tgccttggcc aattgtcttt ctcttttact gagtgattct agttcacctt  64020
ctatagatct gagaatggat gattctccag tcgaaacata ttctaccatg gatccgttta  64080
atttgttgat gaagatggat tcatccttaa atgttttctc tgtaatagtt tccaccgaaa  64140
gactatgcaa agaatttgga atgcgttcct tgtgcttaat gtttccatag acggcttcta  64200
gaagttgata caacatagga ctagccgcgg taacttttat ttttagaaag tatccatcgc  64260
ttctatcttg tttagattta tttttataaa gtttagtctc tccttccaac ataataaaag  64320
tggaagtcat ttgactagat aaactatcag taagttttat agagatagac gaacaattag  64380
cgtattgaga agcatttagt gtaacgtatt cgatacattt tgcattagat ttactaatcg  64440
attttgcata ctctataaca cctgcacaag tctgtagaga atcgctagat gcagtaggtc  64500
ttggtgaagt ttcaactctc ttcttgatta ccttactcat gattaaacct aaataattgt  64560
actttgtaat ataatgatat atattttcac tttatctcat ttgagaataa aaatgttttt  64620
gtttaaccac tgcatgatgt acagatttcg gaatcgcaaa ccaccagtgg ttttatttta  64680
tccttgtcca atgtgaattg aatgggagcg gatgcgggtt tcgtacgtag atagtacatt  64740
cccgttttta gaccgagact ccatccgtaa aaatgcatac tcgttagttt ggaataactc  64800
ggatctgcta tatggatatt catagattga ctttgatcga tgaaggctcc cctgtctgca  64860
gccattttta tgatcgtctt ttgtggaatt tcccaaatag ttttataaac tcgcttaata  64920
tcttctggaa ggtttgtatt ctgaatggat ccaccatctg ccataatcct attcttgatc  64980
tcatcattcc ataattttct ctcggttaaa actctaagga gatgcggatt aactacttga  65040
aattctccag acaatactct ccgagtgtaa atattactgg tatacggttc caccgactca  65100
ttatttccca aaatttgagc agttgatgca gtcggcatag gtgccaccaa taaactattt  65160
ctaagaccgt atgttctgat tttatctttt agaggttccc aattccaaag attcgacggt  65220
acaacattcc aaagatcata ttgtagaata ccgttactgg cgtacgatcc tacatatgta  65280
tcgtatggtc cttccttctc agctagttca caactcgcct ctaatgcacc gtaataaatg  65340
```

```
gtttcgaaga tcttcttatt tagatcttgt gcttccaggc tatcaaatgg ataatttaag  65400
agaataaacg cgtccgctaa tccttgaaca ccaataccga taggtctatg tctcttatta  65460
gagatttcag cttctggaat aggataataa ttaatatcta taattttatt gagatttctg  65520
acaattactt tgaccacatc cttcagtttg agaaaatcaa atcgcccatc tattacaaac  65580
atgttcaagg caacagatgc cagattacaa acggctacct cattagcatc cgcatattgt  65640
attatctcag tgcaaagatt actacacttg atagttccta aattttgttg attactcttt  65700
ttgttacacg catccttata aagaatgaat ggagtaccag tttcaatctg agattctata  65760
atcgctttcc agacgactcg agcctttatt atagatttgt atctcctttc tctttcgtat  65820
agtgtataca atcgttcgaa ctcgtctccc caaacattgt ccaatccagg acattcatcc  65880
ggacacatca acgaccactc tccgtcatcc ttcactcgtt tcataaagag atcaggaatc  65940
caaagagcta taaatagatc tctggttcta tgttcctcgt ttcctgtatt ctttttaaga  66000
tcgaggaacg ccataatatc agaatgccac ggttccaagt atatggccat aactccaggc  66060
cgtttgtttc ctccctgatc tatgtatcta gcggtgttat tataaactct caacattgga  66120
ataataccgt ttgatatacc attggtaccg gagatatagc ttccactggc acgaatatta  66180
ctaattgata gacctattcc ccctgccatt ttagagatta atgcgcatcg ttttaacgtg  66240
tcatagatac cctctatgct atcatcgatc atgttaagta gaaaacagct agacatttgg  66300
tgacgactag ttcccgcatt aaataaggta ggagaagcgt gcgtaaacca tttttcagaa  66360
agtagattgt acgtctcaat agctgagtct atatcccatt gatgaattcc tactgcgaca  66420
cgcattaaca tgtgctgagg tctttcaacg atcttgttgt ttattttcaa caagtaggat  66480
ttttccaaag ttttaaaacc aaaatagttg tatgaaaagt ctcgttcgta aataataacc  66540
gagttgagtt tatccttata tttgttaact atatccatgg tgatacttga aataatcgga  66600
gaatgtttcc catttttagg attaacatag ttgaataaat cctccatcac ttcactaaat  66660
agttttttttg tttccttgtg tagatttgat acggctattc tggcggctag aatggcataa  66720
tccggatgtt gtgtagtaca agtggctgct atttcggctg ccagagtgtc caattctacc  66780
gttgttactc cattatatat tccttgaata accttcatag ctattttaat aggatctata  66840
tgatccgtgt ttaagccata acataatttt ctaatacgag acgtgatttt atcaaacatg  66900
acattttcct tgtatccatt tcgtttaatg acaaacattt ttgttggtgt aataaaaaaa  66960
ttatttaact tttcattaat agggatttga cgtatgtagc gtacaaaatg atcgttcctg  67020
gtatatagat aaagagtcct atatatttga aaatcgttac ggctcgatta aactttaatg  67080
attgcatagt gaatatatca ttaggattta actccttgac tatcatggcg gcgccagaaa  67140
ttaccatcaa aagcattaat acagttatgc ctatcgcagt tagaacggtt atagcatcca  67200
ccatttatat ctaaaaatta gatcaaagaa tatgtgacaa agtcctagtt gtatactgag  67260
aattgacgaa acaatgtttc ttacatattt ttttcttatt agtaactgac ttaatagtag  67320
gaactggaaa gctagacttg attattctat aagtatagat acccttccaa ataatattct  67380
ctttgataaa agttccagaa aatgtagaat tttttaaaaa gttatctttt gctattacca  67440
agattgtgtt tagacgctta ttattaatat gagtgatgaa atccacaccg cctctagata  67500
tcgcctttat ttccacatta gatggtaaat ccaatagtga aactatcttt ttaggaatgt  67560
atggactcgc gtttagagga gtgaacgtct tgggcgtcgg aaaggatgat tcgtcaaacg  67620
aataaacaat ttcacaaatg gatgttaatg tattagtagg aaattttttg acgctagtgg  67680
aattgaagat tctaatggat gatgttctac ctatttcatc cgataacatg ttaatttccg  67740
```

```
acaccaacgg ttttaatatt tcgatgatat acggtagtct ctctttcgga cttatatagc  67800
ttattccaca atacgagtca ttatatactc caaaaaacaa aataactagt ataaaatctg  67860
tatcgaatgg gaaaaacgaa attatcgaca taggtataga atccggaaca ttgaacgtat  67920
taatacttaa ttctttttct gtggtaagta ccgataggtt attgacattg tatggtttta  67980
aatattctat aacttgagac ttgatagata ttagtgatga attgaaaatt atttttatca  68040
ccacgtgtgt ttcaggatca tcgtcgacgc ccgtcaacca accgaatgga gtaaaataaa  68100
tatcattaat atatgctcta gatattagta tttttatcaa tcctttgatt atcatcttct  68160
cgtaggcgaa tgattccatg atcaagagtg atttgagaac atcctccgga gtattaatgg  68220
gcttagtaaa cagtccatcg ttgcaataat aaaagttatc caagttaaag gatattatgc  68280
attcgtttaa agatatcacc tcatctgacg gagacaattt tttggtaggt tttagagact  68340
ttgaagctac ttgtttaaca aagttattca tcgtcgtcta ctattctatt taattttgta  68400
gttaatttat cacatatcac attaattgac tttttggtcc atttttccat acgtttatat  68460
tcttttaatc ctgcgttatc cgtttccgtt atatccaggg atagatcttg caagttaaat  68520
agaatgctct taaataatgt cattttctta tccgctaaaa atttaaagaa tgtataaacc  68580
tttttcagag atttgaaact cttaggtggt gtcctagtac acaatatcat aaacaaacta  68640
ataaacattc cacattcaga ttccaacagc tgattaactt ccacattaat acagcctatt  68700
ttcgctccaa atgtacattc gaaaaatctg aataaaacat cgatgtcaca atttgtatta  68760
tccaatacag aatgtctgtg attcgtgtta aaaccatcgg agaaggaata aaaataaaaa  68820
ttattatagt ggtggaattc agttggaata ttgcctccgg agtcataaaa ggatactaaa  68880
cattgttttt tatcataaat tacacatttc caatgagaca aataacaaaa tccaaacatt  68940
acaaatctag aggtagaact tttaattttg tctttaagta tatacgataa gatatgttta  69000
ttcataaacg cgtcaaattt ttcatgaatc gctaaggagt ttaagaatct catgtcaaat  69060
tgtcctatat aatccacttc ggatccataa gcaaactgag agactaagtt cttaatactt  69120
cgattgctca tccaggctcc tctctcaggc tctattttca tcttgacgac ctttggattt  69180
tcaccagtat gtattccttt acgtgataaa tcatcgattt tcaaatccat ttgtgagaag  69240
tctatcgcct tagatacttt ttcccgtagt cgaggtttaa aaaaatacgc taacggtata  69300
ctagtaggta actcaaaaac atcatatata gaatggtaac gcgtctttaa ctcgtcggtt  69360
aactctttct tttgatcgag ttcgtcgcta ctattgggtc tgctcaggtg ccccgactct  69420
actagttcca acatcatacc gataggaata caagacactt tgccggcggt tgtagattta  69480
tcatatttct ccactacata tccgttacaa tttgttaaaa atttagatac atctatattg  69540
ctacataatc cagctagtga atatatatga cataataaat tggtaaatcc tagttctggt  69600
attttactaa ttactaaatc tgtatatctt tccatttatc atggaaaaga atttaccaga  69660
tatcttcttt tttccaaact gcgttaatgt attctcttac aaatattcac aagatgaatt  69720
cagtaatatg agtaaaacgg aacgtgatag tttctcattg gcggtgtttc cagttataaa  69780
acatagatgg cataacgcac acgttgtaaa acataaagga atatacaaag ttagtacaga  69840
agcacgtgga aaaaaagtat ctcctccatc actaggaaaa cccgcacaca taaacctaac  69900
cgcgaagcaa tatatataca gtgaacacac aataagcttt gaatgttata gttttctaaa  69960
atgtataaca aatacagaaa tcaattcgtt cgatgagtat atattaagag gactattaga  70020
agctggtaat agtttacaga tattttccaa ttccgtaggt aaacgaacag atactatagg  70080
```

tgtactaggg aataagtatc catttagcaa aattccattg gcctcattaa ctcctaaagc 70140
acaacgagag atattttcag cgtggatttc tcatagacct gtagttttaa ctggaggaac 70200
tggagtgggt aagacgtcac aggtacccaa gttattgctt tggtttaatt atttatttgg 70260
tggattctct actctagata aaatcactga ctttcacgaa agaccagtca ttctatctct 70320
tcctaggata gctttagtta gattgcatag caataccatt ttaaaatcat tgggatttaa 70380
ggtactagat ggatctccta tttctttacg gtacggatct ataccggaag aattaataaa 70440
caaacaacca aaaaaatatg gaattgtatt ttctacccat aagttatctc taacaaaact 70500
atttagttat ggcactctta ttatagacga agttcatgag catgatcaaa taggagatat 70560
tattatagca gtagcgagaa agcatcatac gaaaatagat tctatgtttt taatgactgc 70620
cacgttagag gatgaccgag aacggctaaa agtattttta cctaatcccg catttataca 70680
tattcctgga gatacactgt ttaaaattag cgaggtattt attcataata agataaatcc 70740
atcttccaga atggcataca tagaagaaga aaagagaaat ttagttactg ctatacagat 70800
gtatactcct cctgatggat catccggtat agtctttgtg gcatccgttg cacagtgtca 70860
cgaatataaa tcatatttag aaaaaagatt accgtatgat atgtatatta ttcatggtaa 70920
ggtcttagat atagacgaaa tattagaaaa agtgtattca tcacctaatg tatcgataat 70980
tatttctact ccttatttgg aatccagcgt tactatacgc aatgttacac acatttatga 71040
tatgggtaga gtttttgtcc ccgctccttt tggaggatcg caacaattta tttctaaatc 71100
tatgagagat caacgaaaag gaagagtagg aagagttaat cctggtacat acgtctattt 71160
ctatgatctg tcttatatga agtctataca gcgaatagat tcagaatttc tacataatta 71220
tatattgtac gctaataagt ttaatctaac actccccgaa gatttgttta taatccctac 71280
aaatttggat attctatggc gtacaaagga atatatagac tcgttcgata ttagtacaga 71340
aacatggaat aaattattat ccaattatta tatgaagatg atagagtatg ctaaacttta 71400
tgtactaagt cctattctcg ctgaggagtt ggataacttt gagaggacgg gagaattaac 71460
tagtattgta cgagaagcca ttttatctct aaatttacga attaagattt taaattttaa 71520
acataaagat gatgatacgt atatacactt ttgtaaaata ttattcggtg tctataacgg 71580
aacaaacgct actatatatt atcatagacc tctaacggga tatatgaata tgatttcaga 71640
tactatattt gttcctgtag ataataacta aaaatcaaac tctaatgacc acatcttttt 71700
ttagagatga aaaattttcc acatctcctt ttgtagacac gactaaacat tttgcagaaa 71760
aaagtttatt agtgtttaga taatcgtata cttcatcagt gtagatagta aatgtgaaca 71820
gataaaaggt attcttgctc aatagattgg taaattccat agaatatatt aatcctttct 71880
tcttgagatc ccacatcatt tcaaccagag acgttttatc caatgattta cctcgtacta 71940
taccacatac aaaactagat tttgcagtga cgtcgtacct ggtattccta ccaaacaaaa 72000
ttttactttt agttctttta gaaaattcta aggtagaatc tctatttgcc aatatgtcat 72060
ctatggaatt accactagca aaaaatgata gaaatatata ttgatacatc gcagctggtt 72120
ttgatctact atactttaaa aacgaatcag attccataat tgcctgtata tcatcagctg 72180
aaaaactatg ttttacacgt attccttcgg catttctttt taatgatata tcttgtttag 72240
acaatgataa agttatcatg tccatgagag acgcgtctcc gtatcgtata aatatttcat 72300
tagatgttag acgcttcatt aggggtatac ttctataagg tttcttaatc agtccatcat 72360
tggttgcgtc aagaactact atcggatgtt gttgggtatc tctagtgtta cacatggcct 72420
tactaaagtt tgggtaaata actatgatat ctctattaat tatagatgca tatatttcat 72480

```
tcgtcaagga tattagtatc gacttgctat cgtcattaat acgtgtaatg taatcatata  72540
aatcatgcga tagccaagga aaattcaaat agatgttcat catataatcg tcgctataat  72600
tcatattaat acgttgacat tgactaattt gtaatatagc ctcgccacga agaaagctct  72660
cgtattcagt ttcatcgata aaggataccg ttaaatataa ctggttgccg atagtctcat  72720
agtctattaa gtggtaagtt tcgtacaaat acagaatccc taaaatatta tctaatgttg  72780
gattaatctt taccataact gtataaaatg gagacggagt cataactatt ttaccgtttg  72840
tacttactgg aatagatgaa ggaataatct ccggacatgc tggtaaagac ccaaatgtct  72900
gtttgaagaa atccaatgtt ccaggtccta atctcttaac aaaaattacg atattcgatc  72960
ccgatatcct ttgcattcta tttaccagca tatcacgaac tatattaaga ttatctatca  73020
tgtctattct cccaccgtta tataaatcgc ctccgctaag aaacgttagt atatccatac  73080
aatggaatac ttcatttcta aaatagtatt cgttttctaa ttctttaatg tgaaatcgta  73140
tactagaaag ggaaaaatta tctttgagtt ttccgttaga aaagaaccac gaaactaatg  73200
ttctgattgc gtccgatttc gttgctgaat taatggattt acaccaaaaa ctcatataac  73260
ttctagatgt agaagcattc gctaaaaaat tagtagaatc aaaggatata agtagatgtt  73320
ccaacaagtg agcaattccc aagatttcat ctatatcatt ctcgaatccg aaattagaaa  73380
ttcccaagta gatatccttt ttcatccgat cgttgatgaa aatacgaact ttattcggta  73440
agacaatcat ttactaagga gtaaaatagg aagtaatgtt cgtatgtcgt tatcatcgta  73500
taaattaaag gtgtgttttt taccattaag tgacattata attttaccaa tattggaatt  73560
ataatatagg tgtatttgcg cactcgcgac ggttgatgca tcggtaaata tagctgtatc  73620
taatgttcta gtcggtattt catcatttcg ctgtctaata atagcgtttt ctctatctgt  73680
ttccattaca gctgcctgaa gtttattggt cggataatat gtaaaataat aagaaataca  73740
tacgaataac aaaaataaaa taagatataa taaagatgcc atttagagat ctaattttgt  73800
ttaacttgtc caaattccta cttacagaag atgaggaatc gttggagata gtgtcttcct  73860
tatgtagagg atttgaaata tcttataatg acttgataac ttactttcca gataggaaat  73920
accataaata tatttctaaa gtatttgaac atgtagattt atcggaggaa ttaagtatgg  73980
aattccatga tacaactctg agagatttag tctatcttag attgtacaag tattccaagt  74040
gtatacggcc gtgttataaa ttaggagata atctaaaagg catagttgtt ataaaggaca  74100
ggaatattta tattagggaa gcaaatgatg acttgataga atatctcctc aaggaataca  74160
ctcctcagat ttatacatat tctaatgagc gcgtccccat aactggttca aaattaattc  74220
tttgtggatt ttctcaagtt acatttatgg cgtatacaac gtcgcatata acaacaaata  74280
aaaaggtaga tgttctcgtt tccaaaaaat gtatagatga actagtcgat ccaataaatt  74340
atcaaatact tcaaaattta tttgataaag gaagcggaac aataaacaaa atactcagga  74400
agatatttta ttcggtaaca ggtggccaaa ctccataatt tgctttttct atttcggatt  74460
ttagaatttc caaattcacc agcgatttat cggttttggt gaaatccaag gatttattaa  74520
tgtccacaaa tgccatttgt tttgtctgtg gattgtattt gaaaatggaa acgatgtagt  74580
tagatagatg cgctgcgaag tttcctatta gggttccgcg cttcacgtca cccagcatac  74640
ttgaatcacc atcctttaaa aaaaatgata agatatcaac atggagtata tcatactcgg  74700
attttaattc ttctactgca tcactgacat tttcacaaat actacaatac ggtttaccga  74760
aaataatcag tacgttcttc atttatgggt atcaaaaact taaaatcgtt actgctggaa  74820
```

```
aataaatcac tgacgatatt agatgataat ttatacaaag tatacaatgg aatatttgtg  74880
gatacaatga gtatttatat agccgtcgcc aattgtgtca gaaacttaga agagttaact  74940
acggtattca taaaatacgt aaacggatgg gtaaaaaagg gagggcatgt aaccctttttt  75000
atcgatagag gaagtataaa aattaaacaa gacgttagag acaagagacg taaatattct  75060
aaattaacca aggacagaaa aatgctagaa ttagaaaagt gtacatccga aatacaaaat  75120
gttaccggat ttatggaaga agaaataaag gcagaaatgc aattaaaaat cgataaactt  75180
acatttcaaa tatatttatc tgattctgat aacataaaaa tatcattgaa tgagatacta  75240
acacatttca acaataatga gaatgttaca ttattttatt gtgatgaacg agacgcagaa  75300
ttcgttatgt gtctcgaggc taaaacacat ttctctacca caggagaatg gccgttgata  75360
ataagtaccg atcaggatac tatgctattt gcatctgctg ataatcatcc taagatgata  75420
aaaaacttaa ctcaactgtt taaatttgtt ccctcggcag aggataacta tttagcaaaa  75480
ttaacggcgt tagtgaatgg atgtgatttc tttcctggac tctatggggc atctataaca  75540
cccaccaact taaacaaaat acaattgttt agtgatttta caatcgataa tatagtcact  75600
agtttggcaa ttaaaaatta ttatagaaag actaactcta ccgtagacgt gcgtaatatt  75660
gttacgttta taaacgatta cgctaattta gacgatgtct actcgtatat tcctccttgt  75720
caatgcactg ttcaagaatt tatattttcc gcattagatg aaaaatggaa tgaatttaaa  75780
tcatcttatt tagaaagcgt gccgttaccc tgtcaattaa tgtacgcgtt agaaccacgc  75840
aaggagattg atgtttcaga agttaaaact ttatcatctt atatagattt cgaaaatact  75900
aaatcagata tcgatgttat aaaatctata tcctcgatct tcggatattc taacgaaaac  75960
tgtaacacga tagtattcgg catctataag gataatttac tactgagtat aaatagttca  76020
ttttacttta acgatagtct gttaataacc aatactaaaa gtgataatat aataaatata  76080
ggttactaga ttaaaaatgg tgttccaact cgtgtgctct acgtgcggta aagatatttc  76140
tcacgaacga tataaattga ttatacgaaa aaaatcatta aaggatgtac tcgtcagtgt  76200
aaagaacgaa tgttgtaggt taaaattatc tacacaaata gaacctcaac gtaacttaac  76260
agtgcaacct ctattggata taaactaata tggatccggt taattttatc aagacatatg  76320
cgcctagagg ttctattatt tttattaatt ataccatgtc attaacaagt catttgaatc  76380
catcgataga aaaacatgtg ggtatttatt atggtacgtt attatcggaa cacttggtag  76440
ttgaatctac ctatagaaaa ggagttcgaa tagtcccatt ggatagtttt tttgaaggat  76500
atcttagtgc aaaagtatac atgttagaga atattcaagt tatgaaaata gcagctgata  76560
cgtcattaac tttattgggt attccgtatg gatttggtca taatagaatg tattgtttta  76620
aattggtagc tgaatgttat aaaaatgccg gtattgatac atcgtctaaa cgaatattgg  76680
gcaaagatat ttttctgagc caaaacttca caaacgataa tagatggata aagatatatg  76740
attctaataa tttaacattt tggcaaattg attaccttaa agggtgagtt aatatgcata  76800
actactcctc cgttgttttt tccctcgttc tttttcttaa cgttgtttgc catcactctc  76860
ataatgtaaa gatattctaa aatggtaaac ttttgcatat cggacgcaga aattggtata  76920
aatgttgtaa ttgtattatt tcccgtcaat ggactagtca cagctccatc agttttatat  76980
cctttagagt atttctcact cgtgtctagc attctagagc attccatgat ctgtttatcg  77040
ttgatattgg ccggaaagat agattttttta tttttttatta tattactatt ggcaattgta  77100
gatataactt ctggtaaata tttttctacc ttttcaatct cttctatttt caagccggct  77160
atatattctg ctatattgtt gctagtatca atacctttttc tggctaagaa gtcatatgtg  77220
```

```
gtattcacta tatcagtttt aactggtagt tccattagcc tttccacttc tgcagaataa  77280
tcagaaattg gttctttacc agaaaatcca gctactataa taggctcacc gatgatcatt  77340
ggcaaaatcc tatattgtac cagattaatg agagcatatt tcatttccaa taattctgct  77400
agttcttgag acattgattt atttgatgaa tctagttggt tctctagata ctctaccatt  77460
tctgccgcat acaataactt gttagataaa atcagggtta tcaaagtgtt tagcgtggct  77520
agaatagtgg gcttgcatgt attaaagaat gcggtagtat gagtaaaccg ttttaacgaa  77580
ttatatagtc tccagaaatc tgtggcgtta catacatgag ccgaatgaca tcgaagattg  77640
tccaatattt ttaatagctg ctctttgtcc attatttcta tatttgactc gcaacaattg  77700
tagataccat taatcaccga ttcctttttc gatgctggac aatagcacaa ttgtttagct  77760
ttggactcta tgtattcaga attaatagat atatctctca atacagattg cactatacat  77820
tttgaaacta tgtcaaaaat tgtagaacga cgctgttctg cagccattta actttaaata  77880
atttacaaaa atttaaaatg agcatccgta taaaaatcga taaactgcgc caaattgtgg  77940
catatttttc agagttcagt gaagaagtgt ctataaatgt agactcgacg gatgagttaa  78000
tgtatatttt tgccgccttg ggcggatctg taaacatttg ggccattata cctctcagtg  78060
catcagtgtt ctaccgagga gccgaaaaca ttgtgtttaa tcttcctgtg tccaaggtaa  78120
aatcgtgttt gtgtagtttt cacaatgatg ccatcataga tatagaacct gatctggaaa  78180
ataatctagt aaaactttct agttatcatg tagtaagtgt cgattgtaac aaggaactga  78240
tgcctattag gacagatact actatttgtc taagtataga tcaaaagaaa tcttatgtgt  78300
ttaattttca caagtatgaa gaaaaatgtt gtggtagaac cgtcattcat ctagaatggt  78360
tgttgggctt tatcaagtgt attagtcagc atcagcatct ggctattatg tttaaagatg  78420
acaatattat tatgaagact cctggtaata ctgatgcatt ttccagggaa tattctatga  78480
ctgaatgttc tcaagaacta caaaagtttt ctttcaaaat agctatctcg tctctcaaca  78540
aactacgagg attcaaaaag agagtcaatg tttttgaaac tagaatcgta atggataatg  78600
acgataacat tttaggaatg ttgttttcgg atagagttca atcctttaag atcaacatct  78660
ttatggcgtt tttagattaa tactttcaat gagataaata tgggtggcgg agtaagtgtt  78720
gagctcccta aacgggatcc gcctccggga gtacccactg atgagatgtt attaaacgtg  78780
gataaaatgc atgacgtgat agctcccgct aagcttttag aatatgtgca tataggacca  78840
ctagcaaaag ataaagagga taaagtaaag aaaagatatc cagagtttag attagtcaac  78900
acaggacccg gtggtctttc agcattgtta agacaatcgt ataatggaac cgcacccaat  78960
tgctgtcgca cttttaatcg tactcattat tggaagaagg atggaaagat atcagataag  79020
tatgaagagg gtgcagtatt agaatcgtgt tggccagacg ttcacgacac tggaaaatgc  79080
gatgttgatt tattcgactg gtgtcagggg gatacgttcg atagaaacat atgccatcag  79140
tggatcggtt cagcctttaa taggagtgat agaactgtag agggtcaaca atcgttaata  79200
aatctgtata ataagatgca aacattatgt agtaaagatg ctagtgtacc aatatgcgaa  79260
tcatttttgc atcatttacg cgcacacaat acagaagata gcaaagagat gatcgattat  79320
attctaagac aacagtctgc ggactttaaa cagaaatata tgagatgtag ttatcccact  79380
agagataagt tagaagagtc attaaaatat gcggaacctc gagaatgttg ggatccagag  79440
tgttcgaatg ccaatgttaa tttcttacta acacgtaatt ataataattt aggactttgc  79500
aatattgtac gatgtaatac tagcgtgaac aacttacaga tggataaaac ttcctcatta  79560
```

```
agattgtcat gtggattaag caatagtgat agattttcta ctgttcccgt caatagagca  79620
aaagtagttc aacataatat taaacattcg ttcgacctaa aattgcattt gatcagttta  79680
ttatctctct tggtaatatg gatactaatt gtagctattt aaatgggtgc cgcggcaagc  79740
atacagacga cggtgaatac actcagcgaa cgtatctcgt ctaaattaga acaagaagcg  79800
aatgctagtg ctcaaacaaa atgtgatata gaaatcggaa atttttatat ccgacaaaac  79860
catggatgta acctcactgt taaaaatatg tgctctgcgg acgcggatgc tcagttggat  79920
gctgtgttat cagccgctac agaaacatat agtggattaa caccggaaca aaaagcatac  79980
gtgccagcta tgtttactgc tgcgttaaac attcagacga gtgtaaacac tgttgttaga  80040
gattttgaaa attatgtgaa acagacttgt aattctagcg cggtcgtcga taacaaatta  80100
aagatacaaa acgtaatcat agatgaatgt tacggagccc caggatctcc aacaaatttg  80160
gaatttatta atacaggatc tagcaaagga aattgtgcca ttaaagcgtt gatgcaattg  80220
acgactaagg ccactactca aatagcacct agacaagttg ctggtacagg agttcagttt  80280
tatatgattg ttatcggtgt tataatattg gcagcgttgt ttatgtacta tgccaagcgt  80340
atgctgttca catccaccaa tgataaaatc aaacttattt tagccaataa ggaaaacgtc  80400
cattggacta cttacatgga cacattcttt agaacttctc cgatggttat tgctaccacg  80460
gatatgcaaa actgaaaata tattgataat attttaatag attaacatgg aagttatcgc  80520
tgatcgtcta gacgatatag tgaaacaaaa tatagcggat gaaaaatttg tagattttgt  80580
tatacacggt ctagagcatc aatgtcctgc tatacttcga ccattaatta ggttgtttat  80640
tgatatacta ttatttgtta tagtaattta tatttttacg gtacgtctag taagtagaaa  80700
ttatcaaatg ttgttggcgt tggtggcgct agtcatcaca ttaactattt tttattactt  80760
tatactataa tagtactaga ctgacttcta acaaacatct cacctgccat aaataaatgc  80820
ttgatattaa agtcttctat ttctaacact attccatctg tggaaaataa tactctgaca  80880
ttatcgctaa ttgacacatc ggtgagtgat atgcctataa agtaataatc ttctttgggc  80940
acatatacca gtgtaccagg ttctaacaac ctatttactg gtgctcctgt agcatacttt  81000
ttctttacct tgagaatatc catcgtttgc ttggtcaata gcgatatgtg atttttttatc  81060
aaccactcga aaaagtaatt ggagtgttca tatcctctac gggctattgt ctcatggccg  81120
tgtatgaaat ttaagtaaca cgactgtggt agatttgttc tatagagccg gttgccgcaa  81180
atagatagaa ctaccaatat gtctgtacaa atgttaaaca ttaattgatt aacagaaaaa  81240
acaatgttcg ttctgggaat agaaaccaga ttaaaacaaa attcgttaga atatatgcca  81300
cgtttataca tggaatataa aataactaca gtttgaaaaa taacagtatc atttaaacat  81360
ttaacttgcg gggttaattt cacaacttta ctgtttttga actgttcaaa atatagcata  81420
gatccgtgag aaatacgttt agccgccttt aatagaggaa atcccaccgc ctttctggat  81480
ctcaccaacg acgatagttc tgaccagcaa ctcatttctt catcatccac ctgttttaac  81540
atataatagg caggagatag atatccgtca ttgcaatatt ccttctcgta ggcacacaat  81600
ctaatattga taaaatctcc attctcttct ctgcatttat tatcttgttt cggtggctga  81660
ttaggctgta gtcttggttt aggctttggt atatcgttgt tgaatctatt ttggtcatta  81720
aatctttcat ttcttcctgg tatattttta tcacctcgtt tggttggatt tttgtctata  81780
ttatcgtttg taacatcggt acgggtattc atttatcaca aaaaaaactt ctctaaatga  81840
gtctactgct agaaaacctc atcgaagaag ataccatatt ttttgcagga agtatatctg  81900
agtatgatga tttacaaatg gttattgccg gcgcaaaatc caaatttcca agatctatgc  81960
```

```
tttctatttt taatatagta cctagaacga tgtcaaaata tgagttggag ttgattcata  82020
acgaaaatat cacaggagca atgtttacca caatgtataa tataagaaac aatttgggtc  82080
taggagatga taaactaact attgaagcca ttgaaaacta tttcttggat cctaacaatg  82140
aagttatgcc tcttattatt aataatacgg atatgactgc cgtcattcct aaaaaaagtg  82200
gtaggagaaa gaataagaac atggttatct tccgtcaagg atcatcacct atcttgtgca  82260
ttttcgaaac tcgtaaaaag attaatattt ataaagaaaa tatggaatcc gcgtcgactg  82320
agtatacacc tatcggagac aacaaggctt tgatatctaa atatgcggga attaatgtcc  82380
tgaatgtgta ttctccttcc acatccataa gattgaatgc catttacgga ttcaccaata  82440
aaaataaact agagaaactt agtactaata aggaactaga atcgtatagt tctagccctc  82500
ttcaagaacc cattaggtta aatgattttc tgggactatt ggaatgtgtt aaaaagaata  82560
ttcctctaac agatattccg acaaaggatt gattactata aatggagaat gttcctaatg  82620
tatactttaa tcctgtgttt atagagccca cgtttaaaca ttctttatta agtgtttata  82680
aacacagatt aatagtttta tttgaagtat tcgttgtatt cattctaata tatgtatttt  82740
ttagatctga attaaatatg ttcttcatgc ctaaacgaaa aatacccgat cctattgata  82800
gattacgacg tgctaatcta gcgtgtgaag acgataaatt aatgatctat ggattaccat  82860
ggatgacaac tcaaacatct gcgttatcaa taaatagtaa accgatagtg tataaagatt  82920
gtgcaaagct tttgcgatca ataaatggat cacaaccagt atctcttaac gatgttcttc  82980
gcagatgatg attcattttt taagtatttg gctagtcaag atgatgaatc ttcattatct  83040
gatatattgc aaatcactca atatctagac tttctgttat tattattgat ccaatcaaaa  83100
aataaattag aagccgtggg tcattgttat gaatctcttt cagaggaata cagacaattg  83160
acaaaattca cagactttca agattttaaa aaactgttta acaaggtccc tattgttaca  83220
gatggaaggg tcaaacttaa taaaggatat ttgttcgact ttgtgattag tttgatgcga  83280
ttcaaaaaag aatcctctct agctaccacc gcaatagatc ctgttagata catagatcct  83340
cgtcgcgata tcgcattttc taacgtgatg gatatattaa agtcgaataa agtgaacaat  83400
aattaattct ttattgtcat catgaacggc ggacatattc agttgataat cggccccatg  83460
ttttcaggta aaagtacaga attaattaga cgagttagac gttatcaaat agctcaatat  83520
aaatgcgtga ctataaaata ttctaacgat aatagatacg gaacgggact atggacgcat  83580
gataagaata attttgaagc attggaagca actaaactat gcgatgtctt ggaattaatt  83640
acagatttct ccgtgatagg tatcgatgaa ggacagttct ttccagacat tgttgaattc  83700
tgtgagcgta tggcaaacga aggaaaaata gttatagtag ccgcactcga tgggacattt  83760
caacgtaaac cgtttaataa tattttgaat cttattccat tatctgaaat ggtggtaaaa  83820
ctaactgctg tgtgtatgaa atgctttaag gaggcttcct tttctaaacg attgggtgag  83880
gaaaccgaga taaaaataat aggaggtaat gatatgtatc aatcggtgtg tagaaagtgt  83940
tacatcgact cataatatta tattttttat ctaaaaaact aaaaataaac attgattaaa  84000
ttttaatata atacttaaaa atggatgttg tgtcgttaga taaaccgttt atgtattttg  84060
aggaaattga taatgagtta gattacgaac cagaaagtgc aaatgaggtc gcaaaaaaac  84120
tgccgtatca aggacagtta aaactattac taggagaatt attttttctt agtaagttac  84180
agcgacacgg tatattagat ggtgccaccg tagtgtatat aggatctgct cccggtacac  84240
atatacgtta tttgagagat catttctata atttaggagt gatcatcaaa tggatgctaa  84300
```

```
ttgacggccg ccatcatgat cctattctaa atggattgcg tgatgtgact ctagtgactc  84360
ggttcgttga tgaggaatat ctacgatcca tcaaaaaaca actgcatcct tctaagatta  84420
ttttaatttc tgatgtaaga tccaaacgag gaggaaatga acctagtacg gcggatttac  84480
taagtaatta cgctctacaa aatgtcatga ttagtatttt aaaccccgtg gcatctagtc  84540
ttaaatggag atgcccgttt ccagatcaat ggatcaagga cttttatatc ccacacggta  84600
ataaaatgtt acaacctttt gctccttcat attcagctga aatgagatta ttaagtattt  84660
ataccggtga gaacatgaga ctgactcgag ttaccaaatt agacgctgta aattatgaaa  84720
aaaagatgta ctaccttaat aagatcgtcc gtaacaaagt agttgttaac tttgattatc  84780
ctaatcagga atatgactat tttcacatgt actttatgct gaggaccgtg tactgcaata  84840
aaacatttcc tactactaaa gcaaaggtac tatttctaca acaatctata tttcgtttct  84900
taaatattcc aacaacatca actgaaaaag ttagtcatga accaatacaa cgtaaaatat  84960
ctagcaaaaa ttctatgtct aaaaacagaa atagcaagag atccgtacgc ggtaataaat  85020
agaaacgtac tactgagata tactaccgat atagagtata atgatttagt tactttaata  85080
accgttagac ataaaattga ttctatgaaa actgtgtttc aggtatttaa cgaatcatcc  85140
ataaattata ctccggttga tgatgattat ggagaaccaa tcattataac atcgtatctt  85200
caaaaaggtc ataacaagtt tcctgtaaat tttctataca tagatgtggt aatatctgac  85260
ttatttccta gctttgttag actagatact acagaaacta atatagttaa tagtgtacta  85320
caaacaggtg atggtaaaaa gactcttcgt cttcccaaaa tgttagagac ggaaatagtt  85380
gtcaagattc tctatcgccc taatatacca ttaaaaattg ttagattttt ccgcaataac  85440
atggtaactg gagtagagat agccgataga tctgttattt cagtcgctga ttaatcaatt  85500
agtagagatg agataagaac attataataa tcaataatat atcttatatc ttatatctta  85560
tatcttgttt agaaaaatgc taatattaaa atagctaacg ctagtaatcc aatcggaagc  85620
catttgatat ctataatagg gtatctaatt tcctgattta aatagcggac agctatattc  85680
tcggtagcta ctcgtttgga atcacaaaca ttatttacat ctaatttact atctgtaatg  85740
gaaacgtttc ccaatgaaat ggtacaatcc gatacattgc attttgttat attttttttt  85800
aaagaggctg gtaacaacgc atcgcttcgt ttacatggct cgtaccaaca ataatagggt  85860
aatcttgtat ctattcctat ccgtactatg cttttatcag gataaataca tttacatcgt  85920
atatcgtctt tgttagcatc acagaatgca taaatttgtt cgtccgtcat gataaaaatt  85980
taaagtgtaa atataactat tatttttata gttgtaataa aaagggaaat ttgattgtat  86040
actttcggtt ctttaaaaga aactgacttg ataaaaatgg ctgtaatctc taaggttacg  86100
tatagtctat atgatcaaaa agagattaat gctacagata ttatcattag tcatgttaaa  86160
aatgacgacg atatcggtac cgttaaagat ggtagactag gtgctatgga tggggcatta  86220
tgtaagactt gtgggaaaac ggaattggaa tgtttcggtc actggggtaa agtaagtatt  86280
tataaaactc atatagttaa gcctgaattt atttcagaaa ttattcgttt actgaatcat  86340
atatgtattc actgcggatt attgcgttca cgagaaccgt attccgacga tattaaccta  86400
aaagagttat cgggacacgc tcttaggaga ttaaaggata aaatattatc caagaaaaag  86460
tcatgttgga acagcgaatg tatgcaaccg tatcaaaaaa ttactttttc aaagaaaaag  86520
gtttgtttcg tcaacaagtt ggatgatatt aacgttccta attctctcat ctatcaaaag  86580
ttaatttcta ttcatgaaaa gttttggcca ttattagaaa ttcatcaata tccagctaac  86640
ttattttata cagactactt tcccatccct ccgttgatta ttagaccggc tattagtttt  86700
```

```
tggatagata gtatacccaa agaaaccaat gaattaactt acttattagg tatgatcgtt  86760
aagaattgta acttgaatgc tgatgaacag gttatccaga aggcggtaat agaatacgat  86820
gatattaaaa ttatttctaa taacactacc agtatcaatt tatcatatat cacatccggc  86880
aaaaataata tgattagaag ttatatcgtc gcccggcgaa aagatcagac cgctagatct  86940
gtaattggtc ccagtacatc tatcaccgtt aatgaggtag gaatgcccgc atatattaga  87000
aatacactta cagaaaagat atttgttaat gcctttacag tggataaagt taaacaacta  87060
ttagcgtcaa accaagttaa attttacttt aataaacgat taaaccaatt aacaagaata  87120
cgccaaggaa agtttatcaa aaataaaata catttattgc ctggtgattg ggtagaagta  87180
gctgttcaag aatatacaag tattattttt ggaagacagc cgtctctaca tagatacaac  87240
gtcatcgctt catctatcag agctaccgaa ggagatacta tcaaaatatc tcccggaatt  87300
gccaactctc aaaatgctga tttcgacgga gatgaagaat ggatgatatt agaacaaaat  87360
cctaaagctg taattgaaca aagtattctt atgtatccga cgacgttact caaacacgat  87420
attcatggag cccccgttta tggatctatt caagatgaaa tcgtagcagc gtattcattg  87480
tttaggatac aagatctttg tttagatgaa gtattgaaca tcttggggaa atatggaaga  87540
gagttcgatc ctaaaggtaa atgtaaattc agcggtaaag atatctatac ttacttgata  87600
ggtgaaaaga ttaattatcc gggtctctta aaggatggtg aaattattgc aaacgacgta  87660
gatagtaatt ttgttgtggc tatgaggcat ctgtcattgg ctggactctt atccgatcat  87720
aagtcgaacg tggaaggtat caactttatt atcaagtcat cttatgtttt taagagatat  87780
ctatctattt acggttttgg ggtgacattc aaagatctga gaccaaattc gacgttcact  87840
aataaattgg aggccatcaa cgtagaaaaa atagaactta tcaaagaagc atacgccaaa  87900
tatctcaacg atgtaagaga cgggaaaata gttccattat ctaaagcttt agaggcggac  87960
tatgtggaat ccatgttatc caacttgaca aatcttaata tccgagagat agaagaacat  88020
atgagacaaa cgctgataga tgatccagat aataacctcc tgaaaatggc caaagcgggt  88080
tataaagtaa atcccacaga actaatgtat attctaggta cgtatggaca acaaaggatt  88140
gatggtgaac cagcagagac tcgagtattg ggtagagttt taccttacta tcttccagac  88200
tctaaggatc cagaaggaag aggttacatt cttaattctt taacaaaagg attaacaggt  88260
tctcaatatt acttttcgat gctggttgcc agatctcaat ctactgatat cgtctgtgaa  88320
acatcacgta ccggaacact ggctagaaaa atcattaaaa agatggagga tatggtggtc  88380
gacggatacg gacaagtagt tataggtaat acgctcatca agtacgccgc caattatacc  88440
aaaattctag gctcagtatg taaacctgta gatcttatct atccagatga gtccatgact  88500
tggtatttgg aaattagtgc tctgtggaat aaaataaaac agggattcgt ttactctcag  88560
aaacagaaac ttgcaaagaa gacattggcg ccgtttaatt tcctagtatt cgtcaaaccc  88620
accactgagg ataatgctat taaggttaag gatctgtacg atatgattca taacgtcatt  88680
gatgatgtga gagagaaata cttctttacg gtatctaata tagattttat ggagtatata  88740
ttcttgacgc atcttaatcc ttctagaatt agaattacaa aagaaacggc tatcactatc  88800
tttgaaaagt tctatgaaaa actcaattat actctaggtg gtggaactcc tattggaatt  88860
atttctgcac aggtattgtc tgagaagttt acacaacaag ccctgtccag ttttcacact  88920
actgaaaaaa gtggtgccgt caaacaaaaa cttggtttca acgagtttaa taacttgact  88980
aatttgagta agaataagac cgaaattatc actctggtat ccgatgatat ctctaaactt  89040
```

```
caatctgtta agattaattt cgaatttgta tgtttgggag aattaaatcc aaacatcact  89100
cttcgaaaag aaacagatag gtatgtagta gatataatag tcaatagatt atacatcaag  89160
agagcagaaa ttaccgaatt agtcgtcgaa tatatgattg aacgattcat ctcctttagc  89220
gtcattgtaa aggaatgggg tatggaaaca ttcattgagg atgaggataa tattagattt  89280
actgtctacc taaatttcgt tgaaccggaa gaattgaatc ttagtaagtt tatgatggtt  89340
cttccgggtg ccgccaacaa gggcaagatt agtaaattca agattcctat ctctgattat  89400
acgggttatg acgacttcaa tcaaacaaaa aagctcaata agatgactgt agaactcatg  89460
aatctaaaag aattgggttc tttcgatttg gaaaacgtca acgtgtatcc tggagtatgg  89520
aatacatacg atatcttcgg tatcgaggcc gctcgtgaat acttgtgcga agccatgtta  89580
aacacctatg gagaagggtt cgattatctg tatcagcctt gtgatcttct cgctagttta  89640
ctatgtgcta gttacgaacc agaatcagtg aataaattca agttcggcgc agctagtact  89700
cttaagagag ctacgttcgg agacaataaa gcattgttaa acgcggctct tcataaaaag  89760
tcagaaccta ttaacgataa tagtagctgc cactttttta gcaaggtccc taatatagga  89820
actggatatt acaaatactt tatcgacttg ggtcttctca tgagaatgga aaggaaacta  89880
tctgataaga tatcttctca aaagatcaag gaaatggaag aaacagaaga cttttaattc  89940
ttatcaataa catatttttc tatgatctgt cttttaaacg atggattttc cacaaatgcg  90000
cctctcaagt ccctcataga atgatacacg tataaaaaat atagcatagg caatgactcc  90060
ttatttttag acattagata tgccaaaatc atagccccgc ttctatttac tcccgcagca  90120
caatgaacca acacgggctc gtttcgttga tcacatttag ataaaaaggc ggttacgtcg  90180
tcaaaatatt tactaatatc ggtagttgta tcatctacca acggtatatg aataatatta  90240
atattagagt taggtaatgt atatttatcc atcgtcaaat ttaaaacata tttgaactta  90300
acttcagatg atggtgcatc catagcattt ttataatttc ccaaatacac attattggtt  90360
acccttgtca ttatagtggg agatttggct ttgtgcatat ctccagttga acgtagtagt  90420
aagtatttat acaaactttt cttatccatt tataacgtac aaatggataa aactacttta  90480
tcggtaaacg cgtgtaattt agaatacgtt agagaaaagg ctatagtagg cgtacaagca  90540
gccaaaacat caacacttat attctttgtt attatattgg caattagtgc gctattactc  90600
tggtttcaga cgtctgataa tccagtcttt aatgaattaa cgagatatat gcgaattaaa  90660
aatacggtta acgattggaa atcattaacg gatagcaaaa caaaattaga aagtgataga  90720
ggtaaacttc tagccgctgg taaggatgat atattcgact tcaaatgtgt ggatttcggc  90780
gcctatttta tagctatgcg attggataag aaaacatatc tgccgcaagc tattaggcga  90840
ggtactggag acgcgtggat ggttaaaaag gcggcaaagg tcgatccatc tgctcaacaa  90900
ttttgtcagt atttgataaa acacaagtct aataatgtta ttacttgtgg taatgagatg  90960
ttaaatgaat taggttatag cggttatttt atgttaccgc attggtgttc cgattttagt  91020
aatatggaat agtgttagat aaatgcggta acgaatgttc ctgtaaggaa ccataacagt  91080
ttagatttaa cgttaaagat gagcataaac ataataaaca aaattacaat caaacctata  91140
acattaatat caaacaatcc aaaaaatgaa atcagtggag tagtaaacgc gtacataact  91200
cctggataac gtttagcagc tgccgttcct attctagacc aaaaatttgg tttcatgttt  91260
tcgaaacggt attctgcaac aagtcgagga tcgtgttcta catatttggc ggcgttatcc  91320
agtatctgcc tattgatctt catttcgttt tcgattctgg ctatttcaaa ataaaatccc  91380
gatgatagac ctccagactt tataatttca tctacgatgt tcagcgccgt agtaactcta  91440
```

```
ataatatagg ctgataagct aacatcatac cctcctgtat atgtgaatat ggcatgattt  91500
ttgtccatta caagctcggt tttaacttta ttgcctgtaa taatttctct catctgtagg  91560
atatctattt ttttgtcatg cattgccttc aagacgggac gaagaaacgt aatatcctca  91620
ataacgttat cgttttctac aataactaca tattctacct ttttattttc taactcggta  91680
aaaaaattag aatcccatag ggctaaatgt ctagcgatat ttcttttcgt ttcctctgta  91740
cacatagtgt tacaaaaccc tgaaaagaag tgagtatact tgtcatcatt tctaatgttt  91800
cctccagtcc actgtataaa cgcataatcc ttgtaatgat ctggatcatc cttgactacc  91860
acaacatttc tttttctgg cataacttcg ttgtccttta catcatcgaa cttctgatca  91920
ttaatatgct catgaacatt aggaaatgtt tctgatggag gtctatcaat aactggcaca  91980
acaataacag gagttttcac cgccgccatt tagttattga aattaatcat atacaactct  92040
ttaatacgag ttatattttc gtctatccat tgtttcacat tgacatattt cgacaaaaag  92100
atataaaatg cgtattccaa tgcttctctg tttaatgaat tactaaaata tacaaacacg  92160
tcactgtctg gcaataaatg atatcttaga atattgtaac aatttatttt gtattgcaca  92220
tgttcgtgat ctatgagttc ttcttcgaat ggcataggat ctccgaatct gaaaacgtat  92280
aaataggagt tagaataata atatttgaga gtattggtaa tatataaact ctttagcggt  92340
ataattagtt tttttctctc aatttctatt tttagatgtg atggaaaaat gactaatttt  92400
gtagcattag tatcatgaac tctaatcaaa atcttaatat cttcgtcaca cgttagctct  92460
ttgaagtttt taagagatgc atcagttggt tctacagatg gagtaggtgc aacaattttt  92520
tgttctacac atgtatgtac tggagccatt gttttaacta taatggtgct tgtatcgaaa  92580
aactttaatg cagatagcgg aagctcttcg ccgcgacttt ctacgtcgta attgggttct  92640
aacgccgatc tctgaatgga tactagtttt ctaagttcta atgtgattct ctgaaaatgt  92700
aaatccaatt cctccggcat tatagatgtg tatacatcgg taaataaaac tatagtatcc  92760
aacgatccct tctcgcaaat tctagtctta accaaaaaat cgtatataac cacggagatg  92820
gcgtatttaa gagtggattc ttctaccgtt ttgttcttgg atgtcatata ggaaactata  92880
aagtccgcac tactgttaag aatgattact aacgcaacta tatagttcaa attaagcatt  92940
ttggaaacat aaaataactc tgtagacgat acttgacttt cgaataagtt tgcagacaaa  93000
cgaagaaaga acagacctct cttaatttca gaagaaaact ttttttcgta ttcctgacgt  93060
ctagagttta tatcaataag aaagttaaga attagtcggt taatgttgta tttcattacc  93120
caagtttgag atttcataat attatcaaaa gacatgataa tattaaagat aaagcgctga  93180
ctatgaacga aatagctata tggttcgctc aaaaatatag tcttgttaaa cgtggaaacg  93240
ataactgtat ttttaatcac gtcagcggca tctaaattaa atataggtat atttattcca  93300
cacactctac aatatgccac accatcttca taataaataa attcgttagc aaaattatta  93360
attttagtga aatagttagc gtcaactttc atagcttcct tcaatctaat ttgatgctcg  93420
cacggtgcga attccactct aacatccctt ttccatgcct caggttcatc gatctctata  93480
atatctagtt ttttgcgttt cacaaacaca ggctcgtctc tcgcgatgag atctgtatag  93540
taactatgta aatgataact agatagaaag atgtagctat atagatgacg atcctttaag  93600
agaggtataa taactttacc ccaatcagat agactgttgt tatggtcttc ggaaaaagaa  93660
tttttataaa tttttccagt attttccaaa tatacgtact taacatctaa aaaatcctta  93720
atgataatag gaatggataa tccgtctatt ttataaagaa atacatatcg cacattatac  93780
```

```
ttttttttgg aaatgggaat accgatgtgt ctacataaat atgcaaagtc taaatatttt  93840
ttagagaatc ttagttggtc caaattcttt tccaagtacg gtaatagatt tttcatattg  93900
aacggtatct tcttaatctc tggttctagt tccgcattaa atgatgaaac taagtcacta  93960
tttttataac taacgattac atcacctcta acatcatcat ttaccagaat actgatcttc  94020
ttttgtcgta aatacatgtc taatgtgtta aaaaaaagat catacaagtt atacgtcatt  94080
tcatctgtgg tattcttgtc attgaaggat aaactcgtac taatctcttc tttaacagcc  94140
tgttcaaatt tatatcctat atacgaaaaa atagcaacca gtgtttgatc atccgcgtca  94200
atattctgtt ctatcgtagt gtataacaat cgtatatctt cttctgtgat agtcgatacg  94260
ttataaaggt tgataacgaa aatattttta tttcgtgaaa taaagtcatc gtaggatttt  94320
ggacttatat tcgcgtctag taaatatgct tttatttttg gaatgatctc aattagaata  94380
gtctctttag agtccattta aagttacaaa caactaggaa attggtttat gatgtataat  94440
tttttagtt tttatagatt ctttattcta tacttaaaaa atgaaaataa atacaaaggt  94500
tcttgagggt tgtgttaaat tgaaagcgag aaataatcat aaattatttc attatcgcga  94560
tatccgttaa gtttgtatcg taatggcgtg gtcaattaca aataaagcgg atactagtag  94620
cttcacaaag atggctgaaa tcagagctca tctaaaaaat agcgctgaaa ataaagataa  94680
aaacgaggat attttcccgg aagatgtaat aattccatct actaagccca aaaccaaacg  94740
agccactact cctcgtaaac cagcggctac taaaagatca accaaaaagg aggaagtgga  94800
agaagaagta gttatagagg aatatcatca aacaactgaa aaaaattctc catctcctgg  94860
agtcagcgac attgtagaaa gcgtggctgc tgtagagctc gatgatagcg acggggatga  94920
tgaacctatg gtacaagttg aagctggtaa agtaaatcat agtgctagaa gcgatctttc  94980
tgacctaaag gtggctaccg acaatatcgt taaagatctt aagaaaatta ttactagaat  95040
ctctgcagta tcgacggttc tagaggatgt tcaagcagct ggtatctcta gacaatttac  95100
ttctatgact aaagctatta caacactatc tgatctagtc accgagggaa aatctaaagt  95160
tgttcgtaaa aaagttaaaa cttgtaagaa gtaaatgcgt gcactttttt ataaagatgg  95220
taaactcttt accgataata attttttaaa tcctgtatca gacgataatc cagcgtatga  95280
ggttttgcaa catgttaaaa ttcctactca tttaacagat gtagtagtat atgaacaaac  95340
gtgggaggag gcgttaacta gattaatttt tgtgggaagt gattcaaaag gacgtagaca  95400
atacttttac ggaaaaatgc atgtacagaa tcgcaacgct aaaagagatc gtatttttgt  95460
tagagtatat aacgttatga aacgaattaa ttgttttata aacaaaaata taaagaaatc  95520
gtccacagat tccaattatc agttggcggt ttttatgtta atggaaacta tgttttttat  95580
tagatttggt aaaatgaaat atcttaagga gaatgaaaca gtagggttat taacactaaa  95640
aaataaacac atagaaataa gtcccgatga aatagttatc aagtttgtag gaaaggacaa  95700
agtttcacat gaatttgttg ttcataagtc taatagacta tataaaccgc tattgaaact  95760
gacggatgat tctagtcccg aagaatttct gttcaacaaa ctaagtgaac gaaaggtata  95820
cgaatgtatc aaacagtttg gtattagaat caaggatctc cgaacgtatg gagtcaatta  95880
tacgttttta tataattttt ggacaaatgt aaagtccata tctcctcttc cgtcaccaaa  95940
aaagttaata gcattaacta tcaaacaaac tgctgaagtg gtaggtcata ctccatcaat  96000
ttcaaaaaga gcttatatgg caacgactat tttagaaatg gtaaaggata aaaatttttt  96060
agatgtagta tctaaaacta cgttcgatga attcctatct atagtcgtag atcacgttaa  96120
atcatctacg gatggatgat atagatcttt acacaaataa ttacaagacc gataaatgga  96180
```

```
aatggataag cgtatgaaat ctctcgcaat gacagctttc ttcggagagc taaacacatt  96240
agatattatg gcattgataa tgtctatatt taaacgccat ccaaacaata ccattttttc  96300
agtggataag gatggtcagt ttatgattga tttcgaatac gataattata aggcttctca  96360
atatttggat ctgaccctca ctccgatatc tggagatgaa tgcaagactc acgcatcgag  96420
tatagccgaa caattggcgt gtgcggatat tattaaagag gatattagcg aatatatcaa  96480
aactactccc cgtcttaaac gatttataaa aaaataccgc aatagatcag atactcgcat  96540
cagtcgagat acagaaaagc ttaaaatagc tctagctaaa ggcatagatt acgaatatat  96600
aaaagacgct tgttaataag taaatgaaaa aaaactagtc gtttataata aaacacgata  96660
tggatgccaa cgtagtatca tcttctacta ttgcgacgta tatagacgct ttagcgaaga  96720
atgcttcgga attagaacag aggtctaccg catacgaaat aaataatgaa ttggaactag  96780
tatttattaa gccgccattg attactttga caaatgtagt gaatatctct acgattcagg  96840
aatcgtttat tcgatttacc gttactaata aggaaggtgt taaaattaga actaagattc  96900
cattatctaa ggtacatggt ctagatgtaa aaaatgtaca gttagtagat gctatagata  96960
acatagtttg ggaaaagaaa tcattagtga cggaaaatcg tcttcacaaa gaatgcttgt  97020
tgagactatc gacagaggaa cgtcatatat ttttggatta caagaaatat ggatcctcta  97080
tccgactaga attagtcaat cttattcaag caaaaacaaa aaactttacg atagacttta  97140
agctaaaata ttttctagga tccggtgccc aatctaaaag ttctttatta cacgctatta  97200
atcatccaaa gtcaaggcct aatacatctc tggaaataga attcacacct agagacaatg  97260
aaacagttcc atatgatgaa ctaataaagg aattgacgac tctatcacgt catatattta  97320
tggcttctcc agagaatgta attctttctc cgcctattaa cgcgcttata aaaaccttta  97380
tgttgcctaa acaagatata gtaggtttgg atctggaaaa tctatatgcc gtaactaaga  97440
ctgacggcat tcctataact atcagagtta catcaaacgg gttgtattgt tattttacac  97500
atcttggtta tattattaga tatcctgtta agagaataat agattccgaa gtagtagtct  97560
ttggtgaggc agttaaggat aagaactgga ccgtatatct cattaagcta atagagcctg  97620
tgaatgcaat caatgataga ctagaagaaa gtaagtatgt tgaatctaaa ctagtggata  97680
tttgtgatcg gatagtattc aagtcaaaga aatacgaagg tccgtttact acaactagtg  97740
aagtcgtcga tatgttatct acatatttac caaagcaacc agaaggtgtt attctgttct  97800
attcaaaggg acctaaatct aacattgatt ttaaaattaa aaaggaaaat actatagacc  97860
aaactgcaaa tgtagtattt aggtacatgt ccagtgaacc aattatcttt ggagaatcgt  97920
ctatctttgt agagtataag aaatttagca acgataaagg ctttcctaaa gaatatggtt  97980
ctggtaagat tgtgttatat aacggcgtta attatctaaa taatatctat tgtttggaat  98040
atattaatac acataatgaa gtgggtatta agtccgtggt tgtacctatt aagtttatag  98100
cagaattctt agttaatgga gaaatactta aacctagaat cgataaaacc atgaaatata  98160
ttaactcaga agattattat ggaaatcaac ataatatcat agtcgaacat ttaagagatc  98220
aaagcatcaa aataggagat atctttaacg aggataaact atcggatgtg ggacatcaat  98280
acgccaataa tgataaattt agattaaatc cagaagttag ttattttacg aataaacgaa  98340
ctagaggacc gttgggaatt ttatcaaact acgtcaagac tcttcttatt tctatgtatt  98400
gttccaaaac atttttagac gattccaaca aacgaaaggt attggcgatt gattttggaa  98460
acggtgctga cctggaaaaa tacttttatg gagagattgc gttattggta gcgacggatc  98520
```

```
cggatgctga tgctatagct agaggaaatg aaagatacaa caaattaaac tctggaatta  98580
aaaccaagta ctacaaattt gactacattc aggaaactat tcgatccgat acatttgtct  98640
ctagtgtcag agaagtattc tattttggaa agtttaatat catcgactgg cagtttgcta  98700
tccattattc ttttcatccg agacattatg ctaccgtcat gaataactta tccgaactaa  98760
ctgcttctgg aggcaaggta ttaatcacta ccatggacgg agacaaatta tcaaaattaa  98820
cagataaaaa gacttttata attcataaga atttacctag tagcgaaaac tatatgtctg  98880
tagaaaaaat agctgatgat agaatagtgg tatataatcc atcaacaatg tctactccaa  98940
tgactgaata cattatcaaa aagaacgata tagtcagagt gtttaacgaa tacggatttg  99000
ttcttgtaga taacgttgat ttcgctacaa ttatagaacg aagtaaaaag tttattaatg  99060
gcgcatctac aatggaagat agaccgtcta caaaaaactt tttcgaacta aatagaggag  99120
ccattaaatg tgaaggttta gatgtcgaag acttacttag ttactatgtt gtttatgtct  99180
tttctaagcg gtaaataata atatggtatg ggttctgata tccccgttct aaatgcatta  99240
aataattcca atagagcgat ttttgttcct ataggacctt ccaactgtgg atactctgta  99300
ttgttaatag atatattaat acttttgtcg ggtaacagag gttctacgtc ttctaaaaat  99360
aaaagtttta taacatctgg cctgttcata aataaaaact tggcgattct atatatactc  99420
ttattatcaa atctagccat tgtcttatag atgtgagcta ctgtaggtgt accatttgat  99480
tttctttcta atactatata tttctctcga agaagttctt gcacatcatc tgggaataaa  99540
atactactgt tgagtaaatc agttattttt tttatatcga tattgatgga catttttata  99600
gttaaggata ataagtatcc caaagtcgat aacgacgata acgaagtatt tatactttta  99660
ggaaatcaca atgactttat cagattaaaa ttaacaaaat taaaggagca tgtatttttt  99720
tctgaatata ttgtgactcc agatacatat ggatctttat gcgtcgaatt aaatgggtct  99780
agttttcagc acggcggtag atatatagag gtggaggaat ttatagatgc tggaagacaa  99840
gttagatggt gttctacatc caatcatata tctaaagata tacccgaaga tatgcacact  99900
gataaatttg tcatttatga tatatacact tttgacgctt tcaagaataa acgattggta  99960
ttcgtacagg tacctccgtc gttaggagat gatagtcatt tgactaaccc gttattgtca 100020
ccgtattatc gtaattcagt agccagacaa atggtcaata atatgatttt taatcaagat 100080
tcatttttaa aatatttatt agaacatctg attagaagcc actatagagt ttctaaacat 100140
ataacaatag ttagatacaa ggataccgaa gaattaaatc taacgagaat atgttataat 100200
agagataagt ttaaggcgtt tgtattcgct tggtttaacg gcgtttcgga aaatgaaaag 100260
gtactagata cgtataaaaa ggtatctaat ttgatataat gaattcagtg actgtatcac 100320
acgcgccata tactattact tatcacgatg attgggaacc agtaatgagt caattggtag 100380
agttttataa cgaagtagcc agttggctgc tacgagacga gacgtcgcct attcctgata 100440
agttctttat acagttgaaa caaccgctta gaaataaacg agtatgtgtg tgtggtatag 100500
atccgtatcc gaaagatgga actggtgtac cgttcgaatc accaaatttt acaaaaaaat 100560
caattaagga gatagcttca tctatatcta gattaaccgg agtaattgat tataaaggtt 100620
ataaccttaa tataatagac ggggttatac cctggaatta ttacttaagt tgtaaattag 100680
gagaaacaaa aagtcacgcg atttactggg ataaaatttc taagttactg ctgcagcata 100740
taactaaaca cgttagtgtt ctttattgtt tgggtaaaac agatttctcg aatatacggg 100800
ccaagttaga atccccggta actaccatag tcggatatca tccagcggct agagaccgcc 100860
aattcgagaa agatcgatca tttgaaatta tcaacgtttt actggaatta gacaacaagg 100920
```

cacctataaa ttgggctcaa gggtttattt attaatgctt tagtgaaatt ttaacttgtg 100980
ttctaaatgg atgcggctat tagaggtaat gatgttatct ttgttcttaa gactataggt 101040
gtcccgtcag cgtgcagaca aaatgaagat ccaagatttg tagaagcatt taaatgcgac 101100
gagttagaaa gatatattga gaataatcca gaatgtacac tattcgaaag tcttagggat 101160
gaggaagcat actctatagt cagaattttc atggatgtag atttagacgc gtgtctagac 101220
gaaatagatt atttaacggc cattcaagat tttattatcg aggtgtcaaa ctgtgtagct 101280
agattcgcgt ttacagaatg cggtgccatt catgaaaatg taataaaatc catgagatct 101340
aatttttcat tgactaagtc tacaaataga gataaaacaa gttttcatat tatcttttta 101400
gatacgtata ccactatgga tacattgata gctatgaaac gaacactatt agaattaagt 101460
agatcatctg aaaatccact aaccagatcg atagacactg ccgtatatag gagaaaaaca 101520
actcttcggg ttgtaggtac taggaaaaat ccaaattgcg acactattca tgtaatgcaa 101580
ccacctcatg ataatataga agattaccta ttcacttacg tggatatgaa caacaatagt 101640
tattactttt ctctacaaca acgattggag gatttagttc ctgataagtt atgggaacca 101700
gggtttattt cattcgaaga cgctataaaa agagtttcaa aaatattcat taattctata 101760
ataaacttta atgatctcga tgaaaataat tttacaacgg taccactggt catagattac 101820
gtaacacctt gtgcattatg taaaaaacga tcgcataaac atccgcatca actatcgttg 101880
gaaaatggtg ctattagaat ttacaaaact ggtaatccac atagttgtaa agttaaaatt 101940
gttccgttgg atggtaataa actgtttaat attgcacaaa gaattttaga cactaactct 102000
gttttattaa ccgaacgagg agaccatata gtttggatta ataattcatg gaaatttaac 102060
agcgaagaac ccttgataac aaaactaatt ttgtcaataa gacatcaact acctaaggaa 102120
tattcaagcg aattactctg tccgaggaaa cgaaagactg tagaagctaa catacgagac 102180
atgttagtag attcagtgga gaccgatacc tatccggata aacttccgtt taaaaatggt 102240
gtattggacc tggtagacgg aatgttttac tctggagatg atgctaaaaa atatacgtgt 102300
actgtatcaa ccggatttaa atttgacgat acaaagttcg tcgaagacag tccagaaatg 102360
gaagagttaa tgaatatcat taacgatatc caaccattaa cggatgaaaa taagaaaaat 102420
agagagctat atgaaaaaac attatctagt tgtttatgtg gtgctaccaa aggatgttta 102480
acattctttt ttggagaaac tgcaactgga aagtcgacaa ccaaacgttt gttaaagtct 102540
gctatcggtg acctgtttgt tgagacgggt caaacaattt taacagatgt attggataaa 102600
ggacctaatc catttatcgc taacatgcat ttgaaaagat ctgtattctg tagcgaacta 102660
cctgattttg cctgtagtgg atcaaagaaa attagatctg acaatattaa aaagttgaca 102720
gaaccttgtg tcattggaag accgtgtttc tccaataaaa ttaataatag aaaccatgcg 102780
acaatcatta tcgatactaa ttacaaacct gtttttgata ggatagataa cgcattaatg 102840
agaagaattg ccgtcgtgcg attcagaaca cacttttctc aaccttctgg tagagaggct 102900
gctgaaaata atgacgcgta cgataaagtc aaactattag acgaggggtt agatggtaaa 102960
atacaaaata atagatatag attcgcattt ctatacttgt tggtgaaatg gtacagaaaa 103020
tatcatgttc ctattatgaa actatatcct acacccgaag agattcctga ctttgcattc 103080
tatctcaaaa taggtactct gttagtatct agctctgtaa agcatattcc attaatgacg 103140
gacctctcca aaaagggata tatattgtac gataatgtgg ttactcttcc gttgactact 103200
ttccaacaga aaatatccaa gtattttaat tctagactat ttggacacga tatagagagc 103260

```
ttcatcaata gacataagaa atttgccaat gttagtgatg aatatctgca atatatattc 103320
atagaggata tttcatctcc gtaaatatat gctcatatat ttatagaaga tatcacatat 103380
ctaaatgaat accggaatca tagatttatt tgataatcat gttgatagta taccaactat 103440
attacctcat cagttagcta ctctagatta tctagttaga actatcatag atgagaacag 103500
aagcgtgtta ttgttccata ttatgggatc aggtaaaaca ataatcgctt tgttgttcgc 103560
cttggtagct tccagattta aaaaggttta cattctagtg ccgaacatca acatcttaaa 103620
aattttcaat tataatatgg gtgtagctat gaacttgttt aatgacgaat tcatagctga 103680
gaatatcttt attcattcca caacaagttt ttattctctt aattataacg ataacgtcat 103740
taattataac ggattatctc gctacaataa ctctattttt atcgttgatg aggcacataa 103800
tatctttggg aataatactg gagaacttat gaccgtgata aaaaataaaa acaagattcc 103860
tttttacta ttgtctggat ctcccattac taacacacct aatactctgg gtcatattat 103920
agatttaatg tccgaagaga cgatagattt tggtgaaatt attagtcgtg gtaagaaagt 103980
aattcagaca cttcttaacg aacgcggtgt gaatgtactt aaggatttgc ttaaaggaag 104040
aatatcatat tacgaaatgc ctgataaaga tctaccaacg ataagatatc acggacgtaa 104100
gtttctagat actagagtag tatattgtca catgtctaaa cttcaagaga gagattatat 104160
gattactaga cgacagctat gttatcatga aatgtttgat aaaaatatgt ataacgtgtc 104220
aatggcagta ttgggacaac ttaatctgat gaataattta gatactttat ttcaggaaca 104280
ggataaggaa ttgtacccaa atctgaaaat aaataatggc gtgttatacg gagaagaatt 104340
ggtaacgtta aacattagtt ccaaatttaa atactttatt aatcggatac agacactcaa 104400
cggaaaacat tttatatact tttctaattc tacatatggc ggattggtaa ttaaatatat 104460
catgctcagt aatggatatt ctgaatataa tggttctcag ggaactaatc cacatatgat 104520
aaacggcaaa ccaaaaacat ttgctatcgt tactagtaaa atgaaatcgt ctttagagga 104580
tctattagat gtgtataatt ctcctgaaaa cgatgatggt agtcaattga tgtttttgtt 104640
ttcatcaaac attatgtccg aatcctatac tctaaaagag gtaaggcata tttggtttat 104700
gactatccca gatacttttt ctcaatacaa ccaaattctt ggacgatcta ttagaaaatt 104760
ctcttacgcc gatatttctg aaccagttaa tgtatatctt ttagccgccg tatattccga 104820
tttcaatgac gaagtgacgt cattaaacga ttacacacag gatgaattga ttaatgtttt 104880
accatttgac atcaaaaagc tgttgtatct aaaatttaag acgaaagaaa cgaatagaat 104940
atactctatt cttcaagaga tgtctgaaac gtattctctt ccaccacatc catcaattgt 105000
aaaagtttta ttgggagaat tggtcagaca attttttat aataattctc gtattaagta 105060
taacgatacc aagttactta aaatggttac atcagttata aaaaataaag aagacgctag 105120
gaattacata gatgatattg taaacggtca cttctttgta tcgaataaag tatttgataa 105180
atctctttta tacaaatacg aaaacgatat tattacagta ccgtttagac tttcctacga 105240
accatttgtt tggggagtta actttcgtaa agaatataac gtggtatctt ctccataaaa 105300
ctgatgagat atataaagaa ataaatgtcg agctttgtta ccaatggata cctttccgtt 105360
acattggaac ctcatgagct gacgttagac ataaaaacta atattaggaa tgccgtatat 105420
aagacgtatc tccatagaga aattagtggt aaaatggcca agaaaataga aattcgtgaa 105480
gacgtggaat tacctctcgg cgaaatagtt aataattctg tagttataaa cgttccgtgt 105540
gtaataacct acgcgtatta tcacgttggg gatatagtca gaggaacatt aaacatcgaa 105600
gatgaatcaa atgtaactat tcaatgtgga gatttaatct gtaaactaag tagagattcg 105660
```

ggtactgtat catttagcga ttcaaagtac tgcttttttc gaaatggtaa tgcgtatgac 105720
aatggcagcg aagtcactgc cgttctaatg gaggctcaac aaggtatcga atctagtttt 105780
gtttttctcg cgaatatcgt cgactcataa aaaagagaat agcggtaagt ataaacacga 105840
atactatggc aataattgcg aatgttttat tctcttcgat atatttttga taatatgaaa 105900
aacatgtctc tctcaaatcg gacaaccatc tcataaaata gttctcgcgc gctggagagg 105960
tagttgctgc tcgtataatc tctccagaat aatatacttg cgtgtcgtcg ttcaatttat 106020
acggatttct atagttctct gttatataat gcggttttcc atcatgatta gacgacgaca 106080
atagtgttct aaatttagat agttgatcag aatgaatgtt tattggcgtt ggaaaaatta 106140
tccatacagc gtctgcagag tggttgatag ttgttcctag atatgtaaaa taatccaact 106200
tactaggcag caaattgtct agataaaata ctgaatcaaa cggtgcagac gtattggcgg 106260
atctaatgga atccaattga ttaactatct tttgaaaata tacattttta tgatccaata 106320
cttgtaagaa tatagaaata atgataagtc catcatcgtg tttttttgcc tcttcataag 106380
aactatattt tttcttattc caatgaacaa gattaatctc tccagagtat ttgtacacat 106440
ctatcaagtg attggatcca taatcgtctt cctttcccca atatatatgt agtgatgata 106500
acacatattc attggggaga aaccctccac ttatatatcc tcctttaaaa ttaatcctta 106560
ctagttttcc agtgttctgg atagtggttg gtttcgactc attataatgt atgtctaacg 106620
gcttcaatcg cgcgttagaa attgcttttt tagtttctat attaatagga gatagttgtt 106680
gcggcatagt aaaaatgaaa tgataactgt ttaaaaatag ctcttagtat gggaattaca 106740
atggatgagg aagtgatatt tgaaactcct agagaattaa tatctattaa acgaataaaa 106800
gatattccaa gatcaaaaga cacgcatgtg tttgctgcgt gtataacaag tgacggatat 106860
ccgttaatag gagctagaag aacttcattc gcgttccagg cgatattatc tcaacaaaat 106920
tcagattcta tctttagagt atccactaaa ctattacggt ttatgtacta caatgaacta 106980
agagaaatct ttagacggtt gagaaaaggt tctatcaaca atatcgatcc tcactttgaa 107040
gagttaatat tattgggtgg taaactagat aaaaaggaat ctattaaaga ttgtttaaga 107100
agagaattaa aagaggaaag tgatgaacgt ataacagtaa aagaatttgg aaatgtaatt 107160
ctaaaactta caacacggga taaattattt aataaagtat atataagtta ttgcatggcg 107220
tgttttatta atcaatcgtt ggaggattta tcgcatacta gtatttacaa tgtagaaatt 107280
agaaagatta aatcattaaa tgattgtatt aacgacgata aatacgaata tctgtcttat 107340
atttataata tgctagttaa tagtaaatga acttttacag atctagtata attagtcaga 107400
ttattaagta taatagacga ctagctaagt ctattatttg cgaggatgac tctcaaatta 107460
ttacactcac ggcattcgtt aaccaatgcc tatggtgtca taaacgagta tccgtgtccg 107520
ctattttatt aactactgat aacaaaatat tagtatgtaa cagacgagat agtttctct 107580
attctgaaat aattagaact agaaacatgt ttagaaagaa acgattattt ctgaattatt 107640
ccaattattt gaacaaacag gaaagaagta tactatcgtc attttttttct ctagatccag 107700
ctactactga taatgataga atagacgcta tttatccggg tggcataccc aaaaggggtg 107760
agaatgttcc agagtgttta tccagggaaa ttaaagaaga agttaatata gacaattctt 107820
ttgtattcat agacactcgg ttttttattc atggcatcat agaagatacc attattaata 107880
aattttttga ggtaatcttc tttgtcggaa gaatatctct aacgagtgat caaatcattg 107940
atacatttaa aagtaatcat gaaatcaagg atctaatatt tttagatccg aattcaggta 108000
atggactcca atacgaaatt gcaaaatatg ctctagatac tgcaaaactt aaatgttacg 108060
gccatagagg atgttattac gaatcattaa aaaaattaac tgaggatgat tgattagaaa 108120
atataaatta atttaccatc gtgtattttt ataacgggat tgtccggcat atcatgtaga 108180
tagttaccgt ctacatcgta tactcgacca tctacgcctt taaatcctct atttattgac 108240
attaatctat tagaattgga ataccaaata ttagtaccct caattagttt attggtaata 108300
tttttttag acgatagatc gatggctctt gaaaccaagg ttttccaacc ggactcattg 108360
tcgatcggtg agaagtcttt ttcattagca tgaatccatt ctaatgatgt atgtttaaac 108420
actctaaaca attggacaaa ttcttttgat ttgctttgaa tgatttcaaa taggtcttcg 108480
tctacagtag gcataccatt agataatcta gccattataa agtgcacgtt tacatatcta 108540
cgttctggag gagtaagaac gtgactattg agacgaatgg ctcttcctac tatctgacga 108600
agagacgcct cgttccatgt catatctaaa atgaagatat cattaattga gaaaaaacta 108660
ataccctcgc ctccactaga agagaatacg catgttttaa tgcattctcc gttagtgttt 108720
gattcttggt taaactcagc caccgccttg attctagtat cttttgttct agatgagaac 108780
tctatattag agataccaaa gactttgaaa tatagtaata agatttctat tcctgactga 108840
ttaacaaatg gttcaaagac tagacattta ccatgggatg ctaatattcc caaacataca 108900
tctataaatt tgacgctttt ctcttttaat tcagtaaata gagagatatc agccgcacta 108960
gcatcccctt tcaatagttc tccctttta aaggtatcta atgcggattt agaaaactct 109020
ctatctctta atgaattttt aaaatcatta tatagtgttg ctatctcttg cgcgtattcg 109080
cccggatcac gattttgtct ttcaggaaag ctatcgaacg taaacgtagt agccatacgt 109140
ctcagaattc taaatgatga tatacctgtt tttatttcag cgagtttagc cttttgataa 109200
atttcttctt gctttttcga catattaacg tatcgcatta atactgtttt cttagcgaat 109260
gatgcagacc cttctacgtc atcaaaaata gaaaactcgt tattaactat atacgaacat 109320
agtcctccta gtttggagac taattctttt tcatcgacta gacgtttatt ctcaaatagc 109380
gattggtgtt gtaaggatcc tggtcgtagt aagttaacca acatggtgaa ttcttgcaca 109440
ctattgacga taggtgtagc cgataaacaa atcatcttat ggtttttaa cgcgatggtc 109500
ttagataaaa aattatatac tgaacgagta ggacggatct taccatcttc tttgattaat 109560
gatttagaaa tgaagttatg acattcatca ataatgacgc atattctact cttggaatta 109620
atagttttga tattagtaaa aaatttattt ctaaaatttt gatcatcgta attaataaaa 109680
atacaatcct tcgttatctc tggagcgtat ctgagtatag tgttcatcca aggatcttct 109740
atcaaagcct ttttcaccaa taagataata gcccaatttg tataaatatc cttaagatgt 109800
ttgagaatat atacagtagt cattgtttta ccgacacccg tttcatggaa caataaaaga 109860
gaatgcatac tgtctaatcc taagaaaact cttgctacaa aatgttgata atccttgagg 109920
cgtactacgt ccgaccccat catttcaacg ggcatattag tagttctgcg caatgcataa 109980
tcgatatagg ccgcgtgtga tttactcatt tatgagtgat aagtaataac tatgttttaa 110040
aaatcacagc agtagtttaa ctagtcttct ctgatgtttg ttttcgatac tttttgaatc 110100
agaagtcata ctagaataaa gcaacgagtg aacgtaatag agagcttcgt atactctatt 110160
cgaaaactct aagaacttat taatgaattc cgtatccact ggattgttta aaatactaaa 110220
ttgaacactg ttcacatcct tccaagaaga agacttagtg acggacttaa catgagacat 110280
aaataaatcc aaattttttt tacaaacatc actagccacc ataatggcgc tatctttcaa 110340
ccagctatcg cttacgcatt ttagcagtct aacattttta aagagactac aatatattct 110400
catagtatcg attacacctc taccgaataa agttggaagt ttaataatac aatatttttc 110460
gtttacaaaa tcaaataatg gtcgaaacac gtcgaaggtt aacatcttat aatcgctaat 110520
gtatagattg ttttcagtga gatgattatt agatttaata gcatctcgtt cacgtttgaa 110580
cagtttattg cgtgcgctga ggtcggcaac tacggcgtcc gctttagtac tcctcccata 110640
atactttacg ctattaatct ttaaaatttc atagacttta tctagatcgc tttctggtaa 110700
catgatatca tgtgtaaaaa gttttaacat gtcggtcggc attctattta gatcattaac 110760
tctagaaatc tgaagaaagt aattagctcc gtattccaga ctaggtaatg ggcttttacc 110820
tagagacaga ttaagttctg gcaatgtttc ataaaatgga agaaggacat gcgttccctc 110880
ccggatattt tttacaattt catccattta caactctata gtttgttttc attattatta 110940
gttattatct cccataatct tggtaatact taccccttga tcgtaagata ccttatacag 111000
gtcattacat acaactacca attgtttttg tacataatag attggatggt tgacatccat 111060
ggtggaataa actactcgaa cagatagttt atctttcccc ctagatacat tagccgtaat 111120
agttgtcggc ctaaagaata tctttggtgt aaagttaaaa gttagggttc ttgttccatt 111180
attgcttttt gtcagtagtt cattataaat tctcgagatg ggtccgttct ctgaatatag 111240
aacatcattt ccaaatctaa cttctagtct agaaataata tcggtcttat tcttaaaatc 111300
tattcccttg atgaagggat cgttaatgaa caaatccttg gcctttgatt cggctgatct 111360
attatctccg ttatagacgt tacgttgact agtccaaaga cttacaggaa tagatgtatc 111420
gatgatgttg atactatgtg atatgtgagc aaagattgtt ctcttagtgg catcactata 111480
tgttccagta atggcggaaa actttttaga aatgttatat ataaaagaat tttttcgtgt 111540
tccaaacatt agcagattag tatgaagata aacactcata ttatcaggaa cattatcaat 111600
ttttacatac acatcagcat cttgaataga aacgatacca tcttctggaa cctctacgat 111660
ctcggcagac tccggataac cagtcggtgg accatcgcta acaataacta gatcatccaa 111720
caatctactc acatatgcat ctatataatc tttttcatct tgtgagtacc ctggatacga 111780
aataaattta ttatccgtat ttccataata aggtttagta taaacagaga gagatgttgc 111840
cgcatgaact tcagttacag tcgccgttgg ttggtttatt tgacctatta ctctcctagg 111900
tttctctata aacgatggtt taatttgtac attcttaacc atatatccaa taaagctcaa 111960
ttcaggaaca taaacaaatt ctttgttgaa cgtttcaaag tcgaacgaag agtcacgaat 112020
aacgatatcg gatactggat tgaaggttac cgttacggta atttttgaat cggatagttt 112080
aagactgctg aatgtatctt ccacatcaaa cggagtttta atataaacgt atactgtaga 112140
tggttcttta atagtgtcat taggagttag gccaatagaa atatcattaa gttcactaga 112200
atatccagag tgtttcaaag caattgtatt attgatacaa ttattatata attcttcgcc 112260
ctcaatttcc caaataacac cgttacacga agagatagat acgtgattaa tacatttata 112320
tccaacatat ggtacgtaac cgaatcttcc catacctta acttctggaa gttccaaact 112380
cagaaccaaa tgattaagcg cagtaatata ctgatcccta atttcgaagc tagcgatagc 112440
ctgattgtct ggaccatcgt ttgtcataac tccggataga gaaatatatt gcggcatata 112500
taaagttgga atttgactat cgactgcgaa gacattagac cgtttaatag agtcatcccc 112560
accgatcaaa gaattaatga tagtattatt cattttctat ttaaaatgga aaaagcttac 112620
aataaactcc gtagagaaat atctataatt tgtgagtttt ccttaaagta acagcttccg 112680
taaacgccgt ctttatctct tagtaggttt attgtattta tgacctttc cttatcttca 112740 tagaatacta aaggcaacaa agaaattttt ggttcttctc taagagctac gtgagactta 112800
accatagaag ccaacgaatc cctacatatt ttagaacaga aataccctac ttcaccaccc 112860
ttgtatgtct caatactaat aggtctaaaa accaaatctt gattacaaaa ccaacactta 112920
tcaattacac tatttgtctt aatagacaca tctgccatag atttataata ctttggtagt 112980
atacaagcga gtgcttcttc tttagcgggc ttaaagactg ctttaggtgc tgaaataacc 113040
acatctggaa ggcttactcg cttagccatt taattacgga actatttttt tatacttcta 113100
atgagcaagt agaaaacctc tcatctacaa aaacgtactc gtgtccataa tcctctacca 113160
tagtaacacg tttttagat ctcatatgtg ctaaaaagtt ttcccatact aattggttac 113220
tattattttt cgtataattt ttaacagttt gaggttttag atttttagtt acagaagtga 113280
tatcgaatat tttatccaaa aagaatgaat aattaattgt cttagaagga gtgttttctt 113340
ggcaaaagaa taccaagtgc ttaaatattt ctactacttc attaatcttt tctgtactca 113400
gattcagttt ctcatctttt acttgattga ttatttcaaa gactaactta taatcctttt 113460
tatttattct ctcgttagcc ttaagaaaac tagatacaaa atttgcatct acatcatccg 113520
tggatatttg attttttcc atgatatcca agagttccga gataatttct ccagaacatt 113580
gatgagacaa taatctccgc aatacatttc tcaaatgaat aagtttatta gacacgtgga 113640
agtttgactt tttttgtacc tttgtacatt tttgaaatac cgactcgcaa aaaatacaat 113700
attcatatcc ttgttcagat actataccgt tgtgtctaca accgctacat aatcgtagat 113760
tcatgttaac actctacgta tctcgtcgtc caatatttta tataaaaaca ttttatttct 113820
agacgttgcc agaaaatcct gtaatatttt tagtttttg ggctgtgaat aaagtatcgc 113880
cctaatatgg ttaccgtctt ccgccaatat agtagttaaa ttatccgcac atgcagaaga 113940
acaccgctta ggcggattca gtacaatgtt atatttttcg taccaactca tttaaatatc 114000
ataatctaaa atagttctgt aatatgtcta gcgctaatat attgatcata atcctgtgca 114060
taaattaaga tacaacaatg tctcgaaatc atcgacatgg cttcttccat agttagaaga 114120
tcgtcgtcaa agttagcaac gtgattcatc aacatttgct gttttgaggc agcaaatact 114180
gaaccgtcgc cattcaacca ttcataaaaa ccatcgtctg aatccattga taatttcttg 114240
tactggtttt tgagagctcg catcaatcta gcatttctag ctcccggatt gaaaacagaa 114300
agaggatcgt acatccaggg tccattttct gtaaatagaa tcgtataatg tcccttcaag 114360
aagatatcag acgatccaca atcaaagaat tggtctccga gtttgtaaca aacagcggac 114420
tttaacctat acatgatacc gtttagcata atttctggtg atacgtcaat cggagtatca 114480
tctattagag atctaaagcc ggtgtaacat tctccaccaa acatattctt attctgacgt 114540
cgttctacat aaaacatcat tgctccatta acgataacag gggaatgaac agcactaccc 114600
atcacattag ttcccaatgg atcaatgtgt gtaactccag aacatcttcc atagcctatg 114660
ttaggaggag cgaacaccac tcttccacta ttgccatcga atgccataga ataaatatcc 114720
ttggaattga tagaaatcgg actgtcggat gttgtgatca tcttcatagg attaacaact 114780
atgtatggtg ccgcctgaag tttcatatcg taactgatgc cgtttatagg tctagccaca 114840
gaaaccaacg taggtctaaa tccaactata gacaaaatag aagccaatat ctgttcctca 114900
tctgtcataa cttgagagca tccagtatga ataatcttca ttagatgggg atctaccgca 114960
tcatcatcgt tacaataaaa aattcccatt ctaatgttca taattgcttt tctaatcatg 115020
gtatgcatgt ttgctctctg aatctctgtg gaaattagat ctgatacacc tgtaatcact 115080
atcggattat cctccgtaag acgattaacc aacaacatat aattataaga ctttactttt 115140
ctaaattcat aaagttgctg gattaggcta taggtgtctc catgtacata cgcgttctcg 115200
agcgcaggaa gtttaatacc gaatagtgcc atcagaatag gatgaatata gtaattagtt 115260
tctggttttc tataaataaa agacaaatct tgtgaactag acatatcggt aaaatgcatg 115320
gattggaatc gtgtagtcga cagaagaata tgatgattag atggagagta tattttatct 115380
aactctttga gttggtcacc gattctagga ctagctcgag aatgaataag tactaaagga 115440
tgagtacatt tcacagaaac actagcattg ttcaatgtgc tctttacatg ggtaaggagt 115500
tgaaatagct cgtttctatt tgttctgaca atatttagtt tattcataat gttaagcata 115560
tcctgaatag taaagttaga tgtgtcatac ttgttagtag ttagatattt agcaattgca 115620
ttcccatcat ttctcaatct cgtactccaa tcatgcgtag atgctacttc atctatagaa 115680
accatacaat cctttttgat aggctgttga gattgattat ttcctgcacg tttaggtttg 115740
gtacgttgat ttctagcccc tgcggatata aagtcatcgt ctacaatttg ggacaatgaa 115800
ttgcatacac tacaagacaa agatttatca gaagtgtgaa tatgatcttc atctactaaa 115860
gaaagagttt gattagtata actagatttt agtcctgcgt tagatgttaa aaaaacatcg 115920
ctattgacca cggcttccat tatttatatt cgtagttttt actcgaaagc gtgattttaa 115980
tatccaatct tattactttt ggaatcgttc aaaacctttg actaattgta gaatttgatc 116040
tattgcccta cgcgtatact cccttgcatc atatacgttc gtcaccagat cgtttgtttc 116100
ggcctgaagt tggtgcatat ctctttcaac attcgacatg agatccttaa gggccatatc 116160
gtctagattt tgttgagatg ctgctcctgg atttggattt tgttgtgctg ttgtacatac 116220
tgtaccacca gtaggtgtag gagtacatac agtggccaca ataggaggtt gaggaggtgt 116280
aaccgttgga gtagtacaag aaatacttcc atccgattgt tgtgtacatg tagttgttgg 116340
taacgtctga gaaggttggg tagatggcgg tgtcgtcgtc ttttgatctt tattaaattt 116400
agagataata tcctgaacag cattgctcgg cgtcaacgct ggaaggagtg aactcgccgg 116460
cgcatcagta tctgcagaca gccaatcaaa aagattagac atatcagatg atgtattagt 116520
ttgttgtcgt ggttttggtg taggagcagt actactaggt agaagaatag gagccggtgt 116580
agctgttgga accggctgtg gagttatatg aatagttggt tgtagcggtt ggataggctg 116640
tctgctggcg gccatcatat tatctctagc tagttgttct cgcaactgtc tttgataata 116700
cgactcttga gactttagtc ctatttcaat cgcttcatcc tttttcgtat ccggatcctt 116760
ttcttcagaa taatagattg acgactttgg tgtagaggat tctgccagcc tctgtgagaa 116820
cttgttaaag aagtccattt aaggctttaa aattgaattg cgattataag attaaatggc 116880
agacacagac gatattatcg actatgaatc cgatgatctc accgaatacg aggatgatga 116940
agaagaggaa gaagatggag agtcactaga aactagtgat atagatccca aatcttctta 117000
taagattgta gaatcagcat ccactcatat agaagatgcg cattccaatc ttaaacatat 117060
agggaatcat atatctgctc ttaaacgacg ctatactaga cgtataagtc tatttgaaat 117120
agcgggtata atagcagaaa gctataactt gcttcaacga ggaagattac ctctagtttc 117180
agaattttct gacgaaacga tgaagcaaaa tatgctacat gtaattatac aagagataga 117240
ggagggttct tgtcctatag tcatcgaaaa gaacggagaa ttgttgtcgg taaacgattt 117300
tgacaaagat ggtctaaaat tccatctaga ctatattatc aaaatttgga aacttcaaaa 117360
acgatattag aatttatacg aatatcgttc tctaaatgtc acaatcaagt ctcgcatgtt 117420
cagcaattta ttgtcgtact ttatatcgtg ttcattaacg atatcttgca aaatagtaat 117480

```
gattctatct tccttcgata gatattcttc agagattatt gtcttatatt ctttcttgtt 117540
atcagatatg aatttgataa gactttgaac attattgata cccgtctgtt taattttttc 117600
tacagatatt ttagttttgg cagattctat cgtatctgtc aatagacatc caacatcgac 117660
attcgacgtc aattgtctat aaatcaacgt ataaatttta gaaataacat tagcgaattg 117720
ttgtgcgttg atgtcgttat tttgaaacag tatgatttta ggtagcattt tcttaacaaa 117780
gagaacgtat ttattgttac tcagttgaac agatgatata tccagattac taacgcatct 117840
gattccgtat accaaacttt cagaagaaat ggtatacaat tgtttgtatt cattcaatgt 117900
ctctttttca gaaattagtt tagagtcgaa tactgcaata attttcaaga gatagttttc 117960
atcagataag attttattta gtgtagatat gataaaacta ttgttttgtt ggagaacttg 118020
atacgccgcg ttctctgtag tcgacgctct caaatgggaa acaatctcca ttattttttt 118080
ggaatcggat acaatatctt cggtatcttg acgcagtcta gtatacatag agttaagaga 118140
gattagagtt tgtacattaa gcaacatgtc tctaaatgtg gctacaaact tttccttttt 118200
cacatcatct agtttattat ataccgattt cacaacggca ccagatttaa ggaaccagaa 118260
tgaaaaactc tgataactac aatatttcat catagttacg attttatcat cttctatagt 118320
tggtgtaata gcgcatacct ttttctccaa gactggaacc aacgtcataa aaatgtttaa 118380
atcaaaatcc atatcaacat ctgatgcgct aagaccagtc tcgcgttcaa gattatcttt 118440
actaatggtg acgaactcat cgtatagaac tctaagtttg tccattattt atttacagat 118500
ttagttgttt aatttatttg tgctcttcca gagttgggat agtatttttc taacgtcggt 118560
attatattat taggatctac gttcatatgt atcataatat taatcatcca cgttttgata 118620
aatctatctt tagcttctga aataacgtat ttaaacaaag gagaaaaata tttagctacg 118680
gcatcagacg caataacatt ttttgtaaat gtaacgtatt tagacgacag atcttcgtta 118740
aaaagttttc catctatgta gaatccatcg gttgttaaca ccattcccgc gtcagattga 118800
ataggagttt gaatagtttg ttttggaaat agatccttca ataacttata gttgggtggg 118860
aaaaaatcga ttttatcact agactctttc tttttttacta tcattacctc atgaactatt 118920
tcttgaatga gtatatgtat tttctttcct atatcggacg cgttcattgg aaaatatacc 118980
atgtcgttaa ctataagaat atttttatcc tcgtttacaa actgaataat atcagatgta 119040
gttcgtaaac gaactatatc atcaccagca caacatctaa ctatatgata tccactagtt 119100
tcctttagtc gtttattatc ttgttccata ttagcagtca ttccatcatt taagaaggcg 119160
tcaaagataa tagggagaaa tgacattttg gattctgtta cgactttacc aaaattaagg 119220
atatacggac ttactatctt tttctcaacg tcgatttgat gaacacacga tgaaaatgtg 119280
cttctatgag attgatcatg tagaaaacaa caagggatac aatatttccg catatcatga 119340
aatatattaa gaaatcccac cttattatat ttccccaaag gatccatgca cgtaaacatt 119400
atgccgttat cattaataaa gacttctttc tcatcggatc tgtaaaagtt gttactgatt 119460
tttttcattc caggatctag ataattaata atgatgggtt ttctattctt attctttgta 119520
ttttggcata tcctagacca gtaaacagtt tccactttgg taaaatcagc agacttttga 119580
acgctattaa acatggcatt aatggcaata actaaaaatg taaaatattt ttctatgtta 119640
ggaatatggt ttttcacttt aatagatata tggtttttgg ccaaaatgat agatattttt 119700
ttatccgagg atagtaaaat attattagtc gccgtctcta taaaaatgaa gctagtctcg 119760
atatccaatt ttattctaga attgatagga gtcgccaaat gtaccttata cgttatatct 119820
cccttgatgc gttccatttg tgtatctata tcggacacaa gatctgtaaa tagttttacg 119880
```

ttattaatca tcacggtatc gccgtcgcta gataacgcta atgtaccatc caagtcccaa 119940
atggagagat ttaactgttc atcgtttaga ataaaatgat taccggtcat attaataaag 120000
tgttcatcgt atctagataa caacgactta taattaatgt ccaagtcttg aactcgctga 120060
atgatctttt ttaacccagt tagttttaga ttggtacgaa atatattgtt aaactttgat 120120
tctacagtaa tgtccaaatc tagttgtgga aatacttcca tcaacattgt ttcaaacttg 120180
ataatattat tatctacatc ttcgtacgat ccaaattccg gaatagatgt atcgcacgct 120240
ctggccaccc agataaccaa aaagtcacac gctccaggat atacattgta taaaaagcta 120300
tcgtttttta gtagggtttt tttctgcgtg tatacgaagg gattaaaaat agtattatca 120360
acgtaactat attccaaatt attcttatga gaatagataa taatatcgtc cttaatatct 120420
aacaaatttc ctaaatatcc ctttaattga gtcattcgaa gcgtcaatag aatatgtctc 120480
ttaactattt ccggctgttg tatatttaaa tgacttcgta aaaaataata tatgggcgac 120540
ttctcatcta tgtaatcata tggagtgaga tatagggctc gttctacctc ctgcccctta 120600
cccacctgta ataccaattg cggacttact atatatcgca tatttatatc gtggggtaaa 120660
gtgaaaatct actaccgatg atgtaagtct tacaatgttc gaaccagtac cagatcttaa 120720
tttggaggcc tccgtagaac taggggaggt aaatatagat caaacaacac ctatgataaa 120780
ggagaatagc ggttttatat cccgcagtag acgtctattc gcccatagat ctaaggatga 120840
tgagagaaaa ctagcactac gattcttttt acaaagactt tattttttag atcatagaga 120900
gattcattat ttgttcagat gcgttgacgc tgtaaaagac gtcactatta ccaaaaaaaa 120960
taacattata gtggcgcctt atatagcact tttaactatc gcatcaaaag gatgcaaact 121020
tacagaaaca atgattgaag cattctttcc agaactatat aatgaacata gtaagaaatt 121080
taaattcaac tctcaagtat ccatcatcca agaaaaactc ggataccagt ttggaaacta 121140
tcacgtttat gattttgaac cgtattactc tacagtagct ctggctattc gagatgaaca 121200
ttcatctggc atttttaata tccgtcaaga gagttatctg gtaagttcat tatctgaaat 121260
aacatataga ttttatctaa ttaatctaaa atctgatctt gttcaatgga gtgctagtac 121320
gggcgctgta attaatcaaa tggtaaatac tgtattgatt acagtgtatg aaaagttaca 121380
actggtcata gaaaatgatt cacaatttac atgttcattg gctgtggaat caaaacttcc 121440
aataaaatta cttaaagata gaaatgaatt atttacaaaa ttcattaacg agttaaaaaa 121500
gaccagttca ttcaagataa gcaaacgcga taaggatacg ctattaaaat attttactta 121560
ggactggagt tagaatttat agacgactca tttcgtttat cattgttact accatcatta 121620
ttagtattct tcttgtcatc ttgttcagaa atatacagca atgctatacc taatactaaa 121680
tacattatca tgctcgcaat ggctctaaca acaacgaacc aaaatgaatt tggtcgtagc 121740
ttttgttcac aaaaatacat aaagaaatgt ctacataaat ctatggcgcc attggctact 121800
tgaaatagcg ccagtcctcc tacagatttt aatatagctg tataacatga catttattca 121860
tcatcaaaag agacagagtc accatctgtc atatttagat tttttttcat gtgttcaaag 121920
tatcctctac tcatttcatt ataatagttt atcatactta gaattttagg acggatcaat 121980
gagtaagact tgactagatc gtcagtagta atttgtgcat cgtctattct gcatccgctt 122040
cgtcgaataa tgtatagcat cgctttgaga ttctccatag ctatcaagtc tttatacaat 122100
gacatggaaa tatctgtgaa tactttatac ttctccaaca tcgatgcctt aacatcatcg 122160
cctactttag cattgaaaat acgttctatt gtgtagatgg atgtagcaag atttttaaac 122220
aacaatgcca tcttacacga tgattgcctc aagtctccaa tcgtttgttt agaacgatta 122280
gctacagagt ccaatgcttg gctgactagc atattattat ctttagaaat tgtattcttc 122340
aatgaggcgt ttatcatatc tgtgatttcg ttagtcatat tacagtctga ctgggttgta 122400
atgttatcca acatatcacc tatggatacg gtacacgtac cagcatttgt aataatccta 122460
tctaagatgt tgtatggcat tgcgcagaaa atatcttctc ctgtaatatc tccactctcg 122520
ataaatctac tcagattatt cttaaatgcc ttattctctg gagaaaagat atcagtgtcc 122580
atcatttcat taatagtata cgcagaaaag ataccacgag tatcaattct atccaagata 122640
cttatcggtt ccgagtcaca gataatggtt tcctctcctt cgggagatcc tgcatagaaa 122700
tatctaggac aatagtttct atactgtctg taactctgat aatctctaaa gtcactaact 122760
gataccatga aattgagaag atcaaacgct gaagtaatta atttttctgc ctcgttttta 122820
ctacaactag ttttcatcaa tgtagtgacg atgtattgtt tagttacttt tggtctaata 122880
ctgatgatag agatattatt acttcccata atggatcttc tagtagtcac cttaaagccc 122940
attgatgcga atagcagata gataaagtct tggtatgact cctttctaat atagtacgga 123000
ctacctttgt cacccaactt tatacccaca taagccataa caacctcttt aatagccgtt 123060
tcatgaggtt tatcagccat gagcctgagt agttggaaga atctcatgaa tcccgtctca 123120
gaaagtccta tatgcatgat agatttatct ttcctgggaa actctcgtat agtcatagat 123180
gaaatactct tcaaagtttc tgaaataaga ttagtaacag tcttacctcc gactactcta 123240
ggtaacaaac aaactctaat aggtgttttc tctgcggaga taatatcaga aaggatagag 123300
caataagtag tattattgtg attataaaga ccgaatacat aacaggtaga atttataaac 123360
atcatgtcct gaaggttttt agacttgtat tcctcgtaat ccataccgtc ccaaaacatg 123420
gatttggtaa ctttgatagc cgtagatctt tgttccttcg ccaacaggtt aaagaaatta 123480
ataaagaatt tgttgtttct atttatgtcc acaaattgca cgtttggaag cgccacggtt 123540
acattcactg cagcattttg aggatcgcga gtatgaagta cgatgttatt gtttactggt 123600
atatctggaa agaaatctac cagtctagga ataagagatt gatatcgcat agaaatagta 123660
aagtttataa tctcatcatc gaagagcatt ttgttaccat tgtaataaat atccactctg 123720
tcatatgtat aaatgaagta ctgttcaaac atgatgagat gtttatatgt tggcatagta 123780
gtgagatcga cgtttggtaa tggcaatgta ttaagattaa ctccataatg tctagcagca 123840
tctgcgatgt tataagcgtc gtcaaagcgg ggtcgatctt gtattgttat atattgtcta 123900
acacctataa gattatcaaa atcttgtctg cttaatacac cgttaacaat ttttgccttg 123960
aattctttta ttggtgcatt aataacatcc ttatagagga tgttaaacaa ataagtgtta 124020
tcaaagttaa gatctggata tttcttttct gctagaacat ccattgagtc ggagccatct 124080
ggtttaatat aaccaccgat aaatctagct ctgtattctg tatccgtcaa tctaatatta 124140
agaaggtgtt gagtgaaagg tggaagatcg taaaagctgt gagtattaat gataggatta 124200
gtttccgaac taatgttaat tggggtatta ataatatcta tatttccagc gttaagtgta 124260
acattaaaca gttttaattc acgtgacgtg gtatcaatta aataattaat gcccaatttg 124320
gatatagcag cctgaagctc atcttgttta gttacggatc ctaatgagtt attaagcaat 124380
atatcgaacg gatgaacgaa ggttgtttta agttggtcgc atactttgta atctagacat 124440
agatgcggaa gaacggtaga aactatacga aataaatatt cagagtcctc taattgatca 124500
agagtaacta ttgacttaat aggcatcatt tatttagtat taaatgacga ccgtaccagt 124560
gacggatata caaaacgatt taattacaga gttttcagaa gataattatc catctaacaa 124620
aaattatgaa ataactcttc gtcaaatgtc tattctaact cacgttaaca acgtggtaga 124680
tagagaacat aatgccgccg tagtgtcatc tccagaggaa atatcctcac aacttaatga 124740
agatctattt ccagatgatg attcaccggc cactattatc gaacgagtac aacctcatac 124800
tactattatt gacaatactc cacctcctac gtttcgtaga gagttattaa tatcggaaca 124860
acgtcaacaa cgagaaaaaa gatttaatat tacagtatcg aaaaatgctg aagcaataat 124920
ggaatctaga tctatgataa cttctatgcc aacacaaaca ccatccttgg gagtagttta 124980
tgataaagat aaaagaattc agatgttaga ggatgaagtg gttaatctta gaaatcaacg 125040
atctaataca aaatcatctg ataatttaga taattttacc aaaatactat ttggtaagac 125100
tccgtataaa tcaacagaag ttaataagcg tatagccatc gttaattatg caaatttgaa 125160
cgggtctccc ttatcagtcg aggacttgga tgtttgttca gaggatgaaa tagatagaat 125220
ctataaaacg attaaacaat atcacgaaag tagaaaacga aaaattatcg tcactaacgt 125280
gattattatt gtcataaaca ttatcgagca ggcattgcta aaactcggat ttgaagaaat 125340
caaaggactg agtaccgata tcacttcaga aattatcgat gtggagatcg gagatgactg 125400
cgatgctgta gcatcaaaac taggaatcgg taacagtccg gttcttaata ttgtattgtt 125460
tatactcaag atattcgtta aacgaattaa aattatttaa tttaatacat tcccatatcc 125520
agacaacaat cgtctggatt aatctgttcc tgtcgtctca taccggacga catattaatc 125580
tttttattag tgggcatctt tttagatggt ttctttttcc cagcattaac tgattcgata 125640
cctagaagat cgtgattgat ctctccgacc attccacgaa cttctaattg gccgtctctg 125700
acggtaccat aaactatttt accagcatta gtaacagctt ggacaatctg accatccatc 125760
gcattgtacg atgtagtagt aactgttgtt ctacgtctag gagcaccaga agtatttttg 125820
gagcccttgg atgttgatgt agaagaagac gaggattttg attttggttt acatgtaata 125880
cattttgaac tctttgattt tgtatcacat gcgccggcag tcacatctgt ttgagaatta 125940
agattattgt tgcctccttt gacggctgca tctccaccga tttgcgctag tagattttta 126000
agctgtggtg taatcttatt aactgtttcg atataatcat cgtaactgct tctaacggct 126060
aaattttttt tatccgccat ttagaagcta aaaatatttt tatttatgca gaagatttaa 126120
ctagattata caatgaacta atatgatcct tttccagatt atttacaaac ttggtatttt 126180
ttggttctgg aggaggcgaa tttaaattcg gacttggatt cggattttgt aagttcttga 126240
tcttattata catcgagtat aggatggcga cagtaactgc tacacaaata ccgatcaaaa 126300
gaagaatacc aatcatttat tgacaataac ttcactattg atcaagtatg caatatatca 126360
tcttttcact aaataagtag taataatgat tcaacaatgt cgagatatat ggacgataat 126420
aatttagttc atggaaatat cgctatgatt ggtgtgaatg actccgctaa ctctgtgggg 126480
tgcgcagtgc tttccccaca tagaataaat tagcattccg actgtgataa taataccaag 126540
tataaacgcc ataatactca atactttcca tgtacgagtg ggactggtag acttactaaa 126600
gtcaataaag gcgaagatac acgaaagaat caaaagaatg attccagcga ttagcacgcc 126660
ggaaaaataa tttccaatca taagcatcat gtccatttaa ctaataaaaa ttttaaatcg 126720
ccgaatgaac aaagtggaat ataaaccata taaaaacaat agtttgtact gcaaaaataa 126780
tatctatttt tgttttcgaa gatatggtaa aattaaatag tagtacacag catgttataa 126840
ctaacagcag caacggctcg taattactta tcatttacta gacgaaaagg tggtgggata 126900
ttttcttgct caaataatac gaatatatca cccatccatt ttatgcgatg tttatatact 126960
ctaatcttta atagatctat agacgacggg tttaccaaca atatagattt tatcgattca 127020
tctaatttaa acccttcctt aaacgtgaat gatctattat ctggcataac gatgacccta 127080
cctgatgaat cggacaatgt actgggccat gtagaataaa ttatcaacga attatcgtct 127140
acgaacattt atatcatttg ttttaatttt aggacgcgaa taaatggata taaaatagaa 127200
aataacagat attacaacca gtgttatggc cgcgcccaac caggtaggca gttttatttt 127260
atcttttact acaggttctc ctggatgtac gtcaccaacg gcggacgtag ttctagtaca 127320
attagacgta agttccgctt gggaattttt taacgctaaa gagttaacgt taatcgtaca 127380
cccaacgtat ttacatctag ttctttgaac atcttgatta taatataacc attttctatc 127440
tctagattcg tcggtgcact catgtaacca acatacccta ggtcctaaat atttatctcc 127500
ggaattagat tttggataat tcgcgcacca acaatttcta tttcctttat gatcgttaca 127560
aaagacgtat aatgccgtat ccccaaaagt aaaataatca ggacgaataa ttctaataaa 127620
ctcagaacaa tatctcgcat ccatatgttt ggagcaaata tcggaataag tagacatagc 127680
cggtttccgt tttgcacgta accattctaa acaattgggg tttccaggat cgtttctaca 127740
aaatccagtc atgaaatcgt cacaatgttc tgtcttgtaa ttattattaa atatttttgg 127800
acagtgtttg gtatttgtct tagaacaaca ttttgccacg ctatcactat cgcccaggag 127860
ataatccttt tttataaaat gacatcgttg cccggatgct atataatcag tggcgtgttt 127920
taaatcctta atatattcag gagttacctc gttctgataa tagattaatg atccaggacg 127980
aaatttgaaa gaactacatg gttctccatg aattaataca tattgtttag caaattcagg 128040
aactataaaa ctactacaat gatctatcga cataccatct atcaaacaaa acttgggttt 128100
aatttctccc ggagatgttt cataatagta cgtataactt tcttctgcaa acttaacagc 128160
tctattatat tcaggataat taaaacctaa ttccatatat ttgtctcgta tatctgctat 128220
tcctggtgct attttgattc tattaagagt aacagctgcc cccattctta ataatcgtca 128280
gtatttaaac tgttaaatgt tggtatatca acatctacct tatttcccgc agtataaggt 128340
ttgttgcagg tatactgttc aggaatggtt acatttatac ttcttctata gtcctgtctt 128400
tcgatgttca tcacatatgc aaagaacaga ataaacaaaa taatgtaaga aataatatta 128460
aatatctgtg aattcgtaaa tacattgatt gccataataa ttacagcagc tacaatacac 128520
acaatagaca ttcccacagt gttgccatta cctccacgat acatttgagt tactaagcaa 128580
taggtaataa ctaagctagt aagaggcaat agaaaagatg agataaatat catcaatata 128640
gagattagag gagggctata tagagccaag acgaacaaaa tcaaaccgag taacgttcta 128700
acatcattat ttttgaagat tcccaaataa tcattcattc ctccataatc gttttgcatc 128760
atacctccat ctttaggcat aaacgattgc tgctgttcct ctgtaaataa atctttatca 128820
agcactccag cacccgcaga gaagtcgtca agcatattgt aatatcttaa ataactcatt 128880
tatatattaa aaaatgtcac tattaaagat ggagtataat ctttatgccg aactaaaaaa 128940
aatgacttgt ggtcaacccc taagtctttt taacgaagac ggggatttcg tagaagttga 129000
accgggatca tcctttaagt ttctgatacc taagggattt tacgcctctc cttccgtaaa 129060
gacgagtcta gtattcgaga cattaacaac gaccgataat aaaatcacta gtatcaatcc 129120
aacaaatgcg ccaaagttat atcctcttca acgcaaagtc gtatctgaag tagtttctaa 129180
tatgaggaaa atgatcgaat caaaacgtcc tctatacatt actcttcact tggcgtgtgg 129240
atttggtaag actattacca cgtgttatct tatggctaca cacggtagaa aaaccgtcat 129300
ttgcgtaccc aataaaatgt taatacatca atggaagaca caggtagagg cagtcggatt 129360
ggaacataag atatccatag atggagtaag tagtctatta aaggaactaa agactcaaag 129420
tccggatgta ttaatagtag tcagtagaca tctgacaaac gatgcctttt gtaaatatat 129480
caataagcat tatgatttgt tcatcttgga tgaatcacat acgtataatc tgatgaacaa 129540
tacagcagtt acaagatttt tagcgtatta tcctccgatg atgtgttatt ttttaactgc 129600
tacacctaga ccatctaacc gaatttattg taacagtatt attaatattg ccaagttatc 129660
cgatctaaaa aaaactatct atgcggtaga tagttttttt gagccatatt ccacagacaa 129720
tattagacat atgataaaac gattagatgg accatctaat aaatatcata tatatactga 129780
gaagttatta tctgtagacg agcctagaaa tcaacttatt cttaataccc tggtagaaga 129840
attcaagtca ggaactatta atcgcatttt agttattact aaactacgtg aacatatggt 129900
attcttctac aaacgattat tagatctttt cggaccagag gttgtattta taggagacgc 129960
ccaaaataga cgtactccag atatggtcaa atcaatcaag gaactaaata gatttatatt 130020
cgtatccacc ttattttatt ccggtactgg tttagatatt cctagtttgg attcgttgtt 130080
catttgctcg gcagtaatca acaatatgca aatagagcaa ttactaggga gggtatgtcg 130140
agaaacagaa ctattagata ggacggtata tgtatttcct aacacatcca tcaaagaaat 130200
aaagtacatg ataggaaatt tcatgcaacg aattattagt ctgtctgtag ataaactagg 130260
atttaaacaa aaaagttatc ggaaacatca agaatccgat cccacttctg tatgtacaac 130320
atcctccaga gaagaacgtg tattaaatag aatatttaac tcgcaaaatc gttaagaagt 130380
ttaagcgacg atccgcatgc tgcgcaggcc agtgtattac ccctcatagt attaatataa 130440
tccaatgata cttttgtgat gtcggaaatc ttaaccaatt tagactgaca ggcagaacac 130500
gtcatgcaat catcatcgtc atcgataact gtagtcttgg gcttcttttt gcggctcttc 130560
attccggaac gcacattggt gctatccatt taggtagtaa aaaataagtc agaatatgcc 130620
ctataacacg atcgtgcaaa acctggtata tcgtctctat ctttatcaca atatagtgta 130680
tcgacatttt tattattatt gacctcgttt atcttggaac atggaatggg aacatttttg 130740
ttatcaacgg ccacctttgc cttaattcca gatgttgtaa aattataact aaacagtcta 130800
tcatcgacac aaatgaaatt cttgtttaga cgtttgtagt ttacgtatgc ggctcgttcg 130860
cgtctcattt tttcagatat tgcaggtact ataatattaa aaataagaat gaaataacat 130920
aggattaaaa ataaagttat catgacttct agcgctgatt taactaactt aaaagaatta 130980
cttagtctgt acaaaagttt gagattttca gattctgcgg ctatagaaaa gtataattct 131040
ttggtagaat ggggaacatc tacttactgg aaaataggcg tgcaaaaggt agctaatgtc 131100
gagacgtcaa tatctgatta ttatgatgag gtaaaaaata aaccgtttaa tattgatccg 131160
ggctattaca ttttcttacc ggtatatttt gggagcgtct ttatttattc gaagggtaaa 131220
aatatggtag aacttggatc tggaaactct tttcaaatac cagatgatat gcgaagtgcg 131280
tgtaacaaag tattagacag cgataacgga atagactttc tgagatttgt tttgttaaac 131340
aatagatgga taatggaaga tgctatatca aaatatcagt ctccagttaa tatatttaaa 131400
ctagctagtg agtacggatt aaacataccc aaatatttag aaattgaaat agaggaagac 131460
acattatttg acgacgagtt atactctatt atagaacgct cttttgatga taaatttcca 131520
aaaatatcca tatcgtatat taagttggga gaacttagac ggcaagttgt agactttttc 131580
aaattctcat tcatgtatat tgagtccatc aaggtagatc gtataggaga taatattttt 131640
attcctagcg ttataacaaa atcaggaaaa aagatattag taaaagatgt agaccattta 131700

```
atacgatcta aggttagaga acatacattt gtaaaagtaa aaaagaaaaa cacattttcc 131760
attttatacg actatgatgg gaacggaaca gaaactagag gagaagtaat aaaacgaatt 131820
atagacacta taggacgaga ctattatgtt aacggaaagt atttctctaa ggttggtagt 131880
gcaggcttaa agcaattgac taataaatta gatattaatg agtgcgcaac tgtcgatgag 131940
ttagttgatg agattaataa atccggaact gtaaaacgaa aaataaaaaa ccaatcagca 132000
tttgatttaa gcagagaatg tttgggatat ccagaagcgg attttataac gttagttaat 132060
aacatgcggt tcaaaataga aaattgtaag gttgtaaatt tcaatattga aaatactaat 132120
tgtttaaata acccgagtat tgaaactata tatggaaact ttaaccagtt cgtctcaatc 132180
tttaatgtcg tcaccgatgt caaaaaaaga ttattcgagt gaaataatat gcgcctttga 132240
tataggtgca aaaaatcctg ccagaactgt tttagaagtc aaggataact ccgttagggt 132300
attggatata tcaaaattag actggagttc tgattgggaa aggcgcatag ctaaagattt 132360
gtcacaatat gaatacacta cagttcttct agaacgtcag cctagaaggt cgccgtatgt 132420
taaatttatc tattttatta aaggcttttt atatcataca tcggctgcca aagttatttg 132480
cgtctcgcct gtcatgtctg gtaattcata tagagatcga aaaaagagat cggtcgaagc 132540
atttcttgat tggatggaca cattcggatt gcgagactcc gttccggata gacgcaaatt 132600
agacgatgta gcggatagtt tcaatttggc tatgagatac gtattagata aatggaatac 132660
taattataca ccttataata ggtgtaaatc tagaaattac ataaaaaaaa tgtaataacg 132720
ttagtaacgc cattatggat aatctattta cctttctaca tgaaatagaa gatagatatg 132780
ccagaactat ttttaacttt catctaataa gttgcgatga aataggagat atatatggtc 132840
ttatgaaaga acgcatttcc tcagaggata tgtttgataa tatagtgtat aataaagata 132900
tacatcctgc cattaagaaa ctagtgtatt gcgacatcca acttactaaa cacattatta 132960
atcagaatac gtatccggta tttaacgatt cttcacaagt gaaatgttgt cattatttcg 133020
acataaactc agataatagc aatattagct ctcgtacagt agagatattt gagagggaaa 133080
agtcatctct tgtatcatat attaaaacta ccaataagaa gagaaaggtc aattacggcg 133140
aaataaagaa aactgttcat ggaggcacta atgcaaatta cttttccggt aaaaagtctg 133200
acgagtatct gagtactaca gttagatcca acattaatca accttggatc aaaaccattt 133260
ctaagagaat gagagtagat atcattaatc actctatagt aacgcgtgga aaaagctcta 133320
tattacaaac tatagaaatt atttttacta atagaacatg tgtgaaaata ttcaaggatt 133380
ctactatgca cattattcta tccaaggaca aggatgaaaa ggggtgtata cacatgattg 133440
acaaattatt ctatgtctat tataatttat ttctgttgtt cgaagatatc atccaaaacg 133500
agtactttaa agaagtagct aatgttgtaa accacgtact cacggctacg gcattagatg 133560
agaaattatt cctaattaag aaaatggctg aacacgatgt ttatggagtt agcaatttca 133620
aaataggggat gtttaacctg acatttatta agtcgttgga tcataccgtt ttcccctctc 133680
tgttagatga ggatagcaaa ataaagtttt ttaaggggaa aaagctcaat attgtagcat 133740
tacgatctct ggaggattgt ataaattacg tgactaaatc cgagaatatg atagaaatga 133800
tgaaggaaag atcgactatt ttaaatagca tagatataga aacggaatcg gtagatcgtc 133860
taaaagaatt gcttctaaaa tgaaaaaaaa cactgattca gaaatggatc aacgactcgg 133920
atataagttt ttggtgcctg atcctaaagc cggagttttt tatagaccgt tacatttcca 133980
atatgtatcg tattctaatt ttatattgca tcgattgcat gaaatcttga ccgtcaagcg 134040
gccactctta tcgtttaaga ataatacaga acgaattatg atagaaatta gcaatgttaa 134100
```

agtgactcct ccagattact cacctataat cgcgagtatt aaaggtaaga gttatgacgc 134160
attagccacg ttcactgtaa atatctttaa agaggtaatg accaaagagg gtatatccat 134220
cactaaaata agtagttatg agggaaaaga ttctcatttg ataaaaattc cgctactaat 134280
aggatacggg aataaaaatc cacttgatac agccaagtat cttgttccta atgtcatagg 134340
tggagtcttt atcaataaac aatctgtcga aaaagtagga attaatctag tagaaaagat 134400
tacaacatgg ccaaaattta gggttgttaa gccaaactca ttcactttct cgttttcctc 134460
cgtatcccct cctaatgtat taccgacaag atatcgccat tacaagatat ctctggatat 134520
atcacaattg gaagcgttga atatatcatc gacaaagaca tttataacgg tcaatattgt 134580
tttgctgtct caatatttat ctagagtgag tctagaattc attagacgta gtttatcata 134640
cgatatgcct ccagaagttg tctatctagt aaacgcgata atagatagtg ctaaacgaat 134700
tactgaatct attactgact ttaatattga tacatacatt aatgacctgg tggaagctga 134760
acacattaaa caaaaatctc agttaacgat taacgagttc aaatatgaaa tgctgcataa 134820
ctttttacct catatgaact atacacccga tcaactaaag ggattttata tgatatcttt 134880
actaagaaag tttctctact gtatcttcca cacttctaga tatccagata gagattcgat 134940
ggtttgtcat cgcatcctaa cgtacggcaa atattttgag acgttggcac atgatgaatt 135000
agagaattac ataggcaaca tccgaaacga tatcatgaac aatcacaaga acagaggcac 135060
ttacgcggta aacattcatg tactaacaac tcccggactt aatcatgcat tttctagtct 135120
attgagtgga aagttcaaaa agtcagacgg tagttatcga acacatcctc actattcatg 135180
gatgcagaat atttctattc ctaggagtgt tggattttat ccggatcaag taaagatttc 135240
aaagatgttt tctgtcagaa aataccatcc aagtcaatat ctttactttt gttcatcaga 135300
cgttccggaa agaggtcctc aggtaggttt agtatctcaa ttgtctgtct tgagttccat 135360
tacaaatata ctaacgtctg agtatttgga tttggaaaag aaaatttgtg agtatatcag 135420
atcatattat aaagatgata taagttactt tgaaacagga tttccaatca ctatagaaaa 135480
tgctctagtc gcatctctta atccaaatat gatatgtgat tttgtaactg actttagacg 135540
tagaaaacgg atgggatttt tcggtaactt ggaggtaggt attactttag ttagggatca 135600
catgaatgaa attcgcatta atattggagc gggaagatta gtcagaccat tcttggttgt 135660
ggataacgga gagctcatga tggatgtgtg tccggagtta gaaagcagat tagacgacat 135720
gacattctct gacattcaga aagagtttcc gcatgtcatc gaaatggtag atatagaaca 135780
atttactttt agtaacgtat gtgaatcggt tcaaaaattt agaatgatgt caaaggatga 135840
aagaaagcaa tacgatttat gtgactttcc tgccgaattt agagatggat atgtggcatc 135900
ttcattagtg ggaatcaatc acaattctgg acccagagct attcttggat gtgctcaagc 135960
taaacaagct atctcttgtc tgagctcgga tatacgaaat aaaatagaca atggaattca 136020
tttgatgtat ccagagaggc caattgtcat tagtaaggct ttagaaactt caaagattgc 136080
ggctaattgc ttcggccaac atgttactat agcattaatg tcgtacaaag gtatcaatca 136140
agaggatgga attatcatca aaaaacaatt tattcagaga ggcggtctcg atatagttac 136200
cgcaaagaaa catcaagtag aaattccatt ggaaaacttt aataacaaag aaagagatag 136260
gtctaacgcc tattcaaaat tagaaagtaa tggattagtt agactgaatg ctttcttgga 136320
atccggagac gctatagcac gaaatatctc atcaagaact cttgaagatg attttgctag 136380
agataatcag attagcttcg atgtttccga gaaatatacc gatatgtaca aatctcgcgt 136440

```
tgaacgagta caagtagaac ttactgacaa agttaaggta cgagtattaa ccatgaaaga 136500
aagaagaccc attctaggag acaaatttac cactagaacg agtcaaaagg gaacagtcgc 136560
gtatgtcgcg gatgaaacgg aacttccata cgacgaaaat ggtatcacac cagatgtcat 136620
tattaattct acatccatct tctctagaaa aactatatct atgttgatag aggttatttt 136680
aacagccgca tattctgcta agccgtacaa caataaggga gaaaaccgac ctgtctgttt 136740
tcctagtagt aacgaaacat ccatcgatac atatatgcaa ttcgctaaac aatgttatga 136800
gcattcaaat ccgaaattgt ctgatgaaga attatcggat aaaatctttt gtgaaaagat 136860
tctctatgat cctgaaacgg ataagcctta tgcatccaaa gtatttttg gaccaattta 136920
ttacttgcgt ctgaggcatt taactcagga caaggcaacc gttagatgta gaggtaaaaa 136980
gacgaagctc attagacagg cgaatgaggg acgaaaacgt ggaggaggta tcaagttcgg 137040
agaaatggag agagactgtt taatagcgca tggtgcagcc aatactatta cagaagtttt 137100
gaaagattcg gaagaagatt atcaagatgt gtatgtttgt gaaaattgtg gagacatagc 137160
agcacaaatc aaaagtatta atacatgtct tagatgttca aaacttaatc tctctcctct 137220
cttaacaaaa attgatacca cgcacgtatc taaagtattt cttactcaaa tgaacgccag 137280
aggcgtaaaa gtcaaattag atttcgaacg aagacctcct tcgttttata aaccattaga 137340
taaagttgat ctcaagccgt cttttctggt gtaatattct agtttggtag tagatacata 137400
tcaatatcat caaattcgag atccgaatta taaaatgggc gtggattgtt aactatagaa 137460
tcggacgtct gatattcgaa aatctgtgga gtttcaggtt ttggtggagg tgtaactgct 137520
acttgggata ctgaagtctg atattcagaa agctggggga tgttctggtt cggcatccac 137580
cgatggtgtc acatcactaa tcggttcggt aacgtctgtg gatggaggtg ctacttctac 137640
agaacctgta gcctcagttg tcaacggagc tacttcaatg cgaggaaatg tataatttgg 137700
taatggtttc tcatgtggat ctgaagaaga ggtaagatat ctactagaaa gataccgatc 137760
acgttctagt tctcttttgt aaaacttaac tttttctttc tcagcatcta gttgatattc 137820
caacctcttc acgttactac gttcagattc caattcacgt tcgcatgggt tacctccgca 137880
gtttttacga gcgatttcac gttcagcctt catgcgtctc tccctctctc tatcgagttt 137940
atcagagcag tctttctgaa ggcgatcgaa ctccataaat ttctccaacg ctttgattgt 138000
ttccatagat ttccgaagtt cagcttttag gactgtgatt ctttttcttt cgaattcaca 138060
gctggatgta caaccgtttc cattaccgcc atctctaagt ttcttttcta gatcggcaac 138120
atttcatccc catgcctttt acattcctcg agtctactgt cgtcgaaata tcgttccagc 138180
tccttttcga catcaataac tttagcacgt tgtctctcaa gctctctttt gtagttatct 138240
gattccctgg cacgtttaag atcttcatgc aattgagtca gctcttaact tcctctcttg 138300
cttcttcgtc atagtactta caatcactat gggatccatt gttaccacgt ctacactcgg 138360
cgagctcgcg tttaagagat tcaatttccc gtttgtattg gtccatgttt ccattgctac 138420
caccattaga tttacaggct gctagttgtc gttcgagatc agaaatacgg gttttcttgg 138480
aattgatttc gtcgatgtac ttggcatcga aacacttatt aagttctttt tccaattcta 138540
cgattttatt tctttcgcga gtcaattccc tcctgtagta actatctgtt ttgtcagatt 138600
cacgctctct acgtagactt tcttgcaagt tactaatttg ttccctagca cgtccgagtt 138660
tagttttata tgctgaatag agttctgatt catcctttga gcagatctct agcgatcgtt 138720
taagattcct gattctagtc tttagcctat ttacctcctc agaagatgtt ccgttaccgt 138780
tgcgtttaca ctcgttaagc tgtctatcaa gatccatgat tctatctcta agacgttgca 138840
```

tctctctttc catatcagca ttgctttcat tattacgtct gcagtcactc aactgtcttt 138900
caatatctga gattctatct ctaagacgtc gcatctctct ctgtttcggc attggtttca 138960
ttattacgtc tacagtcgtt caactgtctt tcaagatctg atattctaga ttggagtctg 139020
ctaatctctg tagcattttc acggcattca ctcagttgtc tttcaagatc tgagatttta 139080
gattggagtc tgctaatctc tgtaagattt cctcctccgc tctcgatgca gtcggtcaac 139140
ttattctcta gttctctaat acgcgaacgc agtgcatcaa cttcttgcgt gtcttcctgg 139200
ttgcgtgtac attcatcgag tctagattcg agatctctaa cgcgtcgtcg ttcttcctca 139260
agttctctgc gtactacaga aagcgtgtcc ctatcttgtt gatatttagc aatttctgat 139320
tctagagtac tgattttgct tacgtagtta ctaatagttg tcttggcctt atcaagatcc 139380
tccttgtatt tgtcgcattc cttgatatcc ctacgaagtc tggacagttc ccattcgaca 139440
ttacgacgtt tatcgatttc agctcggaga tcgtcatcgc gttgttttag ccacatacga 139500
ctgagttcaa gttctcgttg acaagatcca tctacttttc cattcctaat agtatccagt 139560 tcctttteta gttctgaacg catttctcgt tccctatcaa gcgattctct caattctcgg 139620
atagtcttct tatcaatttc taataaatct gaaccatcat ctgtcccatt ttgaatatcc 139680
ctgtgttctt tgatctcttt tgtaagtcgg tcgattcttt cggttttata aacagaatcc 139740
ctttccaaag tcctaatctt actgagttta tcactaagtt ctgcattcaa ttcggtgagt 139800
tttctcttgg cttcttccaa ctctgtttta aactctccac tatttccgca ttcttcctcg 139860
catttatcta accattcaat tagtttatta ataactagtt ggtaatcagc gattcctata 139920
gccgttcttg taattgtggg aacataatta ggatcttcta atggattgta tggcttgata 139980
gcatcatctt tatcattatt agggggatgg acaaccttaa ttggttggtc ctcatctcct 140040
ccagtagcgt gtggttcttc aataccagtg ttagtaatag gcttaggcaa atgcttgtcg 140100
tacgcgggca cttcctcatc catcaagtat ttataatcgg gttctacttc agaatattct 140160
tttctaagag acgcgacttc gggagttagt agaagaactc tgtttctgta tctatcaacg 140220
ctggaatcaa tactcaagtt aaggatagcg aatacctcat cgtcatcatc cgtatcttct 140280
gaaacaccat catatgacat ttcatgaagt ctaacgtatt gataaataga atcagattta 140340
gtattaaaca gatccttaac ctttttagta aacgcatatg tatattttag atctccagat 140400
ttcataatat gatcacatgc cttaaatgtc agtgcttcca tgatataatc tggaacacta 140460
atgggtgacg aaaaagatac agcaccatat gctacgttga taaataaatc tgaaccacta 140520
agtagataat gattaatgtt aaggaaaaga aaatattcag tgtataggta tgtcttggcg 140580
tcatatcttg tactaaacac gctaaacagt ttgttaatgt gatcaatttc caatagatta 140640
attagagcag caggaatacc aacaaacata ttaccacatc cgtattttct atgaatatca 140700
catatcatgt taaaaaatct tgatagaaga gcgaatatct cgtctgactt aatgagtcgt 140760
agttcagcag caacataagt cataactgta aatagaacat actttcctgt agtgttgatt 140820
ctagactcca catcaacacc attattaaaa atagttttat atacatcttt aatctgctct 140880
ccgttaatcg tcgaacgttc tagtatacgg aaacactttg atttcttatc tgtagttaat 140940
gacttagtga tatcacgaag aatattacga attacatttc ttgtttttct tgagagacct 141000
gattcagaac tcaactcatc gttccatagt tttctacct cagtggcgaa atctttggag 141060
tgcttggtac atttttcaat aaggttcgtg acctccattt attataaaaa atttattcaa 141120
aacttaacta caatcgggta attataagat cgtagatctc ccatgtggcg gaatactacc 141180

```
atctatcgca tgtggatgga cagtaggtaa tggccatggg aacagtaatg attgcatatt 141240
tatctttctt gccagtatta ctgcatattg tcccaatgtt tcgatgtgat gttctaacct 141300
atcaactgcc gctgtatcac aacaatagtg tccgatgaaa ttaagattat gatccaatgt 141360
gtttaatata tgattatcaa gtcttatacg atccgcgtct tttttgacag gatcaggttc 141420
ttctacagga agaagtttcg gcctcttatg atattcatgt ctgggaaacg gtggtctagg 141480
gtgaggctcc ggtatcggag tgggttttgg attataatca tcatcgtcta tgacatcatc 141540
atcatcttcg acttcgatat ttattttgct atcttgatga tgtcctgtat cagttgcatt 141600
ttcagcactc gactgaatat tagcgcattc attgtctatt attaccatat ttctaaaccc 141660
aaaatgtatg tgttgaacat cagtactatc gttgatgagt cttatagcat gaattcgctt 141720
atcgttatcg ggtttatctt ctgtcacctt agcaattcct tttttattaa actctacata 141780
atcatatcca tttctattgt ttgttctaat ataaacgagt atagcatcat tgctaaattt 141840
ttcaatagta tcgaaaacag aatatcctaa accatataat atatattcag gaacactcaa 141900
actaaatgtc caggattctc ctaaatacgt aaactttaat agtgcgaaat cattcaaaaa 141960
tctaccactt atagatagat agtacataaa tgcgtatagt agtctaccta tctctttatt 142020
atgaaaaccg gcattacgat catatatgtc gtgatatacc tgtgatccgt ttacgttaaa 142080
ccataaatac atgggtgatc ctataaacat gaatttattt ctaattctca gagctatagt 142140
taattgaccg tgtaatattt gcttacatgc atacttgata cgctcattaa taagattttt 142200
atcattgctc gttatttcag aatcgtatat ataaggagta ccatcgtgat tcttaccaga 142260
tattatacaa aatactatat ataaaatata ttgacccacg ttagtaatca tataaatgtt 142320
taacgtttta aattttgtat tcaatgatcc attatcatac gctatcatgg tcttgtaata 142380
ttcattcttt aaaatataat attgtgttag ccattgcatt ggggctccta atggagattt 142440
tttattctca tccattttag gataggcttt cataaagtcc ctaataactt cgtgaataat 142500
gtttctatgt tttctactga tgcatgtatt tgcttcgatt tttttatccc atgtttcatc 142560
tatcatagat ttaaacgcag taatgctcgc aacattaaca tcttgaaccg ttggtacaat 142620
tccgttccat aaatttataa tgttcgccat ttatataact catttttttga atatactttt 142680
aattaacaaa agagttaagt tactcatatg gacgccgtcc agtctgaaca tcaatctttt 142740
tagccagaga tatcatagcc gctcttagag tttcagcgtg attttccaac ctaaatagaa 142800
cttcatcgtt gcgtttacaa cacttttcta tttgttcaaa ctttgttgtt acattagtaa 142860
tcttttttttc caaattagtt agccgttgtt tgagagtttc ctcattgtcg tcttcatcgg 142920
ctttaacaat tgcttcgcgt ttagcctctg gctttttagc agcctttgta gaaaaaaatt 142980
cagttgctgg aattgcaaga tcgtcatctc cggggaaaag agttccgtcc atttaaagta 143040
cagattttag aaactgacac tctgcgttat ttatatttgg tacaacacat ggattataaa 143100
tattgatgtt aataacatca gaaaatgtaa agtctataca ttgttgcatc gtgttaaatt 143160
ttctaatgga tctagtatta ttgggtccaa cttctgcctg aaatccaaat atggaagcgg 143220
atacaaaacc gtttcctgga taaaccacac atctccactt ttgctttaca tcagaaattg 143280
tgtcgttgac atcttgaact ctcctatcta atgccggtgt tccacctata gattttgaat 143340
attcgaatgc tgcatgagta gcattaaatt ccttaatatt gccataattt tcatatattg 143400
agtaaccctg gataaaaagt aaacacaccg cagccgtcgc taccacaata aaaaaaattg 143460
atagagagtt catttataat ctattagaag ctgacaaaat ttttttacac gcatcagaca 143520
atgctttaat aaatagttca acatctactt ttgtcatatc gaaccgatgg tatgattcta 143580
```

acctagaatt acatccgaaa aagttgacta tgttcatagt cattaagtca ttaacaaaca 143640
acattccaga ctctggatta taagacgata ctgtttcgtc acaattacct accttaatca 143700
tgtgattatg aatattggct attagagcac cttctaagaa atctataata tctttgaaac 143760
acgatttaaa atcaaaccac gaatatactt ctacgaagaa agttagttta cccataggag 143820
aaataactat aaatggagat ctaaatacaa aatccggatc tatgatagtt ttaacattat 143880
tatattctct attaaatacc tccacatcta aaaatgttaa ttttgaaact atgtcttcgt 143940
ttattaccgt acctgaacta aacgctataa gctctattgt ttgagaactc tttaaacgat 144000
attcttgaaa tacatgtaac aaagtttcct ttaactcggt cggtttatct accatagtta 144060
cagaatttgt atccttatct ataatataat aatcaaaatc gtataaagtt atataattat 144120
cgcgttcaga ttgggatctt ttcaaataga ctaaaaaccc catttctcta gtaagtatct 144180
tatgtatatg tttgtaaaat atcttcatgg tgggaatatg ctctaccgca gttagccatt 144240
cctcattgac agcggtagat gtattagaca aaactattcc aatgtttaac aagggccatt 144300
ttacgagatt attaaatcct tgtttgataa atgtagccaa tgagggttcg agttcaacga 144360
cgattgaatt ctcttcccgc ggatgctgca tgatgaacga cgggatgttg ttcgattgat 144420
ttggaattct ttttcgactt tttgtttata ttaaatattt taaaatttat agcggatagc 144480
aattcatgta ccacggataa tgtagacgcg tattgcgcat cgatatcttt attattagat 144540
aaatttatca ataaatgtga gaagtttgcc tcgttaaggt cttccattta aatattatat 144600
aaacatttgt gtttgtatct tattcgtctt ttatggaata gttttttact agtaaagctg 144660
caattacaca ctttgtccgt aaaacataaa tataaacacc agcttttatc aatcgttcca 144720
aaaagtcgac ggcggacatt tttaacatgg catctatttt aaatacactt aggtttttgg 144780
aaaaaacatc attttataat tgtaacgatt caataactaa agaaaagatt aagattaaac 144840
ataagggaat gtcatttgta ttttataagc caaagcattc taccgttgtt aaatacttgt 144900
ctggaggagg tatatatcat gatgatttgg ttgtattggg gaaggtaaca attaatgatc 144960
taaagatgat gctattttac atggatttat catatcatgg agtgacaagt agtggagcaa 145020
tttacaaatt gggatcgtct atcgatagac tttctctaaa taggactatt gttacaaaag 145080
ttaataatta tgatgataca ttttttgacg acgatgattg atcgctattg cacaattttg 145140
tttttttact ttctaatata gcgtttagat tctttttcat gtgcgaatat tgatttacta 145200
aaatatctat gtttaacttt tgttctataa cgtccttatc ggcggtatcg gtacatatac 145260
gtaattcacc ttcacaaaat acggagtctt cgataataat agccaatcga ttattggatc 145320
tagctgtctg tatcatattc aacatgttta atatatcctt tcgtttcccc tttacaggca 145380
tcgatcgtag catattttcc gcgtctgaga tggaaatgtt aaaactacaa aaatgcgtaa 145440
tgttagcccg tcctaatatt ggtacgtgtc tataagtttg gcatagtaga ataatagacg 145500
tgtttaaatg ccttccaaag tttaagaatt ctattagagt attgcatttt gatagtttat 145560
cgcctacatc atcaaaaata agtaaaaagt gtgctgattt tttatgattt tgtgcgacag 145620
caatacattt ttctatgtta cttttagttc gtatcagatt atattctaga gattcctgac 145680
tactaacgaa attaatatga tttggccaaa tgtatccatc ataatctggg ttataaacgg 145740
gtgtaaacaa gaatatatgt ttatattttt taactagtgt agaaaacaga gatagtaaat 145800
agatagtttt tccagatcca gatcctcccg ttaaaaccat tctaaacggc atttttaata 145860
aattttctct tgaaaattgt ttttcttgga aacaattcat aattatattt acagttacta 145920
aattaatttg ataataaatc aaaatatgga aaactaaggt tgttagtagg gaggagaaca 145980
aagaaggcac atcgtgacat aaataacatt tattatcatg atgacaccag aaaacgacga 146040
agagcagaca tctgtgttct ccgctactgt ttacggagac aaaattcagg gaaagaataa 146100
acgcaaacgc gtgattggtc tatgtattag aatatctatg gttatttcac tactatctat 146160
gattaccatg tccgcgtttc tcatagtgcg cctaaatcaa tgcatgtctg ctaacgaggc 146220
tgctattact gacgccgctg ttgccgttgc tgctgcatca tctactcata gaaaggttgc 146280
gtctagcact acacaatatg atcacaaaga aagctgtaat ggtttatatt accagggttc 146340
ttgttatata ttacattcag actaccagtt attctcggat gctaaagcaa attgcactgc 146400
ggaatcatca acactaccca ataaatccga tgtcttgact acctggctca ttgattatgt 146460
tgaggataca tggggatctg atggtaatcc aattacaaaa actacatccg attatcaaga 146520
ttctgatgta tcacaagaag ttagaaagta tttttgtgtt aaaacaatga actaatattt 146580
atttttgtac attaataaat gaaatcgctt aatagacaaa ctgtaagtag gtttaagaag 146640
ttgtcggtgc cggccgctat aatgatgata ctctcaacca ttattagtgg cataggaaca 146700
tttctgcatt acaaagaaga actgatgcct agtgcttgcg ccaatggatg gatacaatac 146760
gataaacatt gttatttaga tactaacatt aaaatgtcta cagataatgc ggtttatcag 146820
tgtcgtaaat tacgagccag attgcctaga cctgatacta gacatctgag agtattgttt 146880
agtatttttt ataaagatta ttgggtaagt ttaaaaaaga ccaataataa atggttagat 146940
attaataatg ataaagatat agatattagt aaattaacaa attttaaaca actaaacagt 147000
acgacggatg ctgaagcgtg ttatatatac aagtctggaa aactggttaa aacagtatgt 147060
aaaagtactc aatctgtact atgtgttaaa aaattctaca agtgacaaca aaaaatgaat 147120
taataataag tcgttaacgt acgccgccat ggacgccgcg tttgttatta ctccaatggg 147180
tgtgttgact ataacagata cattgtatga tgatctcgat atctcaatca tggactttat 147240
aggaccatac attataggta acataaaaac tgtccaaata gatgtacggg atataaaata 147300
ttccgacatg caaaaatgct actttagcta taagggtaaa atagttcctc aggattctaa 147360
tgatttggct agattcaaca tttatagcat ttgtgccgca tacagatcaa aaaataccat 147420
catcatagca tgcgactatg atatcatgtt agatatagaa gataaacatc agccatttta 147480
tctattccca tctattgatg tttttaacgc tacaatcata gaagcgtata acctgtatac 147540
agctggagat tatcatctaa tcatcaatcc ttcagataat ctgaaaatga aattgtcgtt 147600
taattcttca ttctgcatat cagacggcaa tggatggatc ataattgatg ggaaatgcaa 147660
tagtaatttt ttatcataaa agttgtaaag taaataataa aacaataaat attgaactag 147720
tagtacgtat attgagcaat cagaaatgat gctggtacct cttatcacgg tgaccgtagt 147780
tgcgggaaca atattagtat gttatatatt atatatttgt aggaaaaaga tacgtactgt 147840
ctataatgac aataaaatta tcatgacaaa attaaaaaag ataaagagtt ctaattccag 147900
caaatctagt aaatcaactg atagcgaatc agactgggag gatcactgta gtgctatgga 147960
acaaaacaat aacgtagata atatttctag gaatgagata ttggacgatg atagcttcgc 148020
tggtagttta atatgggata acgaatccaa tgttatggcg cctagcacag aacacattta 148080
cgatagtgtt gctggaagca cgctgctaat aaataatgat cgtaatgaac agactattta 148140
tcagaacact acagtagtaa ttaatgaaac ggagactgtt aaagtactta atgaagatac 148200
caaacagaat cctaactatt catccaatcc tttcgtaaat tataataaaa ccagtatttg 148260
tagcaagtca aatccgttta ttacagaact taacaataaa tttagtgaga ataatccgtt 148320
tagacgagca catagcgatg attatcttaa taagcaagaa caagatcatg aacacgatga 148380
tatagaatca tcggtcgtat cattggtgtg attagtttcc tttttataaa attgaagtaa 148440
tatttagtat tattgctgcc gtcacgttgt acaaatggag atattccctg tattcggcat 148500
ttctaaaatt agcaatttta ttgctaataa tgactgtaga tattatatag atacagaaca 148560
tcaaaaaatt atatctgatg agatcaatag acagatggat gaaacggtac ttcttaccaa 148620
catcttaagc gtagaagttg taaatgacaa tgagatgtac catcttattc ctcatagatt 148680
atcgacgatt atactctgta ttagttctgt cggaggatgt gttatctcta tagataatga 148740
catcaatgac aaaaatattc taacctttcc cattgatcat gctgtaatca tatccccact 148800
gagtaaatgt gtcgtagtta gcaagggtcc tacaaccata ttggttgtta aagcggatat 148860
acctagcaaa cgattggtaa catcgtttac aaacgacata ctatatgtaa acaatctgtc 148920
actgattaat tatttgccgt tgtctgtatt cattattaga cgagtcaccg actatttgga 148980
tagacacata tgcgatcaga tatttgctaa taataagtgg tattccctta taaccatcga 149040
cgataagcaa tatcctattc catcaaactg tataggtatg tcctctgcca agtacataaa 149100
ttctagcatc gagcaagata ctttaatcca tgtttgtaac ctcgagcatc cgttcgactc 149160
agtatacaaa aaaatgcagt cgtacaattc tctacctatc aaggaacaaa tattgtacgg 149220
tagaattgat aatataaata tgagcattag tatttctgtg gattaataga tttctagtat 149280
ggggatcatt aatcatctct aatctctaaa tacctcataa aacgaaaaaa aagctattat 149340
caaatactgt acggaatgga ttcattctct tctcttttta tgaaactctg ttgtatatct 149400
actgataaaa ctggaagcaa aaaatctgat aaaaagaata agaataagat caaggattat 149460
atggaacacg attattataa aataacaata gttcctggtt cctcttccac gtctactagc 149520
tcgtggtatt atacacatgc ctagtaatag tctctttgcg ttgacggaaa gcagactaga 149580
aataacaggc taaaatgttc agacaccata atagttccca acccagataa taacagagtt 149640
ccatcaacac attcctttaa actcaatccc aaacccaaaa ccgttaaaat gtatccggcc 149700
aattgatagt agataatgag gtgtacagcg catgataatt tacacagtaa ccaaaatgaa 149760
aacactttag taattataag aaatatagac ggtaatgtca tcatcaacaa tccgataata 149820
tgcctgagag taaacattga tggataaaac aaaaatgctc cgcataactc tatcatggca 149880
ataacacaac caaacacttg taaaattcct aaattagtag aaaatacaac ggatatcgat 149940
gtataagtga tctcgagaaa taataagaat aaagtaatgc ccgtaaagat aaacatcaac 150000
attgtttggt aatcattaaa ccaattagta tgaagttgaa ctaatttcac agtagatttt 150060
attccagtat tatccccgca tgtatacgta cctggtaaga tatctttata ttccataatc 150120
aatgagacat cactatctga taacgaatga agtctagcac tagtatgcca tttacttaat 150180
attgtcgtct tggaagtttt attataagtt aaaatatcat ggttatccaa tttccatcta 150240
atatactttg tcggattatc tatagtacac ggaataatga tggtatcatt acatgctgta 150300
tactctatgg tctttgtagt tgttataaca accaacgtat agaggtatat caacgatatt 150360
ctaactcttg acatttttta tttatttaaa atgatacctt tgttatttat tttattctat 150420
tttgctaacg gtattgaatg gcataagttt gaaacgagtg aagaaataat ttctacttac 150480
ttattagacg acgtattata cacgggtgtt aatggggcgg tatacacatt ttcaaataat 150540
aaactaaaca aaactggttt aactaataat aattatataa caacatctat aaaagtagag 150600
gatgcggata aggatacatt agtatgcgga accaataacg gaaatcccaa atgttggaaa 150660
atagacggtt cagacgaccc aaaacataga ggtagaggat acgctcctta tcaaaatagc 150720
aaagtaacga taatcagtca caacggatgt gtactatctg acataaacat atcaaaagaa 150780
ggaattaaac gatggagaag atttgacgga ccatgtggtt atgatttatt cacggcggat 150840
aacgtaattc caaaagatgg tttacgagga gcattcgtcg ataaagacgg tacttatgac 150900
aaagtttaca ttcttttcac tgatactatc ggctcaaaga gaattgtcaa aattccgtat 150960
atagcacaaa tgtgcttaaa cgacgaaggt ggtccatcat cgttgtctag tcatagatgg 151020
tcgacgtttc tcaaagtcga attagaatgt gatatcgacg gaagaagtta tagacaaatt 151080
attcattcta gaactataaa aacagataat gatacgatac tatatgtatt cttcgatagt 151140
ccttattcca agtccgcatt atgtacctat tctatgaata ccattaaaca atctttttct 151200
acgtcaaaat tggaaggata tacaaagcaa ttgccgtctc cagctcctgg tatatgttta 151260
ccagctggaa aagttgttcc acataccacg tttgaagtca tagaaaaata taatgtacta 151320
gatgatatta taaagccttt atctaaccaa cctatcttcg aaggaccgtc tggtgttaaa 151380
tggttcgata taaaggagaa ggaaaatgaa catcgggaat atagaatata cttcataaaa 151440
gaaaattcta tatattcgtt cgatacaaaa tctaaacaaa ctcgtagctc gcaagtcgat 151500
gcgcgactat tttcagtaat ggtaacttcg aaaccgttat ttatagcaga tatagggata 151560
ggagtaggaa tgccacaaat gaaaaaaata cttaaaatgt aatcttaatc gagtacacca 151620
cacgacaatg aacaaacata agacagatta tgctggttat gcttgctgcg taatatgcgg 151680
tctaattgtc ggaattattt ttacagcgac actattaaaa gttgtagaac gtaaattagt 151740
tcatacacca tcaatagata aaacgataaa agatgcatat attagagaag attgtcctac 151800
tgactggata agctataata ataaatgtat ccatttatct actgatcgaa aaacctggga 151860
ggaaggacgt aatgcatgca aagctctaaa tccaaattcg gatctaatta agatagagac 151920
tccaaacgag ttaagttttt taagaagcct tagacgcgga tattgggtag gagaatccga 151980
aatattaaac cagacaaccc catataattt tatagctaag aatgccacga agaatggaac 152040
taaaaaacgg aaatatattt gtagcacaac gaatactccc aaactgcatt cgtgttacac 152100
tatataacaa ttacactaca tttttatcat accactactt cggttagatg ttttagaaaa 152160
aaataaatat cgccgtaccg ttcttgtttt tataaaaata acaattaaca attatcaaat 152220
tttttcttta atattttacg tggttgacca ttcttggtgg taaaataatc tcttagtgtt 152280
ggaatggaat gctgtttaat gtttccacac tcatcgtata ttttgacgta tgtagtcaca 152340
tcgtttacgc aatagtcaga ctgtagttct atcatgcttc ctacatcaga aggaggaaca 152400
gttttaaagt ctcttggttt taatctatta ccgttagttt tcatgaaatc ctttgtttta 152460
tccacttcac attttaaata aatgtccact atacattctt ttgttaattt tactagatcg 152520
tcatgggtca tagaatttat aggttccgta gtccatggat ccaaactagc aaacttcgcg 152580
tatacggtat cgcgattagt gtatacacca actgtatgaa aattaagaaa acagtttaat 152640
agatcaacag aaatatttaa tcctccgttt gatacagatg cgccatattt atggatttcg 152700
gattcacacg ttgtttgtct gaggtgttcg tctagtgttg cttctacgta aacttcgatt 152760
cccatatatt ctttattgtc agaatcgcat accgatttat catcatacac tgtttgaaaa 152820
ctaaatggta tacacatcaa aataataaat aataacgagt acattctgca atattgttat 152880
cgtaattgga aaaatagtgt tcgagtgagt tggattatgt gagtattgga ttgtatattt 152940
tattttatat tttgtaataa gaataaaatg ctaatgtcaa gtttattcca atagatgtct 153000
tattaaaaac atatataata aataacaatg gctgaatggc ataaaattat cgaggatatc 153060

```
tcaaaaaata ataagttcga ggatgccgcc atcgttgatt acaagactac aaagaatgtt 153120
ctagctgcta ttcctaacag aacatttgcc aagattaatc cgggtgaaat tattcctctc 153180
atcactaatc gtaatattct aaaacctctt attggtcaga aatattgtat tgtatatact 153240
aactctctaa tggatgagaa cacgtatgct atggagttgc ttactgggta cgcccctgta 153300
tctccgatcg ttatagcgag aactcatacc gcacttatat ttttgatggg taagccaaca 153360
acatccagac gtgacgtgta tagaacgtgt agagatcacg ctacccgtgt acgtgcaact 153420
ggtaattaaa ataaaaagta atattcatat gtagtgtcaa ttttaaatga tgatgatgaa 153480
atggataata tccatattga cgatgtcaat aatgccggta ttggcataca gttcatcgat 153540
ttttagattt cattcagagg atgtggaatt atgttatggg catttgtatt ttgataggat 153600
ctataatgta gtaaatataa aatataatcc gcatattcca tatagatata attttattaa 153660
tcgcacgtta accgtagatg aactagacga taatgtcttt tttacacatg gttatttttt 153720
aaaacacaaa tatggttcac ttaatcctag tttgattgtc tcattatcag gaaacttaaa 153780
atataatgat atacaatgct cagtaaatgt atcgtgtctc attaaaaatt tggcaacgag 153840
tacatctact atattaacat ctaaacataa gacttattct ctacatcggt ccacgtgtat 153900
tactataata ggatacgatt ctattatatg gtataaagat ataaatgaca agtataatga 153960
catctatgat tttactgcaa tatgtatgct aatagcgtct acattgatag tgaccatata 154020
cgtgtttaaa aaaataaaaa tgaactctta attatgctat gctattagaa atggataaaa 154080
tcaaaattac ggttgattca aaaattggta atgttgttac catatcgtat aacttggaaa 154140
agataactat tgatgtcaca cctaaaaaga aaaaagaaaa ggatgtatta ttagcgcaat 154200
cagttgctgt cgaagaggca aaagatgtca aggtagaaga aaaaaatatt atcgatattg 154260
aagatgacga tgatatggat gtagaaagcg cataatacga tctataaaaa taagtatata 154320
aatacttttt atttactgta ctcttactgt gtagtggtga taccctactc aattattttt 154380
ttaaaaaaat acttattctg attcttctaa ccatttccgt gttcgttcga atgccacatc 154440
gacgtcaaag ataggggagt agttgaaatc tagttctgca ttgttggtac gcacctcaaa 154500
tgtagtgttg gatatcttca acgtatagtt gttgagtagt gatggttttc taaatagaat 154560
tctcttcata tcattcttgc acgcgtacat ttttagcatc catcttggaa ttctagatcc 154620
ttgttctatt cccaatggtt tcatcaatag aagattaaac atatcgtacg aacacgatgg 154680
agagtaatcg tagcaaaagt aagcatttcc tttaatctca gatcccggat actggatata 154740
ttttgcagcc aacacgtgca tccatgcaac atttcctaca tatacccggc tatgcaccgc 154800
gtcatcatcg actgtacgat acataatgtt accgtgttgc ttacattgct cgtaaaagac 154860
tttcgtcaat ttgtctcctt ctccgtaaat tccagtgggt cttaggcaac aagtatacaa 154920
ttttgctcca ttcatgatta cggaattatt ggctttcata accagttgct cggccatacg 154980
tttacttttt gcgtatacat gtcctggtga tatatcataa agggtatgct catggccgat 155040
gaatggatca ccgtgtttat tgggtcctat tgcttccatg ctactagtat agatcaaata 155100
cttgattcct aggtccacac aagctgccaa aatagtctgt gttccataat agtttacttt 155160
catgatttca ttatcggtgt attttccaaa tacatccact agagcagccg tatgaataat 155220
cagatttacc ccatctagcg cttctctcac cttatcaaag tcgtttatat cacattgtat 155280
atagtttata accttaactt tcgaggttat tggttgtgga tcttctacaa tatctatgac 155340
tctgatttct tgaacatcat ctgcactaat taacagtttt actatatacc tgcctagaaa 155400
```

tccggcacca ccagtaaccg cgtacacggc cattgctgcc actcataata tcagactact 155460
tattctattt tactaaataa tggctgtttg tataatagac cacgataata tcagaggagt 155520
tatttacttt gaaccagtcc atggaaaaga taaagtttta ggatcagtta ttggattaaa 155580
atccggaacg tatagtttga taattcatcg ttacggagat attagtcaag gatgtgattc 155640
cataggcagt ccagaaatat ttatcggtaa catctttgta aacagatatg gtgtagcata 155700
tgtttattta gatacagatg taaatatatc tacaattatt ggaaaggcgt tatctatttc 155760
aaaaaatgat cagagattag cgtgtggagt tattggtatt tcttacataa atgaaaagat 155820
aatacatttt cttacaatta acgagaatgg cgtttgatat atcagttaat gcgtctaaaa 155880
caataaatgc attagtttac ttttctactc agcaaaataa attagtcata cgtaatgaag 155940
ttaatgatac acactacact gtcgaatttg atagggacaa agtagttgac acgtttattt 156000
catataataa acataatgac accatagaga taagaggggt gcttccagag gaaactaata 156060
ttggttgcgc ggttaatacg ccggttagta tgacttactt gtataataag tatagtttta 156120
aactgatttt agcagaatat ataagacaca gaaatactat atccggcaat atttattcgg 156180
cattgatgac actagatgat ttggctatta aacagtatgg agacattgat ctattattta 156240
atgagaaact taaagtagac tccgattcgg gactatttga ctttgtcaac tttgtaaagg 156300
atatgatatg ttgtgattct agaatagtag tagctctatc tagtctagta tctaaacatt 156360
gggaattgac aaataaaaaa tataggtgta tggcattagc cgaacatata tctgatagta 156420
ttccaatatc tgagctatct agactacgat acaatctatg taagtatcta cgcggacaca 156480
ctgagagcat agaggataaa tttgattatt ttgaagacga tgattcgtct acatgttctg 156540
ccgtaaccga cagggaaacg gatgtataat ttttttata gcgtgaagga tatgataaaa 156600
aatataattg ttgtatttat cccattctaa tcaccttata tgattctgta acacaataaa 156660
ggagtctcat agatgtatag aggtcagata ctggtttgat aaactgttta ttccacataa 156720
gtatgtttga ctttatggtt agacccgcat actttaacaa atcactgaaa attggagtta 156780
ggtattgacc tctcagaatc agttgccgtt ctggaacatt aaatgtattt tttatgatat 156840
actccaacgc atttatgtgg gcatacaaca agtcattact aatggagtat tccaagagtt 156900
ttagttgtct agtatttaac aagagaagag atttcaacag actgtttatg aactcgaatg 156960
ccgcctcatt gtcgcttata ttgatgatgt cgaattctcc caatatcatc actgatgagt 157020
agctcatctt gttatcggga tccaagtttt ctaaagatgt cattaaaccc tcgatcatga 157080
atggatttat catcatcgtt tttatgttgg acatgagctt agtccgtttg tccacatcta 157140
tagacgacga tttctgaatt atttcatata tccctctctt taactccagg aacttgtcag 157200
gatggtctac tttaatatgt tctcgtctaa gagatgaaaa tctttggatg gttgcacgcg 157260
acttttctct aaaggatgac gttgcccaag atcctctctt aaatgaatcc atcttatcct 157320
tggacaagat ggacagtcta ttttccttag atggtttaat atttttgtta cccatgatct 157380
ataaaggtag acctaatcgt ctcggatgac ctatatattt attttcagtt ttattatacg 157440
cataaattgt aaaaaatatg ttaggtttac aaaaatgtct cgtggggcat taatcgtttt 157500
tgaaggattg gacaaatctg gaaaaacaac acaatgtatg aacatcatgg aatctatacc 157560
ggcaaacacg ataaaatatc ttaactttcc tcagagatcc actgtcactg gaaagatgat 157620
agatgactat ctaactcgta aaaaaaccta taatgatcat atagttaatc tattattttg 157680
tgcaaataga tgggagtttg catcttttat acaagaacaa ctagaacagg gaattacttt 157740
aatagttgat agatacgcat ttctggagt agcgtatgcc gccgctaaag gcgcgtcaat 157800

```
gactctcagt aagagttatg aatctggatt gcctaaaccc gacttagtta tattcttgga 157860
atctggtagc aaagaaatta atagaaacgt cggcgaggaa atttatgaag atgttacatt 157920
ccaacaaaag gtattacaag aatataaaaa aatgattgaa gaaggagata ttcattggca 157980
aattatttct tctgaattcg aggaagatgt aaagaaggag ttgattaaga atatagttat 158040
agaggctata cacacggtta ctggaccagt ggggcaactg tggatgtaat agtgaaatta 158100
catttttat aaatagatgt tagtacagtg ttataaatgg atgaagcata ttactctggc 158160
aacttggaat cagtactcgg atacgtgtcc gatatgcata ccgaactcgc atcaatatct 158220
caattagtta ttgccaagat agaaactata gataatgata tattaaacaa ggacattgta 158280
aattttatca tgtgtagatc aaacttggat aatccattta tctctttcct agatactgta 158340
tatactatta tagatcaaga gaactatcag actgagttga ttaattcatt agacgacaat 158400
gaaattatcg attgtatagt taataagttt atgagctttt ataaggataa cctagaaaat 158460
atagtagatg ctatcattac tctaaaatat ataatgaata atccagattt taaaactacg 158520
tatgccgaag tactcggttc cagaatagcc gatatagata ttaaacaagt gatacgtaag 158580
aatatactac aattgtctaa tgatatccgc gaacgatatt tgtgaaaaat attaaaaaaa 158640
aatacttttt ttattaaatg acgtcgcttc gcgaatttag aaaattatgc tgtgatatat 158700
atcacgcatc aggatataaa gaaaaatcta aattaattag agactttata acagataggg 158760
atgataaata tttgatcatt aagctattgc ttcccggatt agacgataga atttataaca 158820
tgaacgataa acaaattata aaattatata gtataatatt taaacaatct caggaagata 158880
tgctacaaga tttaggatac ggatatatag gagacactat taggactttc ttcaaagaga 158940
acacagaaat ccgtccacga gataaaagca ttttaacttt agaagaagtg gatagttttt 159000
taactacgtt atcatccgta actaaagaat cgcatcaaat aaaattattg actgatgtag 159060
catctgtttg tacatgtaat gatttaaaat gtgtagtcat gcttattgat aaagatctaa 159120
aaattaaagc gggtcctcgg tacgtactta acgctattag tcctcatgcc tatgatgtgt 159180
ttagaaaatc taataacttg aaagagataa tagaaaattc atctaaacaa aatctagact 159240
ctatatctat ttctgttatg actccaatta atcccatgtt agcggaatcg tgtgattctg 159300
tcaataaggc gtttaaaaaa tttccatcag gaatgtttgc ggaagtcaaa tacgatggtg 159360
aaagagtaca agttcataaa aataataacg agtttgcctt ctttagtaga aacatgaaac 159420
cagtactctc tcataaagtg gattatctca aagaatacat accgaaagca tttaaaaaag 159480
ctacgtctat cgtattggat tctgaaattg ttcttgtaga cgaacataat gtaccgctcc 159540
cgtttggaag tttaggtata cacaaaaaga aagaatataa aaactctaac atgtgtttgt 159600
tcgtgtttga ctgtttgtac tttgatggat tcgatatgac ggacattcca ttgtacgaac 159660
gaagatcttt tctcaaagat gttatggttg aaatacccaa tagaatagta ttctcagagt 159720
tgacgaatat tagtaacgag tctcagttaa ctgacgtatt ggatgatgca ctaacgagaa 159780
aattagaagg attggtctta aaagatatta atggagtata cgaaccggga aagagaagat 159840
ggttaaaaat aaagcgagac tatttgaacg agggttccat ggcagattct gccgatttag 159900
tagtactagg tgcttactat ggtaaaggag caaagggtgg tatcatggca gtctttctaa 159960
tgggttgtta cgacgatgaa tccggtaaat ggaagacggt taccaagtgt tcaggacacg 160020
atgataatac gttaagggag ttgcaagacc aattaaagat gattaaaatt aacaaggatc 160080
ccaaaaaaat tccagagtgg ttagtagtta ataaaatcta tattcccgat tttgtagtag 160140
```

aggatccaaa acaatctcag atatgggaaa tttcaggagc agagtttaca tcttccaagt 160200
cccataccgc aaatggaata tccattagat ttcctagatt tactaggata agagaggata 160260
aaacgtggaa agaatctact catctaaacg atttagtaaa cttgactaaa tcttaatagt 160320
tacatacaaa ctaaaaatta aaataacact atttagttgg tggtcgccat ggatggtgtt 160380
attgtatact gtctaaacgc gctagtaaaa catggcgagg aaataaatca tataaaaaat 160440
gatttcatga ttaaaccatg ttgtgaaaga gtttgtgaaa aagtcaagaa cgttcacatc 160500
gacggacaat ctaaaaacaa tacagtgatt gcagatttgc catatctgga taatgctgta 160560
tccgatgtat gcaaatcgat atatatatag tatcaagaat atccagattt gctaatttga 160620
taaagataga tgacgatgac aagactccta ctggtgtata taattatttt aaacctaaag 160680
atgttattcc tgttatcata tctataggaa aggataaaga tgtctgtgaa ctattaatct 160740
catcagacat atcgtgtgca tgcgtggagt taaattcata tcacgtagcc attcttccca 160800
tggatgtttc ctttttacc aaaggaaatg catcattgat tattctcctg tttgatttct 160860
ctatcgatgc ggcacctctc ttaagaagtg taaccgataa taatgttatt atatctagac 160920
accagcgtat acatgacgag cttccgagtt ccaattggtt caagttttac ataagtataa 160980
agtccgacta ttgttctata ttatatatgg ttgttgatgg atctgtgatg catgcgatag 161040
ctgataatag aactcacgca attattagca aaaatatatt agacaatact acgattaacg 161100
atgagtgtag atgctgttat tttgaaccac agattaggat tcttgataga gatgagatgc 161160
tcaatggatc atcgtgtgat atgaacagac attgtattat gatgaattta cctgatgtag 161220
gcgaatttgg atctagtatg ttggggaaat atgaacctga catgattaag attgctcttt 161280
cggtggctgg taatttaata agaaatcgag actacattcc cgggagacga ggatatagct 161340
actacgttta cggtatagcc tctagataat ttttttaagc acgaaataaa aaacataatt 161400
ttaaaccaat ctatttcata ctattttgtg tgatcaccat ggacataaag atagatatta 161460
gtatttctgg tgataaattt acggtgacta ctaggaggga aaatgaagaa agaaaaaaat 161520
atctacctct ccaaaaagaa aaaactactg atgttatcaa acctgattat cttgagtacg 161580
atgacttgtt agatagagat gagatgttta ctattctaga ggaatatttt atgtacagag 161640
gtctattagg cctcagaata aaatatggac gactctttaa cgaaattaaa aaattcgaca 161700
atgatgcgga agaacaattc ggtactatag aagaactcaa gcagaaactt agattaaatt 161760
ctgaagaggg agcagataac tttatagatt atataaaggt acaaaaacag gatatcgtca 161820
aacttactgt atacgattgc atatctatga taggattgtg tgcatgcgtg gtagatgttt 161880
ggagaaatga gaaactgttt tctagatgga aatattgttt acgagcgatt aaactgttta 161940
ttgatgatca catgcttgat aagataaaat ctatactgca gaatagacta gtgtatgtgg 162000
aaatgtcata gaaagttaaa agttaatgag agcaaaaata tataaggttg tattccatat 162060
ttgttatttt tttctgtaat agttagaaaa atacattcga tggtctatct atcagattat 162120
tatgtgttat aaggtacttt ttctcataat aaactagagt atgagtaaga tagtgttttt 162180
caaaacatat aaatctaaaa ttgatggatg agatatacag ctattaattt cgaaaatata 162240
ttttaatctg ataactttaa acatggattt ttgatggtgg tttaacgttt taaaaaaaga 162300
ttttgttatt gtagtatatg ataaatattaa aagatggata taaagaattt gctgactgta 162360
tgtactattt tttacattac tacattggct acggcagata tacctacttc gtcactgcca 162420
cacgctccgg taaacggggc atgtgacgag ggagaatatc ttgataagag gcataatcaa 162480
tgttgtaatc ggtgtccacc tggagaattt gccaaggtta gatgtaatgg taacgataac 162540

```
acaaaatgtg aacgctgccc acctcataca tataccgcaa tccccaatta ctctaatgga 162600
tgtcatcaat gtagaaaatg cccaacagga tcatttgata aggtaaagtg taccggaaca 162660
cagaacagta aatgttcgtg tcttcctggt tggtattgcg ctactgattc ttcacagact 162720
gaagattgtc gagattgtat accaaaaagg agatgtccat gcggatactt tggtggaata 162780
gatgaacaag gaaatcctat ttgtaaatcg tgttgtgttg gtgaatattg cgactaccta 162840
cgtaattata gacttgatcc atttcctcca tgcaaactat ctaaatgtaa ttaattatga 162900
ttttgatgat aatgttacca tacattatat cgctacttgg ttagtgtatt attcagtatg 162960
aagacctatt aataattact tatcttttga cgatcttgtt ataattataa tataaaaact 163020
tatggcatag taacttataa ttgctgacgc gataaattcg taataatctg ttttgttcaa 163080
aggaatctac aggcataaaa ataaaaatat aatttataat atactcttac agcgcgccat 163140
catgaataac agcagtgaat tgattgctgt tattaatgga tttagaaata gtggacgatt 163200
ttgtgatatt agtatagtta ttaatgatga aaggataaac gctcataaac tcatcctatc 163260
tggagcctcc gaatattttt ccattctgtt ttccaataat tttatcgatt ctaatgaata 163320
cgaagttaat ctaagtcatt tagattatca aagtgttaac gatttgatcg attatattta 163380
tgggatacct ttgagcctaa ctaacgataa cgtgaaatat attctttcaa ccgctgattt 163440
tttacaaatt ggatctgcta ttacggagtg tgaaaattac atacttaaaa atctttgttc 163500
tagaaactgt atcgatttct acatatacgc tgataaatat aataacaaga aaatagaatc 163560
agcgtcgttt aacacaatat tacaaaatat tttgagactc atcaacgatg aaaactttaa 163620
atacttaaca gaggaatcaa tgataaaaat tttaagcgat gatatgttaa atataaaaaa 163680
tgaggatttc gccccactaa ttctcattaa atggttagag agtactcaac aaccatgcac 163740
cgtcgagtta cttaaatgcc tcagaatatc attgctttcc ccacaagtta taaaatcact 163800
ttatagtcat cgactggtta gttcaatcta cgaatgtata acattcttaa acaatatagc 163860
attcttggat gaatcatttc ctagatacca tagcatcgag ttgatatcta tcggtataag 163920
taattcgcat gataagattt ccataaactg ctacaatcat aaaaaaaata catgggaaat 163980
gatatcttca cgtagatata ggtgtagttt cgcagtggcc gtcctggata atattattta 164040
tatgatgggt ggatatgatc agtccccgta tagaagttca aaggttatag cgtacaatac 164100
atgtacaaat tcttggatat atgatatacc agagctaaaa tatcctcgtt ctaattgtgg 164160
gggactggct gatgacgaat acatttattg tataggcggc atacgcgatc aggattcatc 164220
gttgacatct agtattgata aatggaagcc atcaaaacca tattggcaga agtatgctaa 164280
aatgcgcgaa ccaaaatgtg atatgggggt tgcgatgtta aacggattaa tatatgttat 164340
aggtggaatc gttaaaggtg acacgtgtac cgacgcacta gagagtttat cagaagatgg 164400
atggatgaag catcaacgtc ttccaataaa aatgtccaat atgtcgacga ttgttcatga 164460
tggcaagatt tatatatctg gaggttacaa caatagtagt gtagttaatg taatatcgaa 164520
tctagtcctt agctataatt cgatatatga tgaatggacc aaattatcat cattaaacat 164580
tcctagaatt aatcccgctc tatggtcagc gcataataaa ttatatgtag gaggaggaat 164640
atctgatgat gttcgaacta atacatctga aacatacgat aaagaaaaag attgttggac 164700
attggataat ggtcacgtgt taccacgcaa ttatataatg tataaatgcg aaccgattaa 164760
acataaatat ccattggaaa aaacacagta cacgaatgat tttctaaagt atttggaaag 164820
ttttataggt agttgataga acaaaataca taattttgta aaaataaatc actttttata 164880
```

ctaatatgac acgattacca atacttttgt tactaatatc attagtatac gctacacctt 164940
ttcctcagac atctaaaaaa ataggtgatg atgcaactct atcatgtaat cgaaataata 165000
caaatgacta cgttgttatg agtgcttggt ataaggagcc caattccatt attcttttag 165060
ctgctaaaag tgacgtcttg tattttgata attataccaa ggataaaata tcttacgact 165120
ctccatacga tgatctagtt acaactatca caattaaatc attgactgct agagatgccg 165180
gtacttatgt atgtgcattc tttatgacat cgcctacaaa tgacactgat aaagtagatt 165240
atgaagaata ctccacagag ttgattgtaa atacagatag tgaatcgact atagacataa 165300
tactatctgg atctacacat tcaccggaaa ctagttctga gaaacctgat tatatagata 165360
attctaattg ctcgtcggta ttcgaaatcg cgactccgga accaattact gataatgtag 165420
aagatcatac agacaccgtc acatacacta gtgatagcat taatacagta agtgcatcat 165480
ctggagaatc cacaacagac gagactccgg aaccaattac tgataaagaa gaagatcata 165540
cagtcacaga cactgtctca tacactacag taagtacatc atctggaatt gtcactacta 165600
aatcaaccac cgatgatgcg gatcttcatg atacgtacaa tgatacagta ccatcaacta 165660
ctgtaggcgg tagtacaacc tctattagca attataaaac caaggacttt gtagaaatat 165720
ttggtattac cgcattaatt atattgtcgg ccgtggcaat tttctgtatt acgtattata 165780
tatgtaataa acgttcacgt aaatacaaaa cagagaacaa agtctagatt tttgacttac 165840
ataaatgtct gggatagtaa aatctatcat attgagcgga ccatctggtt taggaaagac 165900
agccatagcc aaaagactat gggaatatat ttggatttgt ggtgtcccat accactagat 165960
ttcctcgtcc tatggaacga gaaggtgtcg attaccatta cgttaacaga gaggccatct 166020
ggaagggaat agccgccgga aactttctag aacatactga gtttttagga aatatttacg 166080
gaacttctaa aactgctgtg aatacagcgg ctattaataa tcgtatttgt gtgatggatc 166140
taaacatcga tggcgttaga agtcttaaaa atacgtacct aatgccttac tcggtgtata 166200
taagacctac ctctcttaaa atggttgaga ccaagcttcg ttgtagaaac actgaagcta 166260
acgatgagat tcatcgtcgt gtgatgttgg caaaaactga catggatgag gcaggtgaag 166320
ccggtctatt cgacactatt attattgaag atgatgtgaa tttagcatat agtaagttaa 166380
ttcagatact acaggaccgt attagaatgt attttaacac taattagaga cttaagactt 166440
aaaacttgat aattaataat ataactcgtt tttatatgtg tctatttcaa cgtctaatgt 166500
attagttaaa tattaaaact taccacgtaa aacttaaaat ttaaaatgat atttcattga 166560
cagatagatc acacattatg aactttcaag gacttgtgtt aactgacaat tgcaaaaatc 166620
aatgggtcgt tggaccatta ataggaaaag gtggatttgg tagtatttat actactaatg 166680
acaataatta tgtagtaaaa atagagccca aagctaacgg atcattattt accgaacagg 166740
cattttatac tagagtactt aaaccatccg ttatcgaaga atggaaaaaa tctcacaata 166800
taaagcacgt aggtcttatc acgtgcaagg catttggtct atacaaatcc attaatgtgg 166860
aatatcgatt cttggtaatt aatagattag gtgcagatct agatgcggtg atcagagcca 166920
ataataatag actaccaaaa aggtcggtga tgttgatcgg aatcgaaatc ttaaatacca 166980
tacaatttat gcacgagcaa ggatattctc acggagatat taaagcgagt aatatagtct 167040
tggatcaaat agataagaat aaattatatc tagtggatta cggattggtt tctaaattca 167100
tgtctaatgg cgaacatgtt ccatttataa gaaatccaaa taaaatggat aacggtactc 167160
tagaatttac acctatagat tcgcataaag gatacgttgt atctagacgt ggagatctag 167220
aaacacttgg atattgtatg attagatggt tgggaggtat cttgccatgg actaagatat 167280
ctgaaacaaa gaattgtgca ttagtaagtg ccacaaaaca gaaatatgtt aacaatactg 167340
cgactttgtt aatgaccagt ttgcaatatg aacctagaga attgctgcaa tatattacca 167400
tggtaaactc tttgacatat tttgaggaac ccaattacga caagtttcgg cacatattaa 167460
tgcagggtgt atattattaa gtgtggtgtt tggtcgatgt aaaatttttg tcgataaaaa 167520
ttaaaaaata acttaattta ttattgatct cgtgtgtaca accgaaatca tggcgatgtt 167580
ttacgcacac gctctcggtg ggtacgacga gaatcttcat gcctttcctg gaatatcatc 167640
gactgttgcc aatgatgtca ggaaatattc tgttgtgtta gtttataata acaagtatga 167700
cattgtaaaa gacaaatata tgtggtgtta cagtcaggtg aacaagagat atattggagc 167760
actgctgcct atgtttgagt gcaatgaata tctacaaatt ggagatccga tccatgatca 167820
agaaggaaat caaatctcta tcatcacata tcgccacaaa aactactatg ctctaagcgg 167880
aatcgggtac gagagtctag acttgtgttt ggaaggagta gggattcatc atcacgtact 167940
tgaaacagga aacgctgtat atggaaaagt tcaacatgat tattctacta tcaaagagaa 168000
ggccaaagaa atgaatgcac ttagtccagg acctatcatc gattaccacg tctggatagg 168060
agattgtatc tgtcaagtta ctgctgtgga cgtacatgga aaggaaatta tgaaaatgag 168120
attcaaaaag ggtgcggtgc ttccgatccc aaatctggta aaagttaaac ttggggagaa 168180
tgatacagaa aatctttctt ctactatatc ggcggcacca tcgaggtaac cacctctctg 168240
gaagacagcg tgaataatgt actcatgaaa cgtttggaaa ctatacgcca tatgtggtct 168300
gttgtatatg atcattttga tattgtgaat ggtaaagaat gctgttatgt gcatacgcat 168360
ttgtctaatc aaaatcctat accgagtact gtaaaaacaa atttgtacat gaagactatg 168420
ggatcatgca ttcaaatgga ttccatggaa gctctagagt atcttagcga actgaaggaa 168480
tcaggtggat ggagtcccag accagaaatg caggaatttg aatatccaga tggagtggaa 168540
gacactgaat caattgagag attggtagag gagttcttca atagatcaga acttcaggct 168600
ggtgaatcag tcaaatttgg taattctatt aattgttaaa catacatctg tttcagctaa 168660
gcaactaaga acacgtatac ggcagcagct tccttttata ctctcatctt ttaccaacac 168720
aaagggtgga tatttgttca ttggagttga taataataca cacaaagtat ttggattcac 168780
ggtgggttac gactacctca gactggtaga gaatgatata gaaaagcata tcaaaagact 168840
ttgtgttgtg tatttctgtg agaagaaaga ggacatcaag tacgcgtgtc gattcatcaa 168900
ggtatataaa cctggggatg aggctacctc gacatacgtg tgcgctatca aagtggaaag 168960
atgctgttgt gctgtgtttg cagattggcc agaatcatgg tatatggata ctaatggtat 169020
caagaagtat tctccagatg aatgggtgtc acatataaaa ttttaattaa tgtaatagag 169080
aacaaataat aaggttgtaa tatcatatag acaataacta acaattaatt agtaactgtt 169140
atctcttttt taactaacca actaactata tacctattaa tacatcgtaa ttatagttct 169200
taacatctat taatcattaa ttcgcttctt taatttttta taaactaaca ttgttaattg 169260
aaaagggata acatgttaca gaatataaat tatatatgga ttttttttaaa aaggaaatac 169320
ttgactggag tatatattta tctcttcatt atatagcacg cgtgttttcc aatttttcca 169380
catcccatat aatacaggat tataatctcg ttcgaacata cgagaaagtg gataaaacaa 169440
tagttgattt tttatctagg ttgccaaatt tattccatat tttagaatat ggggaaaata 169500
ttctacatat ttattctatg gatgatgcta atacgaatat tataattttt tttctagata 169560
gagtattaaa tattaataag aacgggtcat ttatacacaa tctcgggtta tcatcatcca 169620

```
ttaatataaa agaatatgta tatcaattag ttaataatga tcatccagat aataggataa 169680
gactaatgct tgaaaatgga cgtagaacaa gacatttttt gtcctatata tcagatacag 169740
ttaatatcta tatatgtatt ttaataaatc atggatttta tatagatgcc gaagacagtt 169800
acggttgtac attattacat agatgtatat atcactataa gaaatcagaa tcagaatcat 169860
acaatgaatt aattaagata ttgttaaata atggatcaga tgtagataaa aaagatacgt 169920
acggaaacac accttttatc ctattatgta aacacgatat caacaacgtg gaattgtttg 169980
agatatgttt agagaatgct aatatagact ctgtagactt taatagatat acacctcttc 170040
attatgtctc atgtcgtaat aaatatgatt ttgtaaagtt attaatttct aaaggagcaa 170100
atgttaatgc gcgtaataaa ttcggaacta ctccatttta ttgtggaatt atacacggta 170160
tctcgcttat aaaactatat ttggaatcag acacagagtt agaaatagat aatgaacata 170220
tagttcgtca tttaataatt tttgatgctg ttgaatcttt agattatcta ttatccagag 170280
gagttattga tattaactat cgtactatat acaacgaaac atctatttac gacgctgtca 170340
gttataatgc gtataatacg ttggtctatc tattaaacag aaatggtgat tttgagacga 170400
ttactactag tggatgtaca tgtatttcgg aagcagtcgc aaacaacaac aaaataataa 170460
tggaagtact attgtctaaa cgaccatctt tgaaaattat gatacagtct atgatagcaa 170520
ttactaaaca taaacagcat aatgcagatt tattgaaaat gtgtataaaa tatactgcgt 170580
gtatgaccga ttatgatact cttatagatg tacagtcgct acagcaatat aaatggtata 170640
ttttaaaatg tttcgatgaa atagatatca tgaagagatg ttatataaaa aataaaactg 170700
tattccaatt agttttttgt atcaaagaca ttaatacttt aatgagatac ggtaaacatc 170760
cttctttcgt gaaatgcact agtctcgacg tatacggaag tcgtgtacgt aatatcatag 170820
catctattag atatcgtcag agattaatta gtctattatc caagaagctg gatcctggag 170880
ataaatggtc gtgttttcct aacgaaataa aatataaaat attggaaaac tttaacgata 170940
acgaactatc cacatatcta aaaatcttat aaacactatt aaaatataaa atctaagtag 171000
gataaaatca cactacatca ttgtttcctt ttagtgctcg acagtgtata ctatttttaa 171060
cgctcataaa taaaaatgaa aacgatttcc gttgttacgt tgttatgcgt actacctgct 171120
gttgtttatt caacatgtac tgtacccact atgaataacg ctaaattaac gtctaccgaa 171180
acatcgttta atgataaaca gaaagttaca tttacatgtg atcagggata tcattcttcg 171240
gatccaaatg ctgtctgcga aacagataaa tggaaatacg aaaatccatg caagaaaatg 171300
tgcacagttt ctgattacat ctctgaacta tataataaac cgctatacga agtgaattcc 171360
accatgacac taagttgcaa cggcgaaaca aaatattttc gttgcgaaga aaaaaatgga 171420
aatacttctt ggaatgatac tgttacgtgt cctaatgcgg aatgtcaacc tcttcaatta 171480
gaacacggat cgtgtcaacc agttaaagaa aaatactcat ttggggaata tatgactatc 171540
aactgtgatg ttggatatga ggttattggt gcttcgtaca taagttgtac agctaattct 171600
tggaatgtta ttccatcatg tcaacaaaaa tgtgatatgc cgtctctatc taacggatta 171660
atttccggat ctacattttc tatcggtggc gttatacatc ttagttgtaa aagtggtttt 171720
acactaacgg ggtctccatc atccacatgt atcgacggta aatggaatcc cgtactccca 171780
acatgtgtac gaactaacga aaaatttgat ccagtggatg atggtcccga cgatgagaca 171840
gatttgagca aactctcgaa agacgttgta caatatgaac aagaaataga atcgttagaa 171900
gcaacttatc atataatcat agtggcgttg acaattatgg gcgtcatatt tttaatctcc 171960
gttatagtat tagtttgttc ctgtgacaaa aataatgacc aatataagtt ccataaattg 172020
```

```
ctaccgtgaa tataaatccg ttaaaataat taataattta ataacaaaca agtatcaaaa 172080
gattaaagac ttatagctag aatcaattga gatgtcttct tcagtggatg ttgatatcta 172140
cgatgccgtt agagcatttt tactcaggca ctattataac aagagattta ttgtgtatgg 172200
aagaagtaac gccatattac ataatatata caggctattt acaagatgcg ccgttatacc 172260
gttcgatgat atagtacgta ctatgccaaa tgaatcacgt gttaaacaat gggtgatgga 172320
tacacttaat ggtataatga tgaatgaacg cgatgtttct gtaagcgttg gcaccggaat 172380
actattcatg gaaatgtttt tcgattacaa taaaaatagt atcaacaatc aactaatgta 172440
tgatataatt aatagcgtat ctataattct agctaatgag agatatagaa gcgcttttaa 172500
cgacgatggt atatacatcc gtagaaatat gattaacaag ttgtacggat acgcatctct 172560
aactactatt ggcacgatcg ctggaggtgt ttgttattat ctgttgatgc atctagttag 172620
tttgtataaa taattatttc aatatactag ttaaaatttt aagattttaa atgtataaaa 172680
aactaataac gtttttattt gtaataggtg cattagcatc ctattcgaat aatgagtaca 172740
ctccgtttaa taaactgagt gtaaaactct atatagatgg agtagataat atagaaaatt 172800
catatactga tgataataat gaattggtgt taaattttaa agagtacaca atttctatta 172860
ttacagagtc atgcgacgtc ggatttgatt ccatagatat agatgttata aacgactata 172920
aaattattga tatgtatacc attgactcgt ctactattca acgcagaggt cacacgtgta 172980
gaatatctac caaattatca tgccattatg ataagtaccc ttatattcac aaatatgatg 173040
gtgatgagcg acaatattct attactgcag agggaaaatg ctataaagga ataaaatatg 173100
aaataagtat gatcaacgat gatactctat tgagaaaaca tactcttaaa attggatcta 173160
cttatatatt tgatcgtcat ggacatagta atacatatta ttcaaaatat gatttttaaa 173220
aatttaaaat atattatcac ttcagtgaca gtagtcaaat aacaaacaac accatgagat 173280
atattataat tctcgcagtt ttgttcatta atagtataca tgctaaaata actagttata 173340
agtttgaatc cgtcaatttt gattccaaaa ttgaatggac tggggatggt ctatacaata 173400
tatcccttaa aaattatggc atcaagacgt ggcaaacaat gtatacaaat gtaccagaag 173460
gaacatacga catatccgca tttccaaaga atgatttcgt atctttctgg gttaaatttg 173520
aacaaggcga ttataaagtg gaagagtatt gtacgggact atgcgtcgaa gtaaaaattg 173580
gaccaccgac tgtaacatta actgaatacg acgaccatat caatttgtac atcgagcatc 173640
cgtatgctac tagaggtagc aaaaagattc ctatttacaa acgcggtgac atgtgtgata 173700
tctacttgtt gtatacggct aacttcacat tcggagattc taaagaacca gtaccatatg 173760
atatcgatga ctacgattgc acgtctacag gttgcagcat agactttgtc acaacagaaa 173820
aagtgtgcgt gacagcacag ggagccacag aagggtttct cgaaaaaatt actccatgga 173880
gttcgaaagt atgtctgaca cctaaaaaga gtgtatatac atgcgcaatt agatccaaag 173940
aagatgttcc caatttcaag gacaaaatgg ccagagttat caagagaaaa tttaataaac 174000
agtctcaatc ttatttaact aaatttctcg gtagcacatc aaatgatgtt accacttttc 174060
ttagcatgct taacttgact aaatattcat aactaatttt tattaatgat acaaaaacga 174120
aataaaactg catattatac actggttaac gcccttatag gctctaacca ttttcaagat 174180
gaggtccctg attatagtcc ttctgttccc ctctatcatc tactccatgt ctattagacg 174240
atgtgagaag actgaagagg aaacatgggg attgaaaata gggttgtgta taattgccaa 174300
agatttctat cccgaaagaa ctgattgcag tgttcatctc ccaactgcaa gtgaaggatt 174360
```

```
gataactgaa ggcaatggat tcagggatat acgaaacacc gataaattat aaaaaaagca 174420
atgtgtccgc tgtttccgtt aataatacta tttttgtaac tggcgaatta ttcataaata 174480
actctaatag cacgatcgtg gttaacaata tggaaaaact tgacatttat aaagacaaac 174540
aatggtcgat tatagaaatg cctatggcta gggtatatca cggcatcgac tcgacatttg 174600
gaatgttata ttttgccgga ggtctatccg ttaccgaaca atatggtaat ttagagaaaa 174660
acaacgagat atcttgttac aatcctagaa cgaataagtg gtttgatatt tcatatacta 174720
tttataagat atccatatca tcattgtgta aactaaataa cgtcttctat gtatttagta 174780
aggacattgg atatgtggaa aagtatgatg gtgcacggaa gttagtacat gatcgtctcc 174840
ccgctataaa ggcattatca acttctcctt attgattgaa aatgaaaata taaatagttt 174900
ttatgcatag cagtattacc ctatagtttt attgcttact actaacatgg atacagatgt 174960
tacaaatgta gaagatatca taaatgaaat agatagagag aaagaagaaa tactaaaaaa 175020
tgtagaaatt gaaaataata aaaacattaa caagaatcat ccaagtggat atattagaga 175080
agcactcgtt attaatacca gtagtaatag tgattccatt gataaagaag ttatagaatg 175140
tatcagtcac gatgtaggaa tatagatcat atctactaat ttttataatc gatacaaaac 175200
ataaaaaaca actcgttatt acatagcagg catggaatcc ttcaagtatt gttttgataa 175260
cgatggcaag aaatggatta tcggaaatac tttatattct ggtaattcaa tactctataa 175320
ggtcagaaaa aatttcacta gttcgttcta caattacgta atgaagatag atcacaaatc 175380
acacaagcca ttgttgtctg aaatacgatt ctatatatct gtattggatc ctttgactat 175440
cgacaactgg acacgggaac gtggtataaa gtatttggct attccagatc tgtatggaat 175500
tggagaaacc gatgattata tgttcttcgt tataaagaat ttgggaagag tattcgcccc 175560
aaaggatact gaatcagtct tcgaagcatg cgtcactatg ataaacacgt tagagtttat 175620
acactctcaa ggatttaccc atggaaaaat agaaccgagg aatatactga ttagaaataa 175680
acgtctttca ctaattgact attctagaac taacaaacta tacaagagtg gaaactcaca 175740
tatagattac aacgaggaca tgataacttc aggaaatatc aattatatgt gtgtagacaa 175800
tcatcttgga gcaacagttt caagacgagg agatttagaa atgttgggat attgcatgat 175860
agaatggttc ggtggcaaac ttccatggaa aaacgaaagt agtataaaag taataaaaca 175920
aaaaaaagaa tataaaaaat ttatagctac tttctttgag gactgttttc ctgaaggaaa 175980
tgaacctctg gaattagtta gatatataga attagtatac acgttagatt attctcaaac 176040
tcctaattat gacagactac gtaaactgtt tatacaagat tgaaattata ttcttttttt 176100
tatagagtgt ggtagtgtta cggatattta atattagact atctctatcg cgctacacga 176160
ccaatatcga ttactatgga tatcttctat gaaaggagag aatgtattca tttctccagc 176220
gtcaatctcg tcagtattga caatactgta ttatggagct aatggatcca ctgctgaaca 176280
gctatcgaaa tatgtagaaa aggaggagaa cacggataag gttagcgctc aaaatatctc 176340
attcaaatcc ataaataaag tatatgggcg atattctgcc gtgtttaaag atttcttttt 176400
gggaaaaatt ggcgataagt ttcaaactgt tgacttcact gattgtcgca ctatagatgc 176460
aatcaacaag tgtgtagata tctttactga ggggaaaatc aatccactat tggatgaacc 176520
attgtctcct agcaattagt gccgtatact ttaaagcaaa atggttgacg ccattcgaaa 176580
aggaatttac cagtgattat ccccttttacg tatctccgac ggaaatggta gatgtaagta 176640
tgatgtctat gtacggcgag ctatttaatc acgcatctgt aaaagaatca ttcggcaact 176700
tttcaatcat agaactgcca tatgttggag atactagtat gatggtcatt cttccagaca 176760
```

agattgatgg attagaatcc atagaacaaa atctaacaga tacaaatttt aagaaatggt 176820
gtgactttat ggatgctatg tttatagatg ttcacattcc caagtttaag gtaacaggtt 176880
cgtataatct ggtggatact ctagtaaagt caggactgac agaggtgttc ggttcaactg 176940
gagattatag caatatgtgt aatttagatg tgagtgtcga cgctatgatc cacaaaacgt 177000
atatagatgt caatgaagag tatacagaag cagctgcagc aacttctgta ctagtggcag 177060
actgtgcatc aacagttaca aatgagttct gtgcagatca tccgttcatc tatgtgatta 177120
ggcatgttga tggcaaaatt cttttcgttg gtagatattg ctctccaaca actaattgtt 177180
aaccattttt tttaaaaaaa tagaaaaaac atgtggtatt agtgcaggtc gttgttcttc 177240
caattgcaat tggtaagatg acggccaact ttagtaccca cgtcttttca ccacagcact 177300
gtggatgtga cagactgacc agtattgatg acgtcaaaca atgtttgact gaatatattt 177360
attggtcgtc ctatgcatac cgcaacaggc aatgcgctgg acaattgtat tccacactcc 177420
tctcttttag agatgatgcg gaattagtgt tcatcgacat tcgcgagctg gtaaaaaata 177480
tgccgtggga tgatgtcaaa gattgtacag aaatcatccg ttgttatata ccggatgagc 177540
aaaaaaccat cagagagatt tcggccatca tcggactttg tgcatatgct gctacttact 177600
ggggaggtga agaccatccc actagtaaca gtctgaacgc attgtttgtg atgcttgaga 177660
tgctaaatta cgtggattat aacatcatat tccggcgtat gaattgatga gttgtacatc 177720
ttgacatttt ctttcttctc ttctcccttt cttctcttct cccttcctcc ctcttctccc 177780
tttcccagaa acaaactttt ttacccacta taaaataaaa tgagtatact acctgttata 177840
tttcttccta tattttttta ttcttcattc gttcagactt ttaacgcgcc tgaatgtatc 177900
gacaaagggc aatattttgc atcattcatg gagttagaaa acgagccagt aatcttacca 177960
tgtcctcaaa taaatacgct atcatccgga tataatatat tagatatttt atgggaaaaa 178020
cgaggagcgg ataatgatag aattataccg atagataatg gtagcaatat gctaattctg 178080
aacccgacac aatcagactc tggtatttat atatgcatta ccacgaacga aacctactgt 178140
gacatgatgt cgttaaattt gacaatcgtg tctgtctcag aatcaaatat agatcttatc 178200
tcgtatccac aaatagtaaa tgagagatct actggcgaaa tggtatgtcc caatattaat 178260
gcatttattg ctagtaacgt aaacgcagat attatatgga gcggacatcg acgccttaga 178320
aataagagac ttaaacaacg gacacctgga attattacca tagaagatgt tagaaaaaat 178380
gatgctggtt attatacatg tgttttagaa tatatataca gaggtaaaac atataacgta 178440
accagaattg taaaattaga ggtacgggat aaaataatac cttctactat gcaattacca 178500
gatggcattg taacttcaat aggtagtaat ttgactattg cgtgtagagt atcgttgaga 178560
cctcccacaa cggatgcaga cgtcttttgg ataagtaatg gtatgtatta cgaagaagat 178620
gatggggacg gaaacggtag aataagtgta gcaaataaaa tctatatgac cgataagaga 178680
cgtgttatta catcccggtt aaacattaat cctgtcaagg aagaagatgc tacaacgttt 178740
acgtgtatgg cgtttactat tcctagcatc agcaaaacag ttactgttag tataacgtga 178800
atgtatgttg ttacatttcc atgtcaattg agtttataag aatttttata cattatcttc 178860
caacaaacaa ttgacgaacg tattgctatg attaactccc acgatactat gcatattatt 178920
aatcattaac ttgcagacta tacctagtgc tattttgaca tactcatgtt cttgtgtaat 178980
tgcggtatct atattattaa agtacgtaaa tctagctata gttttattat ttaattttag 179040
ataatatacc gtctccttat ttttaaaaat tgccacatcc tttattaaat catgaatggg 179100

```
aatttctatg tcatcgttag tatattgtga acaacaagag cagatatcta taggaaaggg 179160
tggaatgcga tacattgatc tatgtagttt taaaacacac gcgaactttg aagaatttat 179220
ataaatcatt ccatcgatac atccttctat gttgacatgt atatatccag gaattctttt 179280
attaatgtca ggaaatgtat aaactaaaac attgcccgaa agcggtgcct ctatctgcgt 179340
tatatccgtt cttaacttac aaaatgtaac caatactttt gcatgacttg ttttgttcgg 179400
caacgttagt ttaaacttga cgaatggatt aattacaata gcatgatccg cgcatctatt 179460
aagtttttt actttaacgc ccttgtatgt ttttacagag actttatcta aatttctagt 179520
gcttgtatgt gttataaata taacgggata tagaactgaa tcacctacct tagataccca 179580
attacatttt atcagatcca gataataaac aaattttgtc gccctaacta attctatatt 179640
gttatatatt ttacaattgg ttatgatatc atgtaataac ttggagtcta acgcgcatcg 179700
tcgtacgttt atacaattgt gatttagtgt agtatatcta cacatgtatt tttccgcact 179760
atagtattct ggactagtga taaaactatc gttatatctg tcttcaatga actcatcgag 179820
atattgctct ctgtcatatt catacacctg cataaacttt ctagacatct tacaatccgt 179880
gttattttag gatcatattt acatatttac gggtatatca aagatgttag attagttaat 179940
gggaatcgtc tataataatg aatattaaac aattatatga ggacttttac cacaaagcat 180000
cataaaaatg agtcgtcgtc tgatttatgt tttaaatatc aaccgcgaat caactcataa 180060
aatacaagag aatgaaatat atacatattt tagtcattgc aatatagacc atacttctac 180120
agaacttgat tttgtagtta aaaactatga tctaaacaga cgacaacctg taactgggta 180180
tactgcacta cactgctatt tgtataataa ttactttaca aacgatgtac tgaagatatt 180240
attaaatcat ggagtggatg taacgatgaa aaccagtagc ggacgtatgc ctgtttatat 180300
attgcttact agatgttgca atatttcaca tgatgtagtg atagatatga tagacaaaga 180360
taaaaaccac ttattacata gagactattc caacctatta ctagagtata taaaatctcg 180420
ttacatgtta ttaaaggaag aggatatcga tgagaacata gtatccactt tattagataa 180480
gggaatcgat cctaacttta aacaagacgg atatacagcg ttacattatt attatttgtg 180540
tctcgcacac gtttataaac caggtgagtg tagaaaaccg ataacgataa aaaaggccaa 180600
gcgaattatt tctttgttta tacaacatgg agctaatcta aacgcgttag ataattgtgg 180660
taatacacca ttccatttgt atcttagtat tgaaatgtgt aataatattc atatgactaa 180720
aatgctgttg acttttaatc cgaatttcga aatatgtaat aatcatggat taacgcctat 180780
actatgttat ataacttccg actacataca acacgatatt cttgttatgt taatacatca 180840
ctatgaaaca aatgttggag aaatgccgat agatgagcgt cgtatgatcg tattcgagtt 180900
tatcaaaaca tattctacac gtccggcaga ttcgataact tatttgatga ataggtttaa 180960
aaatataaat atttataccc gctatgaagg aaagacatta ttacacgtag catgtgaata 181020
taataataca cacgtaatag attatcttat acgtatcaac ggagatataa atgcgttaac 181080
cgacaataac aaacacgcta cacaactcat tatagataac aaagaaaatt ccccatatac 181140
cattaattgt ttactgtata tacttagata tattgtagat aagaatgtga taagatcgtt 181200
ggtggatcaa cttccatctc tacctatctt tcgtcgctta tcatactagt catatcctaa 181260
atgttgatca tattccacca aatgattgtg aaagagattg agattaaatc gtctaacaaa 181320
caattagttt ttatgacatt aacatataat aaataaatta atcattattg acttaacgat 181380
gacgaaagtt atcatcatct taggattctt gattattaat acaaattcat tgtctatgaa 181440
atgtgaacaa ggtgtctcat attataattc acaagaatta aagtgttgta aactatgtaa 181500
```

gccaggaaca tattcagatc atcgatgtga taaatacagc gataccattt gtggacattg 181560
tccgagtgac acattcacgt caatatataa tcgttctcct tggtgtcata gttgtagagg 181620
tccatgtggt actaatcgag tagaggtcac accttgtaca cctaccacaa atagaatctg 181680
tcattgtgac tcgaatagtt attgtctcct taaagcttct gatggtaact gtgttacatg 181740
tgctcctaaa acaaaatgtg gtcgtgggta tggaaaaaaa ggagaagatg aaatgggtaa 181800
taccatttgt aagaaatgtc ggaagggtac ttattcagat attgtatctg actctgatca 181860
atgtaaacca atgacaagat aagacttact cgcatctact ggatagacat aaaatatcct 181920
cctcgtaata atgaaatata aatatacact aattattaat atcaataaca atcgagtatt 181980
aatatatagg tcatttttaa atccctttttg ggttccgtcc caaacggcgt ttcggtctgc 182040
gtcgccgcca tggccatgcc gagcctctcc gcgtgctcct ccatcgagga cgacttcaac 182100
tatggcagct cggtggcgtc tgccagcgtg cacatacgaa tggcatttct aagaaaagtc 182160
tacggtatcc tttgtctaca atttctttta acaacggcaa caactgcagt atttttatac 182220
tttgactgca tgcggacatt tatacaaggg agtcctgttc taatattggc atcaatgttc 182280
ggatctatag gcttgatttt cgcattgact ttacacagac ataaacatcc cctgaatctg 182340
tacctgcttt gtggatttac actgtcggaa tctctaacgc tggcctctgt tgttactttc 182400
tatgatgtgc atgtcgttat gcaagctttc atgctgacta ctgcagcgtt tcttgctctg 182460
actacatata ctctacaatc aaagagagat ttcagtaaac ttggagcagg attgtttgct 182520
gctttgtgga ttttaatttt gtcaggactc ttggggatat ttgtgcaaaa tgagacagtg 182580
aagctggtcc tgtctgcttt tggggccctt gtattctgtg gattcattat ctatgacacg 182640
cactcactaa tacataagct ctcgcctgaa gagtatgtgt tagcctctat caatctctac 182700
ttggatatca tcaatctgtt cttgcatctg ttgcagcttt tggaagtatc taataagaaa 182760
taaagtttaa aatagaatta ataaaaacat ataggtcatt ttttaaacat ggattggaaa 182820
ccaaggtagt tagttaatac acacaagata tatttttttc acatcatcca cccatgggta 182880
acaccaaggt tgttagttaa taatatacaa gatatttttt ctcactctga tccatgtaaa 182940
ccaaggacga gataagacac tctcattcct catccacaac ccattaaaaa aatggaaatt 183000
aaagccctct attagcataa acggctacag gtctaccatc aggttaacct tcgtctacct 183060
tcacaatggc ctctccttgt gccaagttca gaccctgtca ttgccacgct actaaggact 183120
ccctgaatac cgtggccgac gtcagacatt gtctgactga atacatcctg tgggtttctc 183180
atagatggac ccatagagaa agcgcagggt ctctctacag gcttctcatc tctttcagaa 183240
ctgatgcaac ggagctcttt ggtggtgagt tgaaggattc acttccgtgg gacaattgcg 183300
tggagatcat taaatgtttc atcagaaatg actccatgaa aaccgccgaa gaacttcgtg 183360
caatcattgg actttgtact caatcagcta tcgtctctgg aagagtcttc aacgataagt 183420
atatcgacat actacttatg ctgcgaaaga ttctgaacga gaacgactat ctcaccctct 183480
tggatcatat ccgcactgct aaatactaaa tctccttcat gctctctcac tacacttttt 183540
atcatcttat gaggaatgat tgccttcgtg aaataggaat aattagcacc agaatagcta 183600
tggattattg tggtagagag tgcactattt tatgtcgtct actggatgaa gatgtgacgt 183660
acaaaaaaat aaaaccagag attgaaacgt gtcacaactt atcaaaacat atagatagac 183720
gaggaaacaa tgcgctacat tgttacgtct tcaataaatg cgatacagac attaagattg 183780
ttcggctgtt actctctcgc ggagtcgaga gactttgtag aaacaacgaa ggattaactc 183840
cgctaggagc atacagtaag catagatacg tcaaatctca gattgtgcat ctactgatat 183900
ccagctattc gaattcctct aacgaactca agtcgaatat aaatgatttc gatctgtatt 183960
cggataatat cgacttacgt ctgctaaaat acctaattgt ggataaacgg atacgtccgt 184020
ccaagaatac gaattatgca atcaatggtc tcggattggt ggatatatac gtaacgacgc 184080
ctaatccgag accagaagta ttgctatggc ttcttaaatc agaatgttac agcaccggtt 184140
acgtatttcg tacctgtatg tacgacagtg atatgtgtaa gaactctctt cattactata 184200
tatcgtctca tagagaatct caatctctat ccaaggatgt aattaaatgt ttgatcgata 184260
acaatgtttc catccatggc agagacgaag gaggatcttt acccatccaa tactactggt 184320
cttgctcaac catagatata gagattgtta aattattaat aaaggatgtg gacacgtgta 184380
gagtatacga cgtcagccct atattagagg cgtattatct aaacaagcga tttagagtaa 184440
ccccatataa tgtagacatg gaaatcgtta atcttcttat tgagagacgt catactcttg 184500
tcgacgtaat gcgtagtatt acttcgtacg attccagaga atataaccac tacatcatcg 184560
ataacattct aaagagattt agacaacagg atgtacaagc catgttgata aactacttac 184620
attacggcga tatggtaagt atacctatca ttcaatgcat gttggataac ggagcaacca 184680
tggataagac gacggacaac aactatcctc tgcacgacta ctttgttaat aataatctcg 184740
tcgatgtaaa cgtcgtaagg tttatcgtgg aaaatatgga cacgcggctg taaatcacat 184800
atcgaacaat ggccgtctat gtatgtacgg tctgatatta tcgagattta ataattgcgg 184860
gtatcactgt tatgaaacca tactgataga tgtatttgat atactaagca agtacatgga 184920
tgatatagat atgatcgata actctactat attacgcggt cgatgtcaat aatatacaat 184980
ttgcaaagcg gttattggaa tatggagcga gtgtcacgct cgataatcaa tacggccatc 185040
cagaaaagca gttacagaag agaaaacaaa acgaagctag ttgatttatt actgagttac 185100
catcccactc tagagactat gattgacgca tttaatagag atatacgcta tctatatcct 185160
gaaccattat tcgcctgtat cagatacgcc ttaatcctag atgatgattt tccttctaaa 185220
gtaaagtatg atatcgccgg tcgtcataag gaactaaagc gctatagagc agacattaat 185280
agaatgaaga atgtctacat atcaggcgtc tccatgtttg atatattatt taaacgaagc 185340
aaacgccaca gattgagata cgcaaagaat ccgacatcaa atggtacaaa aaagaactaa 185400
cgtccatcat tacagaaact gtaaagaaca atgagaggat cgactccata gtggacaaca 185460
ttaatacaga cgataacttg atttcgaaat tacccatgga gatactttat tactccatta 185520
aataatttat catggagcga taatgtcctg tttcatttgt ttccatgaca tattacaaaa 185580
tcgattccgt ccaagatgat aaaaacattt accggcatca taaacacgga gtttatttta 185640
tatgtctcgc ataaacatta ctaaaaaaat atattgttct gtttttcttt ttctttttct 185700
ttttctttcg tacatctcta attatgaaaa agtaaatcat tatgagatgg acgagattgt 185760
acgcatcgtt cgcgatagta tgtggtttat acctaacgta tttatggacg acggtaagaa 185820
tgaaggtcac gtttctgtca acaatgtctg tcatatgtat ttcacgttct ttgatgtgga 185880
tacatcgtct catctgttta agctagttat taaacactgc gatctgaata aacgaggtaa 185940
ctctccatta cattgctata cgatgaatac acgatttaat ccatctgtat taaagatatt 186000
gttacaccac ggcatgcgta actttgatag caaggatgac cactatcaat cgataacaag 186060
atctttgata tactaacgga caccattgat gactttagta aatcatccga tctattgctg 186120
tgttatctta gatataaatt caatgggagc ttaaactatt acgttctgta caaaggatcc 186180
gaccctaatt gcgccgacga ggatgaactc acttctcttc attactactg taaacacata 186240
tccacgttct acgaaagcaa ttattacaag ttaagtcaca ctaagatgcg agccgagaag 186300
cgattcatct acgcgataat agattatgga gcaaacatta acgcggttac acacttacct 186360
tcaacagtat accaaacata gtcctcgtgt ggtgtatgct cttttatctc gaggatacgt 186420
aataatcttg attgtacacc catcatggaa cgattgtgca acaggtcata ttctcataat 186480
gttactcaat tggcacgaac aaaaggaaga aggacaacat ctactttatc tattcataaa 186540
acataatcaa ggatacactc tcaatatact acggtatcta ctagataggt tcgacattca 186600
gaaagacgaa tactataata ccgcctttca aaattgtaac aacaatgttg cctcatacat 186660
cggatacgac atcaaccttc cgactaaaga cggtattcga cttggtgttt gaaaacagaa 186720
acatcatata caaggcggat gttgtgaatg acatcatcca ccacagactg aaagtatctc 186780
tacctatgat taaatcgttg ttctacaaga tgtctctccc tacgacgatt actacgtaaa 186840
aaagatacta gcctactgcc tattaaggga cgagtcattc gcggaactac atagtaaatt 186900
ctgtttaaac gaggactata aaagtgtatt tatgaaaaat atatcattcg ataagataga 186960
ttccatcatc gtgacataag tcgccttaaa gagattcgaa tctccgacac cgacctgtat 187020
acggtatcac agctatctta aagccataca ttcggacaga cacatttcat ttcccatgta 187080
cgacgatctc atagaacagt gccatctatc gatggagcgt aaaagtaaac tcgtcgacaa 187140
agcactcaat aaattagagt ctaccatcgg tcaatctaga ctatcgtatt tgcctccgga 187200
aattatgcgc aatatcatct aaacagtatg ttgtacggaa agaaccatta caaatattat 187260
ccatgataga aagaaaatat ctatatgatt ggagaagtag gaaacaggaa caagacgacg 187320
attactacat tattaaatca tgaagtccgt attatactcg tatatattgt ttctctcatg 187380
tataataata aacggaagag atatagcacc gcatgcacca tccgatggaa agtgtaaaga 187440
caacgaatac aaacgccata atttgtgtcc gggaacatac gcttccagat tatgcgatag 187500
caagactaac acacaatgta cgccgtgtgg ttcgggtacc ttcacatctc gcaataatca 187560
tttacccgct tgtctaagtt gtaacggaag acgcgatcgt gtaacacgac tcacaataga 187620
atctgtgaat gctctcccgg atattattgt cttctcaaag gatcatccgg atgcaaggca 187680
tgtgtttccc aaacaaaatg tggaatagga tacggagtat ccggagacgt catctgttct 187740
ccgtgtggtc tcggaacata ttctcacacc gtctcttccg cagataaatg cgaacccgta 187800
cccagaaata cctttaacta tatcgatgtg gaaattaacc tgtatccagt taacgacaca 187860
tcgtgtactc ggacgaccac taccggtctc agcgaatcca tctcaacgtc ggaactaact 187920
attactatga atcataaaga ctgtaatccc gtctttcgtg aggaatactt ctccgtcctt 187980
aataaggtag caacttcagg tttctttaca ggagaaaggt gtgcactctg aatttcgaga 188040
ttaaatgcaa taacaaagat tcttcctcca aacagttaac gaaagcaaag aatgatacta 188100
tcatgccgca ttcggagaca gtaactctag tgggcgacat ctatatacta tatagtaata 188160
ccaatactca agactacgaa actgatacaa tctcttatca tgtgggtaat gttctcgatg 188220
tcgatagcca tatgcccggt agttgcgata tacataaact gatcactaat tccaaaccca 188280
cccacttttt atagtaagtt tttcacccat aaataataaa tacaataatt aatttctcgt 188340
aaaagtagaa aatatattct aatttattgc acggtaagga agtagaatca taaagaacag 188400
tactcaatca atagcaatta tgaaacaata tatcgtcctg gcatgcatgt gcctggcggc 188460
agctgctatg cctgccagtc ttcagcaatc atcctcatcc tcctcctcgt gtacggaaga 188520
agaaaacaaa catcatatgg gaatcgatgt tattatcaaa gtcacaaagc aagaccaaac 188580

-continued

```
accgaccaat gataagattt gccaatccgt aacggaaatt acagagtccg agtcagatcc 188640

agatcccgag gtggaatcag aagatgattc cacatcagtc gaggatgtag atcctcctac 188700

cacttattac tccatcatcg gtggaggtct gagaatgaac tttggattca ccaaatgtcc 188760

tcagattaaa tccatctcag aatccgctga tggaaacaca gtgaatgcta gattgtccag 188820

cgtgtcccca ggacaaggta aggactctcc cgcgatcact catgaagaag ctcttgctat 188880

gatcaaagac tgtgaggtgt ctatcgacat cagatgtagc gaagaagaga aagacagcga 188940

catcaagacc catccagtac tcgggtctaa catctctcat aagaaagtga gttacgaaga 189000

tatcatcggt tcaacgatcg tcgatacaaa atgcgtcaaa aatctagagt ttagcgttcg 189060

tatcggagac atgtgcaagg aatcatctga acttgaggtc aaggatggat tcaagtatgt 189120

cgacggatcg gcatctgaag gtgcaaccga tgatacttca ctcatcgatt caacaaaact 189180

caaagcgtgt gtctgaatcg ataactctat tcatctgaaa ttggatgagt agggttaatc 189240

gaacgattca ggcacaccac gaattaaaaa agtgtaccgg acactatatt ccggtttgca 189300

aaacaaaaat gttcttaact acattcacaa aaagttacct ctcgcgactt cttctttttc 189360

tgtctcaata gtgtgatacg attatgacac tattcctatt cctattccta tttcctttca 189420

g                                                                 189421
```